US009629883B2

(12) United States Patent
Mira Obrador

(10) Patent No.: US 9,629,883 B2
(45) Date of Patent: Apr. 25, 2017

(54) ANTICARIES COMPOSITIONS AND PROBIOTICS/PREBIOTICS

(75) Inventor: Alejandro Mira Obrador, Valencia (ES)

(73) Assignee: CENTRO SUPERIOR DE INVESTIGACIÓN EN SALUD PÚBLICA (CSISP), Valencia (ES)

( * ) Notice: Subject to any disclaimer, the term of this patent is extended or adjusted under 35 U.S.C. 154(b) by 246 days.

(21) Appl. No.: 13/819,261

(22) PCT Filed: Aug. 31, 2011

(86) PCT No.: PCT/ES2011/070609
§ 371 (c)(1),
(2), (4) Date: May 3, 2013

(87) PCT Pub. No.: WO2012/028759
PCT Pub. Date: Mar. 8, 2012

(65) Prior Publication Data

US 2014/0147426 A1 May 29, 2014

(30) Foreign Application Priority Data

Aug. 31, 2010 (ES) .................................. 201031302

(51) Int. Cl.

| | |
|---|---|
| ***A61K 35/744*** | (2015.01) |
| ***C12R 1/01*** | (2006.01) |
| ***C12R 1/46*** | (2006.01) |
| ***A23L 33/135*** | (2016.01) |
| *C07K 14/195* | (2006.01) |
| *C07K 14/315* | (2006.01) |
| *C12N 1/20* | (2006.01) |
| *C07K 14/47* | (2006.01) |
| *A61K 38/16* | (2006.01) |
| *A61K 38/17* | (2006.01) |

(52) U.S. Cl.
CPC .......... *A61K 35/744* (2013.01); *A23L 33/135* (2016.08); *C12R 1/01* (2013.01); *C12R 1/46* (2013.01); *A23V 2002/00* (2013.01); *A61K 38/164* (2013.01); *A61K 38/1729* (2013.01); *C07K 14/195* (2013.01); *C07K 14/315* (2013.01); *C07K 14/47* (2013.01); *C07K 14/4723* (2013.01); *C12N 1/20* (2013.01)

(58) Field of Classification Search
CPC .............. A61K 35/744; A61K 38/1729; A61K 38/164; A23L 33/135; C07K 14/47; C07K 14/195; C07K 14/4723; C07K 14/315; C12N 1/20; C12R 1/01; C12R 1/46; A23V 2002/00; A23V 2200/312
See application file for complete search history.

(56) References Cited

U.S. PATENT DOCUMENTS

2003/0077814 A1* 4/2003 Oh ............................ 435/252.9
2009/0324547 A1* 12/2009 Wikstrom et al. ........... 424/93.2

FOREIGN PATENT DOCUMENTS

| | | | |
|---|---|---|---|
| EP | 0195672 | A2 | 9/1986 |
| JP | 2002000261 | A | 1/2002 |
| WO | 03070919 | A1 | 8/2003 |
| WO | 2004072093 | A2 | 8/2004 |
| WO | 2005018342 | A1 | 3/2005 |
| WO | 2007077210 | A1 | 7/2007 |

OTHER PUBLICATIONS

Camelo-Castillo, A et al. *Streptococcus dentisani* sp. nov., a novel member of the mitis group. Int. J. Syst. Evol. Microbiol. 2014. 64: 60-65.*
Selwitz, RH et al. Dental caries. Lancet. 2007. 369: 51-59.*
P. D. Marsh, "Microbiology of Dental Plaque Biofilms and Their Role in Oral Health and Caries," Dental Clinics of North America, 54, 441-454 (2010).
P. Marsh, "Dental plaque as a biofilm and a microbioal community—implications for health and disease," BMC Oral Health, 6 (Suppl. 1): S14 (2006).
S. S. Socransky, A. D. et al. "Microbial complexes in subgingival plaque," J Clin Periodontol, 25, 134-144 (Feb. 1998).
R. P. Darveau, "Periodontitis: a polymicrobial disruption of host homeostasis," Nat Rev Microbiol, 8, 481-490 (Jun. 1, 2010).
B. J. Paster et al., "Bacterial Diversity in Human Subgingival Plaque," J Bacteriol, 183, 3770-3783 (Jun. 2001).
S. R. Gill et al., "Metagenomic Analysis of the Human Distal Gut Microbiome," Science, 312, 1355-1359 (Jun. 2, 2006).
K. Kurokawa et al., "Comparaative Metagenomics Revealed Commonly Enriched Gene Sets in Human Gut Microbiomes," DNA Res, 14, 169-181 (Aug. 31, 2007).
P. A. Vaishampayan et al., "Comarative Metagenomics and Polulation Dynamics of the Gut Microbiota in Mother and Infant," Genome Biol Evol,2, 53-66 (2010).
J. Qin et al., "A human gut microbial gene catalogue established by metagenomic sequencing," Nature, 464, 59-67 (Mar. 4, 2010).
J. A. Aas et al., "Defining the Normal Bacterial Flora of the Oral Cacity," J Clin Microbiol, 43, 57215732 (Nov. 2005).
E. A. Grice et al., A diversity profile of the human skin microbiota, Genome Res, 18, 1043-1050 (Jul. 2008).
(Continued)

*Primary Examiner* — Renee Claytor
*Assistant Examiner* — Susan E Fernandez
(74) *Attorney, Agent, or Firm* — Tristan A. Fuierer; Moore & Van Allen, PLLC

(57) ABSTRACT

The present invention discloses different specific bacterial strains isolated from individuals without caries which are characterized in that they present inhibitory activity against cariogenic organisms. The invention also discloses a process for isolating said strains, as well as bioactive peptides, such as anti-microbial peptides of human and bacterial origin, which also show anti-cariogenic activity. Moreover, the present invention also discloses pharmaceutical and/or probiotic/prebiotic compositions, functional foods, mouthwashes, toothpaste, chewing gum, etc., that comprise at least one of the strains and/or at least one of the bioactive peptides described in the invention, or a combination thereof, which are useful in the treatment and/or prevention of infectious diseases of the buccal cavity, preferably caries.

9 Claims, 14 Drawing Sheets

(56) References Cited

OTHER PUBLICATIONS

W. J. Loesche, "Role of *Streptococcus* mutans in human dental decay," Microbiol Rev, 50, 353-380 (Dec. 1986).
M. W. Russell et al., "A Caries Vaccine? The State of the Science of Immunization against Dental Caries," Caries Res, 38, 230-235 (May-Jun. 2004).
Margulies M et al., "Genome sequencing in microfabricated high-density picolitre reactors" Nature, 437, 376-380 (2005).
Gomez-Alvarez V et al., "Systematic artifacts in metagenomes from complex microbial communities," ISME J. , 3(11), 1314-1317 (Nov. 2009).
Zheng Zhang et al., "A Greedy Algorithm for Aligning DNA Sequences," J Comput Biol., 7(1-2) 203-214 (2000).
E. M. Bik et al., Bacterial diversity in the oral cavity of 10 healthy individuals, ISME J, 4, 962-974 (Mar. 25, 2010).
K. T. Konstantinidis et al., "Genomic insights that advance the species definition for prokaryotes," Proc Natl Acad Sci U S A, 102, 2567-2572 (Feb. 15, 2005).
Marchler-Bauer A et al., "CDD: specific functional annotation with the Conserved domain Database," Nucleic Acids Res., 37:D205-10 (Jan. 2009).
Selengut JD et al., "TIGRFAMs and Genome Properties: tools for the assignment of molecular function and biological process in prokaryotic genomes," Nucleic Acids Res., 35:D260-4 (Jan. 2007).
Altschul et al., "Basic Local Alignment Search Tool," J Mol Bio., 215 (3):403-10 (Oct. 5, 1990).
Cole JR. et al., "The Ribosomal Database Project: impoved alignments and new tools for rRNA analysis," Nucleic Acid Res., 37:D141-5 (Jan. 2009).
Huson DH et al., "MEGAN analysis of metagenomic data," Genome Res., 17 (3):377-86 (Mar. 2007).
Brady A and Salzberg SL. "Phymm and PhymmBL: metagenomic phylogenetic classification with interpolated Markov models," Nature Methods., 6 (9): 673-6 (Sep. 2006).
Chen T et al., "The Human Oral Microbiome Database: a web accessible resource for investigating oral microbe taxonomic and genomic information," Database (Oxford) 6 (Jul. 2010).
J. R. Tagg et al., "Bacterial replacement therapy: adapting 'germ warfare' to infection prevention," Trends Biotechnol, 21, 217-223 (May 2003), Abstract Only.
R. B. Merrifield, "Solid Phase Peptide Sunthesis. I. The Synthesis of a Tetrapeptide," J. Am. Chem. Soc., 85 (14): 2149-2154 (1963).
Albericio, F. "Solid-Phase Synthesis: A Practical Guide" (1st ed.). CRC Press. pp. 848. ISBN 0824703596 (2000), This Is a Book; Not Attached.
Konstantinidis KT, Tiedje JM. "Towards a Genome-Based Taxonomy for Prokaryotes," J Bacteriol., Sep. 2005; 187(18): 6258-64.
Goris J et al., "DNA-DNA hybridization values and their relationship to whole-genome sequence similarities," Int J Syst Evol Microbiol., Jan. 2007; 57(Pt 1): 81-91.
Richter M, Rosselló-Móra R. "Shifting the genomic gold standard for the prokaryotic species definition," Proc Natl Acad Sci USA., Nov. 10, 2009; 106(45): 19126-31.
Exterkate RA et al., "Different Response to Amine Fluoride by *Streptococcus* mutans and Polymicrobial Biofilms in a Novel High-Tthroughput Active Attachment Model," Caries Res., 2010; 44(4): 372-9.
Pham LC et al., "Effects of Lactobacillus rhamnosus GG on saliva-derived microcosms," Arch Oral Biol., Feb. 2011; 56(2): 136-47.
Hillman JD et al., "Genetically modified *Streptococcus* mutans for the prevention of dental caries," Antonie Van Leeuwenhoek, 2002; 82(1-4); 361-6. Abstract Only.
Montville TJ., "Mechanistic action of pediocin and nisin: recent progress and unresolved questions," Appl Microbiol Biotechnol, 1998, 50:511-519.
Komatsuzawa H., "Susceptibility of Periodontopathogenic and Cariogenic Bacteria to Defensins and Potential Therapeutic Use of Defensins in Oral Diseases," Current Pharmaceutical Design, 2007, 13, 3084-3095.
International Search Report, Jun. 14, 2012.
Margolis, H.C., et al.; "Composition and Cariogenic Potential of Dental Plaque Fluid," Critical Reviews in Oral Biology and Medicine, 1994, pp. 1-25, vol. 5.
Obata, Junko, et al.; "Identification of the Microbiota in Carious Dentin Lesions Using 16S rRNA Gene Sequencing," Plos One, 2014, pp. 1-16, vol. 9.
Kidd, E.A.M., et al.; "What Constitutes Dental Caries? Histopathology of Carious Enamel and Dentin Related to the Action of Cariogenic Biofilms," J Dent Res, 2004, pp. C35-C38, vol. 83.
Houte, J. Van; "Role of Micro-organisms in Caries Etiology," J Dent Res, 1994, pp. 672-681, vol. 73.
Gluch, Joan; "Sugarfree Chewing Gums and Caries Prevention," Contemporary Oral Hygiene, 2003, p. 1.
Widowati, W. et al.; "Saliva pH Changes in Patients with High and low Caries Risk After Consuming Organic (Sucrose) and Non-Organic (Maltitol) Sugar," The International Medical Journal Malaysia, 2013, pp. 15-21, vol. 12.
Loesche, Walter J.; "Role of *Streptococcus* mutans in Human Dental Decay," Microbiological Reviews, 1986, pp. 353-380, vol. 50.
Richter, Michael, et al.; "Shifting the genomic gold standard for the prokaryotic species definition," PNAS, 2009, pp. 19126-19131, vol. 106.
Law, V., et al.; "Factors influencing oral colonization of mutans *Streptococci* in young children," Australian Dental Journal, 2007, pp. 93-100, vol. 52.
Kolenbrander, Paul E., et al.; "Inhibition of Coaggregation between Fusobacterium nucleatum and Porphyromonas (Bacteroides) gingivalis by Lactose and Related Sugars," Infection and Immunity, 1989, pp. 3204-3209, vol. 57.
Jagathrakshakan, Sri Nisha, et al.; "16S rRNA gene-based metagenomic analysis indentifies a novel bacterial co-prevalence pattern in dental caries," European Journal of Dentistry, pp. 127-132, vol. 9.
Liu, Ya-Ling, et al.; "Progress toward understanding the contribution of alkali generation in a dental biofilms to inhibition of dental caries," International Journal of Oral Science, 2012, pp. 135-140, vol. 4.
Kolenbrander, Paul E., et al.; "Oral multispecies biofilm development and the key role of cell-cell distance," Nat Rev Microbiol., 2010, pp. 471-480, vol. 8; Abstract Only.
Eckert, R., et al.; "Tareted Antimicrobial Treatment to Re-establish a Healthy Microbial Flora for Long-term Protection," Adv Dent Res, 2012, pp. 94-97, vol. 22.

* cited by examiner

A

B

A

B

ANTICARIES COMPOSITIONS AND PROBIOTICS/PREBIOTICS

CROSS-REFERENCE TO RELATED APPLICATIONS

This application is filed under the provisions of 35 U.S.C. §371 and claims the priority of International Patent Application No. PCT/ES2011/070609 filed on 30 Aug. 2011 entitled "ANTICARIES COMPOSITIONS AND PROBIOTICS/PREBIOTICS" in the name of Alejandro MIRA OBRADOR, which claims priority to Spanish Patent Application No. P201031302 filed on 31 Aug. 2010, both of which are hereby incorporated by reference herein in their entirety.

FIELD OF THE INVENTION

The present invention belongs to the field of human health; more specifically, the field of bucco-dental health.

BACKGROUND

The human oral cavity is inhabited by hundreds of bacterial species, most of which are commensal species, necessary to maintain equilibrium in the oral ecosystem. However, some of them play a key role in the development of oral diseases, primarily dental caries and periodontal disease (1). Oral diseases begin with the growth of dental plaque, a biofilm formed by the accumulation of bacteria jointly with glycoproteins from human saliva and polysaccharides secreted by microbes (2). The subgingival plaque, located in the neutral or alkaline subgingival pocket, is typically inhabited by Gram-negative anaerobes and is responsible for the development of gingivitis and periodontitis. The supragingival dental plaque is formed on the surface of the tooth and includes acidogenic and acidophilic bacteria, which, upon fermenting the sugars ingested in the diet, produce acid and lower the pH. When the pH is too acidic (generally with a value less than 5.5), the tooth enamel is de-mineralised and destroyed, and, therefore, these bacteria are responsible for dental caries, which are considered to be the most widespread infectious disease in the world, affecting over 80% of the human population (3). A bad oral health may be associated with other pathologies, such as, for example, stomach ulcers, stomach cancer or cardiovascular diseases, amongst others.

One of the main reasons why, as of today, oral pathogens have still not been eradicated is the difficulty involved in studying microbial communities that inhabit the oral cavity, since, on the one hand, the complexity of the ecosystem (several hundreds of species have been detected, with numerous levels of interaction) makes it difficult to detect the potential pathogenic species (4); moreover, no single etiological agent may be identified, as in classic diseases, following Koch's postulates. This fact has been clearly demonstrated in periodontal disease, where there are at least 3 bacterial species belonging to very different taxonomic groups (the so-called "red complex" of periodontal pathogens) which have been associated with the development and progression of periodontal disease (5). On the other hand, a large proportion of oral bacteria cannot be cultured (6) and, therefore, traditional microbiological methods give an incomplete image of the natural communities that inhabit dental plaque. However, the current development of metagenomic techniques and Next-Generation Sequencing technologies allows for the study of the bacterial community as a whole, by analysing the total DNA of complex microbial samples (Metagenome) without the need to culture the bacteria themselves.

In this regard, pioneering studies in metagenomics have focused on the intestinal ecosystem primarily through a shot-gun approach, wherein the DNA is cloned in small-size plasmids, followed by traditional Sanger-type sequencing (7, 8). More recent approaches include sequencing of the ends of large-size fosmids (9) and use of the "Illumina" sequencing technology, which provides a high coverage of short sequences (10). Studies of the microbiota of the oral cavity, as well as of other human body habitats, such as the skin, the vagina or the respiratory tract, have focused on the sequencing of ribosomal RNA amplicons (11, 12). These studies have provided a substantial improvement of our knowledge about these bacterial communities as compared to prior research based on cultures, but estimates of microbial diversity are hindered by the biases in PCR amplification (i.e. PCR only detects the bacteria that are most similar to those already known, and on the basis of which the amplification primers are used, giving an incomplete image of the diversity present), the cloning bias (a large number of genes are not cloned because they are toxic for the host bacteria and, therefore, this method does not allow for the study of the entire genetic reservoir of the sample) and a low sequence length (the sequences in the Illumina technology have only between 35-70 nucleotides, which in most cases makes a reliable taxonomic or functional assignment impossible), together with the fact that, as mentioned above, a large proportion of oral bacteria cannot be cultured.

In order to resolve the aforementioned problems, the present invention discloses the obtainment of the metagenome of dental plaque by the direct sequencing of metagenomic DNA, using 454-pyrosequencing, thereby eliminating the potential biases imposed by cloning and PCR techniques, and, furthermore, providing access to the entire genetic repertoire of the oral bacterial community under different health conditions, as well as the possibility to analyse which bacterial species amongst those found in the metagenome obtained may be associated with a good oral health, since those individuals who had never suffered from caries exhibit a different bacterial flora than those individuals who had suffered or currently suffer from it. By means of the oral metagenome obtained in the present invention, it is possible to direct the isolation, culture and identification of strains with anti-cariogenic activity from the conglomerate of bacteria in the buccal cavity sample; specifically, the supragingival plaque of individuals who have never suffered from caries, i.e. those strains capable of inhibiting the growth of cariogenic bacteria.

Another strategy disclosed in the present invention is the obtainment of a metagenomic library of fosmids (long DNA inserts, approximately 35-45 Kb) from the dental plaque of individuals who have never suffered from caries. By obtaining said fosmid library, it is possible to isolate and identify the bioactive anti-cariogenic peptides synthesised by the bacteria present in the oral cavity of individuals who have never suffered from caries. In this regard, given that, in the state of the art, *Streptococcus mutans* has been shown to be the main causal agent of caries (13), it is not surprising that most strategies against this disease have been aimed against said microorganism. These strategies have included the development of vaccines using known surface antigens, passive immunisation strategies that may neutralise the bacteria, the co-aggregation of *S. mutans* with probiotic strains and the use of inhibitory proteins specific to *S. mutans*, amongst others (14).

Other different strategies have been those disclosed in different patent documents, which propose the use of different bacterial strains, preferably *S. mutans*, that produce a lower concentration of acid (15), or the use of the same resources, for example, the nutrients, by pathogenic strains and non-pathogenic strains, continuously supplying high concentrations of non-pathogenic bacteria, which results in the displacement of the pathogenic bacteria, provided that they share the same resource (16), or even a lower adherence of cariogenic bacterial strains to the tooth (17). On the contrary, the bioactive strains and peptides disclosed in the present invention have antibiotic activity, preferably anti-cariogenic activity, on their own, against caries-producing microorganisms. On the other hand, patent WO20040072093 (18) discloses a number of anti-microbial agents that are active primarily against Gram-negative microorganisms, but the main causal agents of caries, *S. mutans* and *S. sobrinus*, are Gram-positive microorganisms. Moreover, the *S. mitis* and *S. oralis* isolates that produce the anti-microbial peptides disclosed in WO20040072093 (18) have been isolated from the throat of patients with cystic fibrosis, not from the mouth of people without caries, as in the case of the peptides and/or strains of the invention. Similarly, the therapeutic use of said peptides is aimed at the treatment of respiratory tract diseases and not of caries, as in the case of the bioactive peptides disclosed in the present invention.

In this regard, the main technical characteristics that make the bacterial strains isolated and disclosed in the present invention different from the rest of strains disclosed in the state of the art are that they may be cultured by means of conventional microbiological techniques; that they present inhibitory activity against organisms that produce infectious diseases of the buccal cavity, preferably caries, without the need to be genetically modified; and that they have been isolated from individuals who have never suffered from caries. Consequently, both the anti-cariogenic bacteria themselves and the bioactive anti-cariogenic compounds, preferably peptides, disclosed in the present invention may be used as probiotic and/or prebiotic compositions as such, or as a part of different pharmaceutical compositions used for the treatment of infections of the buccal cavity, such as, for example, caries, periodontitis, etc., or even as functional foods. Moreover, the present invention also discloses a method for the prevention and/or treatment of infectious diseases of the buccal cavity, preferably caries, that comprises the administration of a pharmaceutically effective quantity of at least one of the strains and/or at least one of the anti-microbial compounds, preferably peptides, described above, or of the probiotic or pharmaceutical composition or functional foods that comprise at least one of the strains and/or at least one of the compounds, preferably peptides, of the invention.

DESCRIPTION OF THE INVENTION

Brief Description of the Invention

The existing difficulty in the state of the art in identifying bacterial strains that directly inhibit the growth of pathogenic germs related to the onset of buccal cavity diseases is thus caused by the large quantity of bacterial species in said cavity; consequently, the difficulty involved in isolating, amongst all of them, strains that directly inhibit the growth of pathogenic species, many of which are non-culturable species, has made this problem hard to solve thus far.

The present invention resolves this problem by creating the metagenome of the buccal cavity of individuals who have never suffered from caries. The creation of said metagenome, using massive sequencing, preferably pyrosequencing, of the DNA present in the samples taken from the buccal cavity of said individuals who have never suffered from caries, makes it possible to identify the genera and species of the bacteria that are most frequent in the bacterial population present in the buccal cavity of said individuals. This quantification of the frequency of each bacteria in the sample had not been possible, thus far, using culture, cloning or PCR techniques, since these techniques only identify part of the bacteria and the proportions of those that are identified is biased due to the methodology itself (primarily due to the preferable culture, cloning or amplification of certain species, respectively).

In principle, the invention has been based on human beings, but could be applied to any superior mammal, especially pets or livestock, or even wild fauna. It would be sufficient to determine the characteristic metagenome of each species, in individuals who have never suffered from caries, as a representative disease of the typical buccal cavity diseases. Once the bacterial strains that are most frequent in the buccal cavity of healthy individuals have been identified from the data obtained from the metagenome, the following step of the present invention consists of culturing the samples obtained from the buccal cavity of these individuals, in the favourable culture media and under favourable conditions, such that the most frequent genera and species identified in the metagenome of the mammalian species under study may develop.

A second alternative to resolve the problem mentioned above consists of attempting to isolate compounds, especially active peptides, secreted, amongst others, by the bacterial strains present in the buccal cavity of individuals who have never suffered from caries and which present direct inhibitory activity against the growth of cariogenic species. In the present invention, direct inhibitory capacity is defined as the capacity to completely inhibit growth, by creating inhibition haloes in lawn cultures of said pathogenic species, due to their antibiotic action, without ruling out the fact that, in addition to said inhibition caused by their antibiotic effect, the strains and compounds may exert their anti-microbial effect, preferably anti-cariogenic effect, by hindering the cariogenic action by other routes, such as modifying the optimal pH for the growth of said cariogenic strains, hindering their adherence to the teeth, etc.

To this end, the invention has started, once again, from buccal cavity samples taken from healthy individuals, but, in this alternative, it has not only focused on compounds of bacterial origin that may be secreted, amongst others, by the aforementioned isolated strains. Moreover, compounds secreted by other bacterial strains may exist which are not culturable and, therefore, cannot be isolated using the strategy proposed above. Finally, in addition to compounds of bacterial origin from the population of bacterial strains that inhabit the buccal cavity, said cavity also contains compounds secreted by the cells of the mammals themselves, particularly human beings, whereon the present invention is preferably based. Some of these compounds may have a direct inhibitory activity against the growth of cariogenic microorganisms. To this end, the samples obtained from the buccal cavity of healthy individuals were lysed, the DNA thereof was extracted, fosmids were constructed with said fragments and cloned in a host cell that may be cultured and assayed in cultures of cariogenic species, in order to observe whether inhibition haloes against the growth of the pathogenic cariogenic species are produced.

It must be noted that, although the isolated inhibitory strains and compounds have been obtained from samples of the buccal cavity and are active against pathogenic caries-producing (cariogenic) bacterial species, given their inhibitory capacity against the growth of pathogenic bacteria that preferably inhabit the buccal cavity, in principle the bacterial strains and compounds isolated could be found in other parts of the body and produce or be associated with other diseases. For this reason, an object of the present invention is the use of the strains and compounds isolated as medicaments, particularly as anti-microbial agents and, more specifically, as anti-bacterial agents.

Therefore, the present invention discloses the isolation of culturable bacterial strains and compounds, primarily bioactive peptides, with an inhibitory capacity against the growth of pathogenic microorganisms involved in the onset of buccal cavity diseases. Throughout the present invention, the onset of caries has been taken as a representative disease of diseases typical of the buccal cavity, but the invention may be applied to any infectious disease attributable to pathogenic microorganisms of the buccal cavity. For this reason, the present invention preferably focuses on the isolation of bacterial strains and compounds, primarily bioactive peptides, with an inhibitory capacity against the growth of pathogenic microorganisms, particularly those involved in the onset of caries.

The process for isolating culturable bacterial strains with anti-cariogenic capacity is based on obtaining the oral metagenome of individuals who have never suffered from caries, in order to determine which type of bacteria said individuals present most frequently in their buccal cavity and analyse which of them are associated with a good oral health, by inhibiting the growth of cariogenic bacteria. Said process has made it possible to isolate, characterise, culture and deposit different strains with anti-cariogenic activity in the Spanish Type Culture Collection (CECT): CECT 7746, CECT 7747, CECT 7773, CECT 7774 and CECT 7775. By means of sequence homology analysis, it was concluded that four of the strains that present anti-cariogenic activity and which were deposited in the CECT, specifically strains CECT 7746, 7747, 7773 and 7775, belonged to the same bacterial genus: *Streptococcus*; therefore, in addition to their functionality (anti-cariogenic activity) and the process for the obtainment thereof, said strains share a structural and taxonomic similarity, since they belong, as previously mentioned, to the same bacterial genus, *Streptococcus.*

On the other hand, the process for isolating and characterising bioactive anti-cariogenic peptides is based on obtaining a fosmid metagenomic library from individuals who have never suffered from caries. Using said method, it is possible to characterise the peptides with anti-cariogenic capacity produced by the bacteria found in individuals who have never suffered from caries, including non-culturable bacteria, as well as by the anti-microbial compounds, for example, of the defensin type, synthesised by the individuals themselves. Said peptides are assayed in order to determine their inhibitory activity against the growth of cariogenic bacteria, such as, for example, *S. mutans* or *S. sobrinus.*

Another aspect of the present invention discloses different specific culturable bacterial strains, CECT 7746, CECT 7747, CECT 7773, CECT 7774 and CECT 7775, isolated from individuals with an excellent oral health who have never suffered from caries, characterised in that they present inhibitory activity against organisms that produce infectious diseases of the buccal cavity, preferably against caries-producing microorganisms. From the metagenome of the bacteria present in the dental plaque of individuals who had never suffered from caries, the genera and species of the bacteria that appeared most frequently in healthy individuals who had never suffered from caries were identified by homology with the existing bacterial DNA libraries. The bacteria that appeared most frequently in individuals without caries and which appeared to be absent or with a very low frequency in individuals with caries belonged to one of the following genera: *Rothia, Globicatella, Johnsonella, Kingella, Cardiobacterium, Phocoenobacter, Mannheimia, Haemophilus, Neisseria, Streptococcus* and *Aggregatibacter*; the genus *Streptococcus* being amongst the most abundant. In this regard, the preferred bacterial strains of the invention are strains CECT 7746, CECT 7747, CECT 7773 and CECT 7775, all of them belonging to the genus *Streptococcus.*

Another aspect disclosed in the present invention describes bioactive compounds, preferably peptides, which inhibit the growth of organisms that produce infectious diseases of the buccal cavity, preferably caries-producing microorganisms. Specifically, it describes peptides encoded by DNA sequences included in any of the following fosmid inserts with inhibitory activity against organisms that produce infectious diseases of the buccal cavity, preferably caries-producing microorganisms: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 14.

More specifically, the peptides encoded by the DNA sequences included in the fosmid inserts with inhibitory activity against organisms that produce infectious diseases of the buccal cavity: SEQ ID NO: 2, SEQ ID NO: 3, SEQ ID NO: 4 and SEQ ID NO: 5, are characterised in that they are of bacterial origin and have characteristics similar to those of bacteriocins. Similarly, the peptides encoded by the DNA sequences included in the fosmid inserts with inhibitory activity against organisms that produce infectious diseases of the buccal cavity: SEQ ID NO: 1, SEQ ID NO: 6, SEQ ID NO: 7, SEQ ID NO: 13 and SEQ ID NO: 14, are characterised in that they are of human origin and have characteristics similar to those defensins.

More specifically, the invention discloses 2 specific peptides: SEQ ID NO: 8, an anti-microbial peptide of human origin with characteristics similar to those defensins; SEQ ID NO: 9, a peptide of bacterial origin with characteristics similar to those of bacteriocins.

Moreover, the invention discloses solid, powdery (for direct intake or in solution) or pasty compositions for buccal hygiene, such as toothpaste, chewing gum, candy, bars, etc., or liquid mouthwash solutions, such as collutories, syrups, drinks, etc., or probiotic and/or prebiotic food compositions the composition whereof comprises either the strains and/or the compounds, preferably peptides, of the invention, with inhibitory activity against organisms that produce infectious diseases of the buccal cavity, preferably caries-producing microorganisms. In a preferred embodiment of the invention, the strains and/or peptides of the invention are added to compositions that present anti-microbial activity against the flora of the buccal cavity and which may be commercially found, such as collutories of the Listerine® type, said collutories showing an improved inhibitory effect against organisms that produce infectious diseases of the buccal cavity, preferably caries-producing microorganisms, when the strains and/or peptides of the invention are added to the composition thereof.

A preferred embodiment of the invention are probiotics/prebiotics or functional foods, the composition whereof comprises the strains and/or the compounds, preferably peptides, of the invention, with inhibitory activity against organisms that produce infectious diseases of the buccal cavity, preferably caries-producing microorganisms. The concept of probiotics or functional foods includes, without being limited thereto: dairy products, such as yogurts, for example, juices, solid foods, such as sweets, for example, as well as teas, herbalist and parapharmacy products, such as vitamin complexes, with nutritional supplements, etc.

For purposes of the present invention, the following terms are explained:

Infectious disease of the buccal cavity: for purposes of the present invention, the infectious diseases of the buccal cavity are preferably caries, periodontitis, gingivitis and halitosis.

Probiotics: for purposes of the present invention, the term probiotic refers to the use of live microorganisms that are added to foods (milk, yogurts, etc.), dietary supplements (in the form of capsules, tablets, pills, powder, etc.) or others, which remain active and exert their physiological effects on the subject that ingests the food or similar product containing said probiotic. Ingested in sufficient quantities they have beneficial effects, in this case, on buccal health.

Prebiotics: for purposes of the present invention, the term prebiotic refers to the use of substances that are added to foods, chewing gum, dietary supplements or others, which exert an effect on the composition of the oral microbiota, favouring the establishment of bacteria that are beneficial for oral health and/or hindering the establishment of pathogenic bacteria.

Metagenome: represents the genomes of all the bacteria that are present in a sample, an individual or an ecosystem, etc.

Microbiome: is the set of microbes or bacteria that co-exist with human beings.

Bioactive anti-microbial compounds: are compounds such as biologically active peptides, proteins, antibiotics, pigments, etc. that are found in vertebrates and invertebrates and act as natural antibiotics, being a part of the innate immune response. Some of these compounds, for example peptides, are produced by human beings, such as, for example, defensins and cathelicidins, amongst others. They are active against bacteria, fungi and cloistered viruses.

Bacteriocins: are biologically active peptides secreted by bacteria that have bactericidal properties against other species that are closely related to the producing strain, or against strains that are phylogenetically distant from the producing strain.

Phosmids: circular DNA fragments that may be easily introduced into the host cells, generally bacterial cells, and transport bacterial or human DNA fragments.

Functional foods: are defined as those foods that are prepared not only for their nutritional characteristics, but also to fulfil a specific function, such as improving health or reducing the risk of contracting diseases. To this end, biologically active compounds, such as minerals, vitamins, fatty acids, bacteria with beneficial effects, dietary fibre and antioxidants, etc., are added thereto.

Culturable bacterial strains: culturable bacterial strains are considered to be those that grow in pure culture and keep growing in a stable manner, in an artificial laboratory culture medium under standard aerobiosis or anaerobiosis conditions.

DETAILED DESCRIPTION OF THE INVENTION

Figure 1:
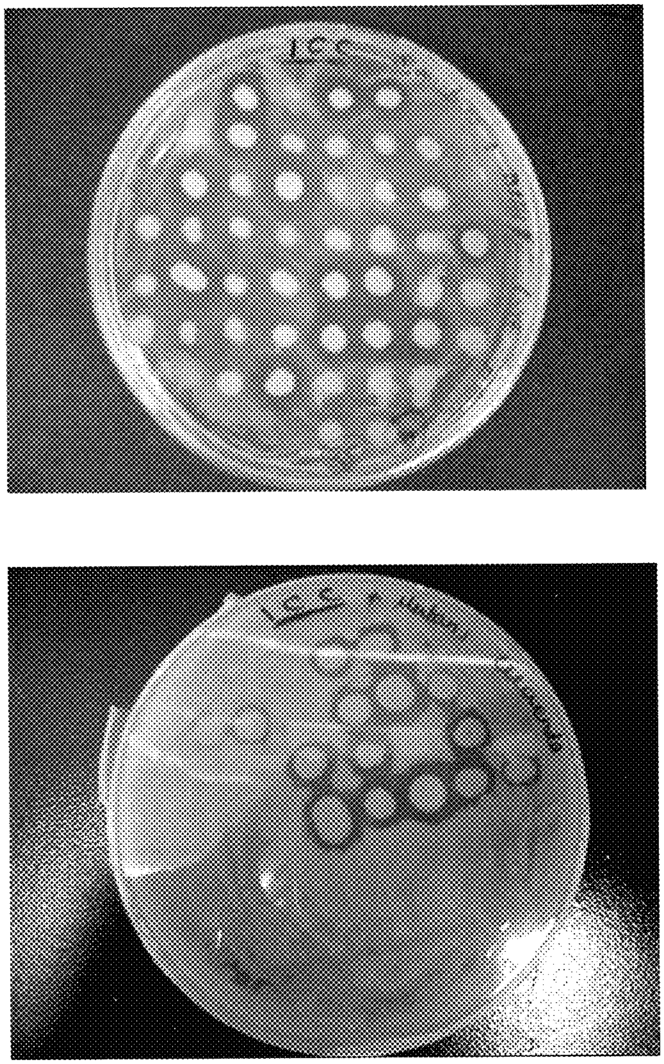
FIG. 1. A. Photograph of a Petri dish, which shows the initial screening of the clones of *E. coli* that contain the fosmids from DNA from the dental plaque of individuals without caries which produce inhibition haloes on a lawn culture of *S. mutans*. B. Photograph of a Petri dish, which shows the confirmation screening of the clones of *E. coli* that contain the fosmids from DNA from the dental plaque of individuals without caries that had produced inhibition haloes on a lawn culture of *S. mutans*.

An object of the present invention is a culturable anti-microbial bacterial strain selected from any of the following: CECT 7746, CECT 7747, CECT 7773, CECT 7774 and CECT 7775. In a preferred embodiment, the bacterial strains of the invention are characterised in that they belong to the genus *Streptococcus*, selected from: CECT 7746, CECT 7747, CECT 7773 or CECT 7775. In another preferred embodiment, the anti-microbial bacterial strains disclosed in the invention present inhibitory activity against the growth of organisms that produce infectious diseases of the buccal cavity, preferably, caries-producing organisms. In a preferred embodiment, the strains of the invention are characterised in that, in addition to competitively growing to occupy the tooth, they are capable of producing inhibitory substances against the growth of cariogenic bacteria.

Another object of the present invention relates to the culturable anti-microbial bacterial strains selected from any of the following: CECT 7746, CECT 7747, CECT 7773, CECT 7774 and CECT 7775, or a combination thereof, for use as a medicament. In a preferred embodiment, the anti-microbial bacterial strains disclosed in the invention are characterised in that they belong to the genus *Streptococcus* and are selected from: CECT 7746, CECT 7747, CECT 7773 or CECT 7775.

Another object of the present invention relates to the use of at least one of the culturable anti-microbial bacterial strains selected from any of the following: CECT 7746, CECT 7747, CECT 7773, CECT 7774 and CECT 7775, or a combination thereof, in the manufacturing of a medicament. In a preferred embodiment, said use is characterised in that the bacterial strain belongs to the genus *Streptococcus*, selected from: CECT 7746, CECT 7747, CECT 7773 or CECT 7775.

Another object of the present invention relates to a culturable anti-microbial bacterial strain selected from any of the following: CECT 7746, CECT 7747, CECT 7773, CECT 7774 and CECT 7775, or a combination thereof, for use as an anti-microbial agent, preferably an anti-bacterial agent. In a preferred embodiment, the anti-microbial bacterial strain is characterised in that it belongs to the genus *Streptococcus* and is selected from: CECT 7746, CECT 7747, CECT 7773 or CECT 7775.

Another object of the present invention relates to the use of at least one of the culturable anti-microbial bacterial strains selected from any of the following: CECT 7746, CECT 7747, CECT 7773, CECT 7774 and CECT 7775, or a combination thereof, in the manufacturing of an anti-microbial composition, preferably an anti-bacterial composition. In a preferred embodiment, said use is characterised in that the bacterial strain belongs to the genus *Streptococcus* and is selected from: CECT 7746, CECT 7747, CECT 7773 or CECT 7775.

Another object of the present invention relates to a culturable anti-microbial bacterial strain selected from any of the following: CECT 7746, CECT 7747, CECT 7773, CECT 7774 and CECT 7775, or a combination thereof, for use in the treatment of infectious diseases of the buccal cavity, preferably the treatment of caries. In a preferred embodiment, the bacterial strain of the invention is characterised in that it belongs to the genus *Streptococcus* and is selected from: CECT 7746, CECT 7747, CECT 7773 or CECT 7775.

Another object of the present invention relates to the use of at least one of the culturable anti-microbial bacterial strains selected from any of the following: CECT 7746, CECT 7747, CECT 7773, CECT 7774 and CECT 7775, or a combination thereof, in the preparation of a composition designed for the treatment of infectious diseases of the buccal cavity, preferably the treatment of caries. In a preferred embodiment, the use of the strains of the invention is characterised in that the culturable bacterial strain belongs to the genus *Streptococcus* and is selected from: CECT 7746, CECT 7747, CECT 7773 or CECT 7775.

Another object of the present invention relates to the culturable anti-microbial bacterial strains selected from any of the following: CECT 7746, CECT 7747, CECT 7773, CECT 7774 and CECT 7775, or a combination thereof, for use as a probiotic or functional food designed to improve buccal health, preferably to prevent caries. In a preferred embodiment, the strains of the invention are characterised in that they belong to the genus *Streptococcus*, selected from: CECT 7746, CECT 7747, CECT 7773 or CECT 7775.

Another object disclosed in the present invention relates to the use of at least one of the culturable anti-microbial bacterial strains selected from any of the following: CECT 7746, CECT 7747, CECT 7773, CECT 7774 and CECT 7775, or a combination thereof, in the preparation of a probiotic or a functional food designed to improve buccal health, preferably to prevent caries. In a preferred embodiment, the use of at least one of the aforementioned bacterial strains is characterised in that said strains belong to the genus *Streptococcus* and are selected from: CECT 7746, CECT 7747, CECT 7773 or CECT 7775.

Another object disclosed in the present invention relates to a probiotic/prebiotic composition or functional food that comprises at least one culturable anti-microbial strain, as mentioned throughout the present invention, as well as the anti-cariogenic substances, compounds or molecules secreted by said strains.

Another object disclosed in the present invention relates to a medical-pharmaceutical composition or a composition designed for buccal health that comprises at least one culturable anti-microbial strain as described throughout the present invention or the anti-cariogenic substances, compounds or molecules secreted by said strains.

Another object disclosed in the present invention relates to an anti-microbial compound that comprises SEQ ID NO: 8 or an anti-microbial compound encoded by a DNA sequence that comprises any of the following sequences: SEQ ID NO: 1, SEQ ID NO: 6, SEQ ID NO: 7, SEQ ID NO: 13, SEQ ID NO: 14.

Another object disclosed in the present invention relates to an anti-microbial compound that consists of SEQ ID NO: 8 or an anti-microbial compound encoded by a DNA sequence that consists of any of the following sequences: SEQ ID NO: 1, SEQ ID NO: 6, SEQ ID NO: 7, SEQ ID NO: 13, SEQ ID NO: 14. In a preferred embodiment of the invention, the anti-microbial compounds described above present inhibitory activity against the growth of organisms that produce infectious diseases of the buccal cavity, preferably caries-producing organisms. In another preferred embodiment, said anti-microbial compounds are peptides.

Another object of the present invention relates to the anti-microbial compounds mentioned in the preceding paragraphs, or a combination thereof, for use as a medicament.

Another object disclosed in the present invention relates to the use of at least one anti-microbial compound as described above, or a combination thereof, in the manufacturing of a medicament.

Another object of the present invention relates to the anti-microbial compounds described above, or a combination thereof, for use in the manufacturing of an anti-microbial composition, preferably an anti-bacterial composition.

Another object disclosed in the present invention relates to the use of at least one anti-microbial compound as described above, or a combination thereof, in the manufacturing of an anti-microbial composition, preferably an anti-bacterial composition.

Another object of the present invention relates to the anti-microbial compounds described above, or a combination thereof, for use in the treatment of infectious diseases of the buccal cavity, preferably the treatment of caries.

Another object disclosed in the present invention relates to the use of at least one anti-microbial compound as described above, or a combination thereof, in the preparation of a composition designed for the treatment of infectious diseases of the buccal cavity, preferably an anti-caries composition.

Another object of the present invention relates to the anti-microbial compounds mentioned above, in the present invention, for use as a prebiotic or a functional food designed to improve buccal health, preferably to prevent caries.

Another object disclosed in the present invention relates to the use of at least one anti-microbial compound as described above, or a combination thereof, in the preparation of a prebiotic or a functional food designed to improve buccal health, preferably to prevent caries.

Another object disclosed in the present invention relates to a probiotic/prebiotic composition or functional food that comprises at least one anti-microbial compound as described throughout the present invention.

Another object disclosed in the present invention relates to a medical-pharmaceutical composition or composition for buccal health that comprises at least one anti-microbial compound as described throughout the present invention.

Another object disclosed in the present invention relates to an anti-microbial compound that comprises sequence SEQ ID NO: 9 or an anti-microbial compound encoded by a DNA sequence that comprises any of the following sequences: SEQ ID NO: 2, SEQ ID NO: 3, SEQ ID NO: 4, SEQ ID NO: 5.

Another object disclosed in the present invention relates to an anti-microbial compound that consists of sequence SEQ ID NO: 9 or an anti-microbial compound encoded by a DNA sequence that consists of any of the following sequences: SEQ ID NO: 2, SEQ ID NO: 3, SEQ ID NO: 4, SEQ ID NO: 5. In a preferred embodiment, said anti-microbial compounds present inhibitory activity against the growth of organisms that produce infectious diseases of the buccal cavity, preferably, caries-producing organisms. In another preferred embodiment, the anti-microbial compounds described above are characterised in that they are peptides. In another preferred embodiment, the anti-microbial compounds described above are characterised in that they inhibit the production of acid, preferably lactic acid, in the buccal cavity.

Another object disclosed in the present invention relates to an anti-microbial compound as described above, or a combination thereof, for use as a medicament.

Another object of the present invention relates to the use of at least one anti-microbial compound as described in the present invention, or a combination thereof, in the manufacturing of a medicament.

Another object of the present invention relates to an anti-microbial compound as mentioned above, or a combination thereof, for use in the manufacturing of an anti-microbial composition, preferably an anti-bacterial composition.

Another object of the present invention relates to the use of at least one anti-microbial compound as described above, or a combination thereof, in the manufacturing of an anti-microbial composition, preferably an anti-bacterial composition.

Another object disclosed in the present invention relates to an anti-microbial compound, as described above, or a combination thereof, for use in the treatment of infectious diseases of the buccal cavity, preferably the treatment of caries.

Another object disclosed in the present invention relates to the use of at least one anti-microbial compound as described above, or a combination thereof, in the preparation of a composition designed for the treatment of infectious diseases of the buccal cavity, preferably an anti-caries composition.

Another object of the present invention relates to the anti-microbial compounds as described above, or a combination thereof, for use as prebiotics or functional foods designed to improve buccal health, preferably to prevent caries.

Another object disclosed in the present invention relates to the use of at least one anti-microbial compound as described above, or a combination thereof, in the preparation of a prebiotic or a functional food designed to improve buccal health, preferably to prevent caries.

Another object disclosed in the present invention relates to a probiotic/prebiotic composition or functional food that comprises at least one anti-microbial compound as described in the present invention.

Another object disclosed in the present invention relates to a medical-pharmaceutical composition or a composition for buccal health that comprises at least one anti-microbial compound as described in the present invention.

Another object disclosed in the present invention relates to a process for isolating culturable anti-microbial bacterial strains, preferably with inhibitory activity against the growth of organisms that produce infectious diseases of the buccal cavity and, more preferably, caries-producing organisms, characterised in that it comprises:

a) Obtaining samples from the supragingival dental plaque of individuals who have never suffered from caries.

b) Seeding the samples in the adequate media and under the adequate conditions so as to grow and isolate only those bacteria that are most frequent in individuals who have never suffered from caries, estimating the latter by means of pyrosequencing of the metagenome.

c) Culturing the isolated strains in a growth medium for cariogenic bacteria and selecting, after an appropriate culture time, those strains that present inhibition haloes against said growth.

In a preferred embodiment, the process described above is characterised in that, in step b), the bacteria that are most frequent in individuals who have never suffered from caries are estimated by means of pyrosequencing of the metagenome, a technique that makes it possible to estimate the proportions of each bacterial species. In another preferred embodiment, the process described above is characterised in that, in step c), bacteria belonging to the following genera are preferably selected: *Streptococcus, Rothia, Neisseria, Globicatella, Johnsonella, Haemophilus, Kingella, Cardiobacterium, Mannheimia, Phocoenobacter* and *Aggregatibacter*. Specifically, the following strains are selected: CECT 7746, CECT 7747, CECT 7773, CECT 7774 and CECT 7775. More specifically, bacteria belonging to the genus *Streptococcus* are selected, preferably those belonging to the following species: *S. sanguis, S. oralis, S. mitis, S. infantis* or new species that have not been described but belong to the *Streptococcus* subgroup that includes these four species. More specifically, at least one anti-microbial bacterial strain is selected from: CECT 7746, CECT 7747, CECT 7773 or CECT 7775.

Another object disclosed in the present invention relates to a method for the prevention and/or treatment of infectious diseases, preferably of the buccal cavity and, more preferably, caries, which comprises the administration of a quantity that is effective to inhibit the growth of the pathogenic microorganisms, preferably cariogenic microorganisms, habitually present in said cavity, of at least one of the culturable anti-microbial strains described in the present invention; or the probiotic/prebiotic composition or the functional foods described in the present invention which comprise said strains; or the medical-pharmaceutical composition or the composition for buccal health described in the present invention which comprise said strains.

Another object of the present invention relates to a process for obtaining anti-microbial compounds, preferably with inhibitory activity against the growth of organisms that produce infectious diseases of the buccal cavity and, more preferably, caries-producing organisms, characterised in that it comprises:

a) Obtaining samples from the supragingival dental plaque of individuals who have never suffered from caries.

b) Lysing said samples and extracting intact genomic DNA therefrom.

c) From the remaining DNA extracted, preparing a metagenomic library of vectors, preferably plasmids or fosmids, capable of being inserted into, and expressing the extracted DNA that they carry, in a host cell.

d) Inserting the vectors into a host cell.

e) Seeding the clones of host cells that contain the vectors in a culture with caries-producing microorganisms and selecting, after an appropriate culture time, those clones that present growth inhibition haloes.

f) Sequencing the DNA of the vectors of the clones that exhibit inhibitory activity, synthesising and/or purifying the compound encoded by said DNA.

In a preferred embodiment, the process described above is characterised in that the concentration of the DNA extracted is at least 300 μg/ml. In another preferred embodiment, said process is characterised in that, following the DNA extraction process, fosmids are constructed that contain DNA with a size range of preferably between 35 and 45 kb. In another preferred embodiment, said fosmids contain DNA with a size smaller than 1 kb. In another preferred embodiment, said process is characterised in that the host cell wherein the fosmids are inserted is *E. coli.*

In another preferred embodiment, said process is characterised in that the culture of the microorganism whereon the clones with the DNA inserts contained in the fosmids are seeded is of a cariogenic bacteria, preferably *S. mutans* or *S. sobrinus*. In another preferred embodiment, said process is characterised in that the DNA sequence of the fosmids is selected from sequences that comprise: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 14, or combinations thereof. In another preferred embodiment, said process is characterised in that the DNA sequence of the fosmids is selected from sequences that consist of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 14, or combinations thereof.

In another preferred embodiment, said process is characterised in that at least one anti-microbial peptide comprising a sequence selected from SEQ ID NO: 8 or SEQ ID NO: 9, or an anti-microbial compound encoded by a DNA sequence that comprises any of the following: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 14, are obtained. In another preferred embodiment, said process is characterised in that at least one anti-microbial peptide consisting of a sequence selected from SEQ ID NO: 8 or SEQ ID NO: 9, or an anti-microbial compound encoded by a DNA sequence that consists of any of the following: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 13, SEQ ID NO: 14, are obtained.

In another preferred embodiment, the DNA sequences of fosmids SEQ ID NO: 1, SEQ ID NO: 6, SEQ ID NO: 7, SEQ ID NO: 13 and SEQ ID NO: 14, and the anti-microbial peptide with SEQ ID NO: 9 are of bacterial origin, preferably bacteriocins. In another preferred embodiment, the DNA sequences of fosmids SEQ ID NO: 2, SEQ ID NO: 3, SEQ ID NO: 4 and SEQ ID NO: 5 are of human origin, preferably defensins/cathelicidins.

Another object disclosed in the present invention relates to a method for the prevention and/or treatment of infectious diseases, preferably of the buccal cavity and, more preferably, caries, which comprises the administration of a quantity that is effective to inhibit the growth of the pathogenic microorganisms habitually present in said cavity, of at least one anti-microbial compound as described throughout the present invention; or the probiotic/prebiotic composition or the functional foods which comprise at least one of the anti-microbial compounds described in the present invention, or the medical-pharmaceutical composition or the composition for buccal health which comprises at least one of the anti-microbial compounds described in the present invention.

Deposit of Microorganisms in Accordance with the Budapest Treaty

The microorganisms used in the present invention were deposited in the Spanish Type Culture Collection (CECT), located in the Research Building of the University of Valencia, Campus Burjassot, Burjassot 46100 (Valencia, Spain), with deposit nos.:

CECT 7746: bacterial strain of the genus *Streptococcus* deposited on 7 Jun. 2010.

CECT 7747: bacterial strain of the genus *Streptococcus* deposited on 7 Jun. 2010.

CECT 7773: bacterial strain of the genus *Streptococcus* deposited on 22 Jul. 2010.

CECT 7774: bacterial strain of the genus *Rothia* deposited on 22 Jul. 2010.

CECT 7775: bacterial strain of the genus *Streptococcus* deposited on 22 Jul. 2010.

The purpose of the examples listed below is to illustrate the invention without limiting the scope thereof.

Example 1

Obtainment of the Metagenome of Supragingival Dental Plaque

In the first place, samples of the supragingival dental plaque were taken from volunteers who have never suffered from caries, and, for comparative purposes, similar samples were taken from volunteers who had previously suffered from caries and volunteers who suffer from caries and, moreover, present lesions in said caries, after signing the informed consent. The sampling process was approved by the Clinical Research Ethics Committee of the General Directorate of Public Health of the Valencian Regional Government (GSP-CSISP). The buccal health condition of each volunteer was evaluated by a dentist following the recommendations and the nomenclature of the Studies in Buccal Health of the World Health Organisation (WHO), and the samples were taken using sterile probes. The volunteers were asked not to brush their teeth for 24 hours prior to the taking of samples.

In order to study the microbial diversity in the dental plaque and obtain the metagenome thereof, the material collected from the plaque of the surfaces of all the teeth of each individual was mixed in order to subsequently lyse it and obtain the total DNA of each dental plaque. The DNA was extracted using the MasterPure™ Complete DNA and RNA Purification Kit (Epicentre Biotechnologies), following the manufacturer's instructions and adding a treatment with lysozyme (1 mg/ml at 37° C. for 30 minutes) during the lysis step. The DNA concentration was measured with NanoDrop (Thermo Scientific) and the samples chosen must preferably have a DNA concentration greater than 300 μg/ml and a total quantity of at least 5 μg (due to the sensitivity threshold of the equipment and the processes involved in the pyrosequencing). Moreover, the DNA samples were run through an agarose gel in order to verify the integrity of the genomic DNA extracted from the volunteers' dental plaques. Subsequently, the pyrosequencing of said extracted DNA was performed by means of the GS FLX-Titanium Chemistry sequencer (Roche). Pyrosequencing consists of the fragmentation of DNA into fragments of about 500-800 nucleotides by means of nitrogen under pressure, adding adapters at the ends which make it possible to anchor the DNA to spheres of less than one micrometer in diameter. The spheres are introduced into an specific oil that acts as a microreactor, in order to perform an emulsion PCR (emPCR), where the DNA integrated in each sphere is amplified.

Following an enrichment of the spheres that have amplified the DNA, the solution is placed on titanium plates in the GS FLX sequencer (Roche), where the pyrosequencing reaction takes place. This reaction consists of the transformation of each pyrophosphate molecule released by polymerase upon adding a nucleotide in a light beam, by means of a set of enzymes such as luciferase. This light beam is proportional to the number of nucleotides added and, in this manner, a high-sensitivity chamber translates the light pulses into the corresponding DNA sequence (19). The average length of said DNA was 425 pb. Those sequences artifactually replicated by means of the 454-pyrosequencing technique that appeared systematically were eliminated from the set of final data through the "454 Replicar Filter" (20), such that the number of reads of a given sequence was related only to the frequency thereof in the sample.

The quantity of human DNA in the metagenomes ranged between 0.5%-40% in the samples from the supragingival dental plaque (Table 1) and were identified using the human genome database by means of Megablast (21) and eliminated from the set of final data.

TABLE 1

Characteristics of the pyrosequenced oral samples and the metagenome thereof.

| Sample[1] | CAO Index[2] | No. of reads | % human DNA | Total Mbp | Contigs > 5 kbp | Largest contig | 16S reads[3] | Simpson Index[4] | Shannon Index[4] | Chao1 Index[4] |
|---|---|---|---|---|---|---|---|---|---|---|
| NOCA_01P | 0 | 347927 | 40.59 | 77.54 | 13 | 12856 | 543 | 0.93 | 3.19 | 100 ± 24.6 |
| NOCA_03P | 0 | 347927 | 22.76 | 100.13 | 49 | 43857 | 374 | 0.91 | 2.94 | 92 ± 28.4 |
| CA1_01P | 8 (1) | 494659 | 2.23 | 203.71 | 657 | 46856 | 1160 | 0.94 | 3.21 | 120 ± 24.8 |
| CA1_02P | 6 (4) | 315892 | 2.74 | 129.85 | 154 | 15919 | 575 | 0.92 | 3.11 | 85.2 ± 9 |
| CA_04P | 25 (15) | 402049 | 11.54 | 142.37 | 181 | 19835 | 663 | 0.89 | 2.89 | 74.4 ± 9.9 |
| CA_06P | 11 (8) | 354192 | 10.83 | 123.27 | 47 | 51033 | 615 | 0.95 | 3.38 | 129.2 ± 41 |
| CA_06_1.6 | 11 (8) | 305820 | 66.97 | 37.52 | 0 | 3376 | 194 | 0.92 | 3.21 | 77 ± 13.3 |
| CA_05_4.6 | 10 (7) | 291162 | 74.99 | 27.67 | 2 | 29784 | 130 | 0.88 | 2.82 | 55.3 ± 8.3 |

[1]"P" indicates supragingival dental plaque samples. The samples with a number code indicate the tooth wherefrom samples from the caries cavity have been extracted.

[2]Number of dental pieces with caries (C), absent (A) and obstructed (O). The number in parenthesis indicates the number of exposed caries in the patient.

[3]Number of sequences of 16S rRNA detected in the metagenome and assigned by means of the RDP classifier.

[4]Simpson, Shannon, and Chao1 diversity indices, performed at the genus level.

Subsequently, a mean of 425 pbs allowed for the functional assignment in a significant fraction of the metagenome (Table 2). Moreover, the assembly of said reads produced 1103 assemblies ["contigs"] greater than 5 kpb and 354 greater than 10 kpb. We obtained a mean of 129.5 Mpb of high-quality filtered sequences (greater than 100 pb and where over 90% of the nucleotides had a 99.99% accuracy: The probability that the nucleotide read by the pyrosequencer is correct; i.e., a 99.99% accuracy means that only 0.01% of the nucleotides are incorrect (sequencing errors)) for each of the 6 oral samples. In the two samples with caries lesions, about 70% of the sequences pertained to human DNA, and in this case an average of 32.5 Mpb of high-quality filtered reads were obtained.

TABLE 2

Functional assignment of the samples present in the oral metagenome on the basis of different classification systems

| Sample | Dental health[1] | Total reads | cdd (n) [a] | cd (%) | cog (n) [b] | cog (%) | Tfam (n) [c] | Tfam (%) | Seed (n) [d] | seed (%) |
|---|---|---|---|---|---|---|---|---|---|---|
| NOCA_01P | h | 204218 | 126729 | 62 | 108929 | 53 | 82457 | 40 | 111497 | 50 |
| NOCA_03P | h | 244881 | 116575 | 48 | 95327 | 39 | 74356 | 30 | 93391 | 38 |
| CA1_01P | c | 464594 | 321997 | 69 | 280652 | 60 | 214050 | 46 | 271868 | 59 |
| CA1_02P | c | 295072 | 182091 | 62 | 150966 | 51 | 118716 | 40 | 146161 | 55 |
| CA_04P | ac | 339503 | 192003 | 57 | 161384 | 48 | 126281 | 37 | 158887 | 48 |
| CA_06P | ac | 306740 | 182349 | 59 | 151524 | 49 | 119477 | 39 | 146032 | 47 |
| CA_05_4.6 | cav | 70503 | 40999 | 58 | 31864 | 45 | 26245 | 37 | 29625 | 42 |
| CA_06_1.6 | cav | 97722 | 54305 | 56 | 45440 | 46 | 35395 | 36 | 44552 | 46 |

[1]h: healthy individuals without caries; c: individuals with caries in the past; ac: individuals with active caries; cav: samples of caries lesions.
(n): absolute count.
(%): total percentage of reads in the sample that were assigned to a function.
[a] cdd: assignment to conserved domains analysed in the NCBI Conserved Domains database.
[b] cog: assignment to sets of orthologous groups.
[c] Tfam: assignment to Tigr Fams.
[d] seed: assignment to the Seed/MG-RAST subsystems.

Example 2

Construction of the Fosmid Metagenomic Library of Supragingival Dental Plaque Using the samples of intact DNA extracted from the supragingival dental plaque of the healthy volunteers included in the study which had not been used for the pyrosequencing process, the metagenomic library of fosmids (inserts that have a length of preferably between 35-45 kb) of the dental plaque of said volunteers was performed, using, to this end, the EpiFOS™ Fosmid Library Production Kit (Epicentre Biotechnologies), following the instructions provided by the manufacturer. Briefly, in a preferred alternative of the process for constructing the metagenomic library of the invention, the fosmids are inserted into a host, preferably *Escherichia coli*. The library is prepared, as explained above, using the EpiFOS™ Fosmid Library Production Kit (Epicentre), following the manufacturer's instructions with some modifications, such as increasing the ligation time (12 hours in a bath at 20° C.), the use of the total DNA for the insertion, and not the DNA extracted from the pulse-field gel, slightly modifying the DNA extraction process such that the latter breaks as little as possible (use of cut pipette tips, avoiding the vortex, use of Centricom membranes (Millipore) to concentrate the DNA).

Insertion of the DNA into the *E. coli* host is performed by packaging the fosmids in lambda phage particles and subsequently infecting them in Epi300T1R strains of *E. coli*. During the packaging, the ligation product is placed in contact with the viruses for 3 hours at 30° C. in 1 ml of phage buffer. The infection is performed at 37° C. for 30 minutes, by placing the virus particles in contact with the *E. coli* strain. A prior titration is performed in order to select the optimal concentration of colonies in a plate (sufficiently distant so as to be able to seed a single colony with the aid of a sterile stick), by culturing different dilutions of the mixture in LB-agar medium with chloramphenicol.

Subsequently, each colony is inoculated in a 96-well Elisa plate in liquid LB medium with chloramphenicol, where they will be allowed to grow once again prior to being stored. The clones are stored in 96-well Elisa-type plates (Nunc) at a temperature of −80° C. in 19% glycerol, in order to prevent the formation of ice crystals and maintain the integrity of the cells. The fosmids are frozen without being induced to multiple-copy in order to prevent recombination processes between them.

The different *E. coli* clones with the different fosmid inserts are then seeded in cultures of cariogenic bacteria, such as *Streptococcus mutans* or *Streptococcus sobrinus*. Those clones are selected which, in said cultures, present an inhibition halo around the seeding point (FIG. 1). The clones obtained are identified by means of sequence homology of the DNA contained in each fosmid, on the basis of different available public sequence databases. In order to obtain the DNA sequence of each fosmid, the total DNA thereof is extracted by separating it from the vector DNA by means of midiprep kits from QIAGEN, and performing the direct pyrosequencing thereof. This is how the respective ORFs and, subsequently, the peptides encoded thereby, are obtained.

Example 3

Analysis of the Diversity of the Human Oral Metagenome

Once the metagenome of the supragingival dental plaque from individuals with caries and from healthy individuals was obtained following the process described in the present invention, the diversity of said oral metagenome was analysed using three different techniques:

Taxonomic assignment by means of the analysis of the 16S rRNA: the 16S rRNA sequences were extracted from the reads obtained from each metagenome by means of similarity searches with BLASTN (26) against the RDP database (Ribosomal Database Project). The sequences with a size smaller than 200 pb were eliminated. The phylogenetic assignment of the sequences was performed using the RDP Classifier (27), with a confidence threshold of 80%.

Gene taxonomic assignment: the taxonomic assignment of all the ORFs was performed on the basis of the lowest common ancestor (LCA) algorithm, by means of the characteristics described in the MEGAN software (28). In order to obtain the LCA of each sequence, homology searches were performed using the BLASTx database against another customised database that includes non-eukaryotic sequences from the non-redundant NCBI database (NR). For each sequence read, only those results that showed a coincidence of at least 90% were considered in the obtainment of the LCA.

Taxonomic assignment of the reads (PhyMM): said taxonomic assignment is performed using PhymmBL (29), which combines the assignment of sequences by both homology and the composition of nucleotides; to this end, hidden Markov models are used. All the available complete genomes were obtained from the Human Oral Microbiome Database (HOMD) (30), as well as the NCBI database (RefSeq), which contain all the genomes of bacteria and archaea (March 2010), and were used to construct a local database designed to perform taxonomic construction models and homology searches by means of PhymmBL. In this analysis, we only used sequences greater than 200 pb to predict the taxonomic identification. Using said read length, the class-level accuracy of the search with PhymmBL has been estimated to be greater than 75%. All the taxonomic and functional results were analysed in a MySQL database for the subsequent analysis thereof.

The results obtained using these three methods show that a small number of 16S genes in directly sequenced metagenomes are sufficient to describe the main taxonomic groups present in the oral metagenome, without the biases associated with cloning or PCR techniques.

From the samples examined, interesting differences may be observed between healthy and ill individuals. The trend shown by the three methods was that the Bacilli and Gamma-proteobacteria taxonomic groups were the most common in healthy individuals, whereas typically anaerobic taxa, such as Clostridials and Bacteroidets, are more frequent in samples from ill subjects. The reads assigned to Beta-proteobacteria (primarily Neisserials) and phylum TM7 (as yet without a definite name and without any member having been cultured thus far) were present in a very low proportion in samples from ill individuals and, therefore, may be associated with healthy conditions.

Correspondence analysis between the metagenomes, based on the taxonomic assignment of the 16S rRNA reads, showed that the samples from individuals with bad oral health tended to group together, whereas different bacterial consortia may be found in healthy individuals. By means of the present metagenomic study, the invention demonstrates that the genera *Streptococcus* and *Rothia*, more preferably, the genus *Streptococcus*, are prevalent genera in subjects without caries. For this reason, when we select, from the supragingival plaque samples of individuals who had never suffered from caries, those that could have anti-cariogenic activity, the selection was aimed at searching (culture media, culture parameters, microscope morphology of the bacteria, morphology of the colonies, etc.) species belonging to said genera, *Streptococcus* and *Rothia*, more preferably, the genus *Streptococcus*.

One of the powerful applications of the LCA and PhymmBL approaches is that most of the reads with significant coincidences may be assigned to a taxonomic origin and, moreover, to a possible function. By relating the taxonomy and the function, it has been possible to predict the ecological or metabolic role that each bacterial group may play. Using the COG (Cluster of Orthologous Groups) functional classification system, it may be observed that the categories are not evenly distributed, and that certain bacterial groups are especially suited to perform certain functions. For example, a large proportion of genes involved in defence mechanisms (e.g. restriction endonucleases and drug discharge pumps) are encoded by Bacilli, which, jointly with the greater presence of *Streptococci* in people without caries, allowed us to predict that those bacteria could be potential producers of natural inhibitors of human pathogens in a possible replacement therapy strategy for the treatment of buccal infectious diseases.

Example 4

Analysis of the Microbial Richness and Abundance Present in the Human Oral Metagenome Initial studies based on traditional culture techniques and pioneering molecular works, including amplification and cloning of the 16S rRNA gene, predicted a diversity of about 500 different species in the oral cavity (6). The use of last-generation technologies (Next Generation Sequencing, NGS) gave estimates of between 4000 and 19000 operational taxonomic units (OTUs). OTUs are estimates of the number of species on the basis of the DNA sequences, which take into consideration the fact that sequences of the 16S rRNA gene with a similarity lower than a given threshold belong to different species. The threshold used is the standard for the 16S rRNA gene, a 97% sequence identity; thus, if the similarity is greater than 97%, it is considered to be of the same species, but, if it is lower than 97%, it is probably a different species. Longer pyrosequencing reads (250 pbs) in three healthy subjects estimated about 600 OTUs per person, and a recent project attempted to sequence 11447 amplicons with almost the full length of 16S rRNA amplicons using Sanger-type sequencing (22), reducing the estimates to less than 300 OTUs in 10 individuals.

Although our estimates of microbial diversity are closer to those obtained using Sanger-sequenced reads (6,22), the 16S rRNA reads extracted from our metagenomic data identified 186 new OTUs that had not been previously detected by PCR amplification. The rarefaction curves (the saturation in the number of species as the sampling stress increases) and different diversity indices, as described in Table 1 (specifically, the Shannon, Simpson, and Chao1 indices), based on 4254 rRNA reads, indicated an estimate of 73-120 genera for the dental plaque samples (Tables 1 and 2). Clear differences between the samples of volunteers with different health conditions were not observed in regards to the diversity, although the two samples with caries lesions tended to present a lower diversity.

An effective tool to quantify the presence of selected species in metagenomes is sequence recruitment. Those individual metagenomic reads with coincidences greater than a certain identity threshold against a reference bacterial genome are "recruited" to plot a graph that will vary in density depending on the abundance of that organism in the sample. If the mean nucleotide identity shown is greater than 94%, the recruitment has probably been performed against reads from the same species (23).

Upon comparing our metagenomes with the 1117 genomes available thus far, using the Nucmer and Promer v 3.06 algorithms, we have been able to estimate the abundance of these species in our samples. Surprisingly, bacteria related to *Aggregatibacter* and *Streptococcus sanguis* were amongst the most abundant in people without caries, which agrees with the greater PCR amplification frequency of these species in the oral cavity of healthy individuals. The genus *Neisseria* was also frequent in samples from healthy individuals. Moreover, the recruitment graphs indicate that a few taxa are normally dominant in each metagenome, which suggests that, although there is a great bacterial diversity in the oral cavity, a few taxa comprise most of the bacterial cells.

Example 5

Functional Diversity in the Oral Ecosystem

In order to analyse the functional diversity of the organisms that are a part of the oral ecosystem of the individuals analysed in the present invention, all the metagenomic sequence reads obtained were compared to different databases: conserved domain database (CDD) (24), subsystem-based annotation system (SEED) and TigrFams profiles (25).

Correspondence analysis (CoA) of the samples on the basis of the functional assignment of the reads provided similar grouping patterns for the three functional classification systems (CDD, SEED and TigrFams). The samples from ill subjects (with caries) tended to group together, indicating that a similar group of functions were encoded in their metagenomes, and the samples from individuals who had never suffered from caries, jointly with one of the individuals who presented a low number thereof, are separately grouped. When comparing the functional assignment of the oral metagenomes against the intestinal microbiome of adult persons (8), the oral samples are grouped together, indicating that the intestine and the mouth are two different ecosystems in terms of the relative frequencies of the encoded functions. The present invention demonstrates that there are blocks of functions that are over-represented in the intestinal microbiome, whereas others are over-represented in the oral samples.

In the oral samples, the individuals are grouped on the basis of their health condition. From an applied standpoint, it is interesting to note that many functional categories are over-represented in the samples from individuals without caries. These include DNA capture genes involved in competition in Gram-positive bacteria, others involved in the phospholipid metabolism, fructose and mannose-induced phosphotransferase systems, the *Streptococcus* mga regulon, proteins involved in mixed acid fermentation, quorum-sensing genes and bacteriocin-type anti-bacterial peptides. Said bioactive compounds, bacteriocins, are potential anti-caries agents and, therefore, the present invention demonstrates that the dental plaque of individuals who have never suffered from caries is a genetic reservoir of new anti-microbial and potentially anti-cariogenic substances.

Example 6

Inhibition Assays of the Clones Obtained in the Fosmid Library of the Invention on Cariogenic *Streptococcus* Cultures Once the fosmid library of the supragingival dental plaque from individuals who had never suffered from caries was obtained, different clones of *E. coli*, with the different fosmid inserts, were seeded in cultures of cariogenic bacteria, such as *Streptococcus mutans* or *Streptococcus sobrinus*. A replica of the fosmid metagenomic libraries of those volunteers who had never suffered from caries was pinned on said plates, by means of a Nunc 96-pin replicator, such that each Petri dish may host the growth of the 96 clones of each plate in the library, previously induced to multiple copy by means of an inducer (Epicentre Technologies). Using this simple screening, a high-yield activity assay of thousands of clones may be performed during a limited time, selecting those clones that produce an inhibition halo on the cariogenic bacteria (FIG. 1).

The DNA sequences or inserts of these fosmids, as explained in Example 2 of the present invention, are those that potentially produce excreted substances that spread in the agar and prevent the growth of those bacteria that cause dental caries. Subsequently, a second activity screening was performed with the positive clones in order to eliminate the false positives (FIG. 1B). The clones obtained are identified by means of sequence homology of the DNA contained in each fosmid, against different public databases of available sequences.

In order to obtain the DNA sequence of each fosmid, the total DNA thereof is extracted by separating it from the vector DNA by means of midiprep kits from QIAGEN, and performing direct sequencing. The ends of twenty fosmids were sequenced using the classic Sanger technology by means of Reverse (SEQ ID NO: 10 and SEQ ID NO: 11) and T7 (SEQ ID NO: 12) primers of commercial PCC1 Fos vectors. Of the twenty fosmids sequenced, four sequences show homology with bacterial DNA (30%-98%) and five other sequences show 99%-100% homology with human DNA. Therefore, of the sequences of fosmid ends that present inhibitory capacity, four are of bacterial origin and five others are of human origin. In two of the cases (one bacterial and one human), the insert turned out to be of a very short length; for this reason, the sequence of the two ends overlapped, thus obtaining the full length of the insert. The insert of human origin completely sequenced using this process has 244 nucleotides (SEQ ID NO: 1) and the bacterial insert has 666 nucleotides (SEQ ID NO: 2).

The sequence of the other seven inserts was obtained by pyrosequencing, using groups of 2-5 fosmids, and combining their DNA in a 1/16 or 1/8 plate of the Genome Sequencer FLX pyrosequencer (Roche). The sequences obtained were assembled by means of the Newbler programme (Roche) using standard parameters, and the assemblies obtained were related to the corresponding fosmids on the basis of the previously-obtained insert end sequences. The characteristics of the nine inserts are shown in Table 3.

TABLE 3

Characteristics of the DNA inserts of the fosmids with inhibitory capacity against cariogenic bacteria

| Name | Origin | Length of Insert (pb) | Sequence No. |
|---|---|---|---|
| T5A | Human | 244 | SEQ ID NO: 1 |
| S12E | Bacterial | 666 | SEQ ID NO: 2 |
| T1F | Bacterial | 42797 | SEQ ID NO: 3 |
| T4H | Bacterial | 28023 | SEQ ID NO: 4 |
| T9B | Bacterial | 33804 | SEQ ID NO: 5 |
| A5D11 | Human | 45166 | SEQ ID NO: 6 |
| A4H11 | Human | 32692 | SEQ ID NO: 7 |
| W4D | Human | 34079 | SEQ ID NO: 13 |
| T5H | Human | 27661 | SEQ ID NO: 14 |

Example 7

Identification of the Anti-Microbial Peptides in the Short S12E and T5A Fosmids Once the sequences of the seven fosmids were obtained as described in Example 6, the DNA sequence of the two short-length DNA inserts was analysed, to obtain all the ORFs encoded in the 3'-5' and 5'-3' direction. Of these ORFs, we selected those that contained ribosome-binding sequences (with a 3'-end complementary sequence of 16S from *E. coli*) and, therefore, could be efficiently translated, and those that could be excreted, either by the presence of a signal peptide (identified using the SIGNAL-IP software) or by the non-classical secretory pathway (identified using the SECRETOME-P software). Using said methods, a candidate ORF was obtained in the fosmid of human origin (T5A), only 26 amino acids in length (SEQ ID NO: 8), and another candidate ORF was obtained in the fosmid of bacterial origin (S12E), 39 amino acids in length (SEQ ID NO: 9). Moreover, these genes showed an amino acid composition characteristic of anti-microbial peptides, and, furthermore, in the case of T5A, of human origin, the presence of two cysteines that may form a disulfide bridge was observed. This, together with their short length and their net positive charge, suggests that they are bioactive anti-microbial peptides.

Subsequently, said peptides were purified. To this end, they were separated from the rest of the products secreted on the basis of their molecular weight. Thus, 15 ml of each clone induced to multiple copy were cultured in Brain-Heart Infusion (BHI) medium, centrifuging the cells and collecting the supernatant, which was filtered through Millipore filters with a 0.2-micron pore size in order eliminate any bacterial residue. This supernatant, which contains the secreted products, was filtered once again through Amicon 10-kD Millipore filters and the filtrate was run, once again, through Amicon 3-kD Millipore filters, thereby obtaining the fraction between 3 and 10 kD to a volume of 1 ml. The fraction with a size smaller than 3 kD (0-3 kD fraction) was concentrated under cold conditions in a speed-vac to a volume of 1 ml.

Figure 2:
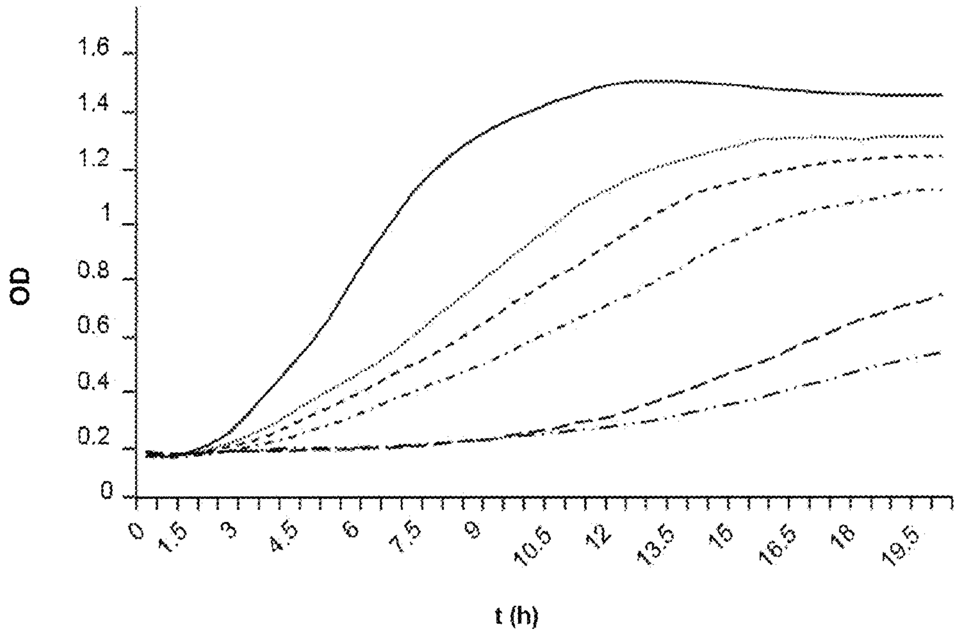
FIG. 2. Growth curves of the *S. mutans* cariogenic bacteria (positive control, without the addition of the inhibitor of cariogenesis, exemplified in the graph as a solid line) in BHI medium (brain-heart infusion), and in BHI medium enriched with 100 μl (dotted line), 150 μl (short-dash line), 200 μl (line with short dashes and dots), 300 μl (long-dash line) or 400 μl (line with long dashes and two dots) of the 3-10-kD fraction of the concentrated supernatant produced by, respectively, 1.5-, 2.25-, 3.0-, 4.5- and 6-ml cultures of cells carrying the S12E fosmid containing the bacteriocin-type anti-microbial peptide of bacterial origin of the invention. The data, taken every half-hour for 19 hours, show the mean of 3 experiments. The X-axis of the graph shows the time, expressed in hours, and the Y-axis shows the optical density (OD) of the bacterial cultures.
Figure 3:
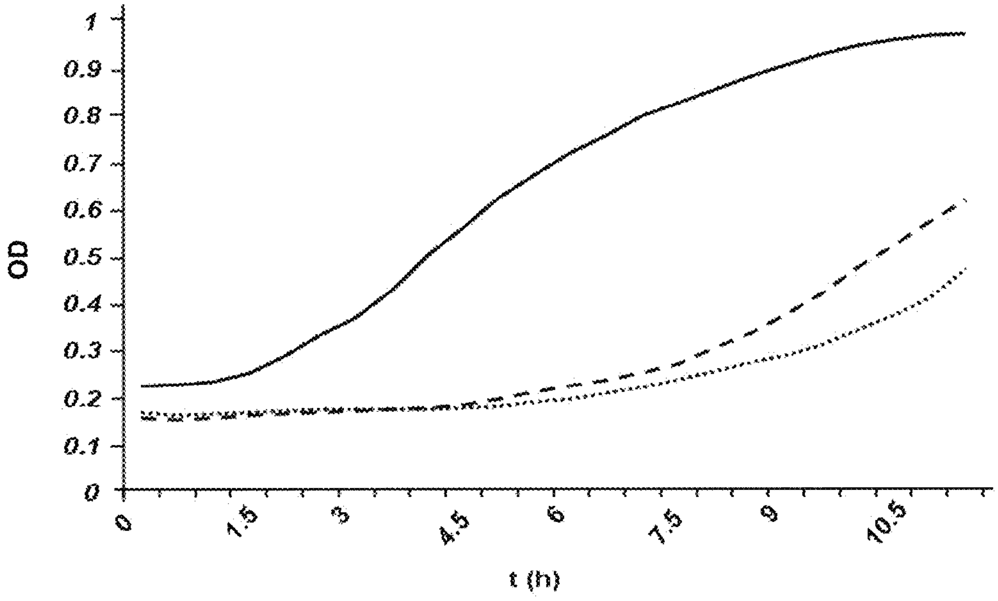
FIG. 3. Growth curves of the *S. mutans* cariogenic bacteria in BHI medium (solid line, positive control without the addition of the inhibitor of cariogenesis) and in BHI medium with 50 μl (dashed line) and 100 μl (dotted line) of the 0-3-kD fraction of the concentrated supernatant produced by, respectively, 2- and 4-ml cultures of cells carrying the T5A fosmid containing the defensin-type anti-microbial peptide of human origin of the invention. The data, taken every half-hour for 12 h, show the mean of 3 experiments. The X-axis of the graph shows the time, expressed in hours, and the Y-axis shows the optical density (OD) of the bacterial cultures.

Subsequently, 50-, 100- and 150-μl volumes of these two fractions, 3-10 kD and 0-3 kD, respectively, were added to a liquid culture of *S. mutans* and to a liquid culture of *S. sobrinus*, and the optical density was measured in a 48-well Fluostar luminometer every half-hour, with each treatment in triplicate, for 12-19 hours. As may be observed in FIGS. 2 and 3, the growth curves of the cariogenic bacteria show that, in the case of the defensin-type anti-microbial peptide of human origin (FIG. 3), the fraction smaller than 3 kD has a dose-dependent inhibitory effect on the cariogenic bacteria, whereas, in the case of the bacteriocin-type anti-microbial peptide of bacterial origin, the 3-10 kD fraction has the dose-dependent inhibitory effect on said cariogenic bacteria (FIG. 2), which agrees with the molecular weights estimated on the basis of the amino acid sequence for each of the fosmids.

Example 8

Figure 4:
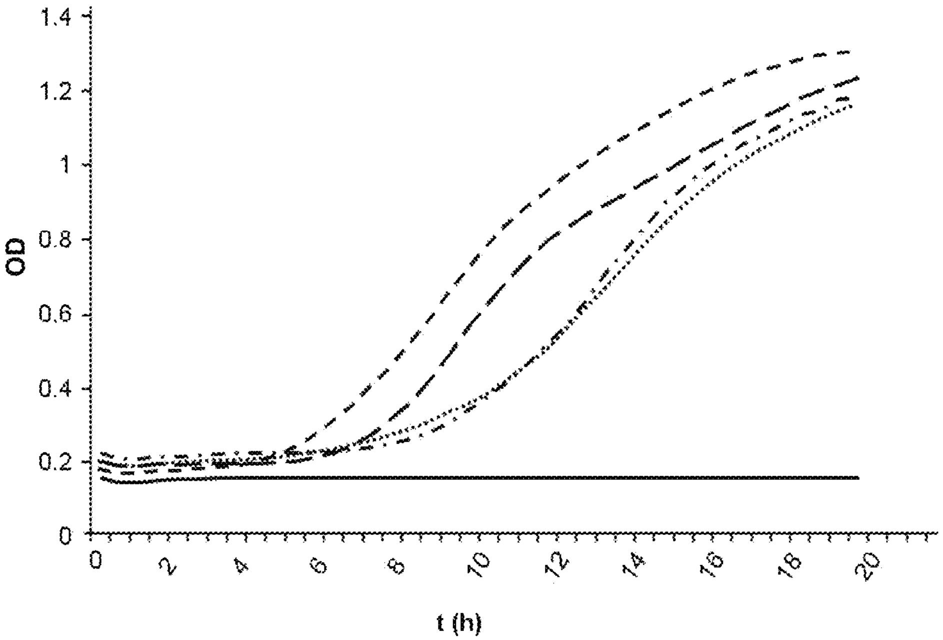
FIG. 4. Growth curves of the *S. mutans* cariogenic bacteria in the presence of Listerine® and the S12E inhibitor of bacterial origin. The data were taken for 19 hours at a temperature of 37° C. in BHI culture medium and represent the mean of 3 experiments. The solid line represents the negative control, without bacteria. The short-dash line represents the positive control, growth of *S. mutans* in the absence of Listerine® and the S12E inhibitor. The long-dash line represents the growth of *S. mutans* in the presence of 100 μl of Listerine®. The dotted line represents the growth of *S. mutans* in the presence of 100 μl of the S12E inhibitor. The line with short dashes and dots represents the growth of *S. mutans* in the presence of 100 μl of Listerine®+100 μl of the S12E inhibitor. The X-axis of the graph shows the time, expressed in hours, and the Y-axis shows the optical density (OD) of the bacterial cultures.

Comparative Assay of the Inhibitory Activity of the Bioactive Peptides of the Invention Against Cariogenic Bacteria In order to compare the inhibitory effect of bacteriocin to that of other competitive products available in the market, the same growth experiments of *S. mutans* in a liquid BHI medium were performed as those described in the preceding example, but now adding: a) 100 μl of one of the leading mouthwashes in the market (Listerine®, which is an anti-dental plaque agent and oral antiseptic), b) 100 μl of the concentrated supernatant (as explained in the preceding example) of the S12E clone containing bacteriocin (3-10-kDa fraction), and c) 100 μl of Listerine®+100 μl of the supernatant of the S12E clone containing bacteriocin. The inhibitory effect of bacteriocin at this concentration, 100 μl, on the growth of *S. mutans* is greater than that of the commercialised product for this bacterial species (FIG. 4) and, moreover, it may be observed, in said FIG. 4, that the addition of bacteriocin to the commercialised product significantly improves the inhibitory activity of said product against *S. mutans*.

Example 9

Analysis of the Cariogenic Activity of the Chemically-Synthesised S12E and T5A Peptides The chemical synthesis of the 2 inhibitory peptides isolated (SEQ ID NO: 8 and 9) was performed in accordance with the solid-phase synthesis method (32 and 33). Peptide synthesis by means of SPPS (Solid-Phase Peptide Synthesis) is the most common method used to synthetically create peptides and proteins in the laboratory, and allows for the synthesis of natural peptides that are difficult to express in bacteria, the incorporation of unnatural amino acids or peptide modification (for example, the formation de disulfide bridges).

In the case of the peptide of human origin, a protecting group, Fmoc-Cys(trt)-OH, was used to protect the —SH groups, which are quite reactive and were relatively frequent in this peptide. The peptides covalently bind to spheres, leaving the N-terminal amino group free, such that it may bind to a single N-protected amino acid. Following the binding, the latter is de-protected and washed. After repeated cycles of binding, washing, de-protection and washing, the peptide chains are constructed. When the peptide is complete, it is released by the addition of a reagent (in this case, anhydrous hydrogen fluoride). The quality control, designed to verify that the peptide synthesised is the correct one and does not contain impurities, was performed by means of mass spectrometry and HPLC.

In order to corroborate that the peptides identified are those responsible for the inhibitory activity against cariogenic bacteria, the S12E (bacteriocins of bacterial origin) and T5A (peptide of human origin with a structure similar to that of defensins) peptides were chemically synthesised, obtaining approximately 4 mg of each of said peptides with a purity greater than 80%. They were totally re-suspended in 0.1% trichloroacetic acid (TCA) and the experiments designed to test the inhibition of liquid cultures of *S. mutans* by said chemically-synthesised compounds were performed.

Figure 5:
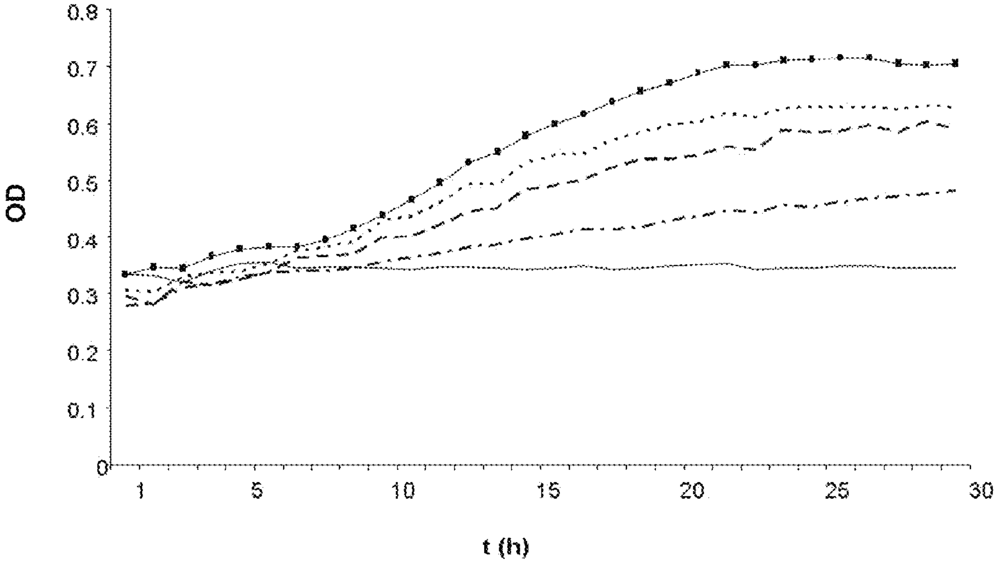
FIG. 5. Growth curves of the *S. mutans* cariogenic bacteria in the presence of the S12E inhibitor (bacteriocin-type anti-microbial peptide of bacterial origin of the invention) chemically synthesised in the laboratory and re-suspended in 0.1% TCA. The data show the growth of *S. mutans*, measured as the absorbance at 600 nm, for 30 minutes, during 30 hours at a temperature of 37° C. in 100 μl of BHI culture medium, of three independent experiments. The solid line represents the negative control, without bacteria. The line with black squares represents the growth of *S. mutans* in BHI culture medium. The dotted line represents the positive control, growth of *S. mutans* in BHI culture medium in the presence of 10 μl of 0.1% TCA. The line with short dashes and dots represents the growth of *S. mutans* in BHI culture medium in the presence of 0.3 mg of the S12E peptide re-suspended in 10 μl of 0.1% TCA. The short-dash line represents the growth of *S. mutans* in BHI culture medium in the presence of 0.03 mg of the S12E peptide re-suspended in 10 μl of 0.1% TCA. The X-axis of the graph shows the time, expressed in hours, and the Y-axis shows the optical density (OD) of the bacterial cultures.
Figure 6:
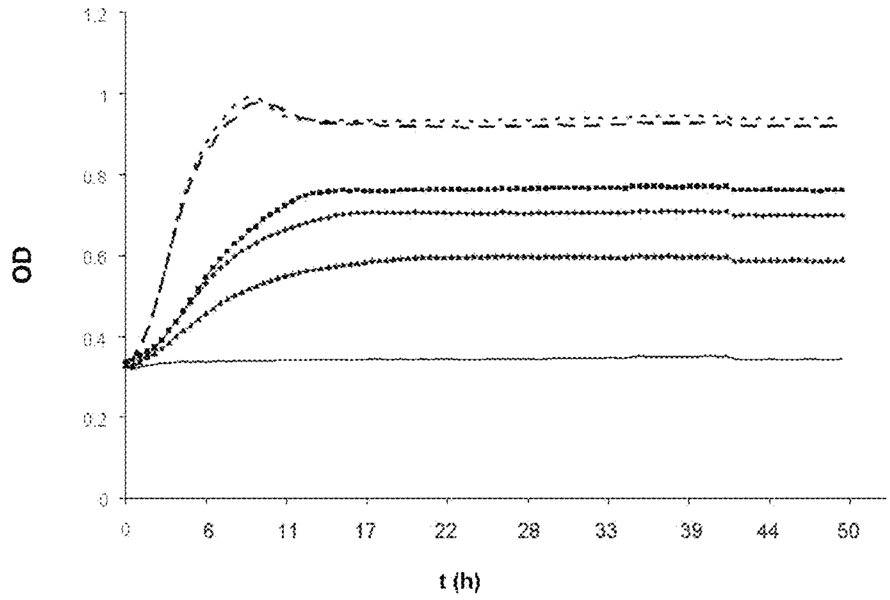
FIG. 6. Growth curves of the *S. mutans* (A) and *S. sobrinus* (B) cariogenic bacteria in the presence of the S12E Inhibitor (bacteriocin-type anti-microbial peptide of bacterial origin of the invention) chemically synthesised in the laboratory and re-suspended in ultrapure water. The data show the growth of *S. mutans*, measured as the absorbance at 600 nm, for 30 minutes, during 48 hours, at a temperature of 37° C. in 200 μl of BHI culture medium, being the mean of three independent experiments. In both graph A and graph B, the solid lines represent the negative control, without bacteria; the dotted lines represent the growth of *S. mutans* (A) or *S. sobrinus* (B) in BHI culture medium. The short-dash line represents the positive control, growth of *S. mutans* (A) or *S. sobrinus* (B) in BHI culture medium in the presence of water. The line with black squares represents the growth of *S. mutans* (A) or *S. sobrinus* (B) in BHI culture medium in the presence of 0.23 mg of the S12E peptide of the invention, re-suspended in ultrapure water. The line with black diamonds represents the growth of *S. mutans* (A) or *S. sobrinus* (B) in BHI culture medium in the presence of 0.047 mg of the S12E peptide of the invention, re-suspended in ultrapure water. The line with black triangles represents the growth of *S. mutans* (A) or *S. sobrinus* (B) in BHI culture medium in the presence of 0.094 mg of the S12E peptide of the invention, re-suspended in ultrapure water. The X-axis of the graph shows the time, expressed in hours, and the Y-axis shows the optical density (OD) of the bacterial cultures.
Figure 6:
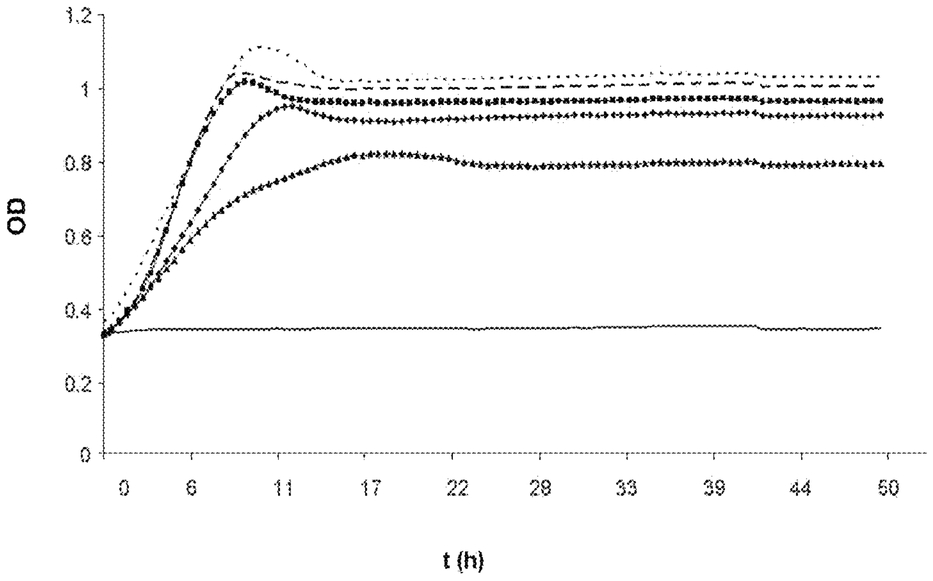

In the case of the bacteriocin-type S12E peptide, of bacterial origin, the inhibitory activity against cultures of *S. mutans* was confirmed, especially at high concentrations (FIG. 5). Subsequently, more S12E peptide was chemically synthesised, now with a purity greater than 95%, and said peptide was re-suspended in ultrapure water, in order to demonstrate that the previously obtained inhibitory effects were not due to TCA, but to the chemically-synthesised S12E peptide itself. Once again, it was observed that treatment of cultures of *S. mutans* and *S. sobrinus* with the chemically-synthesised S12E peptide at a high purity produced a dose-dependent inhibitory effect on both cariogenic bacteria, *S. mutans* (FIG. 6A) and *S. sobrinus* (FIG. 6B).

Figure 7:
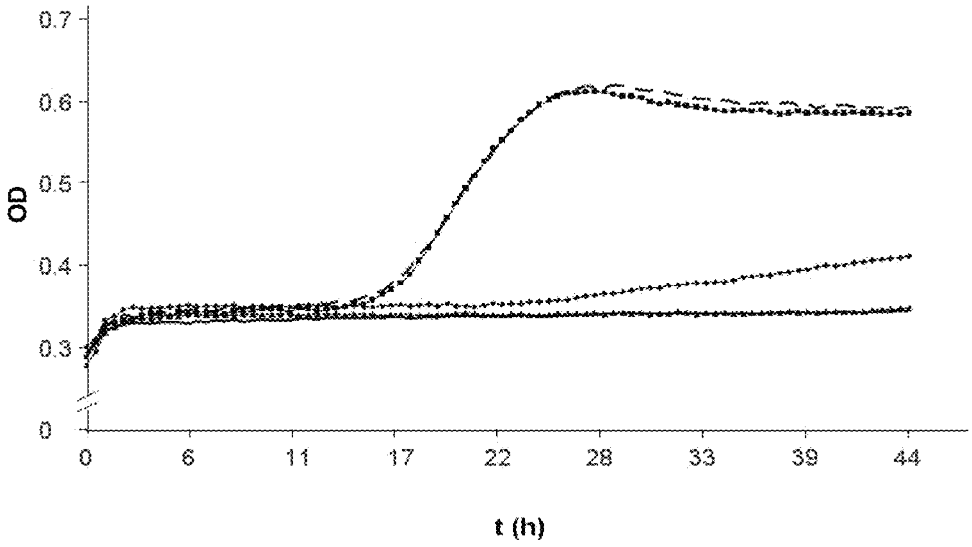
FIG. 7. Growth curves of the *S. mutans* cariogenic bacteria in the presence of 4 μg, 40 μg and 80 μg of the T5A inhibitor of the invention, chemically synthesised in the laboratory and re-suspended in ultrapure water. The data show the growth of *S. mutans*, measured as the absorbance at 600 nm, for 30 minutes, during 44 hours, at a temperature of 37° C. in 200 μl of BHI culture medium, being the mean of three independent experiments. The solid line represents the negative control, without cells. The short-dash line represents the growth of *S. mutans* in BHI culture medium (positive control) with ultrapure water. The line with black squares represents the growth of *S. mutans* in BHI culture medium in the presence of 1 μl of the T5A peptide of the invention (defensin-type anti-microbial peptide of human origin). The line with black diamonds represents the growth of *S. mutans* in BHI culture medium in the presence of 10 μl of the T5A peptide of the invention. The line with black triangles represents the growth of *S. mutans* in BHI culture medium in the presence of 20 μl of the T5A peptide of the invention. The X-axis of the graph shows the time, expressed in hours, and the Y-axis shows the optical density (OD) of the bacterial cultures.

In the case of the T5A peptide (of human origin, defensin-type), at first no inhibitory effect was found. It occurs that this peptide has several reactive amino acids, including two cysteines, the presence whereof is typical in human anti-microbial peptides, and often a disulfide bridge between these two cysteines is necessary for the peptide to be active. For this reason, said peptide was synthesised once again, adding a disulfide bridge between cysteines 3 and 12, and protecting the reactive amino acids during the synthesis. Following these modifications, it was confirmed that this peptide is capable of inhibiting the growth of the cariogenic bacteria, *S. mutans*, at different concentrations, with total inhibition of the growth when the maximum peptide concentration, 80 μg, is added (FIG. 7).

Example 10

Identification of the Inhibitory Genes in Long Fosmids

Figure 8:
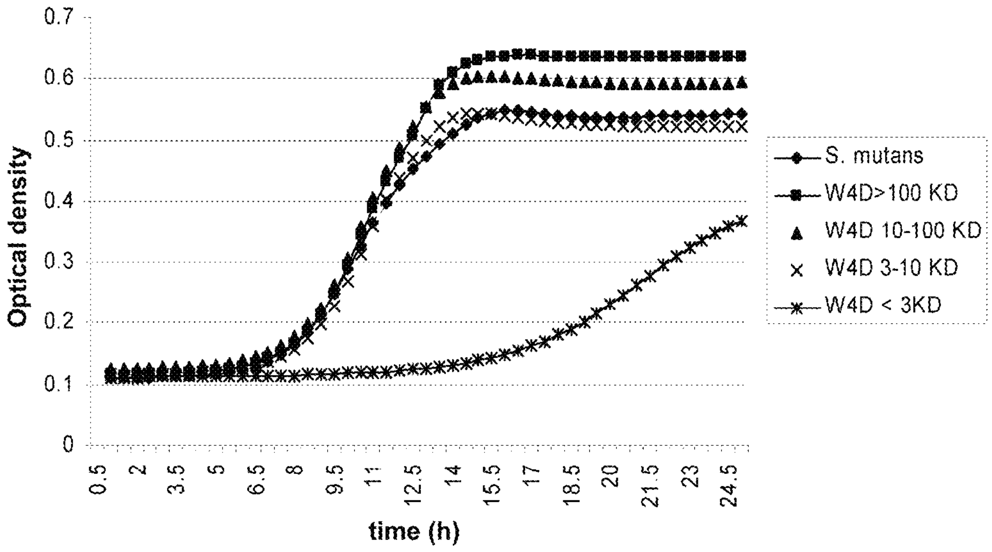
FIG. 8. Growth curves of the *S. mutans* cariogenic bacteria in liquid culture medium in the presence of the supernatants, concentrated 10 times and isolated as a function of their molecular weight, produced by cultures of *E. coli* bacterial cells carrying the W4D fosmid that comprises polynucleotide sequence SEQ ID NO: 13, which encodes a defensin-type anti-microbial peptide of human origin of the invention. The data, taken every half-hour for 24 h, show the mean of 3 experiments. As a control, the graph shows the growth curve of *S. mutans* in the presence of the concentrated supernatant of an untransformed *E. coli* epi300 bacterial culture. The X-axis of the graph shows the time, expressed in hours, and the Y-axis shows the optical density (OD) of the bacterial cultures.
Figure 9:
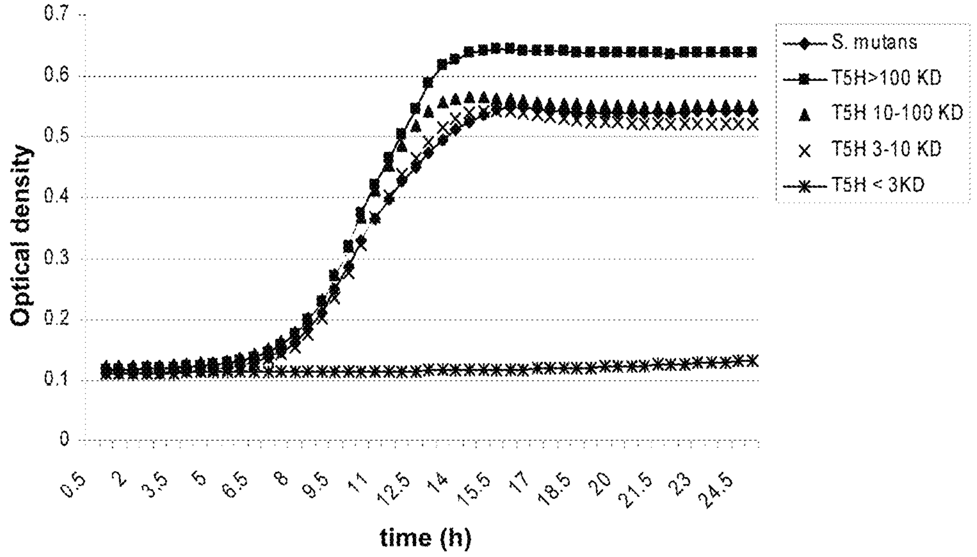
FIG. 9. Growth curves of the *S. mutans* cariogenic bacteria in liquid culture medium in the presence of the supernatants, concentrated 10 times and isolated as a function of their molecular weight, produced by cultures of *E. coli* bacterial cells carrying the T5H fosmid that comprises polynucleotide sequence SEQ ID NO: 14, which encodes the defensin-type anti-microbial peptide of human origin of the invention. The data, taken every half-hour for 24 h, show the mean of 3 experiments. As a control, the graph shows the growth curve of *S. mutans* in the presence of the concentrated supernatant of an untransformed *E. coli* epi300 bacterial culture. The X-axis of the graph shows the time, expressed in hours, and the Y-axis shows the optical density (OD) of the bacterial cultures.
Figure 10:
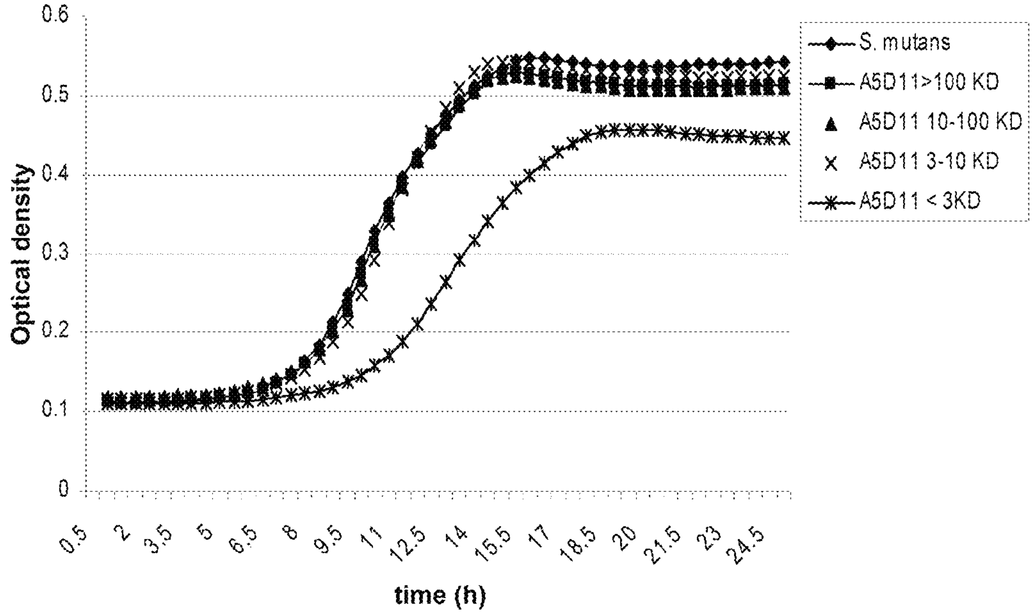
FIG. 10. Growth curves of the *S. mutans* cariogenic bacteria in liquid culture medium in the presence of the supernatants, concentrated 10 times and isolated as a function of their molecular weight, produced by cultures of *E. coli* bacterial cells carrying the A5D11 fosmid that comprises polynucleotide sequence SEQ ID NO: 6, which encodes the defensin-type anti-microbial peptide of human origin of the invention. The data, taken every half-hour for 24 h, show the mean of 3 experiments. As a control, the graph shows the growth curve of *S. mutans* in the presence of the concentrated supernatant of a culture of untransformed *E. coli* epi300 bacteria. The X-axis of the graph shows the time, expressed in hours, and the Y-axis shows the optical density (OD) of the bacterial cultures.
Figure 11:
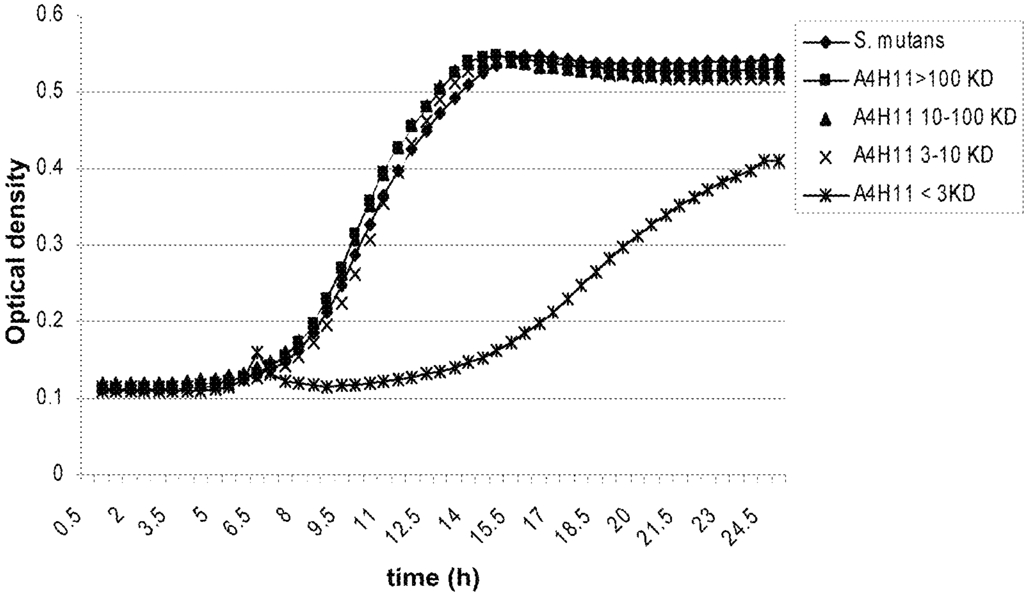
FIG. 11. Growth curves of the *S. mutans* cariogenic bacteria in liquid culture medium in the presence of the supernatants, concentrated 10 times and isolated as a function of their molecular weight, produced by cultures of *E. coli* bacterial cells carrying the A4H11 fosmid that comprises polynucleotide sequence SEQ ID NO: 7, which encodes the defensin-type anti-microbial peptide of human origin of the invention. The data, taken every half-hour for 24 h, show the mean of 3 experiments. As a control, the graph shows the growth curve of *S. mutans* in the presence of the concentrated supernatant of a culture of untransformed *E. coli* epi300 bacteria. The X-axis of the graph shows the time, expressed in hours, and the Y-axis shows the optical density (OD) of the bacterial cultures.

As regards the rest of the potential anti-microbial compounds, DNA was isolated from all the fosmids that produced an inhibition halo, and their ends and the complete insert were sequenced (Table 3). This makes it possible to obtain a catalogue of bacteria that produce anti-microbial substances (not only anti-bacterial peptides), as well as the regions in the human genome which encode them. Inhibition experiments were performed on liquid cultures of *S. mutans*, by adding the concentrated supernatant (as indicated in the preceding examples) produced by the corresponding clones, in fractions of 0-3 kDa, 3-10 kDa, 10-100 kDa and >100 kDa. These experiments reveal that the size fractions that cause inhibition are the 0-3 kDa fraction in the T9B and T4H bacterial fosmids and in the W4D (FIG. 8), T5H (FIG. 9), A5D11 (FIG. 10) and A4H11 (FIG. 11) human fosmids, and the 3-10 kDa fraction in the T1F bacterial fosmid. Therefore, these results once again show that inhibition is produced by small-size peptides, i.e. peptides with a size between 0-3 kDa or 3-10 kDa, which is consistent with the fact that they are anti-bacterial peptides of the bacteriocin type or human defensins/cathelicidins.

Similarly, a search of the ORFs that encode peptides with these sizes (i.e., 0-3 kDa or 3-10 kDa, as the case may be) was performed on the sequences of said fosmids, and the following genes were selected as possible candidates to be the inhibitor-encoding genes: those with a ribosome-binding sequence, the presence of signal peptides and a use of amino acids similar to that of the anti-bacterial peptides and/or with a sequence similar to that of other known anti-bacterial peptides, and/or with hydrophobicity and/or a net positive charge.

Example 11

Identification of Anti-Caries Bacteria

The existence of a small proportion of the adult human population that has never suffered from caries has led to suggest the presence of bacterial species with a potential antagonistic effect against cariogenic bacteria (23). Bacterial replacement of the pathogenic strains by innocuous isolates obtained from healthy individuals has satisfactorily proven to prevent pharyngeal infections and is the basis for probiotics designed to prevent infectious diseases in the intestine and other human ecosystems (31). Metagenomic recruitments of cariogenic bacteria against the oral microbiome of healthy subjects show a total absence of *S. mutans* and *S. sobrinus*. Surprisingly, the lack of detection of cariogenic bacteria is accompanied by an intense recruitment of other species of *Streptococcus* (primarily those similar to *S. sanguis*), *Aggregatibacter* and *Neisseria*, which are the most abundant genera in these individuals.

Given the possibility that isolates of these dominant genera may be involved in antagonistic interactions with cariogenic bacteria, fresh samples of dental plaque were taken from 10 healthy individuals (including the 2 healthy individuals wherefrom the metagenomic sequences were obtained) and used to culture, under optimal growth conditions, species of *Neisseria, Rothia* and *Streptococcus* (specifically, in blood agar, chocolate agar, brucella agar and TSA culture media, under aerobiosis conditions and in anaerobic jars). Following a microscopic examination, diplococci and *streptococci* were selected (in order to maximise the possibility of finding species of *Streptococcus, Rothia* and *Neisseria*), and a set of 249 isolates was obtained.

Figure 12:
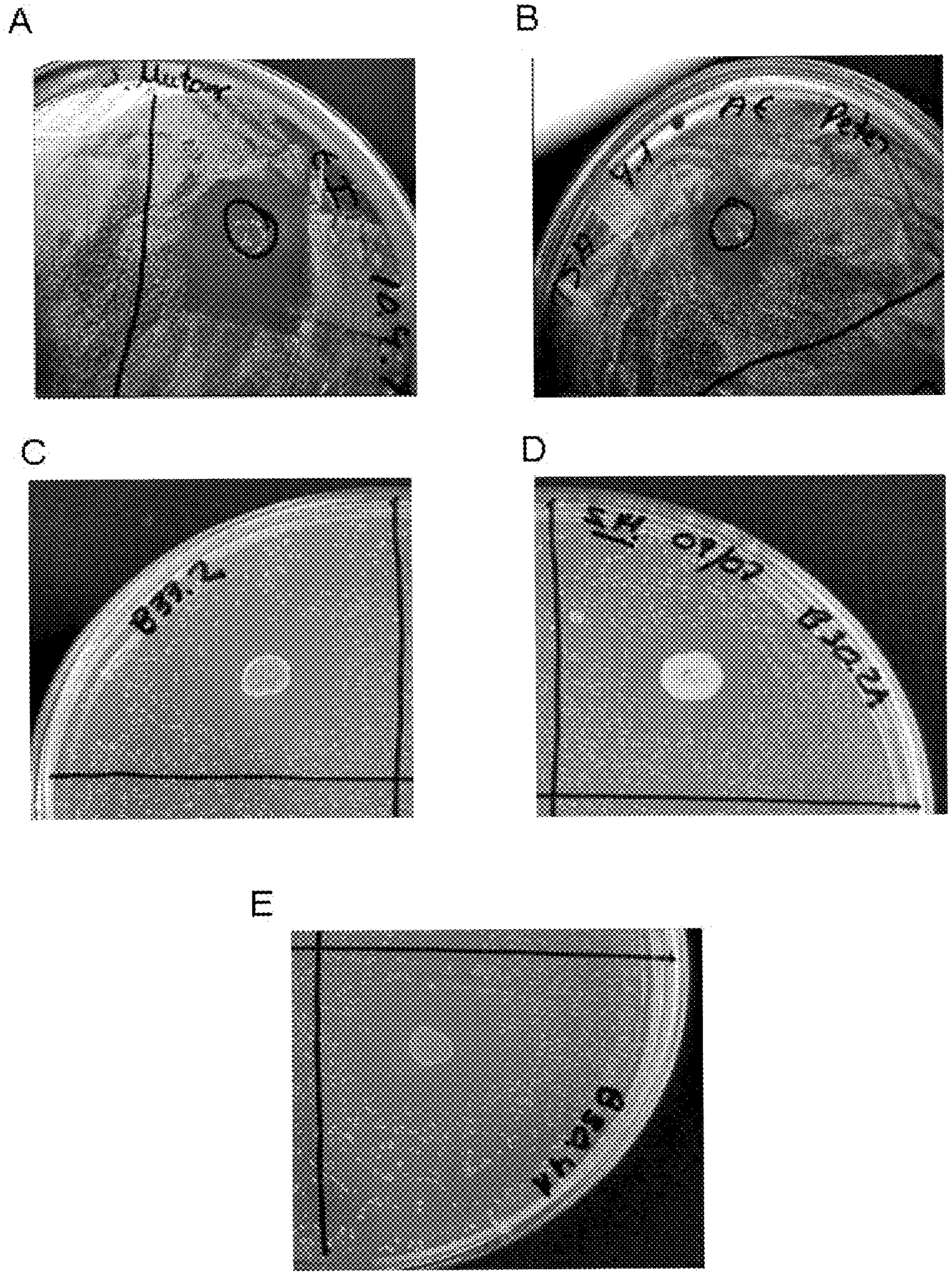
FIG. 12. Photographs of Petri dishes that demonstrate the inhibition of the growth of lawn cultures of *S. mutans* in the presence of the isolates of the CECT 7746 (A), CECT 7747 (B), CECT 7773 (C), CECT 7774 (D) and CECT 7775 (E) strains disclosed in the invention.
Figure 13:
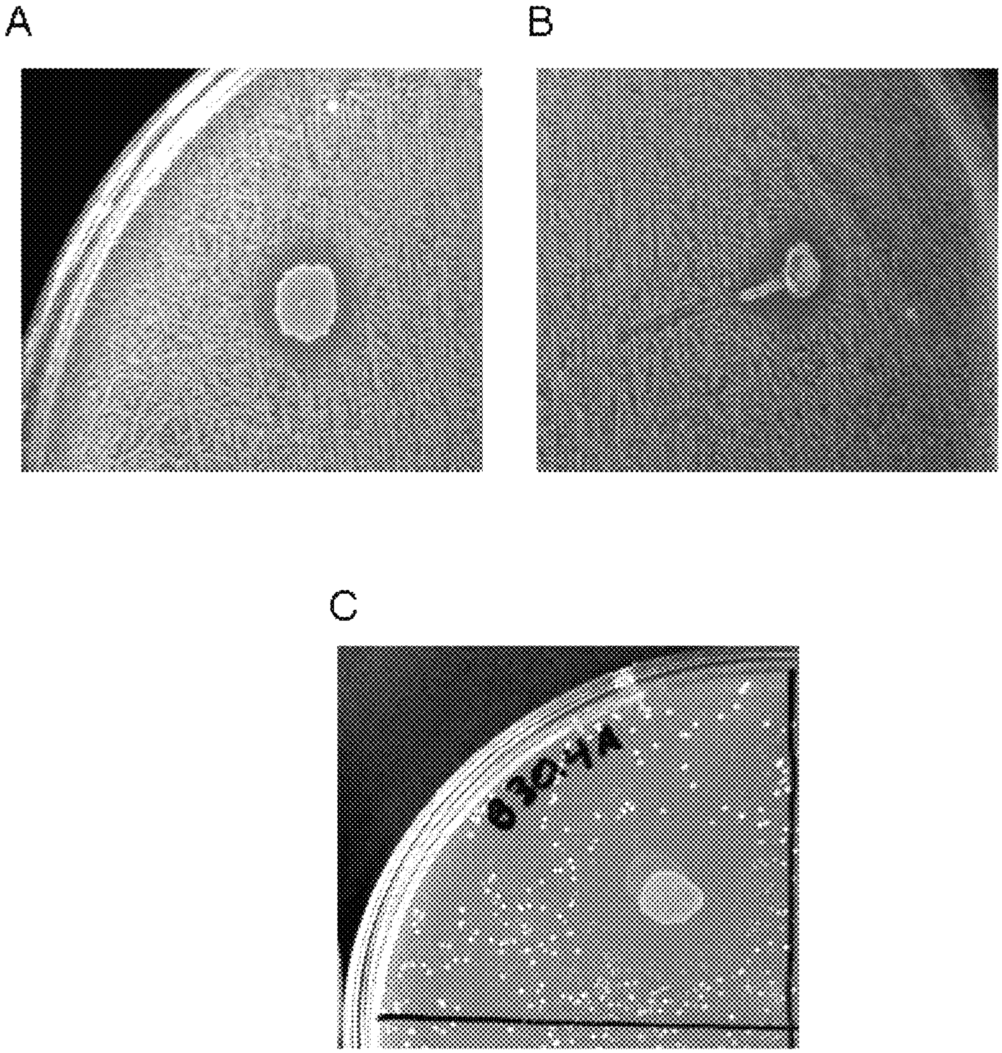
FIG. 13. Photographs of Petri dishes that demonstrate the inhibition of the growth of lawn cultures of *S. sobrinus* in the presence of the isolates of the CECT 7746 (A), CECT 7747 (B) and CECT 7775 (C) strains disclosed in the invention.

Those that were able to grow in the same medium as *S. mutans* and *S. sobrinus* were transferred to lawn cultures in the presence of said cariogenic bacteria. This simple screening identified 16 strains with inhibition haloes (FIGS. 12 and 13). Using PCR techniques and sequencing of the 16S rRNA, most of said strains were identified as belonging to species of *Streptococcus*, showing a 96%-99% sequence identity with the *S. oralis, S. mitis* and *S. sanguis* species or other related species, and also with *Rothia* species, with a 100% sequence identity with the *R. mucilaginosa* species in the 16S gene. The strains that showed inhibition haloes against *S. mutans* and/or *S. sobrinus* were deposited in the CECT, being assigned numbers CECT 7746, CECT 7747, CECT 7773, CECT 7774 and CECT 7775. As previously discussed, strains CECT 7746, CECT 7747, CECT 7773 and CECT 7775 belong to the same bacterial genus *Streptococcus* and, therefore, in addition to the method for obtaining them, share a structural and taxonomic similarity, since they belong to the same bacterial genus.

Specifically, on the basis of the 16S ribosomal gene sequence, said strains, which belong to the bacterial genus *Streptococcus*, are similar to the *S. mitis* (CECT 7746 and CECT 7775) and S. oxalis (CECT 7747 and CECT 7773) species. Sequencing of the complete genome of strains CECT 7746 and 7747 reveals that they are new species of the genus *Streptococcus* (see Example 12), that they are sister strains despite coming from different individuals and, moreover, belong to the *S. mitis/oralis/infantis* cluster of species. The other bacterial strain deposited in the CECT, with number CECT 7774, belongs to the genus *Rothia* and, more specifically, to the *R. mucilaginosa* species. The inhibition haloes against cultures of cariogenic species, *S. mutans* or *S. sobrinus*, of said strains deposited in the CECT may be observed in FIGS. 12 and 13, respectively.

Example 12

Characterisation of Bacterial Strains CECT 7746 and CECT 7747

Characterisation of bacterial strains CECT 7746 and CECT 7747 was performed by means of different techniques. In the first place, the complete genome of these two strains was obtained by means of shot-gun (7, 8) and pair-ends pyrosequencing; the latter consists of breaking the DNA into fragments of about 3000 nucleotides and the sequencing of approximately 200 nucleotides from each end, such that the known distance between these two ends helps in the assembly of the sequences.

In order to obtain the complete genome for each of strains CECT 7746 and CECT 7747, we started from samples collected from each of the cultures of said strains; specifically, a one-fourth culture plate was used for the pyrosequencing experiments by means of the shot-gun system (7, 8), using the GS-FLX pyrosequencer from Roche (Titanium Chemistry), and another one-fourth culture plate was used for the pyrosequencing experiments using the pair-ends system. The sequence quantity obtained for each of the strains using both systems was:

Strain 7746

Shot-gun type: 441.549 reads, with a total of 165,105,921 nucleotides

Pair-ends type: 187.530 reads, with a total of 32,721,622 nucleotides

Strain 7747

Shot-gun type: 28.021 reads, with a total of 5,711,998 nucleotides

Pair-ends type: 305.826 reads, with a total of 51,501,510 nucleotides

The expected genome size for each of the strains was about 2.1 Mb. For strain CECT 7746, the size of the assemblies greater than 500 pb is 2,122,087 pb. In the case of strain CECT 7747, the size of the contigs greater than 500 pb is 1,953,989 pb.

The sequences were filtered and assembled using the Newbler software (Roche), adapted by the inventors with standard parameters, to obtain a total of 109 assemblies >500 pb for strain CECT 7746 and of 51 contigs for strain CECT 7747. Subsequently, said genomes were automatically annotated, to obtain the complete sequence of the genome of said strains CECT 7746 and CECT 7747.

Once the complete genome of strains CECT 7746 and CECT 7747 was obtained, said isolates were taxonomically assigned on the basis of the phylogenetic trees obtained on the basis of the complete sequence of the 16S and 23S rRNA genes, which are the most widespread when preparing bacterial phylogenetic trees.

By linking together the sequences of the 16S and 23S rRNA genes, a single fragment greater than 4,000 nucleotides was obtained, which was aligned with the same fragment of the *Streptococci* species sequenced thus far. The sequences were aligned using the MAFFT free computer software, by aligning the 16S and 23S genes separately, and subsequently linking the alignment together. Afterward, the alignment is purified using the GBlocks free computer software in order to select the conserved informative positions. The tree is obtained using the RAxML programme, by the maximum verisimilitude method, with 500 repeats. The phylogenetic tree obtained showed that both strains are sister strains despite coming from different individuals and, moreover, belong to the *S. mitis/oralis/infantis* cluster of species, and the topology of the tree suggests that they are strains that belong to a new, non-described species.

In order to determine whether said strains belong to different species, the ANI (average nucleotide identity) was used. When the genomes of the sequenced strains are compared, the mean similarity between the homologous genes of the same species at the nucleotide level is greater than 95% (34, 35). In fact, taxonomists accept this 95% ANI value as the limit to separate bacterial isolates belonging to different species and as an alternative to the classic 70% threshold in the DNA-DNA hybridisation value (36). Using the J-species free computer software to determine the ANI values between the two sequenced strains of the invention, CECT 7746 and CECT 7747, and the rest of the *Streptococci* sequenced, it was demonstrated that they are two strains belonging to a new species that has not been described as yet. In the case of the bacterial strain of the invention CECT 7746, there is no strain with a similarity above the 95% threshold and, in the case of the bacterial strain of the invention CECT 7747, only another strain of those sequenced, *Streptococcus* M143, exceeds said threshold. Said strain M143 is a strain that, despite having a draft genome sequence, has not been taxonomically described as a species. The results used to calculate the ANIs were obtained by means of two different methodologies: Mummer and Blast (36), and both methodologies showed almost identical results.

Example 13

Inhibition Assays of Cariogenic Bacteria, *S. mutans*, in the Presence of the Supernatants Obtained from the Cultures of the CECT 7746 and CECT 7747 Strains Disclosed in the Invention The two strains of the invention, CECT 7746 and 7747, were grown in BHI culture medium at a temperature of 37° C. Subsequently, the supernatants of the cultures were collected, in the exponential phase and the stationary phase, being filtered through a 0.2-micron filter, in order to eliminate any bacterial residue. Subsequently, said supernatants were filtered once again by means of centrifugation, using membranes with a pore size of 100, 10 and 3 kDa (Amicon, Millipore), as described in the previous examples shown in the present invention.

Figure 14:
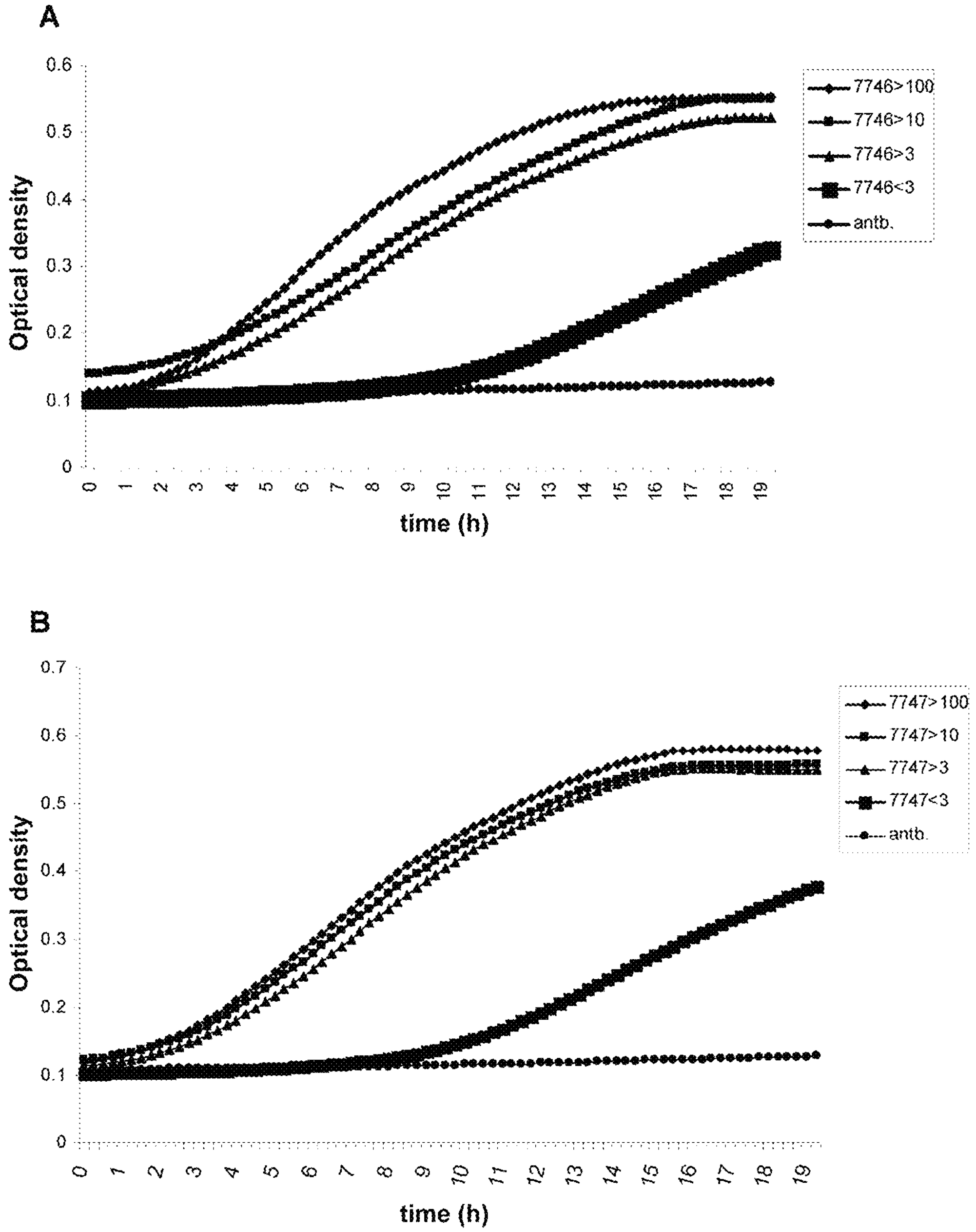
FIG. 14. Growth curves of the *S. mutans* cariogenic bacteria in BHI culture medium in the presence of the supernatants, concentrated 10 times and isolated as a function of their molecular weight, obtained from cultures of strains CECT 7746 (A) and CECT 7747 (B) in the stationary phase. The data, taken every 15 minutes for 20 h, show the mean of 4 experiments. The line marked as antb represents the treatment with the antibiotic chloramphenicol (positive control). The X-axis of the graph shows the time, expressed in hours, and the Y-axis shows the optical density (OD) of the bacterial cultures.

The fraction of the supernatants obtained from each of strains CECT 7746 and 7747, collected in the stationary phase of growth, which produced inhibition of the growth of bacterial cultures of *S. mutans*, was concentrated in the size fraction smaller than 3 kDa for both tested strains, CECT 7746 (FIG. 14A) and CECT 7747 (FIG. 14B). Said results show that the inhibitory substance synthesised by said strains, which presents specific bactericidal effect against cariogenic species, must be of a small size, preferably <3 kDa, as in the case of bacteriocins.

Figure 15:
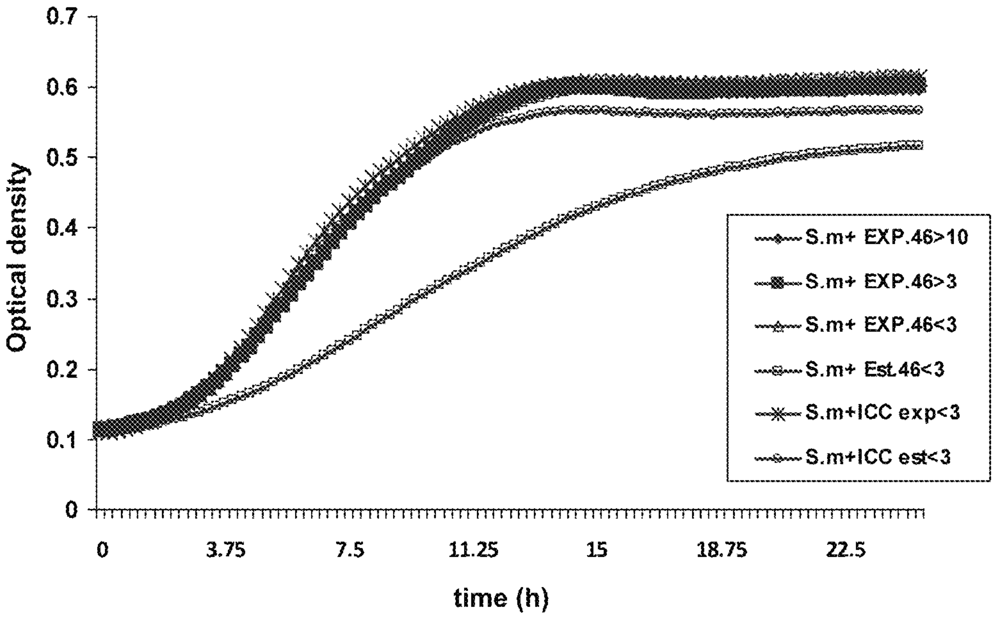
FIG. 15. Growth curves of the *S. mutans* cariogenic bacteria in BHI culture medium in the presence of the supernatants, concentrated 10 times and isolated as a function of their molecular weight, obtained from cultures of strain CECT 7746 in the stationary phase (est) and the exponential phase (EXP). The data, taken every 15 minutes for 24 h, show the mean of 4 experiments. The line marked as clorf represents the treatment with the antibiotic chloramphenicol (positive control). The X-axis of the graph shows the time, expressed in hours, and the Y-axis shows the optical density (OD) of the bacterial cultures.

On the contrary, when the same experiment was performed with samples of the supernatants of cultures of the strains of the invention CECT 7746 and 7747, collected in the exponential phase of growth, no inhibition of the growth of bacterial cultures of *S. mutans* (FIG. 15) was observed, which indicates that the inhibitory agent is only produced in the stationary phase of bacterial growth of the strains of the invention.

Figure 16:
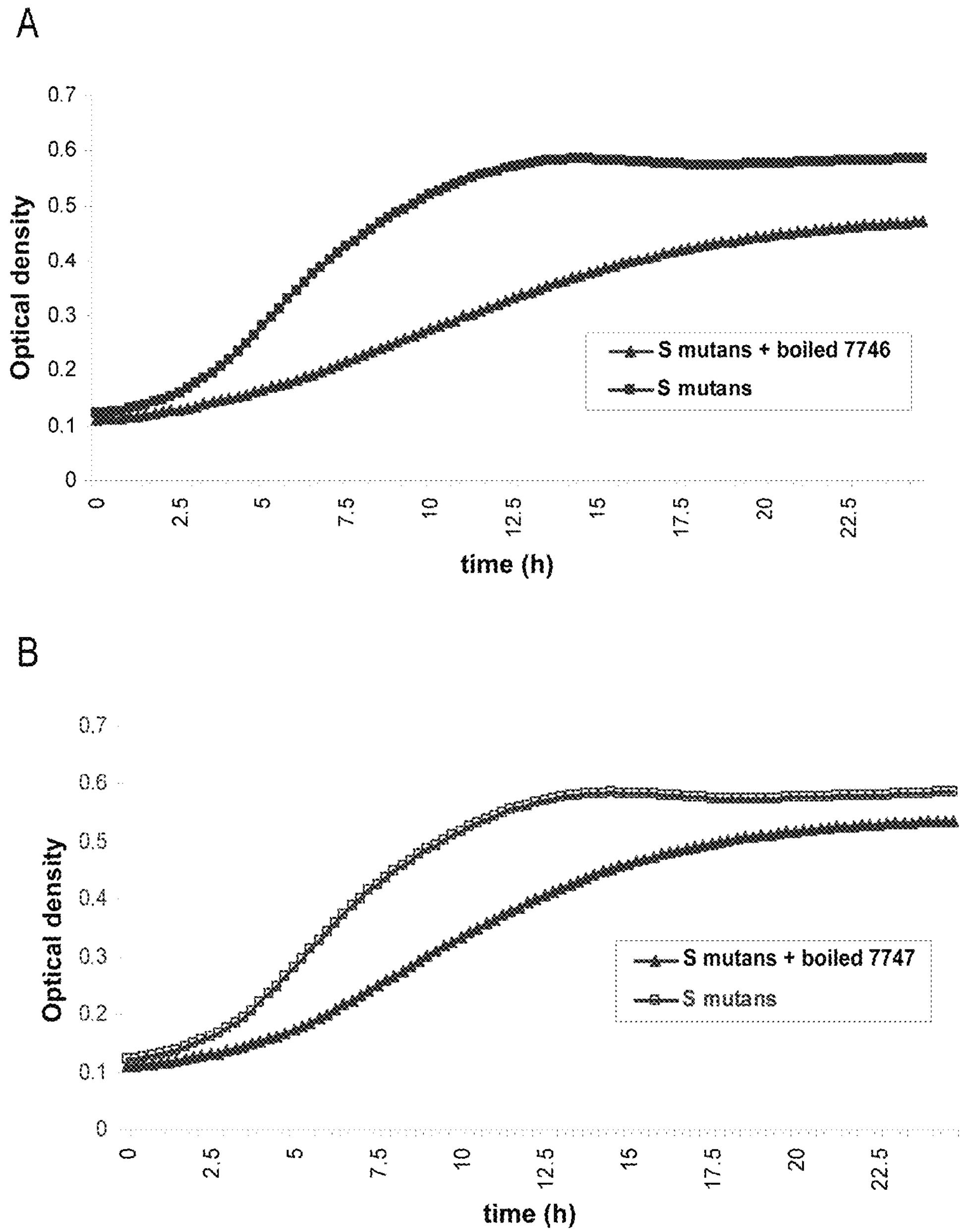
FIG. 16. Growth curves of the *S. mutans* cariogenic bacteria in BHI culture medium in the presence of the supernatant, concentrated 10 times and smaller than 3 kDa, obtained from cultures of strains CECT 7746 (A) and CECT 7747 (B), subjected to a treatment at 100° C. for 10 minutes. The data, taken every 15 minutes for 24 h, show the mean of 4 experiments. The X-axis of the graph shows the time, expressed in hours, and the Y-axis shows the optical density (OD) of the bacterial cultures.

When the samples of the concentrated supernatant obtained in the stationary phase, and smaller than 3 kDa, were subjected to a temperature of 100° C. for 10 minutes, it was verified that the inhibitory activity of said supernatant on cultures of *S. mutans* was maintained and even increased (FIG. 16). These results are consistent with the fact that the inhibitory agent is a bacteriocin and not another type of peptide, since small-size bacteriocins are extremely thermostable and even increase their anti-microbial effect, since they are better eluted in the medium after their aggregates are dissolved through thermal shock.

Subsequently, inhibition assays against cultures of *S. mutans* were performed with the supernatants obtained from the cultures of the bacterial strains of the invention CECT 7746 and CECT 7747, but changing the seeding order and the growth temperature of the cultures of said cariogenic bacteria, in order to verify whether said modifications had any effect on the inhibitory activity of the supernatants of the strains of the invention.

In the first place, culture plates were seeded with the *S. mutans* cariogenic bacteria and, after 24 h had elapsed, the strains of the invention were seeded in the same culture plate. After a time had elapsed, no inhibition haloes were observed. On the contrary, when culture plates were seeded with both strains at the same time, inhibition of the growth of *S. mutans* was observed, as we had previously shown. The greatest inhibition of the growth of cultures of *S. mutans* was observed when the strains of the invention, CECT 7746 and 7747, were seeded first and, 24 h later, the strains of *S. mutans* were seeded, which indicates that there is a greater concentration of the inhibitory agent or substance prior to the growth of the cariogenic bacteria, and that, moreover, the presence of said bacteria is not necessary to activate the production of the inhibitory agent by the strains of the invention.

Subsequently, inhibition experiments against the growth of cariogenic bacteria were performed in a solid medium, by first seeding the strains of the invention with a drop of the culture in a liquid medium in the stationary phase, followed by a tapestry culture of *S. mutans* at different temperatures: 30° C., 33° C. and 36° C. No inhibition of the growth of *S. mutans* was observed at a temperature of 30° C., but inhibition was observed at 33° C., being in fact greater than that obtained at 36° C.

Example 14

Inhibition Assays Against Cariogenic Bacteria, *S. mutans*, Cultured in the Presence of the Supernatants Obtained from the Cultures of the Bacterial Strains of the Invention CECT 7746 and CECT 7747, Under Aerobiosis and Anaerobiosis Conditions In order to determine whether the inhibitory action of the strains of the invention against the growth of cariogenic bacteria was modified by an aerobic or anaerobic environment, inhibition experiments were performed in a solid BHI medium, by first seeding the strains of the invention with a drop of the culture in a liquid medium, in the stationary phase, in an anaerobic jar for 12 h, followed by a tapestry culture of *S. mutans* at 37° C., or followed by seeding with one drop of the culture of *S. mutans* at 37° C.

Figure 17:
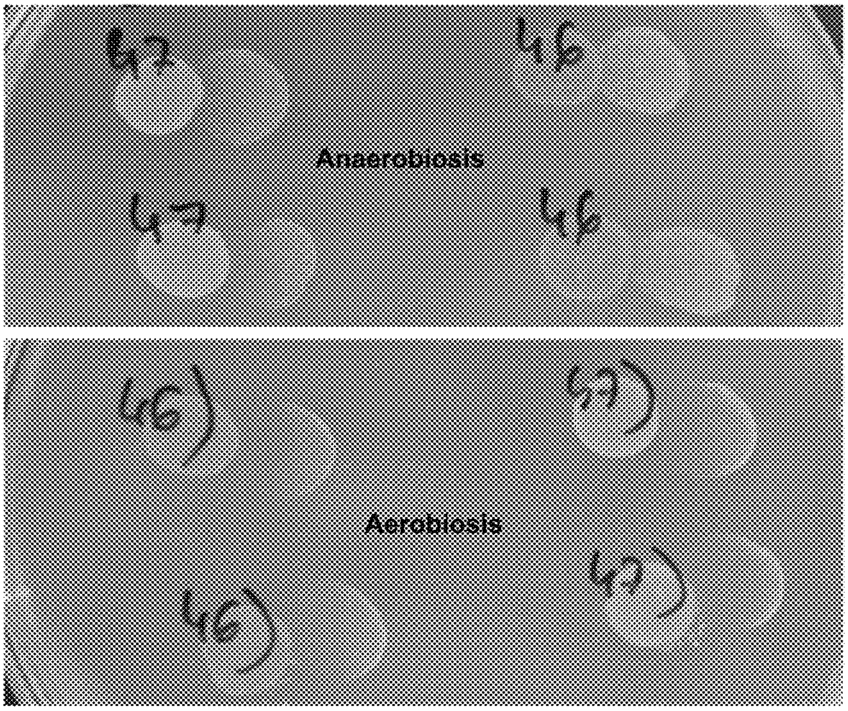
FIG. 17. Photographs of Petri dishes that demonstrate the inhibition of the growth of lawn cultures of *S. mutans* in the presence of the supernatants of cultures of strains CECT 7746 (shown as 46 in the photograph) and CECT 7747 (shown as 47 in the photograph) under aerobiosis and anaerobiosis conditions.

The results of both experiments showed that inhibition of the growth of *S. mutans* is much lower under anaerobic conditions, especially for strain CECT 7746 (FIG. 17). Therefore, the results demonstrate that, for the strains of the invention, the inhibition exerted on cariogenic bacteria is more effective during the aerobic step of formation of the dental plaque, i.e. during the period of adherence and initial formation of the biofilm on the tooth.

Example 15

Anti-Cariogenic Effect of Bacterial Strains CECT 7746 and CECT 7747 and the Supernatants Thereof on the Biofilm in an Artificial Tooth Model In order to demonstrate the anti-cariogenic effect of the bacterial strains disclosed in the present invention, inhibition assays against the production of acid were performed with strains CECT 7746 and CECT 7747 on a biofilm in an artificial tooth model. Said experiments were performed on the Active Attachment biofilm model of the Academic Center for Dentistry Amsterdam (ACTA, Amsterdam). Said biofilm model was described by Exterkate R A et al. (37). Briefly, hydroxyapatite or glass discs are inoculated with human saliva from a volunteer with a high percentage of *S. mutans* (greater than 4%), with or without the presence of the probiotic strain, or the supernatant thereof. In the present assays, strains CECT 7746 and 7747, disclosed in the present invention, were tested, as was strain C7.1, an isolate belonging to species of the *Streptococcus mitis/oralis/infantis* group, obtained from an individual without caries, but which does not produce inhibition of the growth of cariogenic species and, therefore, acts as a negative control.

The human saliva is stored at −80° C. Probiotic strainsCECT 7746 and 7747 and control strain C7.1 are grown in BHI culture medium with sucrose for 12 hours, until a culture density of approximately $4\times10^8$ cfu (Colony-Forming Units) is obtained. Subsequently, the saliva sample is mixed at 50% with the inoculum of the probiotic strains of the invention (CECT 7746 or 7747) or the inoculum of the control strain (C7.1), and applied onto the glass disc.

The biofilms are formed for 48 hours in modified artificial saliva medium (38) under aerobiosis and anaerobiosis, and, once formed, are incubated for 3 hours at a temperature of 37° C. in cysteine peptone water (Sigma-Aldrich, St Louis, USA) containing 0.2% glucose, in order to measure the production of acid. During this incubation period, the strains will produce acid, which is measured by means of a colorimetric reaction: Said biofilm is transferred to an Eppendorf tube and incubated at a temperature of 80° C. for 5 min in order to stop the bacterial metabolism. The quantity of L-lactic acid is enzymatically determined by means of a colorimetric assay using the Spectra Max M2 spectrophotometer (Molecular Devices, USA), following the protocol described by Pham L C et al. (38).

In order to analyse the inhibition of the production of acid by the supernatants, of the strains of the invention (CECT 7746 and 7747) as well as the control strain (C7.1), in the first place, the supernatants of the cultures of said bacterial strains were obtained. To this end, cultures of said strains were grown in BHI medium for 12 hours. Subsequently, the bacterial cells were eliminated by centrifugation and subsequent filtering through pores with a size of 0.2 microns. The medium is filtered through Amicon 100-, 10- and 3-kDa Ultra membranes (Millipore). The fraction smaller than 3 kDa is concentrated to half of its volume in a rotavapor and mixed at 50% with the saliva sample; subsequently, as in the case of the probiotics, the biofilm is formed for 48 hours and incubated for 3 hours in a Buffered Peptone Water culture medium (38) containing 0.2% glucose, so as to be able to measure the production of acid.

Each treatment is repeated in quadruplicate under aerobiosis and anaerobiosis conditions. The experimental groups analysed were:

1. Biofilms formed with saliva inoculum.
2. Biofilms formed with saliva inoculum+CECT 7746.
3. Biofilms formed with strain CECT 7746.
4. Biofilms formed with saliva inoculum+CECT 7747.
5. Biofilms formed with strain CECT 7747.
6. Biofilms formed with saliva inoculum+non-inhibitory *Streptococcus* strain (strain C7.1).
7. Biofilms formed with saliva inoculum+supernatant of strain CECT 7746, which contains the active inhibitory substance.
8. Biofilms formed with saliva inoculum+supernatant of strain CECT 7747, which contains the active inhibitory substance.

9. Biofilms formed with saliva inoculum+supernatant of the non-inhibitory strain (strain C7.1).

10. Biofilms formed with the non-inhibitory *Streptococcus* strain (strain C7.1).

Figure 18:
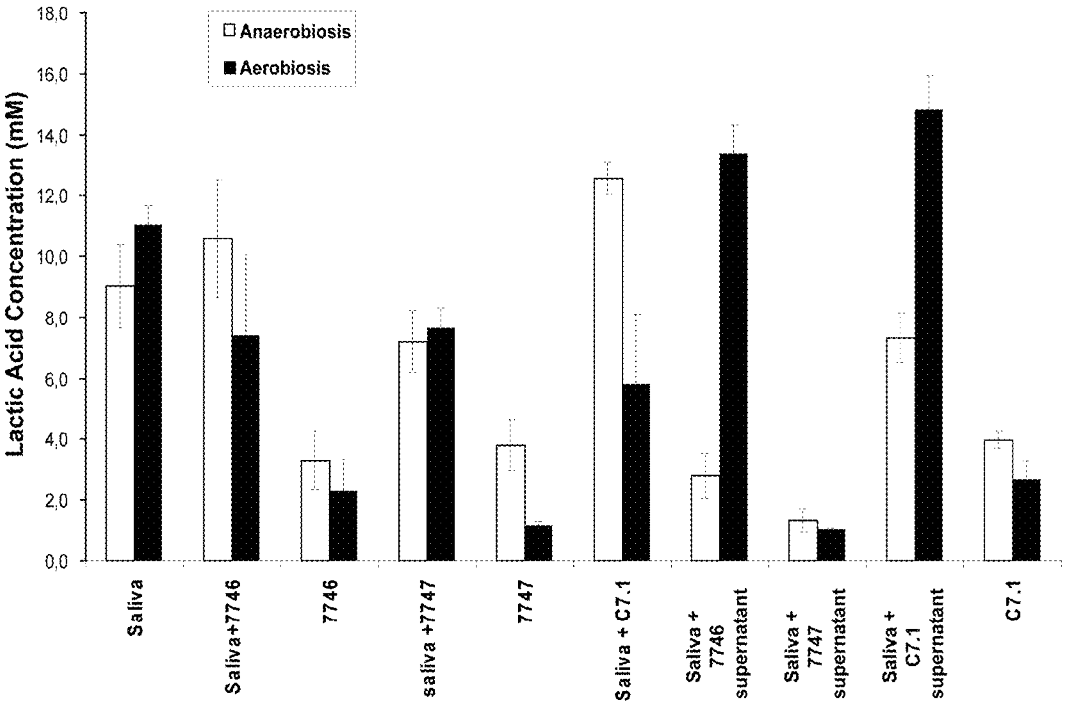
FIG. 18. Concentration of lactic acid, expressed in mM, produced by the biofilm from the culture of human saliva in an artificial tooth model under aerobiosis and anaerobiosis conditions, whereto bacterial strains CECT 7746 and CECT 7747, or their respective supernatants, have been added. For more details, see Example 15. The negative control used was strain C7.1, which is an isolate belonging to the species of the *Streptococcus mitis/oralis/infantis* group, obtained from an individual without caries, but which does not produce inhibition of the growth of cariogenic species.

The results are shown in FIG. 18, and indicate that the monospecific biofilm formed solely by strains CECT 7746 (experimental group 3) or CECT 7747 (experimental group 5) produce a quantity of acid that is significantly lower than that of saliva (experimental group 1). Taking human saliva as the reference value (experimental group 1), the supernatants of strain CECT 7747 (experimental group 8) significantly reduced the production of acid, under both aerobiosis and anaerobiosis, whereas the supernatant of strain CECT 7746 (experimental group 7) reduced the quantity of acid produced by the biofilm only under anaerobiosis conditions. The addition of strain CECT 7747 to the biofilm reduced the production of acid under both aerobiosis and anaerobiosis, whereas the addition of strain CECT 7746 to the biofilm caused a reduction only under aerobiosis.

The reduction of acid, particularly in the case of strain CECT 7747 and the supernatants thereof, is very relevant for the treatment and prevention of dental caries, since the latter is formed due to the production of acid by microorganisms when these ferment the sugars ingested in the diet. Acid pH is precisely what de-mineralises the enamel and produces caries, and, therefore, any acidogenic species, and not only *Streptococci* from the mutans group, could be potentially cariogenic (2). Therefore, the reduction in the production of acid is an indicator that the overall effect of treatment with the probiotic strain or the supernatant thereof is the reduction of acid and, consequently, a lower probability of developing caries.

BIBLIOGRAPHY

1. P. D. Marsh, Dental Clinics of North America 54, 441 (2010).
2. P. Marsh, BMC Oral Health 6, S14 (2006).
3. P. E. Petersen, Zhonghua Kou Qiang Yi Xue Za Zhi 39, 441 (November, 2004).
4. S. S. Socransky, A. D. et al. J Clin Periodontol 25, 134 (February, 1998).
5. R. P. Darveau, Nat Rev Microbiol 8, 481 (Jun. 1, 2010).
6. B. J. Paster et al., J Bacteriol 183, 3770 (June, 2001).
7. S. R. Gill et al., Science 312, 1355 (Jun. 2, 2006).
8. K. Kurokawa et al., DNA Res 14, 169 (Aug. 31, 2007).
9. P. A. Vaishampayan et al., Genome Biol Evol 2010, 53 (2010).
10. J. Qin et al., Nature 464, 59 (Mar. 4, 2010).
11. J. A. Aas et al., J Clin Microbiol 43, 5721 (November, 2005).
12. E. A. Grice et al., Genome Res 18, 1043 (July, 2008).
13. W. J. Loesche, Microbiol Rev 50, 353 (December, 1986).
14. M. W. Russell et al., Caries Res 38, 230 (May-June, 2004).
15. WO 2007/077210 "Probiotic oral health promoting product".
16. WO 2005/018342 "Compositions and methods for the maintenance of oral health".
17. EP 0195672 "Dental caries preventive preparations and methods for preparing said preparations".
18. WO 2004/072093 "Antimicrobial agents".
19. Margulies M et al., Nature 15; 437(7057) (2005).
20. Gomez-Alvarez V et al., ISME J. 3(11) (November 2009).
21. Zheng Zhang et al., J Comput Biol. 7(1-2) (2000).
22. E. M. Bik et al., Isme J (Mar. 25, 2010).
23. K. T. Konstantinidis et al., Proc Natl Acad Sci USA 102, 2567 (Feb. 15, 2005).
24. Marchler-Bauer A et al., Nucleic Acids Res. 37:D205-10 (January 2009).
25. Selengut J D et al., Nucleic Acids Res. 35:D260-4 (January 2007).
26. Altschul et al., J Mol. Bio. 215 (3):403-10 (Oct. 5, 1990).
27. Cole J R. et al., Nucleic Acid Res. 37:D141-5 (January 2009).
28. Huson D H et al., Genome Res. 17 (3):377-86 (March 2007).
29. Brady A and Salzberg S L. Nature Methods. 6 (9): 673-6 (September 2006).
30. Chen T et al., Database (Oxford) 6 (July 2010).
31. J. R. Tagg et al., Trends Biotechnol 21, 217 (May, 2003).
32. R. B. Merrifield (1963), J. Am. Chem. Soc. 85 (14): 2149-2154.
33. Albericio, F. (2000). Solid-Phase Synthesis: A Practical Guide (1st ed.). CRC Press. pp. 848. ISBN 0824703596.
34. Konstantinidis K T, Tiedje J M. J. Bacteriol. 2005 September; 187(18): 6258-64.
35. Goris J et al., Int J Syst Evol Microbiol. 2007 January; 57(Pt 1): 81-91.
36. Richter M, Rosselló-Móra R. Proc Natl Acad Sci USA. 2009 Nov. 10; 106(45): 19126-31.
37. Exterkate R A et al., Res. 2010; 44(4): 372-9.
38. Pham L C et al., Arch Oral Biol. 2011 February; 56(2): 136-47.

The invention claimed is:

1. A method of treating caries, said method comprising administering a therapeutically effective amount of a culturable anti-microbial bacterial strain selected from the group consisting of CECT 7746, CECT 7747, and CECT 7775, or a combination thereof to a patient in need of said treatment.

2. A method of treating caries, said method comprising administering a therapeutically effective amount of a medical-pharmaceutical composition that comprises at least one anti-microbial bacterial strain selected from the group consisting of CECT 7746, CECT 7747, and CECT 7775, or a combination thereof, to a patient in need of said method of treatment.

3. A method of treating caries, said method comprising administering a therapeutically effective amount of a probiotic or prebiotic or functional food comprising a culturable anti-microbial bacterial strain selected from the group consisting of CECT 7746, CECT 7747, and CECT 7775, or a combination thereof, to a patient in need of said method of treatment.

4. A method of treating caries, said method comprising administering a therapeutically effective amount of a mouthwash solution comprising a culturable anti-microbial bacterial strain selected from the group consisting of CECT 7746, CECT 7747, and CECT 7775, or a combination thereof, to a patient in need of said method of treatment.

5. A method of treating caries, said method comprising administering a therapeutically effective amount of a solid, powdery or pasty composition comprising a culturable anti-microbial bacterial strain selected from the group consisting of CECT 7746, CECT 7747, and CECT 7775, or a combination thereof, to a patient in need of said method of treatment.

6. A method of reducing the probability of developing caries in a patient, said method comprising administering a therapeutically effective amount of a medical-pharmaceutical composition that comprises at least one anti-microbial bacterial strain selected from the group consisting of CECT 7746, CECT 7747, and CECT 7775, or a combination thereof, to a patient.

7. A method of reducing the probability of developing caries in a patient, said method comprising administering a therapeutically effective amount of a probiotic or prebiotic or functional food comprising a culturable anti-microbial bacterial strain selected from the group consisting of CECT 7746, CECT 7747, and CECT 7775, or a combination thereof, to a patient.

8. A method of reducing the probability of developing caries in a patient, said method comprising administering a therapeutically effective amount of a mouthwash solution comprising a culturable anti-microbial bacterial strain selected from the group consisting of CECT 7746, CECT 7747, and CECT 7775, or a combination thereof, to a patient.

9. A method of reducing the probability of developing caries in a patient, said method comprising administering a therapeutically effective amount of a solid, powdery or pasty composition comprising a culturable anti-microbial bacterial strain selected from the group consisting of CECT 7746, CECT 7747, and CECT 7775, or a combination thereof, to a patient.

* * * * *

SEQUENCE LISTING

<160> NUMBER OF SEQ ID NOS: 14

<210> SEQ ID NO 1
<211> LENGTH: 244
<212> TYPE: DNA
<213> ORGANISM: Homo sapiens
<220> FEATURE:
<221> NAME/KEY: CDS
<222> LOCATION: (96)..(176)

<400> SEQUENCE: 1
catcatctcc aatctacaga agcggaagcc ggagctaaat agcctgctag aggtcacggt 60
gctgctgccc aacggcggga gcccggattt ctgac atg tct tgc aag aaa gag 113
Met Ser Cys Lys Lys Glu -continued

```
                                    1               5

tcc ctt gga agc aaa tgc aat tat att ctt ctg tgg tat caa cca aca      161
Ser Leu Gly Ser Lys Cys Asn Tyr Ile Leu Leu Trp Tyr Gln Pro Thr
            10                  15                  20

gaa tcc ccc cac taa ggggaactca agataccgat ggaactctag gctggagcgg      216
Glu Ser Pro His
        25

cgggagtttg ccagatactc gtaatctt                                       244


<210> SEQ ID NO 2
<211> LENGTH: 666
<212> TYPE: DNA
<213> ORGANISM: Streptococcus species
<220> FEATURE:
<221> NAME/KEY: CDS
<222> LOCATION: (240)..(359)

<400> SEQUENCE: 2

cccgttcctg ggaacactcg gtggtggatc tggctgaggc gctggtcctg caaaagcggg      60

tgggagaggt tttcgacgcg gtcctaatcg atgtcaatcc gagtccggga tgggaacctt     120

tcagatcgca gacccggcgg tggaggcgaa actgcccgcg gagggccgtg aacccggccg     180

ggcggttcgg gtgcggttgg atgaggtgga tctcagcgag ggcaggacgg tgttctccc      239

atg ccg ttt gag gcc gtt ggg gaa gct aga ctt gct gcc cgg acg agt      287
Met Pro Phe Glu Ala Val Gly Glu Ala Arg Leu Ala Ala Arg Thr Ser
1               5                   10                  15

cgg ccg ggt gat cgc ggc ccg gga aac cgg gct gag gaa agt ccg gac      335
Arg Pro Gly Asp Arg Gly Pro Gly Asn Arg Ala Glu Glu Ser Pro Asp
            20                  25                  30

tcc gca gag cag ggt ggt ggg taa cacccacccg gggtgacccg cgggacagtg     389
Ser Ala Glu Gln Gly Gly Gly
        35

ccacagaaaa caaaccaccc ggcccaacgg ccgggtaagg gtgaaacggt ggtgtaagag     449

accaccagtg cgccgggtga ccggcgcagc tcggtaaacc ccacccggag caagaccaag     509

aaggccagtc cgctggccgc ggaaaccgtc tgagcgctgc tcgcgcgagg tttccgggta     569

ggttgcagga gcccaccggc aacggcgggc ctcagatgga tggtcaccgt cagacaaaat     629

ccggcttaca ggccggctcg tccccgaaag gtcgggt                              666


<210> SEQ ID NO 3
<211> LENGTH: 42797
<212> TYPE: DNA
<213> ORGANISM: Streptococcus species

<400> SEQUENCE: 3

ttacaaagtc ataaccgctc gaaactccta cctgccattt gggcgtgagc gatacgttac      60

ctgagaacat tagcgagttg ttggatatct tattttcgcg tgcctgattg ctataagtaa     120

gcgaatgtgc taaggttatg tcccaaggga taactgcctt gtaaaaggtc ttcttctcat     180

ctttatcctc gccttctttg cggttcttat ccatatcctg cacttcgctt agtggtttcg     240

acgacccaaa gaggtcatca gtacgtcctc ccgctacgtt acccgtttgt ttatctttat     300

tcttgtcttt tttatctttg ttcgagaatg aatagttagt agaaatattg gcgttagtaa     360

gcctaaaaag actaccgccg ttgtctatat tccatttctc catttgtcgt ccgttgttgt     420

ctattgcata agggttcagt gttgccccaa agttcacccc gagcttcccg ttgaagaacg     480

aagtaccccc cgtaatgttc agcggactaa actgcttggt aatcacgttg tagttagaac     540
```

-continued

```
tgaaattgag actgttcaag agcattacct ttttcggctc agcatcagtg ctatcttttt    600
gtttcacttt ggcttcaaag gtgtttgcca atgagaaccc tatcgattgc gactcaccca    660
aacttggcgt accgtagata ccaccctcaa aacgcgtgta ttgtgagcgg ttgccataag    720
cgtccgaaat gtaataatcg taatactggt caaaagaagg attataacca taactcaccg    780
agggtcgcat cacgtggcga atagcttgta ttttagcgtt cttgccaaaa cggaaagtac    840
cgtagatagt agtaccgaga cttgccccga ggttatacgt cataaaacgg tcaaaaccac    900
tgagggtgtc aatgcccacc ttgcccgtat tgctattgaa gtccttacgg tgaatcgtct    960
taaattgcca cgtctcgttt actgatgagt tcaaccctaa agtaacgtat ttaaatagct   1020
tagcagttgt actcaccggt atagagtgtc gcaccccgtt tcttgcctcg tcaaacatct   1080
ttttagtaaa gaacaaactg tcataggtcg aaaaacggtt atcagcttgc atactgtact   1140
ggaaattcaa actcttgata agtccttttt tcgtttgtcc ttcacgagca aaaggataaa   1200
tacgctccat actcgcacgc atcgaaggga gtgtcatatc aatacttttg gtattcgtat   1260
tttgtgaatg cgatgccgat agcgataagt taattgaagg atacgctggg aacgtcttgg   1320
agtacgagat agacgacatc atcgtgttgt tcaaaaagtt tgatgtattc gcttgattat   1380
aagattcttg ataataccta ctattactcg ataagttcac cgaagctgaa aaattagaat   1440
tagggttggc tttaccgtct ttggaatgcg accactggat attgtacata cggctgcctg   1500
aatagtcagg taagcccttc atactgtata tgttattttc aaaagaaaga ttaaaacttc   1560
ccgaatactt atatcgtttc acataagccg attgtgccct aagcccatag ctgccattag   1620
tataatagtc acctgtaagt gaaagatcaa aattgtcgct aatcacaaaa taataaccta   1680
tattttgtaa gaaatagcca cggttattca cctctccaaa agtaggaaaa ataagtccag   1740
atgagcgtcc tgacaccata ggataataag caaatggaat agctaaaggg gtaggaatat   1800
ccactatata catattgcta aaacctgcta taatcttttt cttaggcaca aatttagctt   1860
tgcgtacttt gatgtaataa tcaggatcgt caaggtcttc agcggtagtg ataatcgcat   1920
ttctcataaa gtaagtagag tcattctcct tcttaatgat ctcacctttt atattatttt   1980
cgtcctgctt ggtataagca ttgcggataa tagccttctg gttacgatag ttaaagcgaa   2040
tagaatctgg ctctatcaca tcactaccct gcttaaatac agggtgctga ctgtattctc   2100
ctaaactgtc tttcaaacgt cccgcatata cctctccttt ctcgtaatta atcacatcta   2160
cacccgctgt aatgtcaata ttagtatatt gtacattggt ctcattgtac aagatgattt   2220
cattctttac cctattgaac acaatactat ctttagcctt gtatttcact atgtcttcca   2280
aagcattctt aggtttctta atagtatcgt ttttaagaga atctttagcc ttttctgaag   2340
tctttttagg cttgatacgt cttccacgac gatcgttctt aggttctata gtgtcttttt   2400
taatagtatc gcgtgctacc caaggatagg tatagttaaa accacctgtc ctaaaggcaa   2460
atgattcagc ataccaaaag caacagctta ctactaacaa gctgataata aaagtgagtt   2520
gacgtttata ctgtaacaaa gtttttccga atatagtttt attgaggcga caaaaataca   2580
actttttttt gaaatgccaa gaactacatc gcaacttact attggaaatg gctctactag   2640
cctccttagt taccatttac tacctccttt tacttaaatt gtaatattca taacaaaatc   2700
gcctttttct tgcattttct acaataagtc caataacgaa caataaaccg agaaagaacg   2760
aacaataaac gaagaaaata catacttcac ttattgacga atacttaact aattgaacaa   2820
aacattgaga ataatgcaaa actaaaaatg tttgaacacc acttacctta ttagccagca   2880
actaaaaaaa tctctccttt cattcgtaat tcctaattat tttgtacttt tgcctctact   2940
```

-continued

```
ttaacgaaga aaatgatgat gactctcaaa aatatcaaag tatttattaa aaaatctctc   3000
gtattcaaga ttttagcctt tatcatagcc ttagtgctta tcttgcaggt attccccgaa   3060
aaagcaaaat tcaaatacga atttcgcaaa ggagaacttt ggcaacacga caatttatac   3120
gctccttttg attttcccct aaaaaaaaca gagcaacaaa taaactctga aaaacaacaa   3180
attaccaatc aatctaccgt ttattacaaa caagatacaa ctgcctttat aagtgctaaa   3240
cagaagtttg aacagaaaaa aaatagctat ttcaatcaat tgtctaaaga caaaaaagag   3300
ctcttactcc acaaagctga aacattttta actgaaagct atcacaatgg gataatgctc   3360
aaccctcctg tgttcaaaac ttccgaaatc gcaattatca agcaaaacaa ccaaattgtt   3420
gaagtctctg cctctcgtgt attataccttt caacagctaa ataataccat taaaaactat   3480
ttcaataccg ctccttacaa cgaacatctc aaaaattact acgacctttt ctttgatatc   3540
ctcaccccta atcttgtaat cgaccaaaat tttacccaaa aagccttaaa tcaaaacctc   3600
aaagagattg tctatacgcg tggatgggtg aacaaaggaa aacttatcat cgccaaaggt   3660
gaattagtcg aaggtgaaaa actaaacact ctcttatctc tcaaagaaga atatgaaacc   3720
caaacgtgga gtcaaaataa ctataattgg tcgctatcag gctattacac attagttgct   3780
atagtattga tactaatggt gttatactta aaaatatacg aaaagaaaat atacaaaagc   3840
aatgtcaaat tgagtgttat cttgctcaat atgctcacga tgattctttt cgtcggactc   3900
atctctcgct atttccccga ttatatctat attgtccccg taggaatgat ggtgctcatt   3960
ctcaagtcgt tttcgatct gcgcaccgtc ctctttgtgt atatcagcac catactcatc   4020
acaggcttca ttgtgcccaa tagcttccag tttgtgttca tacaaattgt atctgctatg   4080
gctatcatcc tcactcctaa gggaatgcac taccgattga gcagttttgt atcggcggga   4140
ctcatcaccg ctgcctattt aattatttat atcgctttcc ataccattac cgaaggaaca   4200
ctcaaaggac tagacatttc cttgctcact cttttcattc tcaatggtat aggaatccta   4260
ttttcacaac cttttaccta tatctatgaa cgtacttttg gcttagtatc cgatgtctct   4320
ctcttggaac tttccgacac gaacaccaaa cttttgcgcc aactctccga aaaagctcct   4380
ggtactttcc aacactctat gcaggtggca aatcttgccg aagctgctgc cgccgaaatt   4440
ggcgctaata cgctattggt gcgtgtagga gcactatatc acgacattgg taagatggaa   4500
aaccctattt actttaccga aaaccaaaaa acaagcctca accctcacga ccagctcact   4560
cctgaacaaa gtgctaaggt gattatcaaa cacgttgccg atggtgttga actcgctcat   4620
aaaaataaac tgcctaaacg catcatcgat ttcatcaaaa cccatcacgg acgcagtctt   4680
acctattatt tctatcgcaa agccttagac ctaaatcccg aaggcactaa agaagaagat   4740
ttccgctacc caggtcctat tcctttctcc aaagaaacag ctatactgat gatggctgat   4800
tcagtggagg ccgctactaa aagtcttaaa aaccctactt ttgaagctct taacgagttt   4860
gtcgatcgca tcatcaaaaa acaattagat gacaatcaat ttgctaattc cgatatatct   4920
ttcaaagaaa tcgaagctat caaacgcata tttaaaaaca aactcaccaa tatctaccac   4980
gtgcgtatcg aatatcccga gtaattggca cacttattga catccgattc tccaagtctc   5040
tccgagattc tcaaaaatct aaaataaaca tcaaaaaata tgaaacacta ctttgtatta   5100
ttttcgctaa tatcaacaat ggcaatagca caaaaccaaa cgcctaccgt cgaagttaca   5160
ggtgaaggca tcgtatatgc aaccccccgat atggtaaata tctctatcag tatcgaaaaa   5220
gaagggcttg atttgaagaa tctccgacaa aagaacggtg aagctgtggc tcaagtatta   5280
```

-continued caacttttga gtaaggaact ccctatggag aatttccaaa ccagctatgt atctctttat 5340
aaagatgatt ataacaaact aaacaaatat cgtgtagtgc aaaatatcaa tatcaaatta 5400
gaagatataa gcaagtacga caacttgatg aatgctattt tcgatgcagg agtaaaccga 5460
attgacggca tcagctttgg agtaaaaaac aaagaaaaac tcttacaaga agcacgtatc 5520
gccgctatcg acgatgcccg taaaaaagcg ttactctatg ccgtaagttt agaccaaaat 5580
attggtaaag ctatccaaat caaggaagta aactctcatt tcaacgatat acaacccgtt 5640
gaaagaatga gcaaaatgag tttaggaagt actggaaatg ataatacttt agccgtaggt 5700
aaaatagcta tcgaagctca agtaaatgta gcattcgaac ttttaaaata aattcactat 5760
gggaacacaa gaaattatag cctatatttt agtagcaata gcagcttttt tcttagtaaa 5820
aaaactgttt tttaacaaaa agaaaggctg ttctggcggc gctaattgca actgcggaca 5880
ctaaataatt aaaaaaaatg ccaattcaca aatttgctaa ttgacaaatt attcgtacct 5940
ttgcgccctc aattttaaaa attacaaatt atatctatga ccgctattag aaatatagct 6000
attattgccc acgttgacca cggaaaaact acccttgttg ataaaatctt gcaccactgc 6060
gcactctttc gcgacaatca agattctggc gaactgatat tagataataa cgacctcgaa 6120
cgcgaacgcg gtattaccat cctctctaaa aacgtatctg ttgtttataa agacatcaaa 6180
atcaacatca tcgatacccc tggtcacgcc gactttggtg gtgaggttga acgtgtcctc 6240
aatatggctg atggcgtact tctattagta gatgcctttg aaggtcctat gcctcaaacg 6300
cgatttgtac tccaaaaagc tatcgaaatg aagttgaaac ctattgtggt aatcaacaaa 6360
gtcgataaag aaaactgtac acctgatgag gtacacgaag ctgtattcga cctgatgttt 6420
gaactcggtg ccgaagattg gcaactcgat tttcctactg tctacggttc agcaaaacaa 6480
aactggatgt ccgaagattg gcataaaaaa acagatagca tcgctcctct actcgatatg 6540
gtggtagagc acatccctgc tcctcaaatt gaggaaggta gcttgcaaat gctcatcact 6600
tctcttgatt attctacctt tacaggtcgt atagctatcg gtcgcttgca ccgtggtacc 6660
ctaaaagctg gtatgaatat ttcattagtg aaacgtgatg ggactatcgt aaaatctaaa 6720
attaaagaac tacacctatt tgatggttta ggtcgtaaaa aagtagagga agtacaagca 6780
ggcgacatct gtgcgattgc tggcttagaa ggctttgaaa ttggtgatac catcgccgat 6840
tatgaaaacc ccgaagcact tcctactatt gctatcgatg aacctacaat gagtatgctc 6900
ttcactatca acgattctcc tttcttcggt aaggacggta agttcgtaac ctctcgccat 6960
atcaaagaac gtttggaacg cgaattagaa aaaaacctcg ctttacgagt agaacctacc 7020
gatagtgcag ataagtttat tgtttatggt cgtggggtat tacacctctc agtgcttatt 7080
gaaacaatgc gtcgtgaagg ttatgaatta caaataggtc aacctcaagt tatcatcaaa 7140
gaaatcgatg gcgtaaaatg tgaacctgta gaagaactca ctatcgattt acctgaaaac 7200
gtaagtggta aagcagtcga tttggtaacc cttcgtaaag gtgaaatgct aagtatggaa 7260
cctaaaggtg aacgtatgat tatcaagttc atcattcctt ctcgcggtat cattggcttg 7320
cgtaaccaat tgctcacggc taccgctggt gaggcgatta tccaccaccg tttcttggaa 7380
ttccaacctt tcaaaggtga aatcgcaggt cgtatcaatg ggtcgctcat ctctatggaa 7440
caaggaactg ctatccccta ctctctcgat aaattgcaag accgcggtaa attcttcatt 7500
ttccctggcg aagaaatcta tacagggcaa gtaattggcg aaaactctcg tagtggagat 7560
atcgtcgtga atgttacgaa gactaaaaaa cttacaaacg tacgtgctgc tggttctgat 7620
gaaaaagtga agttagctcc acctattaag ttttcattag aagaagcttt ggaatatatc 7680

-continued caaaaagacg aatacgttga agtaacacca aaaaatatgc gcttgcgtaa aatctactta 7740
gatgaaaatg aacgcaaacg ccacgaaaaa gagtttaaat aattaagcaa atattttcta 7800
aaaacaaaag aggttgccca atattgagta acctcttttt aattgtcata aactttgtca 7860
aagtcccaaa acttcaacaa agtctataaa tctgataatc aatcactttt agagtatgtt 7920
atgtaggaaa gccagcgata gctggtatgt gctgcaaatc cccatataaa taaaactttt 7980
cggacaggct ctttttaatt gtaaactgtt aattatcaat cattaattgt taattgttaa 8040
ttgttttatt gtttcttcaa cagtcttatc atagtcaatc cctaaacctt cttgttgtga 8100
taccaattca cctttttgt taaacacact gatgatatta gaatgcgaga agtccactgg 8160
tgatatttgc ttgtagttca cagcaagtac tgcagcaaac tctcgtgttt gttcttcatt 8220
agaacgaagg aatagccatt gctcatcgtc catttgtctt tctttagcaa aggcttttaa 8280
atgctctggt gtatccgtct tggggtctat actcaccaaa aggtatttca cttgcttgtg 8340
cttatcacca gcttgttcat ctacgcgttt gcgtatttcg cgcatatctt taataaggat 8400
agggcaagcc gtcttgcaag aggtgtagat catcaccacc accaatacat tccctttgag 8460
gtctttaagc tctatgttat ccccattttg ggtcgtccat accgctggca agtgatatac 8520
tgataagtcc gaaaaactat ccgttgcctt tgttgtagta ctatctgtca ccgcctttac 8580
atcagttgtg gatgtgttgc tattgtggtt attacaattg agtaataaca aactcagtaa 8640
aataaaatat agtgtcttca ttaatagtaa tttttctaa ggtttatctt cattttatca 8700
tattttgctt ctaaatcttc taaaaatccc tccaaaacat cggctacatc ttcataattc 8760
tcataaaggt atttatcgtc aattccttgt tccataatcc ctcttatttc tttcaattta 8820
gcccttatat atttatacga gcttgttgtt ccatcatagt atagaaactc ttcaacatat 8880
tctttcaata tatcataatc tgcattagcc tctacaatca tagctttgat atagatattc 8940
accaatgata taattgttaa ctctgccgat tgtttataca cctctactat cacataatta 9000
cagatttcgt ctatatcgtt atatgacata ttctttaagt tgttattatc gcctaataac 9060
aactcacaat cttctataac atctctatat tttgttacaa tatctttcat tattaaagct 9120
acctcctctg catctcccag agatcctcag aattcctcct attttcttaa aatctctcca 9180
aaaattctga aattcatttg tcaattatta tagtaagtca gaattggttt gcaaaatttt 9240
cgtcactaca ttttgccaaa gttttaggtt ttatcaaaat tgattacctg ataatcaatt 9300
acttttaaag tatgttatgt aggggcgttt tgcaaacgcc cctaaaagaa aactttttta 9360
ttcacaatct attttttgtt tgaatataat ttcgtaaatt cgtaattgtc atttattccc 9420
gttaagacaa atagcaatcg cttttgcggc ttgtccccct tcgggggttc gggggctatc 9480
tcgtaattcg tatttcgtaa ctcgtaattt ataaagcaca tctaaacccc atattcagca 9540
tcgtatagtt cgctttgagg ctacctctca gcgcataccg cataaaagct ccatagttag 9600
taaggtcgga agcattgagc gcactcccgc cacaaaaaag agcatcgtct ccttgcttgt 9660
ctttgcgcga gtcccccgag agaagcacac tgttgaagtc cgacacccat tcccatacca 9720
agccgtgcat gtcatacact ccccaatagt tcttgggcgt actgcctact tcctgtaggt 9780
aggtcttggg cgtttgcatg ctccgcacta tatactcttg ataatgtttc ttcttgcggg 9840
catctatact ttgggcatcg gcttgggcta cgtactccca ctcgtcggtt gtcggtagtc 9900
gctttccttc acactcacaa tatttcttgg cagcaaacca cgaaatgtgg gttacagggg 9960
cttgtgcctc cagcggacta aattctaagt cgctcttcca gtgcgaaaga taactcttct 10020

-continued

```
gcgcaaagat tcccttcact cgagaacgct gccactcggg gtgtttctcc aaaaaagctt  10080
tgtattgtgc attggtcact gggtatatat ctagctgaaa gctctttacg tttacgggct  10140
ttgtcgcttt attctcccct ttcactccat acaaaggcac atagcttcct cctttaatcg  10200
ttaccatagg agtagaagtt tgccctaaga gccatccaca aaagcataaa gttattatgt  10260
taattaggta tttttttcatc attatcaccc aattaacgtt tatctcttac tttcttcact  10320
ctttcagggc ttactacggt tttattgttc tcccagttgt gatatacgta ggtgagcaca  10380
tcggctattt gctcaggggt aagtggttga ggaggcatca tactgttgta ctgtttgcca  10440
ttcacagtaa tccctcccgt atgccctttc agtacggtct ctattgctct gtctacatta  10500
gcattcaggt agtcggcttt tgccaaaggc ggaaaagctc cttccaaccc ctgcccttgt  10560
gcctgatgac aagccacaca agtgcgctga tacactttct tcccgtcttc catctgttgt  10620
gccaaagtct tattccctga ctcctgcccc ctatctcctg tcacctgaga cttaaccact  10680
gacacctgat aaggcactgc ctcttgcttg ccgtagatag ctggattttc tctcccttgc  10740
gcgatgagtt gacccaacgc acctttgttg aaagcacgga aaatagcgtg gtctactagc  10800
gtatatgaac caggcacttc tactttgaat tctactatag ctgcccctcc cgcaggaata  10860
actgtcgttt gcacattttc gtttacgagt ttgcctcctt ctacctgcac tcggtcaaag  10920
atttctccta tcacgtggaa agaagaaatg aggttaggtc ctccattccc tacaaaaaga  10980
cgcaccgttt caccagcgtt tacagtaagg gctttatcgc ctgcaatagc tcctactttc  11040
ccgttgaaaa gcacataatc aggcttttcc gcaagggctt tctcttggct gaaggcttgc  11100
aaaccttctg ctccataagc tccttcggta tagaaatcgc cttgcatcac atagtattcc  11160
atatctactg gggcagacc gccttcgggt tctaccaata taagcccata catcccattg  11220
gcaatatgca aaggcacggg cgcttgagca caatgatata caaaaagtcc cgggttcaaa  11280
catttaaagg tgaaggtacg ttgctgtcct ggggctacta acgacgcatc agcacctcct  11340
cctgtacccg ttacagcgtg aaggtcgata ttgtgtgcca atttgttatc tgggtgattt  11400
ttaagtgtaa acgatacttc atctcctaca cgagctcgaa taaaactccc tggcaccgta  11460
ccgccaaatg tccaaaaaag gtatttagta ccatctgtca attcgccttc tttttctatg  11520
atttcaagag taacacttag ttttgtagcc ttccgattgc ctactggcgc tggtacaaaa  11580
ggtggtgaag taagttgggc taccatttct ccctctacgg gaatatcagt ggtagaagta  11640
taagtagttt gttcattaca agcacttaac aataaagaag cactcaatag taataaattg  11700
tatttcataa aatcttttct catcattata gtaccaaatt atatagaagc aattaaaata  11760
cgggggcaaa tataatactt ttttgtctaa taatctctat cccaatatag ctttttagtt  11820
cccattactc ccacaactcc cacagctccc attaaaactg cccgtgcggc tcccaccact  11880
aaaggtcaaa cactgaagtc cgtttcacaa aaaacacatc cttaattctc aacaaagaag  11940
ccaataatag atatacacca aaaccagccc ctaaagtagc aaaagtgcca taaataaaga  12000
aaatacgcac atctttagcg cgtacaccta atttctcagc caatcgtgcc gatactgcaa  12060
agccgtattt ctctaaaaaa aatctaacct ttgaaatcat atctaattat ttgttacccg  12120
ttgtttgctt gtcttaaaaa gtagaattat gccaactccg aagaagataa tcaatgagat  12180
agtcgcatta cgcatattat tcgtaaattg gtctatgagt ccataaacac ccattcctat  12240
tactatccct attttttcag tcacatcgta aaaactgaag aaagaagttg tatctttagt  12300
atcaggcaaa taagccgaat aagtagagcg agaaagcgtt tgtatacctc ccattacaag  12360
tcctactaaa gtagcaatga tgtagaattg tatcggttta tacacgtaat atgaaagtaa  12420
```

```
gcaaattcct acccatatag cattaagccc tattaacacc caaatatttc cccatttgcg  12480
cactgcaata actgtgagtc gtgctcctac tatagctacc aattgaatta tgagcacact  12540
cactattagt cctatagtac tttcttcagc actcgcccat tgtatttctt gttctccaaa  12600
ataggtagct accagcatta cggtttgcac tcccatacta tatacaaaaa aagcaatgag  12660
ataccatttc aatcgtggcg aggtagtgag ttgttgccat actttccgta attccttaaa  12720
tccattaaaa aaaatactct tggtaacttt agctccattt ttcttatatg atggaaggta  12780
gtaaaaagga atactactga accctatcca ccatactcct actgtgataa acgaaatccg  12840
catcgtcgtg agtgtcgttt cggtatcagt agtagtaaaa cctatccatt cgggtttcat  12900
caccattatc aaattgaaaa tcaatagcaa cacactcccc gcgtagccta aactataacc  12960
tttagcactt actgcatcgt attgttcagg cagagcaata tctggcaaat aggaattgta  13020
aaacactata cttccccaaa aacctactac cccacaaaaa taacaaaata aactaaaata  13080
gatgtgttct aacgaaaacc agtacaatcc tatacacgaa attgctccaa tatagacaaa  13140
aaagcgcata aatgtttttt tgttgcctaa atagtcggct ataccactca aaataggcga  13200
gagtaccacc accacagcaa aagccaaagc ggttacaaaa gcgattaccg atgtactttt  13260
gattatcatc ccaaaaaggg ctatatgggt aagccctgca atgcgaaata atagtccgta  13320
aaaaatagga aaaatagtgg aaacgatggt aagtgaatat actgagttcg cccagtcata  13380
aaacgcccaa gcgttgagta gttttttatt gcctctttct aatctgttca tagtttagtg  13440
tttttactg cgtttgttac tccatttttc gagtagataa atcactaaaa aacctgctat  13500
tgctaatagt acagcaatga atatttgagg ttctgtatgg gtgacttctt taaaagtaca  13560
gggcgatatg ctcttctccc acactgccac agcattacct tgagcatctg tatcccattt  13620
caaaacctct ttccaaggcc atactttgtt tagcgacccc acgataaaac cagtcaaccc  13680
tgcaaaagta agagtccgat atttagcaaa caaccatttc agcgccttag aaaaacttaa  13740
aatacccgtg attgctccta ccccaaaaac acttatgagt ttaaaattcc acgaactcaa  13800
agcgtctaaa actgtgtgat aagctcctaa cagcaccaat ataaaagctc ctgaaatccc  13860
tggtaatatc atcgcgcaaa tagccaaagc gccacagaag aaaataaata tcaaattctg  13920
gttaccacca ttcactaagg gtggaataac cgtaataaaa taagcaactc cccccgatat  13980
aagcatcacg agtattgtag ctaaattcca acgcttgatt tcttttatca aaaaaagtac  14040
gctggctatc atcaacccaa agaaaaaagc ccatatcatt ataggttcat tttctaaaag  14100
ccatttcatc cctttggcaa gcgatatgat gctaacccct atccctgcca agagtgctaa  14160
aaaaaaatta ccattaatat gtttccaaaa agctacaatc cctttgctga ataaaagctt  14220
aaatgcttgt aaattgatct tgctaataga ccctacaagc tcttcataaa tccccgatat  14280
aaaggctatg gtacccccag aaactcctgg tacaacatcg gctgctccca ttgccattcc  14340
tttggaagta ataaataaat aatctaaaaa attgcgtttc ataacaattt ataatgtctc  14400
tttctaactt aaacggcgca aagataataa tattttgcta attaatagtc tatcagtatt  14460
gatttgcaaa tttttcgttc tatactatcc gtgtaattcc agtagcgttt gctgccataa  14520
tatatattct ttacgtctaa ctctcattaa gttaacgtca gttcgatata acagaacatt  14580
gatttacagc tttgtaacat aatatattca caaaataatt caccgtcagg tgaaaattcg  14640
tgagataata aaaaataaag acttttatgc actctcaatt tcgtgaaaat tcgtgtaatt  14700
cgtgggagat taaaaatatt ttactgattg ttaaataatt acttactccg aacttatctt  14760
```

-continued aagttacatt gtaggagggg ctaaaagtct caaaatcgta tttacatcta ctttactcgt 14820
cttaaaaaac tctaagattc tccaaaaaaa acacctaata ggaaacctta caataagtta 14880
atcaataaat ttttctatcc atcaaatttg ttaatttgct aattacttcg tatctttgca 14940
aaataaaagc attttcttat gaaaacggaa catcaattac atataaaata taatgttttc 15000
aataaattaa ccgacctgcc tgaaaaagct caaaacctga tgaaacaagc aataaccact 15060
cgcgaaaagg cttacgcccc ttactctaaa ttcaaagtgg gtgccgctgt tttacttaaa 15120
aacggacaaa ctttcgtagg ctccaatcag gaaaatgctg cctacccctc aggtctttgt 15180
gccgaaagag tcgctatata ccaagccgct acccagtatc ccgatgagga aatcgaaatg 15240
atcgcaatct ctggatctgc ccaagaccct actgcctttc ccgtatcgcc ttgtggagct 15300
tgccgccagt cactctccga atacgaaacc aaacaaaaaa acttatcccc gtatatttta 15360
tgggagctga aggcgaaatc gttcaaactg aatctattaa agacctcctg cctttccttt 15420
tcgatggtag cctaatgtaa actaacaact aaaaactata taacgaatga actcagaaga 15480
aattattacc tctgccaaac aaactattac tgaagaagct caagctgttg ctaaactaac 15540
tgattatatc gacgacgatt ttactaagtc agtacaatat atattgcaat ccaaaggtcg 15600
tgtagtgatt acaggtatag gtaaaagcgc tattattgct aataaaatag tagctacaat 15660
gaactctaca ggcacccccg ccatctttat gcacgctgcc gatgcgatcc acggtgactt 15720
gggtattata cagcaagatg atgtggtaat atgtatctct aaaagcggta acacccccga 15780
aataaaagtg ttagtgcctt tgctcaaaag gggtaataat aagctgatag ccattacctc 15840
taataaaaac tctgtcttag ctcaacaagc cgatagtgta ctctacgctc acgttgataa 15900
agaagcttgc cctaataatt tagcccctac gactagcacc acagctcaat tggttttagg 15960
cgatgcttta gcagtttgtc tattggaaat gaaacacttt ggcagtagcg actttgctaa 16020
atatcatcct ggtggtgcat taggaaaacg tttatatcta aaagtatccg atatcgtacc 16080
tcataaccaa aaacctgagg tctctcctga taccgatatt aaaaaggtaa ttgtagaaat 16140
atccgaaaaa atgcttggag taactgccgt actcaacaat catcaaatag taggaatagt 16200
aactgatggt gatatccgcc gaatgcttag taaaacggat agtatcaaag ggcttaccgc 16260
taaagatata atgagcgcta accctaaaac tattgaggtc gattgtttag caattgatgc 16320
cctacaccta atggagaaaa ataaaattac acaactatta gctactaaac aaggtgaata 16380
tgtgggaatt atacacctac acaaccttat tcaagaagga cttatttaaa atctaagaat 16440
attaattatt taaaaatgag agatctatcc aaaatgacaa acattgagga cttgcgtgtc 16500
gtttgtaaac gcaacgtccc taaaatgttc tacgagtatg tagacaccgg ctcttggact 16560
gaagcaacct acaaacaaaa tgtttcagac ttcaacccta tcaaattccg ccaacgtatc 16620
ttagtggata tggataaccg caccctcgaa agtacactcc ttggcaaaaa agtaaaattc 16680
cctgcaatga cggctcctgt gggctttatg ggaatgatgt gggctgacgg tgaaattcac 16740
atggctaaag ctgcccaaaa attcggtatc cctttttaccc tatctactat gtccatctgc 16800
tctatcgagg atttagtaga agctggtgtt gaacctttct ggtttcagct ctatgtaatg 16860
cgcgaccgcg agtttatgaa agaccttatc cgtcgtgcta aagaagctaa atgctctgcc 16920
ttgatgatta ccgtcgattt acaagtctta ggtaaccgcc accgcgatat caaaaacgga 16980
ctttctactc ctcctaagtt caccattcct aatatgttga acctttctac taaaattcct 17040
tggggattgc gctatatctt cggtaatcgc cgctggactt tccgcaatat tgctggacac 17100
gctaaaaacg tatccgacct ctcttcgcta tcttcttgga caaaagaaca attcgaccct 17160

-continued

```
agccttagct ggaaagatat tgccgaaatc aaagaactct ggggaggacc catcatctta  17220
aaaggtatta tgactcctga agatgctata gaggcagtaa aatacggcgc tgatgcaatt  17280
atcgtctcta accacggtgg tcgccagatg gatgacacta tttcaactat aaaagccctt  17340
cccgatatcg taagtgctgt aggtagccaa actgaagtat ggatagactc tggcttctat  17400
acaggtcaaa acatgctcaa ggcttgggct ttaggagcta aaggtattat gcttggtcgt  17460
gctcctgtat atgggctcgg tgcttatggc gaagaagggg taacccgcgc tttgcagata  17520
ctctatgacg aaatggatac tactatggct ttcgctggtc atcgtaacct ccaagatgta  17580
gatagcagta tcttagtaga gggtacttat cctctgccaa gtaatcgata attcaaaaaa  17640
ataatgtacc tttgcccccg caatgagtaa aaagaaaaat ataaccatag aaaatgttat  17700
cgttaccgat gcgggggcta aaggcaaaag cattgctaaa gctcctgatg gtcgcgttat  17760
ttttatcaac aacgctatcc ctggtgatgt agtcgatgta caaactacca aaaaaaaatc  17820
ggcttattac gaggggatcg ctactaaatt ccatgagtat tctaatcgcc gtgtaactcc  17880
cgtatgtacc cattttggct actgtggtgg ctgcaaatgg caagatatga actatgaaag  17940
tcagctgttc tacaaacaaa aagaagtcga aaacaactta gtgcgtttag gaaaaataac  18000
aatccctgaa ctgatgccta ttgtagcttc cgagaatatc tatttctatc gaaataaaat  18060
ggaattctcc ttctccgata tgcgctggct tacccccgaa gaaattcaaa atgccaatac  18120
aattgaacaa cgcaacggtt taggcttcca tatcgctggc gcttgggata aaatcctcga  18180
catcgataaa tgttacttac aagaagatcc ttctaatgcc atacgattgg aaattaagcg  18240
atttgcttta gaaaataata tacctttcta tagcccgcgt cagcaaacag gtgtcttgcg  18300
ttctatgatg atacgcatct cttctacagg cgaaataatg ttggtaatac aattctttag  18360
cgataccaaa aaaggctatt ggttgttaga ccatatcgcc caaacgttcc ctcaaattac  18420
ttctttgcaa tattgtatca acagcaaagg aaacgatgct atctacgacc aagatttaaa  18480
agtctataaa ggcaccgatt gtatttttga ggaaatggaa ggtttgcgct tcaaaatcaa  18540
tgcaaaatct ttttatcaaa caaactctaa acaagcacac aaactatatc aagtaacccg  18600
tgacttcgcc gatttaaaag gatatgaatt ggtatacgac ctctatactg gtacgggtac  18660
tatcgctcag tttgtagcta aaaaagctaa aaaagtaata ggcgtcgaag ctgtacccga  18720
agccattgcc gatgctaaag caaatgctaa ggcaaacggc attgataatg tgagttttta  18780
tgtaggcgat atgaaaaaca tctttaatga tgcttttatc gaagctaatg gtacccccga  18840
tgtaatcatc accgatcctc ctcgcgatgg aatgcacaaa gacgtagtag cgcaaatcct  18900
gcaaatagca ccctctaaga tagtatatgt gagctgtaat agcgctaccc aagcccgtga  18960
tttagcgctc ttaaacgaaa tgtataaggt gacaaaagta caacccgtcg atatgttccc  19020
tcaaacttat cacgttgaaa atgtagtact tttagaaaaa agaactctct cctaaaatct  19080
ctaaaagcaa atgaatatat acgatatcga agctaccaaa atattgctcg aaaagcaacc  19140
taaaataagt atcatccctc acaaaagccc tgatggcgat gccataggta gctgcttagg  19200
gctttatcat tatctcaaat tacatcattg tgatgtaacg gtagtttcac ctaacgattt  19260
tcctgatttt ctcaaatggc tacctgctgc cgatgaaatt cttatttacg acaacaatcc  19320
tgaaaaagct acaaagcaaa tcgaagcctc taaacttatc tttacgctcg atttcaacgc  19380
cctcaaaaga gccgatacac tcactcctct attagagaac tctaaagcta cctttgtgat  19440
gatagaccat catcaagccc ccgacgacta tgccaaagtt actttctcta accctaaagc  19500
```

aagctctact tgcgaaatga tttacacctt tatcgacgca atgggcaata aaaaccaaat 19560
cgataaagaa atagcaactt gcttgtatac aggaataatg acggatacag gtaacttcaa 19620
ataccccacc accactagca acacattcaa aattggcgct ttcttaatag aaaaaggagc 19680
taacaatagc caaatcaata gcaatgtgtt cgataataat tcttacaaca aattgcaatt 19740
acttagcact gctctcaaaa atttggtgta tatcaaggag tacgacactg cttatattac 19800
actcacttct gaggaattgc aaaaatgcga ccatcaaaaa ggtgatactg aaggttttgt 19860
aaactatgga cttacaatta aagatactaa attagccgtc atctttatcc aagaaggcga 19920
ttttgtaaaa atctccttgc gctccaaagg caataacgat gtaaacttgt tcgctcgtaa 19980
atgtttcaat ggcggcggac atatcaatgc cgctggtggg cgattcgacg gctctataga 20040
cgaggcagtt acctatttca aacaagtatt acccgatttt atccacaaaa atatgtaaaa 20100
taatacaatg aatatactta aaaaaataat cattctaagt gccattggca tagttttggt 20160
aagttgtgcc gatcggcaag cacgccatcc tataactaaa aaaacaagta cttttttaaa 20220
agaatcagct atgaaaaata aagctctgtt ggcctccgaa gaagcgctaa tcgattctat 20280
catcaaaaaa gatacacttc actctttcgt cgactctcaa cacggattta agttctacta 20340
tctaaatcaa aatcctgaag ctcattatac tgctcagttt ggcgatattg taacttatga 20400
ttacagcctt tccgatttgc agggtaacca gctttatcaa gaaaaacccg atggtgaata 20460
caaatattat gtagataaag aagaagtatt ccaaggcttg cgttctgcat taaaattgct 20520
aaaagaaaaa gaaagtggcg ttttctattt cccctcaagt gtagcttatg gctatcgtgg 20580
cgataaagat aaaatctctt tcaatcaacc tattatagct aaaatcgaag tcttcaagat 20640
tgaaaaaaat caagaagatg taaaacctcg acccgaataa ataaacatta ttaattaatt 20700
attatattat gagacgactc aattttgtag cattgctctc tgcaatgttt gtatttttca 20760
gttgtaattc gcaaaaaaaa gcctacaagg acttaggtga tggcttattt gctgatatcg 20820
aaactactca aggaaatatc attgtaaaac tcaactacaa agaaactcct ataacagtag 20880
ctaactttgt tactttagcc gaaggtaaaa actctttcgt aaaagccgaa tacaaaggaa 20940
aacctttcta caacggaacg atcttccacc gtgtaatcaa agattttatg atccaaggag 21000
gtgaccctac tggtacaggt atgggcgatc ctggatatcg ttttgaagat gaatttgtcc 21060
ctactttgca acacaataaa aaaggaattt tatcaatggc caatgcaggg cctggtacaa 21120
atggcagtca gtttttcatc actcaagtac ctacccctca cctcaatggt cgtcatactg 21180
tttttggtga aactgttaaa ggtttagaag taatcgatgc aatagctaat actaaaactg 21240
tagctaacaa taaacctgaa aaagatatca aaatcaataa aattacaatt attgctaatg 21300
gtaaagacgc taaaaacttc aatgctgtaa aagtttttga aaactatttc aaagatatcg 21360
ctaaaaaaga acaagaaaag gaagctaaaa ccaaagcagc ggctgctaaa ttcttagaag 21420
aggtaaaaac tcaagaacct caagctaaag cactcccttc tggagtaaaa atatttactt 21480
tagtagaagg taaaggcaaa cagcctaacc acactcaaca agtaatggtt aactatgctg 21540
gatatttggc aaatggtact ctcttcgatt ctaatgtaaa agaaatagaa gaaacttatg 21600
gcaaatacaa tgcaatgcgt gagcaacaag gcggctacca agctttccct atggaatata 21660
gttctaatgc ccctcttata cctggtttta aggaagctct tctaaaaatg aaagtaggtg 21720
acaaagtgcg tgtattcatc cctgctgcct taggctatgg cgaaagaggt gccggtaatg 21780
ttattcctcc taatagcgac ctcattttcg acatcgaaat caccgacata gctaaataac 21840
ccttaaccac taacacctaa aaatggtata caaatttaga gtaatactcg acgttaaaga 21900
agacgttttt agagatatcg caatccaagg agaagctacc ttggaagatt tgcacaatgt 21960
aatcaaccag tcttttggat ttgctggcaa cgaaatggct tcattctacc ttacagatga 22020
cgattggaat caaggtgaag aaatcactct tttcgatgta tccgagagtg gcgaaatacg 22080
cttaatggaa gaaactacta tcgaatcagt agtaagtgaa gacgaaccta aattgttgta 22140
tgtgtacgac tttatgtcaa tgtggacatt cttcgttgaa ttggtagata ttgaagaaga 22200
aaaatctggt gtatcctacc ctgctttgat acacgctcac ggttctatcc ctgccgaagc 22260
ccccgaaaaa tccttcatcg ccgatgattt cgatgagttt gaagacgagt tcaacgattt 22320
cgacctcgat gaagacgatt atggtagttt cagtgaagag gaatactatt aatttcgcta 22380
acatctatct atgcttaact tatatacaac aaacatcgaa accctttcta tccatagggt 22440
aggcaacttg agtaaagggg aacctatttt cttttctgaa aaaccttatg cgttaaacga 22500
cgaaattata ggcttgctaa aagagtattt cttcaaacct tttcgtgaaa aagaagaaaa 22560
ctacttccat tttgtacacg atgccgatgt agaattcaat actctttatc agctggtaac 22620
ccctattttt gaggacgaaa gtacaattca cgaacaatca gggaaaattg ctcaacactt 22680
gtacaaccaa tctaatcatc ctcatatcaa aagtggagaa gtctatatag ccctttttgca 22740
cgatacttat ttggataatg aaaaggtaaa agctgttggt atttttaaat ctgaggtaaa 22800
aaatagcttc ctacagtttg aagaacaagg taaccagtta gaaatgatta tccaagaagg 22860
tgtaaacatc catcgcttgg ataaaggttg tatcattttc aatgtaaata aagaagatgg 22920
ctacaaaata ctttctattg atagtaatcg ctacgatact aaatattggt tagaaaactt 22980
tctaaacgtc gatgctttgg tcgacgataa cttctatact aaaaaatacc tcaagttcag 23040
ccaagatttt gcaaaagatg taatcttgcc cgccgaagat aaaaaagaag aagtactttt 23100
tatgaaccgc gctatcaact acttcgctaa aaatgatgat ttcgaagaaa cctcatttat 23160
gaatgaagta tttgaaaatc ctcaattaat acctgagttc aaacactaca aagtagaaaa 23220
aggccctaag tatcaaatag aagatgtatc tacctttcca atcgctaaca aagctgtctc 23280
cgatgtacgt aaaaaaatta aaaacgtaat cgatttagat acaaatatcc aaatacgtat 23340
ggacttcatc aatcccgaat ctgccgataa gttcatagaa aaaggttggg acgaggaaaa 23400
gcaaatgtat tactatttag tgtacttcaa caaagaacaa aaaggttcat aaaaataacc 23460
tcatcaaaaa taaaatggca tatagttttt tatatgcctt tttttatac ttttgcgttt 23520
taaaaacata aaactatgat tgacgcacat aaattctcaa taggtatatt attacccatt 23580
gaatcttatc aaggggctat ccctaaaatg gaaaatcaaa tacagctaat ccaacgcgca 23640
gaagccttag ggtatgatac tgtatgggta cgcgacatcc ccctctacaa ccccgatttt 23700
aaagaagtag gtcaaatgtt tgacccttgg atatatttag ctcatatagc ttctcttaca 23760
ttctctatca aaataggaat agcaagtgta attctacctt tacgccaccc tctacatgtc 23820
gctaaagctt ccgcaagtct cgatgtattg ttccctaacc gcttcgtaat gggaattgcc 23880
tctggcgacc gtcccgtcga ataccctgct ttcaacaaac cttttgaatt gcgtagcgca 23940
cacataaccg aacatatcga aactcttaaa aaattgtgga gtgtagattt ccctacttac 24000
aataatgatt atggtaccct aatggacaaa gtaggtgatg tactccctaa acctatccat 24060
aaaaatatcc caatctatgc cactggtcac atcggtggta taaacctcaa ttggatagct 24120
aaacacaccg atggctggat ctactatccc cgtgatttct ctttccaaaa aaaaatcgta 24180
gaagattggc acgaagctct caaaaatgaa ggcgaacctg ctaaacctta tatacaaccc 24240

```
atatatatcg accttatgga aaatcctaat tttgaacctc aaactatgga cttaggcttc  24300
cgcctcgggc gtaattacct catcgatatg ttccaagaac tcaaaaaaat aggaataaat  24360
catattatgc tggtactcaa atattgcagc cgcccagctg gtgaggtact cgaagaaatc  24420
ggaaaagaag tattgcctca actcaaataa acacgatgaa aagactcttt tttatactgt  24480
gtttctatgg attcttcact gaaggatata ccaatgatgg tgctttctat atggcaggta  24540
accaactcgt ccccatcaac gaaactgata tttcagtaaa aaaagaaatt ttgtatatca  24600
aaaaaacaca agaatttgca gaagtatcag tctattatga gtttttcaat cctaaagatg  24660
aaaaagaaat catagttggt tttgaggcgg gtatcccttt aggtgatgct gggttttctc  24720
cagtaaatgg gcatcatcct tatatgttcg actttacagt atcgctcaac ggtaacttct  24780
taccttatca aatagctttt gtaaaaaact caacctatac taaaaatcat aaaatacaaa  24840
atatagaccc aaaatctctt gataatgatg tcattggtga tgagttagac tttcaatatg  24900
tttatcattt caaggcaaag tttaaaaaag ggaaaaacat tgtaaaacat acttatagat  24960
ataaactatc aagaggagta tgttattatt acgactttaa ttacgtactt acggcagcca  25020
atcgctgggc taacaagcaa atcgacgatt ttaccctgat cttggatatg ggtgatttcc  25080
aaacagcttc tattcgtaaa actttcttta aaaacactaa tgaatggact ttcaacggaa  25140
taggaaaaat aactgaaaat cctgattata ctaattttta tatccagcaa ggtattttag  25200
tattcgaaaa gaaaaacttt gtacctaagg gagagctttc cgtagaagaa gaaagttcct  25260
actgtcgaga agcaggaagt aatcaaaagt ttatttttc attaggaaaa aaccgagaat  25320
taggcgaccc taccgagaaa actcctgaag aaaaacgcat tatcaggaat ctgccatttg  25380
cacgacgtgg gtatatattt aaggataaaa ctttgcaaga tattttcaaa acagaagatt  25440
ggtatcaacc caacccttcc tatgtacccg aagttgaagc ccttactgaa gaggaaaaac  25500
aactcattaa aacatttaaa taacaccttt tattatgacc atcactcaat atcaatatgt  25560
cttagcagta gccaaataca aaaattttac taccgccgcc gagcatagtt ttgttactca  25620
acctaccttg agtatgcaag tgcagaaatt agaggaggaa ttgggagtta ctattttcga  25680
cagaagtaaa aaacctctac aggttactga aataggtgaa caaattatca aacaagccca  25740
aataatcgta aacgaagctg ggcgaatgaa cgatatcgtc gctcaacaaa aaggctatat  25800
aggaggcgaa ttccgtgtcg gaattatccc taccgtctct cctaccctat tgcctatgtt  25860
ccttactaat tttattaaca aatatcctaa agtttgcctg aaaatcgagg aacaaacaac  25920
cgaaaatatc ttaaaaaaga ttgaagatgg tagttacgac gccggtattt tagctactcc  25980
tctacacaat tcattaatcg tagaacgtcc cttatattat gaaccttttg tcgcttacat  26040
ccctgtaaac caccgcctcc aaaactctaa aactatctac tctgaagatt tagatatcaa  26100
cgatatttta atgcttgagg atggtcattg ctttaaggat agtgtactca atatctgcaa  26160
ccaagatgta atcgattcta aagaacactt ccaactaaaa agtggtagtt ttgaaacttt  26220
agtgcgatta gctaacgaag gcttaggaat gaccctgtta ccctatctac actctttgga  26280
actgaaagag gaagaaaaga aacgcattca ctatttcgcc gaaccctatc ccgctcgcga  26340
aattagctta gtttatcaca aaaatgaact aaaattacaa atcataaaag ctttacacga  26400
tactatagct ggggtaattc gcggagctat tgttttccaa aatgtaaaaa ttattagccc  26460
aacaagagaa aggcacacaa tttgataaag acagaagtta aaaattaaaa aaatagaaaa  26520
aaccatttta tgatgaaaaa tatttcagca gcattatttt tattatttat ctcattcgct  26580
tcttgcagct ttacaagcaa gaagtttgac aatcctaata aggataagga cactgtgcta  26640
```

ttagaaatta ttgagcacgt gctcgaaaat gctcatttta gtcccgtgaa aatggacgac 26700
tctttctcta aaaaagtctt cgatagctat ctgaaaaata tcgacggaca aaaacgctat 26760
tttctccaat ccgatatcaa tgagttcaaa aaatatgaaa accgtttaga tgatgattta 26820
aaaaaaggtg acatctcttt cttcaacctt tcttataatc gtctcaaaca gcgtatgaaa 26880
gaagctgaag gaattactaa agctatcttc gctaaaccta ttgacctcaa tagcaatgaa 26940
actatcaata ccgactacga taaattgcct tttgttaaaa gtaaagccga tttacaaact 27000
cgttggaaac aagtgattat tttcactact ctttctactt acattactaa acaaaaagaa 27060
gaagtaacta agaaagaaaa agatgctaaa tatcagccta aaagcaatca aatactcaaa 27120
aaagaatcta tagagtctac tcaaaaaaca ttggctgata tgtatagtat gtacaacgat 27180
attacacgtg aagagtggtt cgctatgttc gtaaatgcta taaccgaaac ttttgaccct 27240
cactctaact atatggcacc cgacatcaaa gaaggtttcg accgtgatat gtctggcaaa 27300
ttcgaaggta ttggcgctca attacaaaag aaaactgatg gtatagctat tactaatgtg 27360
attttgggag gacctgtttg gaaaggtaaa ctcttggaag taggcgacca aatcctaaaa 27420
gtaggtcaag gcgctgccga acctgttgat gtcgtaggaa tgcgcttaga tgatgccgtt 27480
aaacttatca aaggtccaaa aggtaccgaa gtgcgcctca ctgtaaaacg tgtagatgga 27540
actatcgaag tagtacctat catccgagat gtagtagaaa tcgaagaaac ttacgccaaa 27600
tcagctgtga ttactgccaa tggcaaacgt tacggcctca tcaatctacc taaattctat 27660
attgatttcg aagatgtaaa ccgtcgcaat gccgctaccg atgtagccct cgaaattgaa 27720
aaacttaaaa agaaaatatt gatggcttaa ttgtcgactt gcgttccaat ggcggtggct 27780
ccctaaaaac agtagtcgat ataggaggtc tatttatccc taaaggcccc atcgtacaag 27840
taaaatcatc acgtggtagt cgtgacgttc tctccgacaa cgaccctaaa actcaatggg 27900
atggctcttt agtaatcctt accaatgaac tttccgcttc agcttccgaa atcctagcag 27960
ctgctatgca ggattataaa cgcgctatta tcataggcgg taaacaaacc ttcggtaaag 28020
gtaccgtgca aagcttcata gacctaaatg agttccttcg tcaaaacaat tacggcgacc 28080
ttggagcttt gaaaatcact atccaaaaat tctaccgtat caacggaggc tctacccaac 28140
tcaaaggagt tgaaagtgat attgttgtac ccgataaata caaatatatc gatataggtg 28200
aacgtgatat gcctaacgct atgccttggg ataaaataga acctgctaaa tacactcctt 28260
gggcaaacaa tgccaatttt aatatggcta ttgaaaacag taaaaaacgt attagagaaa 28320
acgaatattt aaaactgata gatgaaaatg ctcaatgggt aaaacaacaa caaaaagatt 28380
atgttttccc actcaactat gaagcctaca aaaaagtaat cgacaaaaac gaagagcaag 28440
ccaaaaagtt taaagctatc agcgactata aatctaactt aaaattctct tctgtagctt 28500
ccgatgaagc taaaattaaa aacagcgaag agttaaaact tcgtcgtgat cgttggcacg 28560
aaagtcttga aaaagacgtc tatatagatg aagctgtaaa agtgttagaa gatttgaaca 28620
aataaaacaa taactaacag attataaaaa cattggtaaa gctaatacct ttaccaatgt 28680
tttttattt ttgggtatat gagaaaattg ttatacettt gcactacaat cttactcttt 28740
agtcaaatta aaatgcattt taaaatcttc attgttatat atctattctg cgttgcgtac 28800
acacaggcac agcaaccaga tagcctttct caacaagaaa ttcacaaaga gttagaagct 28860
atcaaacaat tccgccagaa agattccgta cgcattgcaa tgctcttaaa cgaaatacaa 28920
ctactcataa ataacgacaa acatacatct tcaattacta attcctccac tactaatgaa 28980
aaagaaatgg aaaaactacg caataaaatg cgtggacgac ctattgtttt tgaaaaagat 29040
accttatact atctctatac ttcctatgga ccttatgata ttgatactcg cgtaaaatat 29100
atagaaaata aactcaaaga attatataac gacccctctt tcgccgccga ttctatcaaa 29160
ataaaaccca atggcgacta cctatcagta atgtataacg aaaaaatcat cactcgtgtt 29220
acaatggtag atgcgctctg ggaaaatagc tcccaaactg aattagctca aagatatgct 29280
aatgtaatca aaaatacaat tgtaaaatat aaagaacaaa atagcctaaa aagcatccta 29340
atccgcttgg ctgagttgtt attagtactc ttcatcgctt ttgtacttgt atgggcgatc 29400
aaccgattat tcaatttctt aaaaaaaata acgctcaact ccgaacaccc ctccctcaca 29460
ggtatccgaa ttagaaatta cgaatttatc aaaaaacgag gagttgtaaa agctttagtg 29520
aaattacttg ctatattgcg tatcatattc ttgtttttct tgctaataac tattatacct 29580
ctgattttcg atatcttccc ttctactcaa tacttgtcta aaattatagt acaatggatt 29640
tctgaaccta taaaaaacgt cggtatagca attattggat atttgcctca tttattctat 29700
attgtcatta ttgtagtcat tacacgctac gtattgaaaa tattgcgctt ttttgcttta 29760
gaaatagaaa gaggtatctt aaaaataaaa ggctttcacc ccgaatgggc tcatactact 29820
tatgtgctgg cacgtatgat gttatgggta ttagctttgg taataatgtt ccctcacctc 29880
cctggttccg atagtgatgc ctttaaagga atctctgtct tcttaggggt attgatttct 29940
ttaggatctt cttctgccat ttctaatgcc attgcaggca ttgtaattag ttatatgcgc 30000
ccatttcaag taggtgattg gattaaatct ggagaaatta taggagctgt gatagaaaaa 30060
aacgccttag taacaagatt gaaaactatt aataacgaag atattaccat ccctaattcg 30120
gctatcttga gcggtgcaac tatgaacttc acttctatag gcaaagaaat aggcttagcg 30180
ctaaatgtac aagtaaaagt acgctatgat tattctgata atttagtgga agaactcctt 30240
atagaagctg ctctgaaaac caatggtatt tctcctaaac cacatcttta catttttcaa 30300
atttctctta atgaactaaa tgctatttat gagctcaatg cttatacttt ccaccccgaa 30360
aatatgtatt ttataaaatc agacctaact aaaaatatcc aaagtacttt taggcaagct 30420
aatgtggaga tattctcaac acaatacgta gaaattaaaa ctcccttttc aaatactaaa 30480
aaacaaaatt cataatgaag caacgactga tatttattga tgtaatacgc gcttatgcca 30540
tttgtatgat gttacaaggg cactttatca ctgccttact cgctgaacaa tattgcgacg 30600
aaaataatcc ttactatcat atttggcatt attttacagg tattacagcc cctgtattcc 30660
ttactatttc tggatttatt tttacctatt tactcattcg tgaaggcgaa cgcagtggtg 30720
taggacttaa gaaccctcgt gtaaaaaaag gtgcaaaacg cggattaatg cttatagcag 30780
tagcgtgtat tttgcggaaa agcatctatt tcgtagatat cttgcattgt atagggttag 30840
ccctcatcat aatggtagga ctctacttat tagctcgaaa tcacgtgagg catttccttc 30900
ctacaatgct catcagcatt actttactac ttttcacctt caacgagacc tataaccaat 30960
atgaatactc ttggttaccc caagtggtag ctaattactt tactccaaaa tacggtactt 31020
tctttactat ttttccttgg ttaggttttg taaccttagg aggctttatg ggatcgttat 31080
tttactatta cagaaacgcc aaacatttat atacagtata tacactacta cttattggca 31140
tcggagctat ttttcacttt caatatcaca ctttccattt cctatatagc attactggtt 31200
ggaatcactt tgaaagttta gcacgaaatg gttttctttt cttgagaatg ggcgatactc 31260
tctggacgtt tgcagtattt gtaatcttgc gaaatatact tactgcgcaa ttcttgcaac 31320
gtatcgggca aaatactctt tccatttaca tcattcatag tattgcgctt tatcacttta 31380

-continued ttccatattt caacttagac cattattttc ataagagctt caaccctacc caagcagtaa 31440
taggtgctat tctctttgtg ataactgtgc tcattgtatc gttctactat cacaaattta 31500
gtaaatacat aaaagaaaaa tattctaaaa acaactgata gaaaaattaa aagctttctt 31560
acataaataa cttaaaacta aatacaaatg aaaaaacttt acattttatt attcacaaca 31620
ttcttattag cttgcaatag caaagaacaa gctcaagaac atcccgttgc ccctcctaat 31680
agcaatatta cagtaccaaa agcactacaa aattattaca aaggaattct ttttactaaa 31740
aatggaaaag ctttgtacga tgatttagca gtacttacca tcagcaaaca tactaatttc 31800
ttaagttatt atgatcgtca taagtacctc tacaaagccg acgctagcct taaaaatcct 31860
gaatatgtag tattggtcta caccggcgaa gagcgctatt ggaaagaata taagagtggt 31920
aataataatt ataaacctca aactttcaac accgaacata tttttcctca atcaaaatat 31980
agtaatggag atgccaaagg tgatttacat catctaaaag cttgtgatag taaacttaat 32040
agcagtagag gaaatatacc ttttaccaat ggatccggaa gagctggacg tatcaatagc 32100
gcttggtatc ctggcgatga gtggaaaggt gatgtcgctc gaatgattat gtatatcaat 32160
ttgcgctata acgataaaat cgataataaa attgtaatag gaggtatcga aacactttta 32220
aaatggaatg atgacgatcc tgtttccgac ctcgaacgcc aacgcaacaa tgtaattgaa 32280
caagcccaag gcaaccgcaa tccgtttatc gattttcctc aattagcacg cgctgcttac 32340
aaaaattacc aagagtaata ctatggaaaa tgaacctcta tacacactaa aaaaatattg 32400
gggatacgat aattttcgca actctcaaga agccgtgatc aaatcggttt tagaaggtaa 32460
tgatacctta gccttattgc ctacaggtgg aggaaaatct attacttttc aagtacccgc 32520
tatgatgcgc aaaggtatat gtatagtggt ctctccattg atagctctga tgaccgacca 32580
agttgaagcg cttaaaaaca gagaaatacg tgcattatca ttagccggtg gcctctccta 32640
ccccgagtta gaacgcctgc taaacaacgc tctctatggg caatacaaat tcttatacct 32700
ttctcctgaa cgtctgcaac aggaagtcgt gcgtaattac ctcaaagtaa tgcctatcaa 32760
tctaatagtg atagatgaag ctcattgcgt atcgctctgg ggcaaggatt tccgccctgc 32820
ttatttacag tgtaaatggc tcaaagaaca attccctaat ataccttttat tagctctcac 32880 cgcttctgct acccctcaag tacaacaaga tattttacat caattaggca tcgaaaaagc 32940
aaatgtaatt agtacttctt tagctcgccc taatatagcc tacaaagtat ataaagtaaa 33000
aagcaaattt caccaccttt tgcaactgct aagaacaacc gaaggtacag ctattatata 33060
tttgcgaagt agaaatggtt gtgtacaatt ggcgcgttta ttagaaaacc acaatatttc 33120
agctacttat tttcacggcg ggatccccgc tgaagaaaaa aataacaaac tgagtatgtg 33180
gttgctaaac gacgtacgtg taatggtagc tacaaacgcc tttggtatgg gaatcgacaa 33240
acccgatgtc cgctgggtga ttcattggga tatccctcaa accttagaag attatttcca 33300
agaagcaggt agagcaggta gagatggtaa ccccgccgag gccatcgttt tctacaatga 33360
ggtagatata aaaaatgccg aaaaacttct aaatgaatat cttatagaca ttccttatct 33420
aaaaatcgtt tacagtaaac tcaatagcta cttccaaata gccataggag aaggtaccga 33480
aaatacctat agcttcctat tccccgattt ttgtaaacgc tacaacttat tgcctttaaa 33540
aacttataac gctttacaag tattagatag attttctatc atttccttca accaccattt 33600
ctacaacaaa gttactttcc aaatgaaagc tacccccgaa caattagtga agtatataac 33660
tactcatcgg tatatcaaaa acattactat ttatcttatg aggtgctacg aactgatatt 33720

-continued

```
tcacttccca gtagagttag aaatggctaa attgatggaa cgtaccgaaa aatctcacaa  33780
agaaattatg gggtatttag aaactctgca caacgatgga ataggtgttt taaaatgtga  33840
aactgccgat atacaaatca ttttcaacgt gcctcgcgac gatgatcgca caatcaatag  33900
cattggcaaa cacatcaaag agtataacca ctccaaacga ttattgcaaa acaaagtata  33960
tcaatacttg gaagatgaaa atacttgccg aagtatattc ttattagagt attttggcga  34020
gaaaaatgcg aaaccttgtg gtatatgttc taattgtgtt actcaaatgc actcccctaa  34080
aaccaataaa caaaaaatag aggctgatat ccttcaatta ttatcttcta aatcttttaa  34140
ttgcaacgat ttaataaata cactacccta ctctgttcag cagattaaca ctgtcttaga  34200
cgaacttttt gcaatgaaaa aaataacgtt caacattttt aatgaattgt gcttaaaata  34260
aaatattttt aataagattt tgttttatca tatttattta ctaattttgc cgtgttttat  34320
ccatattatt tggttttaat acaaaagaag atttttacta tgaacgataa cttttcacca  34380
agagttaaaa gaatatttac atatagcaaa gaagaagcag tacgtttagg gcaatctact  34440
gtgggcactg agcatttcat attagcaata cttcaagaaa atgaaggtag tgctatcaat  34500
ttgttacaca acttaaatat cgatatggaa agacttaggc aaaacatcca tacccttact  34560
tcagcgcgcg gtctcaatcc tcctaatttt aacgctgttc actttaccgt gcaagccgaa  34620
agagcaatgc aagctacata tttagaagct aaaagaatgc aatctgatgt gataaatacc  34680
gctcatttac tattgagtat tttacgcaac gaaaatgacc ctactacaaa agttttcaat  34740
aaattaggcc taaactacga aacagcacgc gacagctttc aacctataga ggacaataat  34800
tcaaaacttg ttactcccac aatgcctact aatgaggttg atgaatacga tagagactat  34860
cgcttgcccc acgaaagtag aaacaataga aatctacaag ggcaaggaca gtacaatcaa  34920
cgaaaaaata cagtattaga taatttcggt agagacctaa ccacacttgc tgaacaagga  34980
caattagacc ctgtcgtagg gcgagataaa gaaatagaac gcgtatctca aatattgagc  35040
cgccgcaaaa aaaacaaccc tatcctcatc ggtgaacctg gcgtaggaaa aagtgctatc  35100
gctgaagggt tagctttgcg catcgtacaa agaaaagtgg cacgcatatt gtataacaaa  35160
cgtgttgtaa ctctcgattt agcctcttta gtagctggta caaaataccg aggtcagttt  35220
gaagaacgcc tcaaagcaat aatgaatgaa ctcgaaaaaa atagagacat cattcttttt  35280
atagacgaaa tccacacctt agtgggcgct ggaggagctt caggaagttt agatgcctct  35340
aatatgttca aacctgcctt ggcaagaggc gaaatacaat gtattggagc tactacctta  35400
gacgaatacc gacagtctat cgaaaaagat ggcgctttag aacgccgatt ccaaaaagta  35460
ttagtagaac ctaccagtgt agacgaaacc attcagattc ttcaaaatat caaagctaaa  35520
tacgaagaac accacaatgt aatttatacc gaagatgcta tcgaagcttg cgtaaagctt  35580
accaatcgct atctcaccga tcgctattta cctgataaag ctcttgatgc cttagacgaa  35640
gccggagcgc gaatacatat tatgcaggta aaagtacctc aatatatttt agacgtagaa  35700
gaacgattag aacaagctac acaagccaaa aatagagccg tttctcgtca acagtttgaa  35760
gaagctgcac gccttcgcga taacgaaaaa cacatcgaaa aatcattaat agatctcaac  35820
aaacgatggg acgaggattc taaactacac cgagacactg taactgccga acatatcgcc  35880
gatgtcgttt ctatgatgag tggcatcccc gtgaatagaa tcgctcaaac tgaaattaac  35940
aaactctctg gcttatctga cgctatgaaa tctaaaatca taggacaaga cgaagctata  36000
gaaaaagtcg taaaatctat taaacgcaat cgcacaggtc tcaaagatcc taataaacct  36060
ataggttcct ttattttctt aggacaaaca ggtgttggaa aaactcaact tgccaaagtt  36120
```

```
ctctccaaag aactttttga ctctgaagat gctatggtgc gtatcgatat gagtgagtat  36180
atggaaaaat tctctatctc tcgactcata ggagcacctc caggatatat cggatatgaa  36240
gaaggtggac aacttaccga aaaaatacgc cgcaaacctt actctgtagt actcttagac  36300
gaaatcgaga aagctcaccc cgatgttttc aatatgcttt tgcaagtgtt agacgatggc  36360
ttcctaaccg atagcttagg acgaaaaatc gactttagaa ataccatcat cattatgaca  36420
tctaacatag gcgcccgcca agtaaaagaa ttcggacaag gtgtcggttt tggtacttct  36480
gcacgattgg ctcaatctga ggctaatgaa aaatcaatcg ttgaaaatgc cttgaaaaaa  36540
gtatttgcac ccgagttcct caatcgtatc gacgatgtca tcactttcaa ccctctcagt  36600
aaagaagaca tcttcaaaat tattgatatt gaactctcta aactttattc tcgtatcaac  36660
gatttaggtt accacgtaga actgagtgaa aaagctaaaa actttatagc cgataaaggt  36720
tacgacaaac agtatggagc acgccctcta aaacgcgcta tacaaaaata tattgaagac  36780
cccttggctg aagaaatcgt atctaaccaa atacacgcag gtgacagcat catattcgat  36840
ttagatgaaa aaggtgaaaa cctccttatt actgaaaaga acactaattt aataacttta  36900
taacccctta tttatgtaca ttttaagact tttaggacta tttacactac tattttgctt  36960
ttcttctttt acagaaagca tacaaaaaaa tgaaaagagt actactgtga aagtaagcgc  37020
tgagaatact ctgatagcaa gtaaaaaacc taaaaagaaa acttatagtc ctcctaaaaa  37080
aggaaaaact aaggtagtag cctctactgc taaaggtaaa aaaacacctc ctaaacatag  37140
ggtagcaagc catagtgcta aaaagaaagc cgtagcaaaa aacagaagag cagtagccgc  37200
taaaagaaaa actcctgtaa gaggacgtgc agtagcttcg agaagtaaga ggtatactcc  37260
taaaaaaata agccaacaat acgctgaaaa tatagctatt actgaagaaa atttagatga  37320
tgatttagat gaagaagaac tccttgatga agaagaaatc gtagataata ctgatatcgc  37380
tcttcctgct ctatcaaaaa gtaaagttga tactaaacaa caaaaaaatat tgctcgacac  37440
tgctttttct tacttaggaa ctccttaccg ccacggagga gtctctcgta aaggaatgga  37500
ctgttctggc tttgtaagta ctactttcaa atctatcgct gtacctctct ctcgttcttc  37560
acaagaaatg gctacccaag gacggaaaat acgcttagaa aatgtacaag taggtgattt  37620
attattcttc aaaactactc gccgaaatag aatttctcac gttggtatgg tagtagatgt  37680
agatggtgat gtgaagttca ttcattcttc ctctaaaaga ggggtcgtaa tatcttcatt  37740
aagtgatgct tattacaaaa aagcctttcg tatggcaaaa cgtgtgatgt gagattcgta  37800
aatattccca tattaactat attatttgga ctcataggag ggattgctat taccgatata  37860
atagctccct ctttttgtt tgttataagc agtagtctgt gtttgttagc taccctaaca  37920
atacattacc tattagctac caagcgatat gcttttcgtc gcggaattat attccacata  37980
ggtctcactt ctgtagctgt aggtatgtta ataacgtacc ttcacactcc tacttataac  38040
cctaaacatt acacacaaaa actaaatacc aatgaatatt acaccttaga agccgaggta  38100
atagaaatca tttcacaaac caattatggt actactttta aagctaacct cttaacggca  38160
aaccacaaca ataccgaagg aaaaatcttg tgttttttcc cttctaaaac aattaccgat  38220
gatgtaaatg cattagctcc aaccgataga ttaattttta taggaaaata cacgccctta  38280
tctcccccta aaaatccata tcaatttaat tataaacgat atatggaacg aaaaggagta  38340
tttggttggg tagaagtaat agcgttttct attgttaaaa ataatacagt agattttatg  38400
ggagatattg aaaaaatgcg ttctcatcta actgctataa tcaatcaaaa tttcaatcgc  38460
```

```
gagtctgccg ctctcttaaa tacattactc ttaggaaaac gtagtgattt agatgaaaat  38520
atttatcaac aatatgtaga tgctggtgca gtacatattt tagctatttc gggcttgcac  38580
gtcggaatta tcacggctat acttctatta ctactacaaa aaatgcctaa tttgagattt  38640
tatcgcccat tgcgatactt catcttgtta gcaggattgt ggacttttgc tttaatggct  38700
ggggcttctc cttctgtatt gagagcaact ataatgttta gttttgtagg gttgggtacc  38760
cttatacgcc gaaaacaagg gagattcgat gctttaatgc tctcaatgtt atttttgttg  38820
cttatcaatc cttattattt atatgatgta ggcttccagt tgagttatgc agctgtattt  38880
tctataatga aattctaccc tgtaatgcgc aaatggtggc aacctgaaaa taaatacatc  38940
cgatggattt ggtctttatt tttagtagga ttatctgctc aaatagttgt tttgcccatc  39000
agtttgtact attttcatca atttcctatt ttgttctttg ttgctaactt ggtagtagtg  39060
cctttgttac aacctatact tataggaggt atcattgctc tatgttgggg aagtttaggt  39120
attttgcctt accctataat ttttatctta gaaaaattaa taactctgat gaacatttta  39180
gtagctttta tcgcacatca agaaatgttt atcatacgca atatacottt cacaactccc  39240
ctacttcttt cttctttagt aatagtactg atactcatca tctttgtaca ttataggaaa  39300
tataaagtat tggtagctct tctcgtttct gtacttttgt ttcagggagt acttttctat  39360
cacaaatacc aattggaaac taccgaagaa atgttagtat ttagcaagta taaagataag  39420
ataatcacta ttaggcaagg taataagctg agtatctatc aggtcgatac aacttctatc  39480
aacccaatga taaacaacta cattaaaaac aaaggcatta gtgatattac actttacaaa  39540
atgccctata tattgcgctt caaacaaaaa aactacttac taatggatag tttaggagta  39600
tacccaaaat ccaagcaagt agttattgat agtgttatct tcttacaaaa acctaaaatc  39660
aatttagata gaatgaagcg tgatttatcg cttaggtagt aaggaaagaa taatatacaa  39720
taaaatgatt ataggaatag caatcatttt taaacttaca agtagaataa cacaaagtgc  39780
taaaaataca tacttcaatg cattattctt aaatgaataa tcactgaact tcaatgcaaa  39840
gagggctatt tcagcattca gtaaatatgc actcaacaat gtaattccta ataaaaccca  39900
actattatgc aataaactat caaatagttc agttgattgg tattgcatta taagcggtag  39960
agaaaggata aacattgtat tagctggagt aggaagccct ataaaaccag aagtttgccg  40020
cgtatctata ttaaaattcg ccaatcgata ggctgatgcc aaagtgataa gaaaacctat  40080
ataaggtaag taggctaccc aagttgttgg attttctact acgtaactac tttggttaaa  40140
caactgaaac atcgcaacac ctggtactac tcctgaggta accatatcag ctaaagaatc  40200
taactgtaac cccatttctg atttcacgtg tagcaaacgg gcaaaaaaac catcaaaaaa  40260
atcgaggaaa atacctatcg ctacaaagag agcagcccaa tcaagtgccc ctctcacggc  40320
aaaaacaatc gctacagttc cgcaaaagag gtttcctaaa gtaattaaat tagggatatg  40380
ctttttcatt ttacttacaa tcggcatcta aataatctgg aagatatgat tggtctttct  40440
tctcatcgca atcaggataa gtaaccactc catagttatc acgtacgatt tcatctttag  40500
aaggtttgcc atcgtgatcg tgatcagcgt gacgagcagc aataagtctt actgtaaaaa  40560
ttaaaggtga ataagctggt atttttgcct gactattatt gaagtagcct aaacctgatg  40620
gaatgaagaa cacccctacc cctccatcgg taggagcggt aagtgtacca tctgaatttt  40680
gtgtgagttt ggtcactgaa ggctttaact gagcaactcc ctctctaaat cctctgatag  40740
tacctgaagg acgattggta acaatatttc ccagtaaatc catccaatta gatgctgatt  40800
gagtagtagt ctcatcaaat actgtcaagt tgagtaactg acctttatag tttacatata  40860
```

-continued ccgagtcggc aatagaagtg gtatgggtac tagtaccttc ttgtaatatc atatagtaca 40920
aagtatgacg aatgcgattg ttattggcat caaatacatc caattccatt ttcttcaaat 40980
tactattgtt aaaaatggat tgtgaaacat tagttgtact tgtaaaagta acagcatccg 41040
aaatagctgc cgtagctgaa tatgtgtaag tatgtgtttt taagaatgtt tcaatagctt 41100
gattattttc attcctcact tctgtaacat ctcttggtgg tgttacatta gaactatcgt 41160
ttttcttaca acctgtagtt aatagtaaag ctattacact gatgctaaat agaattttgt 41220
ttatcatata aaatattgtc ttatttttgg ggcgcaagat acaaattatt tcttactttt 41280
gcacctcatt gttattttta aaattataaa agaatgcgaa ttgataaata tttatggtgt 41340
gtacgttact tcaaaacacg taatattgct actgaagctt gtaaaaaagg tcacatcaaa 41400
gtaaatggcg aaacagtaaa accttcacgt gagatttata aaaacgacca aatagtagtg 41460
cgtaaaaacc aaatcaacta ccaattagag gttttagaca tccccgaaag ccgtgtgggg 41520
gctaagttag tagaccttta tcgtcaagat aacactcctc ctgaagcttt tgagcaagcc 41580
gaaatacaaa aactcgctca ggactattac cgcgaaaaag gagaaggtcg ccctactaaa 41640
aaagatcgcc gtgctattga taatctctta aatgattttc aagaagatga cgattgaaat 41700
tcactttgtc aaagtcctaa aactttgaca aagtgaaaaa tataatacta caacaatgta 41760
gggtattttg caggattaac ttcgtgcatt atactgtata tcttctcaat gatgctatcg 41820
acattaggtt tagagaaata atcaccatca gttgcataag caggacggtg gttacctgcc 41880
gccaaggttt gtggtgcact atctaaatac tgataagcat tttgttcttc caaaattttc 41940
tgtaaaatat atgccgaagt agccccaggc atatcttcat caactactaa tagtctattg 42000
gttttctgta tgctcttcac tatatcgtga cgtacatcaa atggcgctaa tgattgtaca 42060
tcaataattt caatatcaat acccaaggca gccaattcat cagcaacctc acacacgata 42120
cgcaaagtag acccgtaaga tactacagta atatcttttc cttcacgaag tgtttctact 42180
acccctatag gagtcttaaa ctcagtgaga ttactaggca acgcttcttt caagcgataa 42240
ccattgaggc attccaccac tacagctggt tgattaccct ccaagagtgt attgtagaac 42300
cccgctgctt tcaccatatt acgtggggtg agaatgtaca tccctcttaa agaagctaac 42360
aatacaccca taggtgaacc cgcgtgccaa ataccttgta aacgatgccc tctcgttctg 42420
ataataagag gtgccatttg cttaccaaaa gtgcgatagt gcagactggc taaatcatca 42480
cttagtgttt gtaatccata aagcccgtca tgctgggctt cggcatctcc acgcctgagc 42540
aggtctccga ggccatcgcc gcgggcgccg acggcgcgat cagcggctca gccacggtca 42600
agatcgttga gcgctacgcc cccgagatcg tggccaccgc ctccgccagc agcgacggga 42660
ccggcaatga ggagcggcgc cactacgcgc tcggggcgct gcgcagcgat ctcgtcgcct 42720
tcaccgccac catgaaggag gccacgcgtc agcactgacg gccgacatca gcaggccgtc 42780
cgggacagca gagggtc 42797

<210> SEQ ID NO 4
<211> LENGTH: 28023
<212> TYPE: DNA
<213> ORGANISM: Streptococcus species

<400> SEQUENCE: 4
tgccatttat aattttcata atagggataa agagaaagcc ttagatccta agcattctcg 60
tgttgtatat cttcctcaat ggggaatacc ttctgagcaa acacgcacga gacctaagga 120

-continued

```
ttataaagaa tcttatcctg aaaaattagc tttggaagaa caagggggca ttattagttg    180
ttggacatat tacaaccata ttgtgaaatg gctcaactct tgtgtagaag ctatgggaag    240
agaaaacaat attgttaagc aactcgttaa aaactatata gaatattgga atagtacaaa    300
ctctaaaaat acttattata tgaatgcatt agaagaagaa ttaaaaacta aagaaaattg    360
gctgattatg ggagaagccg ccaatacaat gaataatcta agaacccgat gggcggaaga    420
ttttagcaat caattagctt ccatagaatg tcattctgat tttcctata acaaagattg    480
tgatgaggcc aactattaca atgattttcg ttggacttat ggaggagcat ggggagatat    540
agcctttatc tatgaaccac acaaagggct ttccatttgg aaagcaggag cgggaaaagc    600
cagagaacgg tataaagaaa gatttgagca tatattccct gattttatga tcagccaaga    660
tagtaatagc aactatttaa tgcatctaaa agatcaaaat gaaattatct tatgtgattc    720
aagagataaa gacgatgtct ttctttggga ataccatgac aaaggaggaa aagtgcgtaa    780
gtttattact gaaaagatca gaaaatatac taatgatcaa gaagttcgaa acttacttaa    840
agaaataaac gattggaaat ttgaaaaaga gcttcaaaac atcgtagtag gggagaattt    900
taaagttgaa aagtataaca catatattga ttttcggtgg ggactaaaaa atagtgattt    960
agataaggat ttagtttttt tatactaccc ttacaataag aaaggttttt gtctttggaa   1020
aaggaatttt ggaaataaaa aagaacaata caaatccctt tttgctgaat ctttctcaga   1080
agactttgaa tgggttgaag ataatacaga ctatattatg aggttaaaag gtaatgcatt   1140
ttctgctatt gggaatgaag aagaaggttt ttcaaaatat gaagcggttg aaaaacttac   1200
tgaaatactt cagaaatata caaacaaacc agaaatagtt gagtttttta aaaaaataaa   1260
tgaagcctcc gaacaataaa actacaaaat ctccccactc ctaagaaaag tggggatatt   1320
tttgcagaaa aatattacgc atggtcgtag tttgtccatt tgcgtatata tctttgccgc   1380
gtggaagaaa gaattaacaa ttaataatta tgcagttgta tttagatgac ttgcgcccta   1440
ctccagaggg ttttgatcgt gtatatagtt acgaggagtt tgtggcctat cttgagagaa   1500
agggcttgcc tgattttatt tcctttgacc acgacttagg ggaagacttc tcgggttatg   1560
actgtgctaa atacttagta gagtactgct tagcgcacca gctctccctg cctgactatc   1620
aagtgcatag ccaaaaccct gtaggtaagg agaatataga acgcttgttg gagaacttta   1680
gaagttttga gggttgattt aaggccatac caagcaaaaa aattaacaat taactacatt   1740
taattaacaa tatatacaaa taattaacgt ttgtctggtc gtagtttgtc ctgttgtgat   1800
ggtatctttg cagcggaaaa ataaatatta cttcttatga ttttagataa ctttactgac   1860
aaacaaaaca tagcttatgc tgatatactt gaagctatga tttgccaaaa tacccgtgag   1920
gaaaaggatt ttgatgagca agagagactt tctgaaagac ggttatacaa tggtaaaaga   1980
attattttca gagagatata tgattataag cgtaattatg tacataaaaa actatatcct   2040
tatggacagg aaatagtaca ccttatttat cctatctata cagaacaggc acaaagagaa   2100
ctctatctgc ccatcaagga acgaatattg gctttaggtt ttcagcccga agctattaca   2160
aagataaccg tacgcttgaa aaactacaat gaaaaagggc agaaactaca agaaacctac   2220
aattggtgta agggattttt tgctgaaaga ggaagtatgg ggattgataa tatccgctat   2280
gatgataggc aaaatatcta ttccagtgaa ggatttaatg cttattggaa cgagaaacga   2340
aacatactgc gtaccattga tttaaatgga aaaaccctta ttgaacaaag ttcttgggac   2400
gcagatgcgt tcaatacagt ggaggtctat cattatgatg atgataaaaa tcttgtacaa   2460
aaaattatca gtaatagaga tggaatcagt aatattataa actattctaa gggaaaaagt   2520
```

-continued

```
agagtgagaa tagtgaaact caatcctaaa aaaccttcta aatacataga agaaggatac   2580
acccaaacta taaaaaaagg agcttatacc tacaaagtag aaagatatta ttatggggat   2640
agtacagatc tgagaaaaag tcttatcgta ttggataacg aagatagaat cgtaagagag   2700
aaaaagacaa actatatcac caaacataag aaaaacaaag aagggaagca aacctttcga   2760
aatatcaaaa cagacgagca tattagtaga tattattata atgagcaagg cgtacttaca   2820
aaggaaatac accttagcac agaccgctct gtagaacttg aagtattgct ttacaattca   2880
caagaacaga aaacagtacg tatttatagg agtaaagacc tcaagcaaga agtcaagtgc   2940
ttagaaaaaa ctgtttatac ctatgatgat aagggaagac ttttattaga aagttctcct   3000
actcacctta cccatcattt ttatacctta gcagaagact atgatgagca tttggaaatc   3060
actataaaaa ccgaattata aaatacttaa ttatgacctt agcttatttt tcagaaaagc   3120
acaaaatagc ctttgccgat gcttttgagg cgatgacttg tggtatgcct agtttcgatt   3180
tcgaagagcc tgctttggaa gagaagaatt ttgacgaaaa tggacgccta ttagaaagac   3240
gctttgtaca ctatgggaga cccagattag tagaacatta tgactatgaa aaaggtatcg   3300
tacataagtc attctatgaa tttggtcgtg agattctgga atttagtttg cctttataca   3360
gtgagcagga attgagagct aaacatatcc ctattaaaga acgagtacaa aacttaggtt   3420
ttacacctga gcaagtgaca gaaattaacc ttaatataaa aagtacagac aaaattggag   3480
gtatacagca agaaactata catggttgcg aggggcattt taaaaaagcg tataggacga   3540
atatagaaaa aagcgcttat gatgaaaaag gtaatatata tgctatagaa gaatatgtat   3600
cttcttgggg agagcaacgt attgagagcc gtacttttga tgtccaaggt aatctgatct   3660
ttcaaggaca ttcttgggaa gaagatactt tacgctctat aaaagtatca ctatataaca   3720
gtaaaagccg agtgatacaa catatagata taggctttaa tggtagtata acacattaca   3780
cctccaaaaa aaatgaggtg atttgcaatg aaataggtcc actttcatat atagaaagcc   3840
acaaaattat agaaaaaata ggtaataaca catgtgaaac gattcgtacg gaaagtgttt   3900
taaagaataa tgagacgatc agtatcctcg atcctaaagg tagactctta aagaaaacag   3960
agattgatta tgaaaatgaa aaaaaagaat gtgaaaggga agaagaatac acttataacg   4020
aattaggagt actcataaag aaaatggaaa actatgtcta ccatggttcg tttttgtgtg   4080
ctcgtattta tggctctgaa accattctct acaatggtca aggtcaaaag atagagcata   4140
gtaaaaaaga tgtacgtgaa agggatataa tatctttaga tcctattata atcgaagatt   4200
caattatctt agaaaaaatct ctttattatt acaatgagca aggtgacctt attcgtgagg   4260
aactgaaaaa atggcgtgct gatgagggta ttgaaaccga tgttgaacac tttactacct   4320
atcattttta cgttaaagat gatgaatacg aagaacattt aaaagttact gtaaaagaaa   4380
atctttaaac atcatttaaa tcaaaatcaa tcctttgtat ttacaactaa aaaattaaaa   4440
attaacctaa cagtagtaat ccaaaaaaat actaatttgc aaattttcta attatctggt   4500
catagtttga ccaaccctta ctgtatcttt gccacaaaaa ataaaaatac acccaaagaa   4560
tatgacatta gataacttta ctcctatcca aaaacttatt tttgtagatg cttttatgac   4620
aatcatttgt aatagttact atcaagaaga aaaagacttt gatagtgaag gtcgccttag   4680
cgaacggcgt tttgtatatc ctgatggcag cctaaaagta cgtgaagctt acgactacaa   4740
gcgatcacgc gtaacaaagt ttttctttga aaataaagaa gaacttcttc gccttacggt   4800
gcctctctat accaatgatg agcagcgtac tatgttcacc cctctcaaag aaagggtaca   4860
```

-continued

```
gcaattaggt ttttcattag agaatattga aagactgtct ctttctcaac agtgtaacga   4920
ccctaaaaac ctcactgaac aaaaagtttt gatagataaa tcttcaaatt atagagaatc   4980
ctttgatatt gaaaatgtca cttatgacat ggaagggagg gtaaattggc gagaaaaata   5040
tgattcctat tacccagaaa aaagtaaagg gcgttatgtt tttgagcgtg atgaaaaaaa   5100
aataatggaa aaaatatttt atgatatatg tgatccttca gtaaagtttt ttagttatga   5160
cgaggaagat aggctagtac aaaaaggaaa tttgtactac gaatattacc acaagaacaa   5220
agctaattgt atcaagatgt gtcctgaaaa acctagaaaa tacagtgaaa taggttactt   5280
gcatactcaa aagaaaggta ctcttactga aaccaccgaa tgtcttactg aatttgggaa   5340
aaccgaaaaa atagtttcta cttttaacca aaaccatcag ttagttagaa aagtagatat   5400
tacctattgc aattacggca aaaacaaaaa ggaatacaga cctcgcaaga aagatattat   5460
tagcaaaact atagaacaga acatctataa ccctgagggc ttattagtaa aacgagaata   5520
tatttctttt gatgatgata tatctaaaat agatagttat agtgttgaat cttttggata   5580
caatgagcaa ggacaaaagg tagaatacaa taagaaaagt gaatataaaa attgtttgga   5640
ggctatagga gaacgcccta acctaaaaat tgaatataaa gacaaaatat tcttagagcg   5700
taccctttat tattacgatt cagaaggaaa cctcactcgt gaggaactga aaaaatggcg   5760
tgctgatgag ggttctgaaa ctgaagttaa ataccttact actcatcgtt tttacgttaa   5820
agatgatgaa tatgaagaac atttagtagt tactgtaaga aaatgataac cttagacaac   5880
tttaccgata cccagaaact catctttgcg gatgcttttg agacgatgac ctgtggcaaa   5940
cccacttcta atcgtcaata tgcttctgaa gaagaaaaat attttgacag taagggtcgc   6000
cttagtgaac gctgttttgt atatcctgat aacaaaggtc tgaaattgcg tgaagtatac   6060
gactacgagc actcgtatat aaactgtttt ttctatgaag caggcgagga gattctcagt   6120
tttattctgc cattctacac tgatgaagaa aagcgtacta tgttcacacc cattaaggaa   6180
aggatattgc aattaggctt tccccctgag cagattgaga aaattgcatt ccaccaaaag   6240
tgcgatgaca gaaagagcct tacctcacaa gaagtttgga cgcattgtaa agggttcttt   6300
gtccaaggaa ataccactta tttaaaaagc tttacttatg acgaaaaggg aaaagaactt   6360
tttatagaag agtatgattc ttgttggggt gaaaaaagat ttagacgcta tactttcgac   6420
cacaatggca atacaattat ggagagaaac tcttgggtta ttgatgattg gccaactcta   6480
aaaacttcta tttatgatga taagaataga ctattggaag agagtggact acactatcaa   6540
tacaaccgag agaatgttac tttattaaca tttccaaccc ctcgaacttt tacctcagaa   6600
ggctatattc atactataaa aagagataat tacacagaaa ctactaagca ctactcggat   6660
ggaagtaagg tagaagaaac aatttctact ttcgaccata aaaaaggtt agtgaaaaaa    6720
gtaagacgta tctattataa agattgggag aaaattagaa aaggaaagta tgccttcaaa   6780
aaagtagaat gtcatgaatg gatagaagaa tacacctata atgaagcagg agtacttata   6840
gaggaagtga ttcactatgt tgattatgaa gattttttgt ctaatggttc ttataggaaa   6900
gaaactattc tctacaatga gcaaggacaa aaggtagaat acaacaagaa aagtcaatat   6960
aaaaatagtt tagagactat aggagaacgc cctaatctaa gaattgaata caaagacaaa   7020
atattcttag agcataccct ttactactat gactctgagg gaaatctcac tcgtgaggaa   7080
ctgaaaaaat ggcgtgctga tgagggggct gaaacagaag ttgaatatct tactatctat   7140
catttttatg ttaaagatga tgaatatgaa gaacatttgg aagttactgt gaaaaaattt   7200
cattagacag ccccttagatc aacaaaaaat agtatatttg taccttaatt tcatataaaa   7260
```

-continued

```
catgaacaca tttaccccag aattacagca atgggcagcc gaagtgatag agaaaatcac   7320
ccccatagct gaagaaattg acttagctta ctacccctta cagtcagaag ctaagatgaa   7380
tcctgaactt ttgattattg gattaaatcc tggatcacaa ggagagtata aagaacaaaa   7440
gacaaatgat aaatgggagt tcaaagatgg taagatgacc actgaacgct tattaaaggg   7500
taatcctttt attgctgaaa aagaggaatg gaaaatcttt agaggactaa acaggattcc   7560
atttatcaag caggcagtag ataccaatga ctactgcttt atgaattatg tgtattttgg   7620
aacttctgat ttcaataaga tcaaaggaca cgctaaagca gttgaaacct gtacagcact   7680
cactaaaaag tttattgaga ttatcaagcc taaacatatt atcgttttag ggttagaggg   7740
tatagaaagc atttctaaga ttgaaaaaac tttgctaaaa ggtaaaagca aacgtcttct   7800
tgtacaagga ggtgatttgt tcggcaaaca aatactgggt atttctcacc cctcttacgc   7860
cgtgtcagca gaagaatacg aggctataga taccaatata aaagagttct atgagggaaa   7920
acctctaact ccctttcctt tcaaatctaa tgtaacaact attgatgttg ataaacttaa   7980
taatctcttg gcgggatcgc ttaactttaa gttgcgtggc aaagatacac aagtatatga   8040
agcacaagta aaaggtgtag gtgatgatgt tttggatttt agaattgacc taagaaaacc   8100
acctgtttat ctttctttcc gttcattagg ataccctaaa gaattaaaaa acaaagaggt   8160
gtataaaaat acctttaaag aaccttttag tcttgaggta aatgcttggt ttgtagaaaa   8220
attcttaaac aactaccctc aggaacaagc tattgagcaa gaaatggctg atgacctcct   8280
atccttatta aaggcgatta aagcacaaca ataattgcct ttgagttctt ttacaaactg   8340
tctaaaaaaa tcttttgggc agtttgtctg tttttatctt ttttaaggat agtcagccac   8400
ataattcgca gataatttta atcttatatg gagtataaac acttttctcc cgaccaaggt   8460
gcaattatat tcactggtat aaaatgctat ctttctatgg ctaatagtac cgtagaagaa   8520
gattttgaca gtaatggaga tctcttagaa cgtcgttatt actatccaga tacagggtat   8580
cttgccctaa gagaaacggt ctttcctgag agaaacgcca tctatttatt ctattacgga   8640
tatagcttgg gacaatgtat gtactttacc ctcccctacg atgaacattt tgataggtta   8700
aactataaaa cagaagatta accccctaaaa ctcctcttca aagaggaaac taactcctaa   8760
accctaacac cttcatgaaa atacaatact tttccgactt acatcttgag tttgaggaca   8820
atctcaactg gattgacaac aatgctatag agcgcgtagg cgatatcctg atcatcgcag   8880
gcgacttgtg tccctttgta cagctctctc gtgtactctt taagagcgag atagctgacc   8940
tatgcaaggg ctacaaaaaa gtattctgga ttcctggcaa ccacgagtac tatatcttta   9000
cacacaacta tgccactacc cgctatgagc agccgatgaa ggaaatcccc aatctctttt   9060
tggtagacaa ctataccgag cgtatcggcc gtacccaact gattctctgt acaatgtgga   9120
gccatatcgg gaggaagaat gctgccaaga ttaagtatgg tatgagtgac ttccactata   9180
tcactgtgca gaaccccgaa aaaggagagg aaatagactc cctacaagta gctgacttca   9240
acgctttcaa caaaacagcg gttaagtttc tcaaaacagc cgtcaaaaag gccacccaag   9300
ccaagaaagc aggtgagata gaccatattg tagtggctac ccactatgtc cctaccctca   9360
agtactaccc acaaatgtac ttgggcagcg tactgaacga tgcttttgtc cttgacctca   9420
ccgatttcat tgaaaagagt gccattgatt attggattta tgggcatcac cactttaatc   9480
aacccgattt cagaattggc aatacggttc tgactaccaa ccaactcggt tatgtgatgc   9540
gtgaagaaaa tgaaggcttc gagtggggac gatatataga agtaggggcg aaagacaatt   9600
```

-continued

```
cgcccataaa taacgaatag tgaataattt tctcctcttc cctctaaaat tttttcttag   9660
tcggtcgtag tttgtccaac tactatctta cctttgtacc cgtaatcaaa aattaaaaaa   9720
aatgaatacg gtaaaaacaa acattcttaa tggacagttc cccataggga cgcttatttt   9780
aggtataggc ggaggagggg ctaatttctt ggactatgtg caaaagaata gcctccagcc   9840
tatccgctta aaggaggaag ttggtaacta tggcatagac aaggtccttg ctgaagttga   9900
caaacgtata tgggaacact tattagaatc actaaccact aatcactaaa aatcatggca   9960
aaaacaatcc aaatagaacg tttagtacgt atagtaagtt tgcttacagc taataaaaag  10020
ggtctgtcag cacaaaaaat cagtgaaaaa ttgaaggaag agggaataaa cttcagtgat  10080
agaaccataa ggagagactt tgatgatata gaaagtgcct ttggtataga gattgtcttt  10140
aatgctaagg aaaaggtatg gacaatagat cctgaaaccc tctcagacca acaactgctc  10200
ttagaccacc tcctgcttat ggaggcctac cgaagggcaa aagatcagca tatcctcctt  10260
gtggaacccc aacccgaaag agggttggag atgcttgacc ctatccttac ggctattgac  10320
aaaaacctct tgattacttt ccactacaag gctttttact cggaagagac caccgaaaga  10380
caggtgttgg cttatgctgt aagggaatac caaggacgct ggtaccttat cgctacggac  10440
gacaaaccgc ctttcaagct caaggcattt gcctttgacc gtatgagcga cctaagagta  10500
acagagacaa aggtaaaacg ccaaaaattg gatatggaaa cgttctttga ccatttctat  10560
gggatctcca tggctgaagg cgaaccatgc caacagatac tcctttcttt caactatgag  10620
caaggacaat atgctaaaac actcaagcta cacccatcgc aagtagttgt ttctgaagac  10680
gataaagagg tgcgcgtaca gctaaccctt gctttttccc atggggaagc tccctacgac  10740
ttagttatgc gactttgctc ttttagtgat tcggtaaagg tactcgctcc cgcctcctta  10800
gcccagcagg ttaaagcgcg tcttaaggca gcatacaaac aatatactta gcaaattgga  10860
aaatttttcg tacatttgtc cctaataaaa tcatataatt atgagcttag aggacaaatg  10920
ggcttccttg gacaaaaaat tggacggaat tctccgcaac cagtcttata ttatccaaaa  10980
ggtcttacta atgcagagcc agttggagca gctttctaca gctgccccag ctaagggaga  11040
cgtacccaaa cctaaagagg tatttcaacc agtaacagac aaagagataa tcccacctat  11100
agaaaaagca ccagcgccaa aggtgcaaga gacaccagcg cccaaagagc aagagacacc  11160
ggcggcaaag acgcaagagg ttgtaacacc aaaggcgcaa gaggtcatag aaaaacctat  11220
ccaaaaggta gctatgcagg cgcctattac ccctcctaag gctgccgctt ctgcttctaa  11280
ggatacgaga gaacctgtga tagagtggtc taaactgatt aaaaaagagg attgggaacg  11340
cttcattggg ggtaatctct ttaataagat tgggattgcc attatcctta ttggggtgtt  11400
tataggggtg aagtactcca tagaccatga ccttatcagt cctaccatgc gtatcatctt  11460
gggttacctc acaggggctg ccctctttgg agtgggctat tacctaaagc ctaagtatga  11520
gaaattcagt gcggtgctcg tcagcggggc aatggcgatt ttctatttcc tgacctatgt  11580
ggcgtatgac ttttaccaga tgttccccac aggggtagct ttcgcactga tgttctttgt  11640
gacggttgcc acgatttggt ttgccctgag ctacagccaa cagattattg cgcttattgg  11700
tatggtaggg ggctatgcgg tgcctttctt gcttagcaat gggggcggac atgtatgggt  11760
actgctctcc tatgtggctt ttatcaatgt ggggatattg attatatcct tctataagca  11820
atggcgctgg ctctatcatt cggcctttgt ctttacttgg gcactttacc tgacccttca  11880
tgtgttcaaa tacaaggata accagggact ttatttctca ttcctattgg tgtattacct  11940
gatcttccat tttgccttca ttgtacgcaa gctctgggca aaggatactt ttaccatagg  12000
```

-continued ggatattctt attttgctat ctaatacctt gttattctat tcgttagggc tatcctttac 12060
ctttgaaaat gtatttgctc agacacgtga ttatctgacg gtattcactt tggccaatgc 12120
acttttccac ttcttggtgt attactatac ccgtagtcgg ggcgcttcca aggagctgaa 12180
gtacctaagt ctcatcttgg ccatttcttt tggaaccctt accataccta tctattttga 12240
aggggtttgg attactctct tctgggcaat ggaagcagga ggtctcttct gggtaggacg 12300
tgccaaaaaa atccgtatgt acgaggtgat ctcctatata gtactccctt tagcgacttt 12360
tagcctttgg actaattgga tagaaatgca agaacatatt gcctcaattc cagagaaggt 12420
aacagctttt ctcaatacta ccttccttaa ctcattgctt tatgtgggta tagtggcggg 12480
gatctcctat atcaataccc gttataggga aaaagcctca gaaaagtttg attatgggat 12540
caatatactc ctatttataa tgctatatgc cactttttat atagagatat ataattattg 12600
ggcgataagg ataaaccaat atgtagtaga agcagataca ggaatgaaag cctatgatag 12660
tttgcagtac tttaagcaaa tgtggcttat tgtctataca gtggcttact ttgcactctt 12720
tacatggata gatacgcgct atattcgcaa ggaaaaaatc ttgtttaaca acttggtttt 12780
caatcttgtt ataggaatga tcatgctcac acaaggcttg tatttgctta gcgaactcag 12840
agggctatac ctaagttata cccctggtat gatgtatgta atcatccgtt atatagctct 12900
attggctttt gctctgttgt tatggcagac gtacaagttg ctcgatgcag aggctatcaa 12960
cttcaaaaac aataaggtac gtgatttggt gctttatggg gttgttctat gggtggtaag 13020
tagcgaatgg ctacactgga cagaactttt gggtgctacg gctaattaca aattgggtct 13080
gagcatctta tgggtgtctt atggtgtgtt catgcttgtg aagggaatac atcagagcaa 13140
aagctatatg cgaatagcca gtatatctgt aattctcttt actttagtca agctattttt 13200
ctatgatata gcgcacctaa gcactatttc cagagtggtg gtattggtca tacttggtgt 13260
attgcttatg atcgcttcct tcctctatgt gaagtatgat aagaaaatac gtaataatga 13320
caagtgacca atgacaagtg accaatgaca agtgaccaat gacaagtgac caatgacaag 13380
tgactaatga ctaataccat aatgggattt gtcactaata acttgtcact aaaaaaagtg 13440
atttaactgc tggtaggttt gattttttt gtatctttgc acggaaattt atagaagtgt 13500
caataggtaa cttttataaa taaaggcaaa ataaagaata cattcataca taaaaataat 13560
ggcacaaata aaggcggctg aagtttcagc gattcttaag aaacaattag caaacttcga 13620
tgcgtcggta tctttagaag aggtagggac ggtattagaa gtaggagatg ggattgctcg 13680
cattttcggt ctctccaaag tggaaaacgg agagcttgtc catttcgaat caggacaaga 13740
aggaatggtg cttaaccttg aagaagatca cgtaggggtg gtactccttg gttcttctac 13800
ccaaataaaa gaaggggaca ccgtaaaacg taccaaaacc atcgcctcta tcaaagtagg 13860
ggaggggatc gtaggacgtg taatcaatac cttaggtgaa cctattgacg gtaaaggccc 13920
tatcttaggc gaactttacg aaatgccttt cgagcgtaag gcgccagggg taatctatcg 13980
ccaacccgta aatgaacctt tgcaaacagg gattaaggct attgatgcta tgattcctat 14040
cggacgcggt cagcgagagc ttgtaatcgg ggacagacag acaggtaaaa ctaccgtatg 14100
tatcgatacc atcctcaacc aaaaagagtt ctacgatgca ggtaatccag tgtattgtat 14160
ctatgtagcc attggtcaaa aagcctctac tgtagcaggg atcgctaaaa ccttggaaga 14220
tgcaggagca cttgcctata ctactatcgt agcggccaat gcttctgacc cagcaccaat 14280
gcaggtatat gctccttttg caggggtagc catagggggaa tacttccgtg atacaggtcg 14340

-continued

```
cccagcgctt attatctatg atgacctttc caagcaagcc atggcttacc gtgaggtatc  14400
cctcttgctt cgtcgcccgc ctggacgtga agcctaccct ggggacgtgt tctacttgca  14460
ctctcgcctc ttggaacgcg ctgctaaggt gattaaggac gacaatgtag cccgcaatat  14520
gaatgacctc cctgattcta tcaaacatct tgtaaagggt ggtggttctc ttaccgcact  14580
tcctgtgata gaaactcaag ctggtgacgt ttccgcttat atcccaacca acgtgatttc  14640
tatcaccgac ggacagatct tcctcgaatc agacctattc aactctgggg tgcgtccagc  14700
aatcaacgtg ggtatctctg tatcccgtgt gggaggttcc gctcagatca agtctatgaa  14760
gaaggtggca ggtaccctta agcttgacca agcacagttc cgcgaattgg cggcttttgc  14820
taagttcggt tctgaccttg atgcagctac cagcaatgta attgagaaag gaaagcgcaa  14880
tgtggaaatc cttaaacaat cttctaatac tccatacaag gtagaagacc aagtagcgat  14940
tatctatgta ggttctaaga acctattgcg ccaagttcca gtagagcgcg tacgtgagtt  15000
tgaaaaagaa tacttggata accttcgcac agctcaccag gatacccttg cagaactcaa  15060
agcaggaaaa atcaatgatg agattacttc tgtattggaa aaagtagcta aagagatagc  15120
tcaaaattat atcgtgaaat aatttttat ttaatattat tggtaatact gccctacaag  15180
tgtagggcag tatttttaat ataaaggaaa atatgagaac attagaagag ttgatcaata  15240
aggaagaacc cggttgggac ttggtacaag aatggttgca agaggccatc aattcttatg  15300
aagtactgcc ccgtgatgct aagcgagcag aaacagaact actgaatgca caaataacta  15360
cccgttcgcc tatgggagct attatctatg aaacgggtgg tattcttata gatggaggct  15420
ggatacacct tttaggctct ggctgtgaga ggttagacag aggaatgttt cagtggaaca  15480
aagggaagtc ttttgagcac tatggggaac ctcctgcatt tcttttggta gcagatgata  15540
tcttaggggg actttttgct atcaatgggg gagcatttgg acaagatgac ttaggacaga  15600
tgtactactt agcccctgat acactcgctt gggaaccaat ggaatgcggc tattcggagt  15660
ttgtcggctg gaccttaagc ggggatatac atctgttcta caagcctttc tattgggaag  15720
gttggcagga ggaagtagct aagctcaatg gaaatcaggt gttttcattc ttccctttcc  15780
tctggacaaa agaaggaaaa cagatagaaa atgtgagccg aaaagtaatt tctatggagg  15840
gaagttatcg tcttacgatg gatatgcaaa gacaactctt ggagaaataa tagaggtatg  15900
gagggattca ctaaggattt ttggatatcg gttgtattac agttcatata tgcctatatt  15960
tggcttattc ttcctttatt gggacttata tattggtgga ggaaaagaaa gaattttctt  16020
aaaggaaaac tttcaccaag taagaaagga acagaaattt ctattacttc agttttaaaa  16080
aacagttaca gagaagcgtt aggacttcct ttgatagaga taacagcaga tacagagatt  16140
tttactgaaa tgggtagtgt agttaagcaa gaaaagctac agaaaaagat atatgtactt  16200
aaaaatcaaa taatcagcag gttggttttc tatgaaaaag taggatatga agaggatata  16260
tttctttcag aggacaaaga attgagaatt gtttttgacc atacagataa ggaggtactc  16320
tatatgtcaa agggagaaga agaaattacc tttgaagaat ttatttatca gtatcaaaaa  16380
ctaataggga aaactcttcc atcaactttg ttttatggac aggtattaca agtctaaaaa  16440
gcaacacgcc cttttccata atgtaagaaa agaggctgtc ctaaatatct ggacagcctt  16500
ctattatttt atgggtttct attttgaacc tttttcaata attttcttca cattcaaaac  16560
tgaacaaatg ataataagag aatttgttac agaagtcaat atgaaatttg ataaatttat  16620
cttttctagc agaagaagat atgagataaa agcctctaaa gccaaacata gaataatcag  16680
aaatataaaa aaaatttca tatatgtgtt ttttaaaaac aacctgctac atctgctaaa  16740
```

-continued gctaacatga gttcgacata aataaaatta tatttttttct cctacagact ccacagagag 16800
aatgatacaa caactaagtg taaatcttaa cagcatgatt acacaaacat agagaatctg 16860
tgaaatccgt gaaaatcagg gagagctttt gtatatcgaa ctcacgttat ttattttctt 16920
ttatatgctt ctatatttgt aataaattca tcaaaaagat agcttgcatc atgagggcct 16980
ggagctgctt cagggtggta ttgtacgctg aatacggggc ggttctttag gcgaataccc 17040
gctacagtac catcgttgag gtgtaggtgg gtgatctcta tattggggtt cttttctgct 17100
aattccttat caacagcaaa accatgattc tgagaggtaa tctcactctt gcctgtaagg 17160
aggttcttta cagggtggtt gattcctctg tggccattgc gcatcttata ggtaggtact 17220
ccttgggaga gggcaatgag ctggtgacct aagcaaatgc caaatacagg cttaccactg 17280
tcaataactt gctgagtaag tgtaatggcc tcggttagtg gttcagggtc gccagggcca 17340
ttggagagga agaagccatc aggggcaaaa gcactaagtt cttcaaaggt agctgtatga 17400
gggaacacct tgatataggc accacgagcc gccaagttgc gcaatatatt gcgcttgata 17460
cccagatcca aggcagccac acgataaggg gcattttcat ctcctacgaa ataagcctcc 17520
ttggtggata cttcaggggc taaggccaag cccttcatgg acggttgcgc cttgagctgg 17580
gctttgagtc cttctatgtt gtccacttcg gtcgagagta ccgcattcat actcccatga 17640
tcacgtatgt aggacaccaa ggcacgagta tccacatcgc ttactacaaa gagattttgt 17700
ctttcaagga aagcacctaa ggactcttca ctgatagggc gggagccata ctcgctaaag 17760
ttacgacata caaggcctgc aatcttcacc ccgtcggatt cgttttcttc ggagaaagct 17820
ccgtaattgc ctatatgaac ggtagccgct accatgattt gcccgaagta ggaggggtcg 17880
gtaaagattt cctgatagcc agtcatccct gtattaaagc agatttcacc aaaagcacta 17940
ccttcttttc ctacggcttt tccatagaaa acagtgccgt cctccaagag gacaattgct 18000
ggtttttttt gtgtatattt cattggataa tcaccatgat tctgtgctgc aaatatacgt 18060
catttttctg actatacttg gtttttttaat taaattttga taggcctgtt ctgttttaga 18120
aatccaaagc gtaccagcat aattgcccac gtagcgaaaa ggtgatatgc cattggttgc 18180
cactatgaag ggcgtgtaaa tcactgattt tcataaatatc tgatagacca gaactacgat 18240
aggggactat gcctatttcc gagaacacac agctgggggc acctatgggc ttgagggtct 18300
ttcggtcaaa tcgctgtgct ttgatccctt gggaaagccc atctcggaat acataaataa 18360
ggtaactctt atccccttgt gtagcccata caaaggtatc tctaatataa gctataaaat 18420
catcacagtg gaagaatcgc tttcctttag gaaaattctt tggatcataa caccaaaaat 18480
caaagccctt tcttgcatac tgataaccta tatagctgct tttattatca ttatttatat 18540
aggaaaagct atcaaattga aagtcctcat cttctttttc ctccaagaga tatttctcta 18600
tacaggtgtc cttgtgaaat tttagatgat aagtcttata atcttctgta taagcgataa 18660
aaatgggctc ctccaaggcg tgagccgtaa ggtcatcccc cagtagaggc gtagtgatag 18720
ctattatagg tgaggggagt aaggcggcta aggattggtt accaacgact ttgccactgg 18780
tggggtttat acaaagcagg ctaaaatcag tacgagatcg cttgctgcta tagatggcat 18840
acatataccc agaagtggta aaggtacttg caatataggc ttcttttagt tcaggtagga 18900
gtgttttctc ttggacggct ctataggcta aactatcttt tgtaacagcc atgggggcat 18960
attttttcca atggacacga ttatctattg tatagagggt atcattcttg gcatagaaat 19020
gattgatata ggtactctta ggaatttcta aggcttgttt taggaactta cgcctttcgg 19080
tatcaagggt gattaagggc aattgttggc tttctatgga aacataacgg cttagataaa 19140
ggtgcttttt agctaccgaa tcataagcat atagggaatt tcggtcactg gtaatttccc 19200
ctaaatattc gagttgctca tagtagcttg taggggtctc tgtaaggggg actactgcag 19260
gggcgttaca taagctaagg tcggtatgga taaccttttg ccaccatgct tgccattgct 19320
tttttttggc gttcttctct ataggaataa aatcaaaagt atcatgtgcc gaatttagga 19380
tacgaagtgc aagctcggct atggaactcg tttcttcttg tacataaatg cctccaccgc 19440
aggtatctaa ctcataacga tgctggatag ttttgcgatt gtccaattct gcgatccact 19500
tagggatatc gcggtattcc caagaaccgg taaagaggtt tttacttata atatgctcat 19560
acagtccgtc tatttttacc tgatattcaa aggtagccac ctgtccgtca gggtcaaggc 19620
aggtggcttt tttggtataa taaagtgctt tatggttggg aaaagcaatg gcttcaaagg 19680
tgatttctcc tttgcatttg agaaaatcat gataaatatc cttgaataca ggcactaata 19740
agatcgtggg ttgtcctacc cgctgggcgg attccttgga gaggttgaca aatacaatat 19800
ttcgaggcgg ggtgatgtcc gctttttcca agacaaagag tctgttttgg atcatttcat 19860
tctctccata gtaggtgtga tcgttatcta tatagccctt gagggttagg gtttcttgcg 19920
cccaaaggcc ataatagggg agcgttataa gcaagaggag caaccacttt ttcatatctt 19980
tattctttta gatttttccg tctgataaaa gacacaatgc ctaaaatcat gacaaacaca 20040
gccgcataat agacaaagtt aggagtaatc actttctctc cgctggcata actatgcaga 20100
ccagagaggt agaaattaac cccgaaatag gtcatcagga tactggcaaa ggccactaca 20160
ctggcaaagt tgaatcccca tatgccacgc aaggagggga caatacgcat atgaatcaca 20220
aaggcataga ccatgatact caccagcgcc caagtctcct tcggatccca accccagtag 20280
cgtccccagc tctcattggc ccattgcgca cccaagaagt tcccaatggt gagcatgata 20340
agtcccacgg taagggctag ttcattgacg atagttagtt catctactac acccttgatt 20400
ttttctcggt tcttcgccgt ggtaagaatc atgagtaaga ggttaatagc tcctaagatc 20460
atacccaagg tgaaagggcc atagctacct acaatcaccg ccacatggag catcagccag 20520
tagctattca gtacaggctg taggttgcct atggaagggt caagccagtt ccagtgggca 20580
atcatcagaa tcatggaggt tacaaaggca gtagaggcga ggcttagtgg tgagcgacgg 20640
gcgaaacaca atccaattcc catggtagcc catgctacgt agatcatact ctcataagca 20700
tcactccatg gggcatggcc tgagatatac cagcggaaag caagccctgc ggtatgtaag 20760
gcaaagagga aaaagagcag tcctgtacat acttgagtgg tgatacgcag cgccttgcgc 20820
tccttaaaga tacgcgcgat aagcacgaca aacatgattg ttcccacata taagtaccag 20880
ctaaagaggc ttttgaagac atcatacttg ttgtaaagaa tctcggcttc tatctgtttt 20940
tcggaaggaa ttaccgcctt acctacagcg cgctggttct gctggagtac agtcaggatc 21000
ttatccgcat cgctgtaatt gcctgtctcc acggcatctt ttacagagga gagataccag 21060
cggaaagcgt gcttgataaa gccagcttcg agggtgtcct gcgtataggt aggattctcg 21120
tagatgtcca atggggaaat ccacttgttg ttagggctgt ccttcagtgg gaaaatgcgc 21180
aacatactcc ccgaaagggc gcgctctaga aggtgcatct tggtatctac ctccttgaac 21240
tcctttggga attggttagg gttggaggta gaataggcct ccactaagta aggattgagt 21300
ttgttgttat attccttatc caagaaatcc aaagctctta cgcgcttaag gccttttttct 21360 acgcctaaaa tcttgtgtag gctgtcgtta tctttttttga tatagaagaa atccacgttg 21420
taccatagct gacgatttag cagcatggag aggaaaactt gattggcgtc tagtccccgg 21480
aaagtatcgg ccttgctgac ttttctgagc aattcagaag caaaggtatt gattggcttc 21540
atacggccat cttcgtcttg gattaccaag tgagcaaagc ggtcggcatg ttccttcttg 21600
acagtagtgg ccttgataag cgagtctatc tgcttgggag tcagttcaaa agaatcatgt 21660
tgggcatagg tgcctacgga aaagagcaaa gccaagaggg taagagcacc tcggcgtttg 21720
tcatagagct ttttgagctt ttgactgagc tggacaaagc gtgtctttcc aaagaacatg 21780
ctggcgataa ggcctatata gagtagggta tagcctatgt aagtgagcaa ggtaccccaa 21840
aaatcgtgat tgacagaaag aatactgcct ttctcatcgg ggaagaaatt ggcttggaag 21900
aagcgatagc ccttatagtt aaggatatta ttcatgtaga tatcatattt gaaagtctcc 21960
tctggtgagg ttacggtcac tttactcttg aaagaggagt aactacgctc ggtgccaggg 22020
tatttgtcgg cgatgaagtc gtccaacttc actttgaaag gcaggggcgt acgcactgaa 22080
ccataactca ggtggaaggt aagtccgcct atctctgttg aggtgggagg gttgatctca 22140
tcacgcctac cgatgacctc cacttctttg gtttcaccct cgcaggtgat actcatcaca 22200
agggcactga gatcacctgc attttgtttt ttctcaggga tagaggtcat gaccattttc 22260
cctttttgca ttggctcagg cagaacaaag cgcatgccgc ctatgttgta caagcagcgg 22320
tattggagag gctgcatact atctttggct acctcaaata ccttttggtc tcccatggtc 22380
atataactac ccatataagg ggtatgaata tagctccctt caggggttat ttgtaggttg 22440
atagctcctt cggtagggtt gttcagcgag atgggcaggc catggaagtt ttcagtagca 22500
ccactcttga ggtagtgttc gtgtccctct ccgccagcgg cctctacaat cttcagatag 22560
aattcacctt ggggatccgc tacaaaggta gcctcggcat gagcgataaa tcgcttgagg 22620
tctatacgga aatcctttcc cttgaagtca gaagaccagc tataggaatt ggaagtaaat 22680
tcggagaaga gcacctcggt ttgtttggct ttgcgtaagg gttgtccctc gtaggagcca 22740
tctacctggg cggtgatata ggtcagctcc gaggtataaa agtcagcctc ctctccctcg 22800
cgtagggcga gcttgccttc gtcgctgatg tagcgggtaa cggcagcccc cacgatgatg 22860
aagatccaag aggcatgcag gacgaaaacc gcccaatttt cgcgcttgag caggcgatag 22920
cggccaatat tcccgataaa gttgatgaca aaaagcgcca tgatgagttc aaaccaccaa 22980
gcgttataga tccagatttt ggctgtgtcg gtattatacc aagtttccac aaaagtaccc 23040
atagcaaggg cagccccata ggccaagaaa agcactgcca ttaggcgagt agaaataagg 23100
aattgcgtaa gtttttaag cattttttga gtgttttcct aaggggcaaa aatacgaaat 23160
ataatgataa aaggcaaaca agttttgagt tttgagttct gaattttgag ttacgacact 23220
gatcacatat tgctaacaac taaccatcgt taattaactt cgttttatta ttacagagaa 23280
ttgtttttac ctctaaaatg ttgtaatttt gcattctgaa aattaagagg taaaaggtta 23340
tagcagacag accctgatcc ctgaaatcct taactaacta taactcatga aaaaacaact 23400
cattcaagcc ctttgggcta ttgccaatgg gcaacctcaa caacaaggag agaaaacagt 23460
ttatccctcc acacgagaac aactcagtgc gatcaagatg cttatgtcct tagaagactg 23520
ggaggagctg ccttctgtag actctataga ggacgaaaag cccgctctcc aagtcttgcc 23580
ttgcactact aaagatactc ctgccgcaca atcctcgaat tctgaagtag tgagaacgcc 23640
tcaaaaaaca gtgaatatag atcagcagac aaccaataca cctcaacagg taaccaatac 23700
acctcaacag acaacaaaac ctacaatcag ttacagacgt acttatcagg agtggtttgc 23760
tcaaaatgaa ttgcttgaaa agctgttact tgaagagaaa gctaaaaaaa cacaagccaa 23820

-continued

```
attaagtaaa aagacaaagt ctaaaagtat accgttagac tcttctgtat aggagactat  23880
agttgtataa tttgaaaaaa cttgagttta ttttttatta tctttgcccc aaaaagcaat  23940
tatgaaaaag acagtcttta tagtgattaa tctttccctt ttgggttgtg cttcccgaca  24000
gatagcaacc tccgacaaaa aagaggtctt atcgcaccaa gaagaggtta taacaaaaat  24060
ccctaataag ccctcactca aagggcaggt aaagcgttat aaggagcgca gttatacccc  24120
tatcttccaa aagctatctc aaaaggattc tattttttcc caatggagtg agacacctta  24180
ctttgagata gaatacctct ttgatcccaa aggaaatata gtaaaggaat gtcagcaagt  24240
gaaagggcaa acggattctt tgtattatat atccgagagt aaatatttgt ataatgagaa  24300
aggaaaattg atgcaaaaaa tcttcaaaga aggagatttt cctgaaacag ataataatca  24360
atataagcat atatattata cgaattatat ttacgatggt aaaaataggc taatagagga  24420
agaagaatgc gattcggatt tactcaaagg agaaaaaatt atatatactt atgacgaata  24480
tggtaatatt atagaaaaaa tttcatttac tgataaaaat aattatttct ataaagaaat  24540
atataatcat gataatgaaa atagacaaat aagttataaa aaaatatatg taactaatgg  24600
atatgaagaa gaaataaaaa agaacacatg gaagtatgat aatttaaata gagttgttga  24660
agaatatgtt tatgaattga gtacaacgca atataaagaa ggaacactta tatatgataa  24720
tactataaga tattatagat acaatactaa tggaaaactc cttgaaataa gagataaata  24780
tcttagtgat agtatattag ctcaaggtgc cactcagggg catacttatt atgcgtatga  24840
tttaaagggt aatctattat gtgagtctaa ttttggagat gggaggcttt gttggcgcaa  24900
gtgttatgat gagtgtcagc accttgtaga agagatttat gttagtcaag aaggagaaat  24960
ctataatagg cagtattatt atcaagaaga tatatatcat aatcctatag aaagacttgt  25020
tataaatgag ggtcctatag aattatatag atacgagata gcgtattatt aaggaataaa  25080
attctcttta gtcgtttgtc atttattatt atttttgtat ttttgcaaca aaataaaaga  25140
ctctatggaa ttatactacg ccttttcagt aattattgtt ttagctgctg tgttctctta  25200
tctgaatgtc aggtatgtaa agctcccgat gaccattggg atcatggtga ttgccatgat  25260
ggtatcggta gggattcgcc ttttcggggg ggctatcttt tcaggtttag cgcataggtt  25320
ggaagcattc ttagaggggt ttaattttac agaaatccta atgagtgcca tgcttaactt  25380
cctacttttt gcagcggcct tgcatatcaa tgtctctgac ctaaaagaat ataagctccc  25440
gatccttact tatgcgacga taagtgtggt actttcggct ttctttatct ctggattact  25500
ctactatatt gcctcttgga tagggataga tatcccttat gtctattgct tacttttttgg  25560
tacgctcatc tcacctaccg accctattgt ggttttggga gtactcaagc aggccgatgt  25620
acctaagcgt attgagacaa agatcacagg tgaatctctc ttcaacgatg gggtagccgt  25680
agtgatgttt gccgtagtgc ttaagctggc taccgacgct acttttgaac cttcgtttaa  25740
tgctataacc aagctcttcc ttttggaagc agggggaggg atatttttag ggctatctt  25800
gggttggatt gcctctgaga tgatgaagaa ggccgatgac taccatgtga gtgttttggt  25860
aacccttgcg gtggtgatgg gtggtttctt gatagccaag gcttcccatg tgtcttcgcc  25920
tttggcgatg gttattgcag ggctttttgt aggtaatgta ggcaagaagg ccagcagcga  25980
ggagaatagg gattacctga gtaagttttg ggcgattgtg gatgagatca tgaacgctat  26040
tctcttcctc tttatcgggt ttgagatgct tttgatagat aatttagaca aacagttcct  26100
cttgggcggg attgccattg tggtatgtct tttaggtcgt gccctggcaa tttatattcc  26160
agctcagaca atcttgcgca aggttagctc ctattcgcga ggttcccta ttaccatggt  26220
```

atggggtggg gtacgtggcg gcgtttctat cgcgctggtg ctttctatcc ctcaggatca 26280
gggggtgatg aaggaaaccc tcttgcaggt tacttatata gtggtgctct tctctatttt 26340
ggtacaggga cttaccgtgg gtaaagtagc caaagatgcc ttgcaccgag atgaggtgat 26400
gattcgcctt aagcgtataa gagccgcaca tcagcgcaag ttaaatacac aaaacgattt 26460
gtaaatgaga tgaatacacg ccattggtta tatatactta gcctatttgc tttagtctgt 26520
tactcttatg cacaagagag gacagattgg gagcgtgaat atctgcacaa gggcgtgaaa 26580
acacttcgta tcaggggcta ccatgtcaag gaaaatggtg cagtagctca aaagggggccg 26640 cttatcgccg agatgaatat agaaaagacc tttgatgcac agggtaacct tgtcaaggaa 26700
atattctttg acgagcgcaa tgcagagacc ttgcgctacg aatataccta tagcaagcag 26760
aaggtaaaga aatacaaact acacttggat cctcaaaggg agaaagtagg cattacagtg 26820
ttcaactgtg atgggagtgg caatgtaacc aaagaagaaa cctatgacgg ggaaggggtt 26880
ttgctctatt ctgccttttt tgtctatgat gatgcaggac gacagaccga aagcaatttc 26940
ctcagggagg atttctcggc taagttcatc tctacctatg accatagagg gaggctctta 27000
gaacaggagc aaaatatagt ggataagggg gagaatattc tcaataaggc caaatatcgc 27060
tacaatagcc atggagattg tgatcgaatc ctctcgctgc tcaatagaaa ttttgctcag 27120
aagaagagtt ttgagtacaa atatgataaa aaagggaact ggattggacg ctttgaatac 27180
caagatggca aacccacaac gattattgaa cgacagatag aatactttta agtgaaaagt 27240
gaaaaatgaa gagtgaaaag taaagccagc gaatacttgg agttgggtat gtgggtgaag 27300
agttatagac aatcggaaga ggattgtaaa aaatgatatg agtaggcgta gaggcaaaat 27360
agcgtaaaca aggtagagac gtgagtttat agcgtctata tttgtagata tttatggcat 27420
ctgttattgt accttataaa aagaaaacta taatatgtat agaatcttct tagtcttttt 27480
agcacttctt ttgtggggat gccccaagca tacacctacc attacggaat tgcctctgac 27540
caatgagata gagcaaaagc tctataacct catcagctgt gcacgttttg acttagataa 27600
gcgagcagaa tttgaggaat ctggttatta ctatgtttat aatgcttgcc ctgtagatga 27660
gaatcctttt ggagaggtgg cactatttct ctatcctaaa aatgagcagt ttgacctgaa 27720
agtagtacag gcggctatgt acagaggaga tgaacaaaag tgggtggatg tggtcttcaa 27780
tcccatcaag gatatgtcac ctgagcagat tgctcaaaac ttcaacgtgc tacttgtgat 27840
tgtgaataaa aaatatttga aagagaatca tactctcgaa tcgggctatg attacaaata 27900
tccgaccaag tacatcacct atagccttaa ggatggcaaa tggactaagg gtcagatagg 27960
ggaaaaaata tcccacgacc ctgaatcatg gatagagtat gtcaacaata tagcaaatat 28020
agc 28023

<210> SEQ ID NO 5
<211> LENGTH: 33804
<212> TYPE: DNA
<213> ORGANISM: Streptococcus species

<400> SEQUENCE: 5
gtgggacgaa gtgtcaatga aacgtggggc gagtccatag atccggcggg aggcaacgtc 60
atacggcatt acagctttga tcttaacccc tcttggaatc ggaaaaattt agccattgtc 120
gcactcatcg gttattacaa tgagaataat atcgccgaat gctttatcga caacgccaca 180
gtttaccgtt tgtccgagat ctccacgggg atcggagaga ttacgacaga tcaaaagtcg 240

-continued

```
acagcatctc aaaaaacttt ttatgactta aacggcaggc aaatcagcgc cgatcatcta    300
tcggcaggca tctacattgt ccgcgagaaa gccccaaatg ggagcgtcaa aacgagcaaa    360
atcatcgtaa gatgaggtct atatatcaaa caacaaatta aatacttatg aacatcttct    420
caattactct tttacagagc aaactattga aaggcgccct tagtagaggc cctcagaaac    480
tcttgttcgc tttattcttc gtgatggctg cgggaattca agcgcaaaac agtggaaacg    540
caggtccgct gcagtggcaa tacgataaag aaacgaaaaa attaaccatc tctggccaag    600
gagcaattcc cgattatgaa gaagacgcac agccttgggc cccatttgcc agagaaataa    660
aaacggcaga agtaggagag ggcgtcacta tgattggcga caacgctttt acctacagct    720
tgaaaatgga aaaaatctca cttcccaaaa cgctgactga gattggctac cacgctttct    780
atagttgcca gaagttagct tcggtttcca ttccggcaac ggtgaaaaaa atcggcgaca    840
gagcctttca agaatgcttt gagctgaaag aaatagaagt agatgagaat aatgcaaatt    900
attcttcgtt agacggcgtc ttatacaaca aaaaagagac gctattgatc cgttatccgg    960
ccggtaagga tgaagatttt accattccga acacagttac caccatcggc gacgatgctt   1020
tttccgactg cgaggcatta ttgcacgtga cgattcccaa tagcgtgacg cgaatcggcg   1080
attacgcctt ctacaagtgt gtaggtttgg aagaaatttc cattcctgcg agcgttacgt   1140
ccatcggcga tggagctttg gccggttgtt catcgctttt gggcattgtt gtcgatgaca   1200
agaactccac ttacacttcc gatgaaggca tattatattc gaaagacaag actcgactca   1260
tccaatatcc tgccggcaaa gacgaaactg acattctcgt tcctgaaggt gtgaaagtga   1320
tcggtatcgg cgcttttgtt agcaccatca acttaaagaa cgttattctt cccgacggac   1380
ttacgaccat cgaagaagac gctttcgccg acggagaggc attgcagacg gtggttatcc   1440
ccgccagcgt aacgcgaatc ggcaatcgag ctttctttgc ttcagaagaa ctcctcaccg   1500
ctaagattcc ggagggcata gagcgcattg gcgacgacgt gttcaatagc tgtaaggcca   1560
tgacctcgat catcatcccc caatcgctca agagcatagg ccgaagtgcc tttgaatatt   1620
gcgtttcttt gggttccatt acccttcccg caggcgttac gagcatcggc cccaaagcct   1680
ttgagggttg cttcttgctg aagacgcttg ttgcgcagat gcccgatccc gaccgtgtga   1740
tgctgggaga tgacgtcttc cgccatgttc cgaaagataa tacaaagaac accttctgcc   1800
aactctacgt gcccgaaggc agcaagcaga aatatgaggc tgctgctcag tggaaagact   1860
tcgcaccaaa catcctcgaa ggtctccccc tcggcattcg tccgcttgaa aatgaacacc   1920
cgatgcgcaa atccggaatt tacagactcg acggtgtgcg ctgccaaggc tcattgcagc   1980
agttgccggc cggcatttac attgtcaatg gcaagaaagt agctaagaaa taacgcgctt   2040
gcgcccttag gcgtatgata tacataagcc ggatggtcgt ttgctctcga ctatccggct   2100
tcttcgtacc tctttataag gaaatatgca agccgatgac acaatatata aagatgcacg   2160
tccgcttccc aacgcggcac tacgggcaat gaggcttctt agcaccacca atggatgcgt   2220
agcgttgcat caggctgtag gcctcggcct tttcactttt caacttaggg attaaagtag   2280
aaaaaagaca aggaatatgt gtgcacgaaa cgggtaatag ggcggccgga acgcagttag   2340
aaccttttt atcacgagaa aaaaggtttg cgctcacgat aaaaagagct ttttctcgtg   2400
ataaaaattg cttacgctcg tgagcgcaaa tgaagcggat gggatatggg gcttcttttg   2460
ggggagcaag cgcgtgaaat aatgggccgg gcagtagcgc tgcggcccgc ccgtcggtca   2520
attatgcgac ggcataaaag atagtccaat ccaagcgggt acggccggca tattttgagg   2580
ctgtaaaggg caagtttatg aggaaaaaca gccgcggaat attcgccatt tcagcattgg   2640
```

```
cggattaagg ctaatcctcg atgaaatggc actttttgcg acgtatgccg cacaaagcgc   2700
ttcacaacaa aggctgctcc tcaagctgcc ggtcgggggc ggacgcaagg cgatgaccga   2760
caaaaaatta cgaaataaag ttgtagacag aaagatcccc tttgctcgga ttccgataaa   2820
aggaagtcgg taaccgaaca aaggggatta tgatgcgctg tgctatcgcc gtggagtggt   2880
cgtgtagccg cagcggaaag aaagcttaca gttttacttt atacgtggaa gtcttgccgc   2940
cggaaacgag acgaacgatg tacgtgcctt tctccaattg cgcgccgagc gggaggagac   3000
ggccgtcagt cgtgtagact tggagcgtat tgtagcggcc gtttacttgg atttgaccat   3060
tcacaatcgc gatggaagct tgctcgcctt ggttgatgtt gcggatgccg gtcgtgttgt   3120
tttcgggaac ggggagtccg tcgttgacgc ctgatttgat gatccagatg cctgacgcgt   3180
catcttcgtt gagtttgttg acgaactcct gctttttcat gtcttcgtag tcgacgccaa   3240
tgccggttga gtagctgctg ccgtcctcca tttttgcgta atagctgttg aaaatcgttg   3300
tcgggaaaga gcccggtacg atgggatcca tcagcgtcgg cgaactataa atcaaagcgc   3360
ctgcttgata gcaattggtg atctcgataa tgcttccgtc gacggcctct tccgtatttc   3420
cgatgatgcc accaatggtg ccgtcggtcg cgctttgttc gttgagagcg ctaacttcgc   3480
cggtgttgta gcaatctctg atggttatgg agcgtttaat ttgtccgatg atgccgccgg   3540
tattggtgct gtgctcctta accgcagcgc ggttgccgca acgctcgatt ttcgtgccgt   3600
cttgcgtgtt ggagccgacg agacctccgg tgatgccgag gtagcacgtg aggggcgcgt   3660
cgttggtgca gtctgcgatt tcgctcgctg cgccggcgat gagtccgccc acaatgccgc   3720
cgccgtaaaa tctgtggcag ttgactacat aatctttacc cgtgtggcaa ttgatgatct   3780
ttgtgccgtc cattcccacg cctacgatgc cgccgatgat gtggtcgcct tcgactttac   3840
cacttgcgat ggtgaggttc ttgatcgtag cgcctttaac gatgccgaag aagccgaaca   3900
tagcgtattg gtcattgtgg aatgtgaagt tgcggatgct gtggttgttg ccatcgaaag   3960
tacccataaa cgggcgaatt cttgtcgggt cgtcagccgt gcgatcaaag ccgttgccga   4020
tggggcgcaa gtcttctacg ccggcgaggt taatatcgtt ctccatacgg aagaatttgc   4080
cggcgaaagt gtttttgtcc tcttccacag ccttggagag ggctttcagg tcatcgacag   4140
tcttcacgag ataagggttg gcctgcgtgc cttcgccgcc actgaaggcc ggcgcttggg   4200
cgctttgacg cagctgtttg cgagcgcctg ctttttgagc ttgtaggtat tgctgcaaag   4260
taagctctac ttgagcctgc atttgctttg gggtgacgtc ggccatagat gatccgggca   4320
gacaaattgc tgctaaagaa agaagcagcg tagcgttaag gtgtttcata tttagatctt   4380
taaatgtttt gttcgtttgc acttttccaa aatctcaata ggcggcgatg cacactcgtg   4440
gcataataaa gctgctcggt ccgctcgcgc tgcgctccgg caacaatgtc ttctgtcggc   4500
gcacctccaa atcttgcttt gataggcaaa acgtgggata agattatggt gcaaatatat   4560
gattttaatt ttaggcaagt agaaaaaatc ccaaaatgta gttaagtttt tcaagttcag   4620
gtttgcattg tcgccaattc ttaggtgaac agttcccaat ttgttcaaaa ataaagaatt   4680
tgtgttgtga ttgattggga aaaagatttg aggcattcgg taactcattt taggcacgcg   4740
aaacgaacaa gcgtgcgcga aagcccgaac ttttacaagt tcgggcttta ttatcttttc   4800
attttcttta ctttgctcag cttagatcta taccatatta tatataggcc cttttgcctt   4860
gccgttttat tgcgccaaga gtttcttaac ccagtcagaa atagcctttc catcggcttt   4920
tccggccaag cgctttgatg cttcgcccat tacgcggccc atatccttca tcgaagttgc   4980
```

-continued

```
ccccgtttcg gcgatgataa gcttcacggc agcttcaagc tcttccggtg tgagggcctt   5040
cggcaaatac tcttcgataa tggtagcctg cgccgcttcc tcttcagcca agtccggccg   5100
gtcttgttcc gtgtaaagtt tcgccgtatc gcggccttgt ttagccagtt tcgacaagat   5160
tttgagcgct tgtgcgtccg tcaacgtgtc gtttgcaccc ggcgccgtct ttgcttcgat   5220
gaaaaacttc ttgatattgc gtagcgtttc aagccgtatt ttatccttag ccttcatagc   5280
tgctacgata tccttgctga tttgttcaaa taagtccata atcaataatg tttatgatga   5340
ttactgttaa tcaaaattga tgataagtgg tgtctcctcc tctttctcgg cgtccgatac   5400
agccgattgc ggcgcttccc ttcgtccggc ttcgagcgct tggcgtattt ggcgggccat   5460
ctccggtgtg cggtttcgcg taggcacact ttcgagcaat tccggcaagt cgccgttgat   5520
catatcctct aattgcaggc ggatgataaa ggcgtgcggg cgcttttggc gctttccaga   5580
accgtaaatg cgctcgcggc gtatcgcccg tttcgtgtgc tcgtcctcag aaagcgcgtc   5640
agtttggtcc gccttctcat tgaagagccc aaagccggat gccagaatcg tcactttgat   5700
ttcgtcgccc atagctgcgt cgggcacgaa accccatttg aaatatgggt tgccatcgaa   5760
gcgcgttgtg aaatgttcta tttcgctcat ttcgtctatg agtaaggctt tgtcggcctc   5820
agaactacaa gtgatggcca tggctatacg cgtggcccgg aagatgtctt tattattgag   5880
caagggcgaa taaagcgcat cgcgaatggc ccgcgtgacg cgctgaggtc ctgtggcgtg   5940
tcccgaagat atgacggcca agccaccttg atgcaaaacc atattcacat cgcggaagtc   6000
gaggttgaca cggccgcgca ttttgatgat ttccacaata ctcccgacgg ctttcgtcag   6060
cgtttcgtcg gctttcttaa aggcattgat gacggtgagg tccggataaa tttctcggag   6120
tcgttcattg ttgatgacga gtatggcatc gacctctttg gccaaccttt cgacgccgtc   6180
taaggcttta tcgacttgcc gctgcaactc aaaaagaaac ggaatcgtca cgatggccac   6240
cgtaagcagc ccgcgcgatt ttgcttctcg cgcaatgatc ggcgaagcgc cggttcccgt   6300
tccaccgccc attcccgcgg tgataaagac catcttcgta tcttcgtcaa aaatgtcatc   6360
gatcgcctcc aaatcgctct cggccagtgc tcgccctgtc tccggatcgc cgccggctcc   6420
aagtccggga ccaagctgca gacgatcagg caccgcacta ctttcaagcg ctttccggtc   6480
cgtattgcag acgaggaagc gtacgtcgtg aagaccctca cagtacatgt tggctacagc   6540
atttccaccg ccgccgccta cgcctatcac tttgatgatc gaagagcgcg tgcagtcgac   6600
aggttcgata aggagttcgt cgttcattgt tggtgttcag cgcagaagcg ctaatgttat   6660
ggtcggtttg ttaactattt ttgtggtgtt tggctgaacg gccggggcgt agttctgtag   6720
ctgcgatggg ttcggctgcc ggccgttttt gcaaaactaa caaaaaaagc gggagattat   6780
ctccttttttg ccgtctaact gaagatttat tttgcgcgat cggtcggcgt gcgccgtcat   6840
accaaaaagc ggcgaaacgg gcgatacagc cagttcatca gtcggcgtaa attcgggtgt   6900
cgatacgaca gacagtcgac aacaacagta ttttcatacg tgttaaacgt atgaagcccc   6960
tgcgaaaagc gcggatcggt agcgtggagg cgcaccccgc taccgacgct ccaacccgtg   7020
tgcggatcat agtttaatgg ctgaagcaga acgccctcgc cgtaatgacg attgcaaatc   7080
tgcgcgggcc gatagagttg ccccccgaag cgaaagaggc tgccggcatt gcgcgcaata   7140
aattccggaa agcgcaaatg agacgtgact tcatacgcat cgccttgctt tttcaaaaaa   7200
tgcagcgttc gcccgtaagg gtccgtatcc atcgagccga tgagccactc ttcgccgccc   7260
gattgatgga atacgacgtc gacaagtggc actttcgtta gcaaacgatc aaagacaaag   7320
gcgtcttgcg cgcgatcgta gcgaaacagg ctatgttcgc cggaagcaat gttttccgga   7380
```

-continued

```
tggatgaaaa tttcgccatc gcggcgcaca atctccggga aactcaaatg cgtgggtaag   7440
ctaagaacgg tctttgcctc gagtacctgc cccgtagtgc gtgctatggt caggcgttcg   7500
atgtgtccct gcaattttcg ctccacataa gcttccacca agagtgtgat ttcgcccggc   7560
gaaacgtcta aaataaacgg atcgccatac caaacgccct tttcgggcgc ttcgatgggc   7620
acgaaacgca aggatgcacc ggccaaaata tcggcaagcg gcgtcgtaac caaggccacg   7680
cgccaacaag agccgaccag cggcgccaag cgttctcgaa gattaggcat aagccgtcat   7740
atataatata atgtgtcaac gcattgcgcg cgttgtgctg ttcgccgtca gtgtgcgtgc   7800
ggtttttgtg gtagcgacac tgattgataa gtctacaaag ctacgaaata aatagcgttg   7860
tcgccgtttc gtatcgctac tttctccgtt ttgagcggaa aagtcaagat cgtcggccgt   7920
cgaagcgcac cttttcaatc tgcccttgct tttagcttgt cttccagtaa gcgctgcgtc   7980
gcgaagtgcc gttttcggaa tacgcattct ctactctctg ctgctgccac atttgacgca   8040
ggccggtggc ggcgcaaaat ggtgcttcgc cgtatggttt tttatgcctg caatgtcatt   8100
tggcgattgt ttggtgccgc caaaccattg tttgctccca ccaaactatt gtttgccccg   8160
accaaaccat cgtttgccgg caccaaatga tacgagacct tgaatatgga ggtacaaaaa   8220
cgaactaatc gggccgatga tttgcgggca actttttcgca ggctatgatc accttttgcc   8280
catcacagag tgtcgtggca aaccaatagt cgtcgccgcc ttcttttacg tggagcttct   8340
ttctgagtgc gtctaccgtc agcggaaagt tgcgcacggt gatgttagcc cgcttcgtgt   8400
cgccgcagaa atctttcagc gctgccttgt tcattgtcgt cgtgcgcaga cagcggaagc   8460
tgcggcccgg aaagtcgacg ataagctgtg tggatgtata taaatgactg ttgggatgca   8520
actttttcaa atcgaatctg agagccggca atttgagtgc gcccgctttc aaaagcgccg   8580
ccgaaggttc gtaaagaaag gtctcaacct cggcagtaaa agtgcaattt gcggcggttt   8640
catcggcagt ttggaaagaa aagtccaccc cgtctcgaca gtgaatcgat ggcgggccgt   8700
ccgtagggcc cagcagcaag agcaagtcct tacattctcc tttttcagca aacacgtgta   8760
cctcgcaaac ccctcccagt tcgctcaccg ccgcgtgcca atcgagcatc ggcgagagtt   8820
tcaggagtgt atagcgcgcc ttttcgcgca gcaagggtaa tatatccatc acgttgggct   8880
cgcaatcggc caaactcacg accttccggc ccgctccatc gcgccgcgcc ggatccagca   8940
agatgaaatc agccggcggc atagtctgca aataagccac gccatcggcg ttgacgaagc   9000
gcgcgttgtg caggcccagc aaggggagat tgtaggccgc caattggcac aaatccgcct   9060
gctgttccac gtaaatcgcc tcgtcaaaca gttgtccgag ataaaaaaag tcaactccga   9120
agccgccggt cagatctacc atccgcccac ctgcgggcaa atggcggcga atgacctccg   9180
ccttatagcg tgcggccaac tcgccggagc attgctccaa cgaaaggcgg cgcggatagc   9240
gaagtcgcgg ctcggcagcc cacgttggta ctttcgcgtt caacttctgc caaccctcga   9300
tctgacgcag gatgtattca gcctcttcgc ggggtcggtc ggcaagcatc agtgccagtg   9360
cgggcacact ctccgtgcgg tgatctcgga taaaagcttc agcgttttcc ataaaaagcc   9420
ctcaaaagcg gcggtttcat cgcttatcgg atgagtttgt agtgcgcctt ggcttgtgcg   9480
cgagttttga aattaaaatg ccaccattcc gtgcgcaaca ctttgaaccc cccgaccgcc   9540
attacgcgcc gcaataagcg cctgttggct acggccgccg gagaaatgcg cttttgtttt   9600
aagaattcct gctctaaatt gacgtgcgac aaacgcccca tatagtcgat cttcgttccc   9660
atcgggatgg tgtcgcccgt cgccgcgttg cagagcgtta tgtctacggc caaaccgtaa   9720
```

-continued

```
ttgtgcaagc ccccgccgtt ggccggattg ctcacgtaaa tgctttttgg cgtccctgcc   9780
acgacattaa acatcttttg ttgcaccgac atcggacgtg cggcatcgta aaccttgagc   9840
gagagatccg gacgcaagcg cttcaactcg gtttgtgccc gtttcagcgc cgcagccgtg   9900
gagggaagga ggtaagccgt gtgaagttct gtataaagaa cctggcccgt gaagttgtcg   9960
gcgcggccat acatcaagct aacctgaatc gtgggatcca cgctgcggag gtcgacgagt  10020
ccttgccgct ccattgacaa ttccgtaggc gtcttcgtag ggacggcggg cgtttttcttc  10080
tgcgcaaaca ggagtgaggc cgctgcgcaa agcaccaaaa gaagcggccg atgcgggcgg  10140
atcatcgcac gtagcgaata tagtcgtcct tgcgcggctt ctcggtcgtc gggagcttgt  10200
cgggataacc cacgatgcaa tgcgcgatgc cttcataatc gccttcgatg ccccaggatt  10260
tgagcagcgc tttgccggct tcgctatcaa attcttgctt ggcgcgatgt atccagcaac  10320
ttcccaaacc cagtgcgtga gcagccaatt gcagattttc cattactgca gatccgtcgt  10380
aaagatacgt gtgtttcgtg cgatcagcca agactacgag cacgacgggc gcgccataaa  10440
acgggtcagc cttggtgccg aggatctcag cattcatttg cgagagctga tcccgcactt  10500
ccttgttcgt gacggcgacg atgatcgccg cttgtgcgcc gcggcccgag gggcaaagg  10560
tgccggcctc catgatcttg tttaaaactt cttccgatgg catttcgggg cggtaagatt  10620
tgcagctccg acgcgttaac aatgcttcta atgcttccat attataaatt ggtaaaacta  10680
tgatgcgatg gtcgccgcgc ttgatggcat attcataatg tatctccatc agaaagttcg  10740
gcgaatctaa atgttttcgg tacaaaaata ctacttctcg acgaaaagat gtaatttggc  10800
agccggaatg acagctgaaa aaactgctcg ataggcttaa agacaaagca agaaggaaac  10860
gttggcaaaa aaacttgcaa aaactggtca aatctaagta actttttccc acaataggcg  10920
tctactttac agagggccac aaaaagagaa caacaacccg gtgaaagaaa tcgatttccg  10980
agaagatctg ctcccgctta aaaacaaact gtaccgctta gcgctcagaa ttacgctcga  11040
tacagccgaa gccgaggatg taacgcaaga tacgctgata cgcgtgtgga caaaacgcga  11100
agaactgggc gctttgaatt ctctggaggc ttattgtctg actgtttgcc gcaacttagc  11160
gctcgatagg cacgacaaaa aagaagccca aaacctctct ctcgatgcag tatacgaggc  11220
agccgatcgc tcgctttccg ctcaggagca attagagcac gacgaaaagc tacgacgcgt  11280
gcacgaatta ttcaatagct tgcccgaaag gcagagaagt gcaatgcaac tgcgcgacat  11340
cgaggggaaa agttacaagg aagtggccga aacgctcggc ataacggagg ataacgtcaa  11400
aataacgctc ttccgcgccc gccaagccat caaaaaacaa tatctaaaag aagaaagtta  11460
tggattataa gtacatcgaa cagctcttgg agcgctattg ggaggcgcaa accacggagg  11520
ccgaggaagc tatcctgaag actttctttg cacagcccga tgtgcccgct gctttggagc  11580
gctatcgtcc gcttttcgct tacgaagaag cgcagcagtc agtcggtttg ggcgccgatt  11640
tcgatgagcg cttgctgaaa ctcattgcgg agcctaccaa ggccgacgag ccgatgcagc  11700
agatgcaaaa gccatcgccc agattaagag taaaagcccg tcgcgtcaat ggcggcatca  11760
gtttccgccc gttctttcaa gctgcagccg cagtggccat cgtcgtgttg gtaggtatcg  11820
gcgcgcagaa gtcgtttaat cgcgataagg aggcttggga ttacaacccc aacaattata  11880
gcgacactta caacaatccg gcgcaggcct accacgtagt agaaagcggc ttgaatatgt  11940
ttcagcgcac cgcctccgcc gattcgacca aggagcaatc gcccgaggtg gaaaaagatc  12000
cgatagtcaa tgaggaatag aatactactg ctgatttgcg gcctgttgat gtgcatcgcg  12060
gcccaagcgc aggtcgaaac ggacttcgct tcaaactact tgaagctgta tgcgacaaac  12120
```

-continued

```
acttcgctct actgcacgac cgtcagcccg acgatgatca accgaatgct ctcgatgaag  12180
accttgccca aggatcggca ggctcagcaa gcgctgcaat gcatcaagag tgtgcgcatc  12240
gtctccaata ataacgctaa cgagacgtcg ggcttgtttg acaaagccaa aagcctgctt  12300
cagcagaaca gcgatcgctt tgcacactac aacgactacg acggcaagac gatttacgtg  12360
cgccgaaagg gcgacacaat tgtagaggcc gtgctgctga caaagactga ggggtgcttg  12420
tacgtagtcg acgtcaccgg caatatgact gaagccgtca tcaaaagctt aataaattcg  12480
taaaacaaga tacaaacact ggtcgatccg catccggcgg agaatataca aaacatcact  12540
gctctattaa aacatcagaa tgagaatgtg ccgcaggcat ttctctccca cgtatccggc  12600
gggatcagaa tagcgggaag ttgacaacga aagttgcgct tcccgttttt cgtacccttt  12660
cgggaaggaa tccgtccttg ccctgcgtcg ctcggctcga ctggctgctc accgtggtca  12720
actgtgggag gacaatgatg attttctgaa atacaaggct ttgccgcgcc gactgctaac  12780
ggtataatga gggctgcaat gcttgacgtt tgcccgacaa aagtcggatt tttttacta   12840
ttgatcgacg ctttttgcac aaggtcctga ctacgtgtgg gcccgcacgg ctttctttga  12900
ggctttcagc tctcttgcag cttttgctat cgtgagcgta aaccttttc atcacgagct   12960
gaaacctttt ttctcgtgag cgcaaacctt ttttatcacg agagcaaggt cgcgaaggcg  13020
aaaggagtgc atcgcgaatg ccatgccgcg cataaaaaat cggcccccgt tgcctgctaa  13080
atgagagcaa cgcggggccg actttacgtc gggcagcgct caaggggcgc tgagtttttt  13140
atttagagcc atacgtggcc tgattcgcca tcgctgtcgt cccaaataaa tttctgatag  13200
tcggtcaaag cctccgtcca agtcaggtta aaggccttca tgatcgcttg tatgagtgcg  13260
ttgccggctg catcgtagtt gttttcgggc actttgctta catccgtgct gctttcaagt  13320
ccgtcaatgt attcttcgcg acttgcgtaa acgacgatgg gcacggtgac gttaatatcc  13380
gaagtgccga aagcctggct gtaagccgag cgcttgtaga atgggtcgaa gtcgctcgca  13440
gccggatctt tcttgccttt gaatgcgtgc cagagctgta tgcgcaggtc aaactttacg  13500
cgattcttta agaaacgcac cgcgcctttg agtcctatcg gattggagcg gcccgtaatt  13560
ttcgcttcgc cgctgtggtg cgttttatcc caaggcgttg tgtccgtata tttatagtca  13620
atgtagttcg tagtctgagt gccgtcggcc aaagctgcgc cggtcatcaa ctcagttgcg  13680
ttggaggtgg tgaaataatg ctgatgcagg ctatcctgtc cgccttctat gaactgattg  13740
ttcataagtt ttcccttctt atcataatat ttgatgaaca aaagatagac gggggccggc  13800
gtaaaattgc tgccggtata gtaattggcc gactggcgca cgaagaacga cttctggctg  13860
ccgtcagcat agccccagcc ttttccttcc ttgttctcga aggcgatttc ttgcaccttt  13920
ttcagatact ttgccttagt ttcggggtcc tgatgagcac ctccttccac gtcgatcttg  13980
ttccagtcgg cgtgcatgtg gcattcgtag agttcaatca ccatcttcgt aggatcttcg  14040
tgacccttct ctccgatagg attgacgggc ttgaccggtt cattgctaca agccgtgaaa  14100
gttacggcga aaaagagggc gaacacggtc gccgagatta gtttgattgc attacgtttc  14160
ataattctct gtgtttataa aatgattatt gtatgtggtt ttttgtctaa aagagccagt  14220
tgacctgcaa gcgaacatcg cggcccatat cgtgagcata gtaacgcgag cggttggtgt  14280
actccttgta aagcttatta aagaggttgt cgaccgtgag cgaaaggcgc agcttttgcc  14340
gcccgccgag tgcccattct gcacctgctt cgacgccaaa aagatggtag gccggcggcg  14400
tgaaattaac caaatcgctg gccggattaa agcgccgctg ttttgcgaca aagcggtggc  14460
```

-continued

```
gcagactgat ccaaggcgac gtctttcccc acttgatgtc gctcagtccg acttcttgat  14520
ccacgcgcca agagggaatg tagggcaaat aagcccgcgt cttgcgctcg ttggcccaaa  14580
tcagcgacgt ttgcagatgg taatgaagga atttcagagg ccgcaaatcg aaagcagcat  14640
cgaaaccgcg gaaaaatgcg tcggtttgct tgtattggaa aagcggatag gagccggaaa  14700
taaccgttat aaactgatgc gtgggctcgt cgtaaatata accgttgatc cattgtacaa  14760
aagcttcagc tttgaggtca aaaagtttgc tctggtagtc agcagatacg atccatttcg  14820
tgctttgctc cgacttcata ttcgcatctc cgactacgaa cattcccgat cccaactcgt  14880
tgccattact gtagagttcg taaacgtgag gtgcccgcca agccaaacca aggttggacg  14940
tcagcgaaaa agcgttggat ggctgcacgt gaaagcccaa gttgtaggaa agattgctga  15000
atttgtgatc tccggtatag agttttccgg tataatcata gcccgcggcg cgcgtctgtt  15060
ggtgatcgaa gcgcacgccg gcctcaccgc tccaaatgcc cttccgatat ttttggatga  15120
gaaaagcccc cgcgtcgtat tcggtgtagt tggggatgag cgaaaccaca cccgtgcccg  15180
cttcgttctt attgcgaatg tgcaagtacg agatgccggc ctccgattgc cagttggcgt  15240
aatctttagt ccattttagc tggttctgaa acgaagttag cgtcatactt actgcgggaa  15300
tgtgggagag attcattcgt cttacgcgaa attccttgcg aatgtcgttt tgaaaggctg  15360
tctgccagaa gaaatgtccc cactttccac cgtccaaaaa cgcttttccg atggccgtat  15420
ggtgtacgac gcggtgataa ggatagagga tgtggcgcga aaacggcagt atgtacgtcg  15480
ggcgtcccgt ttcgatgcgc tcccgtagta gatcctcgct acccagttgg gaactcatca  15540
tcacgccctc cttatgatcg aagaggctgt acgatgtttc gaggcgcagg gggccgtggc  15600
gatagccgag gttcagactc acgtcttgtt ccctgtagcc cgtgttgttc aggacgtaat  15660
ctgccgtccg cgcatcgccg gaattcagat acgtgccctg cacgcgccac gccaagtcgc  15720
ggagaaaagg catcgaacct tcgattgttg cgaccgcatt gtagcgtagg ccgttcgcgc  15780
ctacgagtcc gctgacacta cctccaatat tcgtctcgcc ataaggcagc ggtttttgtt  15840
ctaagataat gatgccgccg agcgcctccg atccatagcg cacagcctcc gcacctttaa  15900
ccacttggat gcgtgcgctg ctgtttttgt caatctccgg cgcgtgatcg aggccccact  15960
gttgaccggt ctgccgcgcg ccgttgttga tcatcaggat tcgattgcca tacatccctt  16020
gtatgaccgg cttggccgta ctcgtgccgg tctgtatcga actgacgccg cccaccttct  16080
cgagtagcga ggcgagcgat tgacccatag cagaggagat cgtccggctg ttgatttgcg  16140
atgcgacagc gttgaccgag acttcgtttt ttgtacccct aacgaccgct tcgcgcagat  16200
tattggcgta ggggcgcaag gcaacgatgc gctggccgcc gctcagcgtc agatcctgcc  16260
aatggagggc ctgcgtcgta taaccgaggg ccgatatttt taagatttcc tgtcggcgcg  16320
gcactgacgg gagttggata aggccggttg aatctgccgt aaacgtggac tgcgcatagg  16380
ataaaagggc gtcttgaatc ggttgacgcg tttcgctgtc aagaaccagt atggccggct  16440
ttgacgtagt gcgaaaattg tcggactgct gtgcaagcac gttttgtgct gccatcaaac  16500
agattaacaa taggccccga aagtagtgaa acttatgagg gttcatctgt aaaaagtaag  16560
ataaaataaa tgattacaaa gtttgcttcc tatcgacaag tgccgataag ggggattctg  16620
cccgcttgca aaggacttcc gtctgctgcc aacgcaatat ttgattcgcg cgtttggaaa  16680
cggccggcgc atcgtagctt ttaggcctta caagccccgc accgcaaaga gcgacaaggc  16740
tgcaagacgg caagaaagca gaataaactt agaataaggg tggagaattg gtgtttaccg  16800
acaagatttg gcggtaaacc gtctgcatca caaagacaaa acgtttgagc ggtatcgatg  16860
```

-continued

```
tgagtggctt tacaaaaacc gtaggtttga aagccgtagc tttctgaaag acaaaatcgc  16920
agacaacgca ggatgcttta atcgtagctc ccgttgtttg ctgcattttg ccgagattgt  16980
cggcgtgaaa gtctgccgtg tggtagtgcg cccctttaag tgtgagcata aaagcgaatg  17040
tcagcaataa catccacgcg taaattcgcc ttatgtgctc tctctttctc attttccttc  17100
aagattagac ttagaagggc tgtaaaaacg gcctaagatg gccttaattc ggaggcaaag  17160
atatagtttt cgtccgaaca ggccattgtc tttgctcgtt attttatact atttaacaga  17220
gaataattga gaaaagggcg agatgggttt aattcgcaat atttatgagc cgattcctgc  17280
gccacagttt cggccttgtc ggccgcttgg gtgcaaatgg gtttttcaaa gttttgtcac  17340
tgtttggtaa ggggactacg ttcgcggcgc gaggtgggcg ttttgttgtt ttgtgctcat  17400
tatatgctga taatgtatcg atatttaagc agtagacttt tatttcgatt cgcacaacac  17460
gtgatggcag cgtttttttt cgtgagaaca aaggtgtacg ctcgcgatga aaaggtctta  17520
cgctcgtgat ggtacactgc gatgatggga atatatcagt ttgtaatgcg aagttttgtg  17580
caactaaaag aggattttcg gtttcgttcg tgcgttggtc tcgtcctgtt tccgtttgcg  17640
gacgttttga aagaccaacc ctaaggggtt gctcaagggt ggggcgcttt aggcagggtt  17700
aaaccgcttc gcattttaac cctgccctgc caaaagacta accccgatgg ggttatttgc  17760
ggcggactga aagggaggta tgaattgtgc ggagcagaga tcatgtttat aaggggtatt  17820
tgctgtggtg ggtaagggct atgggattgc gcggaatata gattgagttt gttgggattg  17880
taataagcgg tgaaacattg gttgttcgat ttaggcggaa gcggtgaaaa tttcattgag  17940
gaatttgagt tgcgaaacgt attgcattca atctaattga taaaaagtcc tatcggtaat  18000
tcaaattata caatgatgga gcgtgcataa ttggcccccg atgctacaaa tagcgacgac  18060
aaccccttag ggttggtctt tcactgtggc agggttgagg agcgtagcgg taaccctacc  18120
actaacgact gaaagtcgtt gttgttgccg attgttattt ggatgttgct cgatgcgttt  18180
tgggtattgg acgtttttta aagaccaacc ctaaggggtt gtcaatcgcg ggggacgtta  18240
ggcagggtta agctgcttcg cattttaacc ctgccctgcc aaaagactaa ccccgatggg  18300
gttatttgag gcggaattgg ttggcaatgg gaggtgcgta ttaacatccg aaactatgga  18360
attgtaattg tgaggtttta tgggatattt tgtagattga aggaagtgag atttgtttgg  18420
aatgattagt aggtcaaatc aaatgtgcat ttatacaatg acagggtagg cataatttga  18480
ccccgatact acaaatcgca acgacaaccc cttagggttg gtctttgggc aggccagggt  18540
taaggcacag cgtaccttaa ccctggataa gcaggcatac atagtgtgca accccttagg  18600
gttggtcttt cactgtggca gggttgagga gcagagcggc aacccggcca ctaacgacgt  18660
gagtcgttgc tcttgtcggt tattatttgg agagtatctg ttgcgttccg aacatcggat  18720
gttttttaaa gaccaaccct aaggggttgt cgatcgcgcg tgacgttagg cagggttaaa  18780
ccgcttcgca ttttaaccct gccctgccaa aagactaacc cctatggggt tatttctggc  18840
ggaatggctt tagagatggg aggtgcgtat aaatacccga agccatggta ttgtatttgt  18900
gaagtttgat gggacatttt gtaggttgaa ggatgggggg attgtttgca atgattagaa  18960
ggtcagatgc aatgtgtatt tatttattga tagtgagcac acaattcgac cccgatgcaa  19020
caattagcga ccacaacccc ttagtgttgg tctttcatcg tcgcagggtt gacgagcgta  19080
tattattgtg tgaggctccg tggtgtgttg gttaggtatg atggaggtat tttgccgtgg  19140
aggcgtgttt tatgtgtttg taaccattcg taatcgatgt ctggtggcgc aatagatgat  19200
```

-continued

```
gcggccgatc tgcgcttaga cgggcaggat acaaaaacgg cagtcgcccg atttgttttg  19260
cgacaaacgg ggcaactgcg tgtagggaga tacgaaaaat cggacgcaag caggttgcgt  19320
ccgatctata aagtttaggg cttaagccaa acgcttttcg agacgttgac gaatagcctt  19380
gatgaagttc tctgagttaa cagcagtcgg cgtgatgcct tccatcaagt taacgaggtc  19440
cttcgttacg ataccttcgt tgagcgtatc gaagcaagct gcttcaagct cgtcagcata  19500
tttaaccaac tcggggaggt tgtcgagctc accacgcttg cggaatgcgc cgctccaagc  19560
gaagatagta gccatcgggt tggtagaagt ttcttcaccg gcgaggtgct tgtagtagtg  19620
gcgcgttacg gtgccgtgag cagcttcgta ttcgtatttt ccgtccggac taacgagtac  19680
gctggtcatc atagcgagag agccgaatgc ggtagatacc atgtcgctca tcacgtcgcc  19740
atcatagttc ttacaagccc agatgtagcc acccttgctg cggattacgc gtgcaacagc  19800
gtcgtcgatc aaggtgtaga agtattccaa gccgcgcttg tcgaattctt ctttgtactc  19860
ttggaatact tcttcgaaga cgatgcggaa ttgtgcgtcg tacttcttag aaatagtatc  19920
cttcgtagag aaccaaaggt cttggttggt atctaaagca tacttgaagc aagagtgtgc  19980
gaaagagcgg attgatttat ccgtgttgtg cataccctgg atgataccgg ggcctttgaa  20040
ttcgtggata acgacttctt ctttcttgcc gcttttgcct tcgaatacga gcttagctgt  20100
gccttcttct tcgttacgga tttctacgcc tttataaacg tcgccatatg cgtgacgagc  20160
gatcgtgatc ggcttctccc agctcttcac tgcaggcttg atagaaggga tcgtgatggg  20220
cgcacggaat acagtaccgt cgagcattga acggatagtt ccgttaggac tcttccacat  20280
ttcatggagt ttgtattcgt ccatacgctg gtggttcggc gtgatggtag cgcactttac  20340
agctacgccg tacttcttcg ttgcttcagc agaatcaaaa gttacttggt cgcgcgtttc  20400
atcgcggtga ggcaaaccta agtcgtagta ttctgctttg aggtcaacga aaggaaggat  20460
cagttcgtcc ttgatcatct tccagagaat tctcgtcatt tcatcaccat ccatctctac  20520
caatggagtg gtcatctgaa ttttttttcat aatgaatgct tatgggttaa attgataaag  20580
ttatttcttg cgttgtgctg cgtagtaatt catcagacag ccttgcgcca agatgtcgcg  20640
ctcgtcggcc gtcaggttgg tgaagaagag gtggatgggg tgtacgcctt cagccgtgat  20700
gacttgtgca tcgatttctt ctttacctgc gaggattgct tcgcggatgc cgggaataaa  20760
taccatatcg cctgctttgt aatcaaacgg cgtttcctta gcgatcgtga acggcacgat  20820
accccaattg atacagttgc tgcggtagcg cttcgtagcg tattcgtagc agatgttagc  20880
gtcgccacct aatactttct ggcaagaagc tgcttgctcg cgtgctgaac catcgccggg  20940
gcggttagca aatacgcaag agccgaacga agtgttgtcg gcagaagcgc ctactttctt  21000
caatgcttcg agaacgtggg cgggcgtctt gcctgcgcgg cgctcgagat cttcgctttg  21060
gatgcgcttg ctcaatccta cgtactcggg tacgcggcga gagagggcga actcagaaag  21120
tttgagtggg ttggagcggt agcttgacgt ttcgccggag gggatcaact cgtcggtcgt  21180
agtaacgggg tcgtggataa cggctgccaa ctctacgagc atattttctg ccatcggata  21240
catcttaggc cagtccttga tgttaggacc atagcgcaac tcttgctgag cgtctgcctt  21300
gccgaagccg ttgtagatac ggtgttcgta aacagtagga tcgaaagcgt aaggcttgta  21360
gtcgttggtg tattcaacgt cagtagctgc tgtgattacg ccgccattag ctgccgttgc  21420
tgcgatagag cgtgcgtcca tcaatgccac gagcgagatc tggccttggc cgggtttaga  21480
accttcgcgg ttggggaagt tacgcgtcgt gtggcgaata ctgaagccgt tgttggacgg  21540
aacgtcgcct gcaccgaagc aaggaccgca gaatgcgggc ttgatgataa cgcctgcttc  21600
```

gagcaatact tctgcaatgt ggttacgagt cgtagcgagg taaacgggca ctgattgggg 21660
atatgcagac atggtgaagt agtcgttgcc gactgacttg ccgcgcataa tagctgctgc 21720
ttcagcaagg ttatcgtacg taccgccggc gcaacctgca atgatacctt ggtcggctac 21780
catcttgccg ttcttcactt tgctaacgag gtcgatttgt actttatcgc catagcgctt 21840
gtgggtatct tcttctacgg cgcgtaagac agcctcgggg ttggcttgga gctcgtgaat 21900
agatacggcg ttggaggggt gataaggcaa tgcgatcatt gattcttgct tcgagaggtc 21960
gatgcgaatc attgagtcgt aatatgctac gtcgcccgga cgcaattctt tgtagaactc 22020
accgcgacgg tgtgtgtcgt agtgcttctt aacttcttcg tctgtgatcc agatagaaga 22080
gaggcaagtc gtctcggtcg tcataatgtc gataccgtta cggaagtcga tcggcagatt 22140
cttcacgccg gggcctgcaa attcgagcac tttgtttttc acaaagccgt tttcaaacac 22200
agcctttacc aaagagatgg ctacgtcgtg aggacctaca cccttgcggg gagcgccttc 22260
gagccaaacc aaaactactt cgggtgcgtt gatatcccaa gtgttgcaaa gcaactgctt 22320
cacgagttcg ccgccgcctt cgccgacgcc catattaccg agcgatccgt agcgcgtgtg 22380
gctgtcagaa cctaaaatca tattgccgca cttcaccatt gcttcgcgtg caaactggtg 22440
gataacggca acgttagcgg gaacgtagat accgccatac ttcttcgctg cagaaaggcc 22500
gaagatatgg tcgtcttcat tgatcgtacc acctacggcg cacaaagagt tgtggcagtt 22560
ggtcatcgcg taagggaggg ggaatttctc caaaccgctg gcgcgcgccg tctgtatgat 22620
accgacgtaa gtgatgtcgt gggacatcat tgcgtcgaac ttaatgcgca ttttattacc 22680
cttacttcca tctacatcgt gtgcacgcag gatgttgtaa gtgatggtgt tttcccttgc 22740
ttcatcgggt gtgggaagac cctttgcgtc tttcgcaaat tcagaaccgt tgagtagata 22800
aactccttct ttaattagtt ctaccatgat agtaatttga aatattatgt tgatttagga 22860
taatatcgcg ttgagcagaa aggtgagtga aagtatatca gcactgccgc ccggagagat 22920
attttctttg atatatcgct gattgagctt gattagagca gcctcggaga agttgctcag 22980
caacgttcgg gcttcttctt tgacctggga cgctatttgc gctcccttgc ggtggagtac 23040
attggtatcg tcgagtgtgg tcattatata taatagggtt ttatgggctg caaaagtgtc 23100
gccctttaat tgtcgtaggt aaggtagcca gttgtcgaaa aggtcgggat agccggcagc 23160
tgcttgggct aatgcgcccc caacgttata ctgtcggcga acggcgtcgc cgtgtgtgcc 23220
tttcggggcg gggaagtcgg aagctaaacg gcagatggcc gtgcgcaggg gctgctcttg 23280
aatgacacca tgtatataat aattgtgtgc ggccgcaatc agcacgagcc ccatggcaaa 23340
gagggcgcct ttgtgtgtgt tgacgttgtt tgtggccaaa agcatttcac gctcggcttc 23400
caagcccaag cggcgcatct cttcagacgt gggcaacttt tcttgatacc ccagctgagc 23460
aagtgctacg aaatgaggat ggagcgcgtg aatgcttcta cacattaagt tgtagtccat 23520
atcttggtga gcaccggcat caatttgatc aactaaacca ggcttcggac ttgtatccaa 23580
ttcgctttgt agagccattg ttgccagttt ggccagcagg taaggaattg tggtaggata 23640
aactttcggc gctgcttcgg aaaatttccc ttcggctaaa gcagttcgca ccgctgaggc 23700
actaatcgct cgatctcctt cgcttaatcg cgccatttct acgacagaaa tgccctcaag 23760
cgggagaatc tcgtgcatca gttcgttgta gcgttgcgtc attgcgtcaa gcggctcact 23820
gcccacaaag cggatcttcg ctcctaaagc gggcgctata cgctttgcgc acagattaag 23880
atctaagctc atctgcgttg cagcggcttc attaagtttt ttgaggaaat aagtggggaa 23940

```
cgttgccgcg gaaatgctat aatcgctgcc ttcgcaaacg ataacgttcc ctatgttgcg  24000
acaacccgct tcgagcatag ccttgcgctc ggtgtaagag aattcggagc gatcctcttt  24060
gacgggaata acaaagagcg tgtcgacttg gcgcgctgct tgggtaatga ggaaatgatg  24120
tccgcatgta aacgggttgg cattcatcac gatgaggcct gacgtgcctt cgcgtcgaag  24180
gctctttaga tagcgctcat acgtaagcca accgctcaag ccgttctcga gtaaaacagc  24240
tttgggagct tcggccagca aatggaagcc gaggctctca aagatctttt gattagaagg  24300
cttggtaaag actttaaccg cctcatattg cctgctcatc gcaatactca tcagatgcga  24360
cacgagcgta gcgctaatgc cttcgtccct caaagtatcg ctcacggcaa tacatttaat  24420
aatgtctttg tccaatccgc ctccggcaag aatctgatcg tcgccaactg ctgtcactac  24480
ggcataatag tccaacgcat ccaagcgcag cccgttggca gcgaggaaag ccgtaacgcg  24540
ctcgcggttt gtgcgaacgg ttaaagggta actttgtatt tcaaagtcgt tggacatagt  24600
ctgcgacaag ttggtctata cgtttgtgta tttcttcttg cgtatggctg tgattacgca  24660
tacaatagcg tgcatctcga tcgcaaagta ggcagcgacg gggagctctt ccgatcgtct  24720
tgcgcgaggc gggtgctccg tccttttgaa taacatctac atcaaacaat cgtccgagcg  24780
gatgctgttc ttctacattg caagctatcg tcttcgcttc gggaatcgag agggagacca  24840
gcagataagc ttcgtagccg gtttccaaat caagttcttc catctgaagg agacgctcgc  24900
caaaagccgt tcgcacagct tcgacggcag ctcgcgctac aatgagagat tgggaattac  24960
gcttcacatt tcccggcata atgaccgtca ggcacacaag cgtcgctaaa gggttttcct  25020
gcagcaatgc ttgctgtttt gcccatctat tttcgcggct ggccagaagt tggtcaagcg  25080
taactcccat aaaggataac tttatccctg tatattgcgg atcacgtcga gtaccgtgtt  25140
gtcacgatac atcacaacgc caaccacttt ttcgccaaac ggcaattctg cgggttggcc  25200
aatgatcttt tctgcgcgtt ctttcaaatc gttcaaatca acaatcttca agccggcagc  25260
gcgaaggcgt tctgccactt ccggacggcg cggattaaca gcgatgccgt attccgttac  25320
gacaacgtca accgtagcac ccggcgtaat caatgtcgtc accttatcta ctacgcacgg  25380
gattctttcg cggagcaagg ggcatacaat aatagaaaga gcagaatctg cagccgtatc  25440
agggtggcca ccgattgcac cacggatgat accatcgcta cctacaagca cgttcacatt  25500
aaagtcaacg tctacctcca aagcagagag gatcacgata tccaaatagt gcgttgcaga  25560
gccttgctcg tcagctgcgg catattcaga agccgaaact tccttgtgga attcattgtt  25620
cttcactgat tcagcagcaa ccttgtcgaa agattgcaca tcgatcaagc gcttaatgag  25680
tccttcttcg tgcatcttaa ccatatgagc cgtgatacca ccgagcgcat agttggcttt  25740
gatgcctttt tcgatcatac tttcgcggat aaacttcact gcagccaaag atgcaccgcc  25800
ggaacccgtc tggatagaga agccatcttt aaagtaacca ctattgatga tcaccttcgc  25860
tgcctgttgt gccaaaagaa tgtcgcgtgg gttcttcgtg tcgcgaatag cgccggaagc  25920
gatctttgaa gaatcgccca ctgattctac ctctacaacg aagtctacct tatgttctga  25980
aatagaatta ggcgtgttcg gatagtctac gaggtcatcc gttatgatta caaccttatc  26040
tgcatattca gcatcaggaa gagcatagcc gagtgaaccg caaatagatt tcggattctc  26100
agagcgagaa tagccggcag catttcccaa cgggtcgcaa gaagaagcgc cgaggaaagc  26160
cacgtcgata tgcaagtcgc cgcgtttgat ggcacttgcg cgatcgccgt gagagcggaa  26220
tacaacaggc tcatccatca agccgtgtga aatctcattg gccaattcgc cgcgaagacc  26280
tgaagtcgac aagcgattga ctacgccgtt gcgaatatgt tcgatcaagg gtttgtgtac  26340
```

-continued

```
gtcctgcaaa cttgaagctg cgatgtgcag attcttgaag cccatctcag ccagtttagc  26400
tacgaccatg ttaaccacct tatcgccacc gcggaagtgg tggtggaaag agatcgtcat  26460
cccatctttc aagccgcttt ggcggatagc ttcctccagc gtaacgactt tcgaacaagt  26520
cttttgatat tctaagcgag gcgtgccgac tttcttaaga tcatcaacaa atgttttttt  26580
gcccactttg gcagctgccg cctcgatcat agcagctctg tcgtttatct tattcattgt  26640
aaatcctcct tagaaattat gcctgacgcg agggccaagt cgatagtacg ttgtgctctg  26700
attactacag ggcggtccac cattttaccg tttacggcaa ttacgccgct accgcgcttt  26760
tcagcttctt taatggcagc aataatcgtt ttagccttct caatggcttt ctccgtcgga  26820
gcaaatactt cgttgacgat ctcaatctgg cgaggattga tgattgactt accgtcgaag  26880
cccaattgct tgatcagctc tacctccttg cggaaagttt ccatatcgtt caagttagag  26940
tagaccgtat caagcgcgtc gatgccggct gcgcgtgcag ctacgacaat ttgttggcga  27000
gcgaagagca actccgttcc ttccggcgag cgttgcgtct tcaagtttgc gcagtagtct  27060
tctgcgccaa gagctatgcc catcatacgt tcagaagcca cggcgatttc gtaagcgttg  27120
acaatgccga gcgtactttc aatggcagcc ataatttttg tgcggccgag gcagccgatt  27180
tctttctcta cgcgctctat ttcgcgttct acctcgcgca cctcttcagc tgtttccgtt  27240
ttcggcatac gaatcacgtg gacgccggct tttacgacag cctcaacgtc tttctttcca  27300
taagccgtat tgagtgggtt gatacgcaca accatttccg tgttgccgta atcgattgtt  27360
ttcagtgcat tgtgtactaa caggcgagcc gcatcttttt cggccatcgt aaccgagtct  27420
tcaaggtcca gcatgattga atcagggccg tagataaaag catcctgcat cattcccgga  27480
ttgtttcccg ggacgaacat catagttctt cttagtcgtt gcatagtatt ccttctaata  27540
gatgttttgt tttcggcatt aagcccatac gtccttgccc gtagcgcgaa cggcagctgc  27600
cgtcactcga gcacgaattg tgcaatccaa ggcccctttg tctgttgctt taaccagtgc  27660
gttgtctacg cccaagtcgg taagcgtctc tgtgattact tttttaattt gctccccgaa  27720
ttggaaagcg acgctgcttt ccagatcaac ctgcagcgtt cctgtttctg aaggtgcgat  27780
ctgaatcaga atatctcccg attcgagcgt acctgcgaaa gcattttttta tatccataat  27840
attttacctg ttaaggatta actgtgtatt cgtcgtaata acggtacaaa tatgcagcct  27900
tttttttatt tgcacaaacc attcttcaaa atattttgtt gttgccgtta tttagttatg  27960
acaaaatggc aattcttgtt tgcttcaatg catttctttt ttactaaagc catctattcg  28020
aagccagtat tttatctttt ctctatcaaa gtgtctcaaa agattatttt attgccatct  28080
tgcacatttt cgccttttat gtggtatatg gctgttttgt tattcttttt tgctgcttac  28140
catctctttt gaatgtttaa ttttgttgcg tctatcagct gtattctacc gcaagaagtc  28200
atatttataa aattattagt caaacgacgc agcagataag ggcttattca ataaactaca  28260
aggaagctca tttctttcgc atacttctgt aatttttgtc gccattttat taaaacagag  28320
gccttggtgt tgtgctgtga ttggggcgac tttctgcgcg attattccat cttgtcgtag  28380
tgcgctttgg acgtggtttt cataattcac atctcctaaa ataaatcatt caaaggctat  28440
tgtgcaactg aaaatttcgc tcgttcattg tttgctcgga ccaaactatc gtttgctgag  28500
aggaaactat ggtttggtgg cagcaaacga tagtttggcc tcggcaaacc ataaaatgat  28560
aaggtgcgga aagggagaga tgcgccttgc gcgcgcattt gttggcgatt ttaatccttt  28620
gtcggcaaca ggattaaagc ttatacgtcc ttgctcgaag cttattcggc aggcagcgaa  28680
```

-continued

```
gggtatttat gcaaagtttc ctccgtttgc aaacttatgg tctgccatat atataatgtg  28740
tatcggcttt cgatgtttga agcggagaat aggaggcgag gcggcgcata cttacactaa  28800
gccggcaagc cgctgcgata aactcgcgcc gttaaggctt acggatggtt taattcgaga  28860
tttagcagat ttaacgtaat aaccggagca aatggttgct cattctgcgc gaaaatatta  28920
aattagcggc agattcaaaa ccaaaaatcg tcgtacacaa atgaaaaaac agcacaacta  28980
ttgcatcctt cttgccggcg gagtaggcaa gcgtctttgg cctctcagca gaaggaatat  29040
gcctaaacag tttctcgatt tctttggcac gggccggacg ctgatacaac agacttacga  29100
gcgtatggct cggttcatac cgaccgaaaa tatctacatc tcgacatttg ccgactacga  29160
gccgatggtt aaagagcagt tgcctgacgt cagccccgac aatatcttat ccgaacctgt  29220
ccaactttct acggcgcctg ccacggtgtg ggcctcttac cacatttcgt tgcgtgatcc  29280
ggaggccaat attttagtaa cgccctgcga ccagctcatc agcgatgaag ctactttcat  29340
tagcgagatg gaggccggtt tggactttgt ggcgaaccac aatgcgatgc tggcgatggg  29400
cgtaaaggca caatgcgcca attcggccta cggttatatt caaatggggc aagaaaagcg  29460
caaagatctc tttgctgtga agtcgtttac ggaaaagcct gatctcgact acgcgcaaaa  29520
atttgtcgat tcgggagagt ttttgtggaa tacgggcctt tatctctgga atgcaagcac  29580
catcgtgctt accctccata ccttgatgcc cgaaatcgac gccctcatca aaaaagaagg  29640
gcccacgttt tcgcaagaaa gcgagattcg cctcgtccgt cagttctatc cgaccaatta  29700
tcaccgctct attgatctcg tagtcttaga taagtgcgaa aatgtctttg tgcaatcgtg  29760
ccgtttcggc tgggcagata tcggttgttg gccggagttg caccgcgcgg cgtcgaaaga  29820
cgtcgacggc aatgccgttt tgggtcagcc ccaagtcttt ttcgcgggca gtcagggcaa  29880
tcttgtttat cttccggccg aaaagcgcgc cgttattcgc ggtcttgacg gcttcttggt  29940
tgcggagcac ggcgatgtgc tcgtaatttg ccctaacgac gaccacgcct tggtgaaaaa  30000
gctcttcaag gaagccgaaa tcgtcttggg cgaaaaatac gtctgacgcg ctctcccgcc  30060
gctcgagttc gctttcccac cgcagcgact taaatcgccg cggtaggagt tcacgccttt  30120
gccgccagga ctttcctttc ccgccgcctt gttttcggcg caacagttgc acgtgtgcgc  30180
cccgtccgcc ttgtttcaac gcaaaaaaag cgctccgccg cgtgcgatca tcgcacgcgg  30240
cggagcggca tattggtgct tgtgtcgccc tttccccaaa aaagaagccg tataaagcag  30300
ataatctttc gtatgtctgc tttttctgtt ttatctttgt ggcaaaatag cattgagaca  30360
aatatggaaa cgaccagaca gcaaaaaata gagcgattga tccaaaaaga attgagcgat  30420
atgttgcagc gccagacgca gcaagcgccc ggcgtactcg taagtgtgag tcgcgtccgg  30480
atttctccgg atctgagcgt ttgccgcgga tatttgagcg tttttccttc agaaagaggc  30540
gaggaaatcg tggccaacat caacgccaac gtaaagacgg tgcgcttcga actgggtaag  30600
cgcgtgcgcc atcagttgcg catcattccc gagttgaaat tcttcatcga cgattcgctc  30660
gattatatcg agcacatcga cgaattgctc aagcaataaa cctgtgcgcc acgcattatg  30720
aatttcccct tctttatcgc ccgccgttat cttttttcta aaaagagaca caacgccatc  30780
aacatcattt cgagcatcgc cgtcggaggt gtggcgctcg ccacgatggc tatggtttgc  30840
gtactctcgg gtttcaacgg cttccacgac ttaatcggcg gcttgtttac gacgattgat  30900
ccgcagcttg aggtcgtgcc caccaagggg aaggtggcgg cggccgacga tccgcatttg  30960
gatgcgattc gtgaggatcc cgctgtggcc gccttttcgg ccacgctcaa cgatgatgcc  31020
ctgattctct tcaaagggcg tccgacggtc attcgcctaa aaggcatcga tgagcgctat  31080
```

gctgacgtga ccggcattcg gcagatcctc tacggcaagg gagattttga acttcaacgc 31140
gctaatctta attacggcat ccccggtttc ggtctggcca attcgcttgg cggtctccag 31200
tttggcgagg tagaaatatg cgtcccgcgc aagggtgagc aaatcaacct gctgaatccc 31260
gccgagaata ttaacgtcgg caccccttcag agttcgaacc tctgcttcca agtttaccag 31320
tcaaaatacg acaacaatta catgctttgt cccctctcct ttgcgcaaga tctgtttgag 31380
aagcaaggct gtatctccgc tttggaactc aaattaaagt cggacgctga cgaggctgat 31440
gtcaaagagc gactgcaaaa gttggccggc cctacgttca aagtaatgga ccgctacgaa 31500
caacaagagg gcactttcaa tgtgatgaaa atcgagaaac tctttgcctt cttcttcctg 31560
actttcattg ccctcgtggc ctgcttcaat atcatcggca gtctctcgat gctcattatc 31620
gacaagcgcg atgacgtgga caccccttcgc catcttggcg caacggataa agatatttta 31680
cgcatcttcc tttttgaggg ccgactcatt acggcgcttg gcgcgatcat cggcctgctt 31740
ttaggcctgt tactctgttt tttacagcaa gaatacggct tgctgcgcct cgggacaacg 31800
gccggtagct ttatcgtcga tgcctatccc gtcagcgtgc gcgctgaaga catcttggtc 31860
atctttgtca ccgtcatcgt cgtaggtttt ctttccgtgc gctatcctgt aagttacctt 31920
ggcaagcgtt tgcttcgcaa tgggcaaacg tcttaaagac aacggactaa caactgatcc 31980
ttatatcctg ttttctgcgt aaaacggcac tgatcgtagc cgctttactt tttgctgctg 32040
tatgcttccg cccttttttct tctcgattta gtttggcaga aagagccgca aggcttatgc 32100
tttatcggcc tgtctgtcga ttttggagaa actttcaccc attaaaaaac gcgcaaagcc 32160
ggtcggcgat gggccgctat cccgattttt acctttacgc tcacgataaa aagcacttac 32220
gctcgtgagc gcagaccttt ttcatcacga gcgcacacct tttttatcac gatgaaaaac 32280
ctcagacgtg ggaacgaggc ggccgatcgt gcagtggggc gaaagacctt ttcgattgtg 32340
cgtggataca taatgcgtgc tactgactcc ccaaaaagaa agccgtaacg gcctgcgaag 32400
catccggcgc gcggggcgga cattgcgcaa aacgtccggc gataggcgga agcagcgtgg 32460
agaggtccgc gcggcccgat ggcgcttgca gggcgcgaaa taggccggcc gatagccaag 32520
atacaaaaaa ctccgcgccc gcccaaagag aatgggcaag cgcggaggca tcaatataat 32580
gaaaaagaaa ttgcttaatc ttcgatcaag tcgtggccgg tcatttcctt gggctgcggc 32640
aggccaagta tgtgcaagat gctcggcgct acatcggcca agacgccatc tttcaccttc 32700
gcacccttat ttgccgtgac gtaaatgaaa ggcacggggt tgagcgagtg agccgtattg 32760
ggcgagccgt ccggattgat tgcgttgtcg gcgttgccgt ggtcagcgat gataatcgtc 32820
tcgtagtcgg tttcgttggc agccgtcacg acctcattca cgcattggtc gatggctatc 32880
acggccttct cgattgcttc gtagacgccc gtgtgaccga ccatatcgcc gttggcaaaa 32940
ttgacaacga tgaagtcgta tttgtttgtg cgaatggctt cgacgagctt atcttttacc 33000
tcgaaagcac tcatttcggg cttcaaatcg taggttgcta ctttcggaga ggctacgagt 33060
atgcggtctt caccttcata gggcgtttcg cgtccgccat tgaagaagaa cgtgacgtgg 33120
gcatatttct ccgtctcggc cgtgtggagc tgcttcaagc cctggttgct cagatattcg 33180
ccgagcgtat tttgtacgtt ctctttgggg aagagaatgt ggacgccttt gaacgatgcg 33240
tcgtagggcg tcatgcaata aaattgcagt cccggtatgg tttgcatacc ttcttcgggc 33300
atatcttgct gcgtgaggac ggtggtcaac tccttggcgc ggtcgttgcg ataattgaag 33360
aaaataacga catcgttggg cttgatacgc ccatcgactt tggcgttaac caagggctcc 33420

```
ataaactcat ccgtgtcctt gttttcctcc gtcgagcggt cgtagcagcc ttgcacagct  33480

gccaccatat ccgtttcctg acgtccttcg ccgttgacga ggttgtcgta agcaatcttc  33540

aatcggttcc agcgcttatc gcggtccatc gcgtagaaac ggccgatgat cgtagccacg  33600

tgtgcgccct gcttgtcgca ttccttttcg agtttttcaa taaagccttt gccgctgcgc  33660

ggatccgtat cgcggccgtc cataaagcag tggacgtaag ttttatcacc gacgccgtaa  33720

gtgccggcta tgtcgatgag cttgaataag tgggacaatt cggaatgcac accgccgtta  33780

gagacgagtc ccataatatg tagt                                          33804
```

<210> SEQ ID NO 6
<211> LENGTH: 45166
<212> TYPE: DNA
<213> ORGANISM: Homo sapiens

<400> SEQUENCE: 6

```
tcgtatgttg tgtggaattg tgagcggata acaatttcac acaggaaaca gctatgacca     60

tgattacgcc aagctattta ggtgagacta tagaatactc aagcttgcat gcctgcaggt    120

cgactctaga ggatcccacg tagatcatgg accataagtc acagttcaat tctgcaacag    180

tgaaaaattg taattttttt tcaccagaat ggaaaagaaa agctatgagc tctagaatat    240

aactcaacaa gaaacgtcag tttaatcaca ccagtcttcc agacatgatt cagtccaccc    300

agtctcacga gcttgtctgc tccaagcaac actggcacgg tttccctttg gcagacagat    360

atatggggtt cccactgatg gtttgtactg tcctttagta cttgacgaat cattgcgatt    420

ggctgtggct tctttctttt ttataatttt ttttttaatt ttactttaag ttccgggata    480

catgtgcaga atgtgcaggt ttgttatgta ggtatacatg tgccatggtg gtttgctgca    540

cctatcagcc tgtcatctag gttttaagcc ctgcatgcat taggtatttg tcctaatgtt    600

ctctctcccc tttccccacc cccaaccccc aagaggtccc ggtgtgtgtt gttcctctcc    660

gtgtccctat gttctcattg ttcagttccc acttgtaagt gagaacatgc ggtgtttggt    720

tttctgttcc tgtgttagtt tgctgagaat gatggcttcc agcttcattg atgtccctgc    780

aaaggacatg atcttattct tttttatggc tgcatagtat tccatggtgt atatgtgtgg    840

ctgtggctat gtgtgtgtgt gtatgtatat gtatagttgt acatatctgt gtaggtggtt    900

gtgcacacac acacacacaa attattcagt ctctctggat ctcataacac tcctcccaaa    960

gctctacata tttattttta atgctggtat tcatggaggt atcatgaaat aaaatacaca   1020

tgttgtagca tgcagtccca tgagatacga acatgcagac acctgtgacg ccactcctgc   1080

cagtcaagat ccagagcttt tccctcttcc cagaaagttc ctcatgccct ttccagccag   1140

cacccacccc ccacagagac aactgctctc ctggcttcta ccaccataga ttagttttgc   1200

ctgttctaga aatgcattta aaaataattg catagtgtgc actcttcggt gcccagtttc   1260

tttcattcaa cataatattt ttgagattca tccatttttt tttgtggttt gctcttacag   1320

actatttgtg ttcctccaaa atgcatgtgt tgaagccctg tgtgatggta ttaggagatg   1380

gggttttgaa agggaattcg ggttagagga agtcacgagg gaggggctgt tgtaatggaa   1440

ttagtgctct tctaaaaaga gacagcaggc tgggcacagt ggctcaagcc tgtaatccca   1500

gcactttggg aggccaaggc aggtggatca ccagaggtca ggagttcaag agcagcctga   1560

ccaacatggc aaatccccat ctctactaaa aaatacaaaa acttagccag gtatggtggc   1620

atgtgcctgt aatcccagct actcgggagg ctaaggcagg agaatagctt gaacccggga   1680

ggcggaggtt gcagtgatca gagatggtgt cactgcactc cagcgtgagc aactgagtga   1740
```

```
gactctgtct caaaaacaaa aaaaaaggag acagtgaagc gttctctctc ttcctctgga   1800
tgtgcacatg caccagggaa tggccacgtg aggacacaat gcgaaggagg ctgtttgcaa   1860
accaggaagg gggatctcac cagaacctgg ccgtgctggc accctgatct tggattttca   1920
acctccagaa ctgttggaac ataacttgat gtttaagcca ccggtgcatg gtattttgtt   1980
gtggctgccc aaatagatgc atccattggc tctttttat tttcaatcca ttgcattgcc    2040
agaccccact aggatccatt tatttattct cctgttcaca ggcatttgga ttatttccag   2100
tttggggcta tcatgaaaaa aatcctgtta tgaggaatct tgaactcttg gttattcttc   2160
ctccgccccc tcccttctct catgctgcca cctcccttac cggttcagaa ttcaagtctg   2220
ggttctaatg gccagcagca tccagcagag ttgtgcggag ccatgtttca tgtctctttg   2280
gtagtttaat gatgggaatt ctcatgaagg acaaaactca aatgaggaag gggaaattta   2340
cattggcatt caggggtaga acttgtccca tgacacatca tttctagtga attacacacc   2400
cttctgcacg gccagttctt atgctgtgga gtcaattaga cgatgcagca ggccctggct   2460
gcttcatggt ggatgatgga gctggctgag aacactgggc cctggggagc aggaagcagg   2520
accattttgg gaaaccttag aatggagaag agtttttagg atacaactct ggaagagaac   2580
tggcctcagt ccacggagca gggtgcagct caggcatgac aggaacatgt gctgggaccc   2640
cagcccagga ccctgcctcc aacgcacctc ctctccatgg ggcactgtct gcttttctca   2700
ctcctacatc agccactcgc tctcggtggc ctccagccac tgtttccttc agaggaagtt   2760
agtaaaaggc acatcctgcc attgttaaac ctctttatcc actgtgctgc tgacacactt   2820
tgtctgaggc tctgtgcaaa gaggtctcat cctatcctga gacgcaggtg tgtacgaggc   2880
tgtcagccct aggaaggcag caatcccacc atccttacac cacacctcaa tgggaaagaa   2940
cctcagccag ggtctccttg attaaaccca attctattct cctgccagtg caggtccctt   3000
gagtcctagc cctctgccct gtctgccctc cagcatcggt ggcgctcgtg gtcttcagag   3060
ctctgatcca ctgttctccc tgctttcctt atgtctgccc aggttggctg aactccattc   3120
taggctgttt caactctacc cttggcctcc cagctgacag gtgcacggtg gccatccttt   3180
ggcatttcca ctctggcact cgctaatgat gaaactgaat acccaagagc tctccttcag   3240
ccacacatag gacagctaga ggtgaccagg agttgccact ctcaggagcc accctcagcc   3300
aatggcaaat gcaaggagga gaataaacac cccagctcct ttgacactag gggcagctc    3360
agaggcatga cccgcgccac ctggccagtt ttcccagctg cccgcaggga tgtcctgctc   3420
cttgatggac gctgtatggg ctgcctccca ttcctttgcc cctgccttca cccccaccac   3480
tacctcctgg gacccaatta cacccagacc ctggtcccca gggctgcttc tgggagcgtg   3540
cagctgaagg cagcagttaa gagccctgct tgaaactttg accttcggca agatctttaa   3600
accgcagcta cctcatctta gaatggggat gatgacaggg cctaacgata tcttcgaatg   3660
gggatggtga cagggcctaa cgatatcttc gaatggggat ggtgacaggg cctaatgata   3720
tcttagaatg gggatggtga cagggcctaa cgatatctta gaatggggat ggtgacaggg   3780
cctaacgata tgggtgactc tatgtggagc gttactgtgt gctgccactg agtcactgtg   3840
cttaacacaa actatgtcaa ggaatttgag tcaaatactg tcacaatgtc cattctacag   3900
atgaagaaaa ggagatcaag accatcctgg ccaacatggt gaaaccccat ctctactaaa   3960
aatacaaaaa aattagccgg gtgtggtggc gggcgcctgt aatccccagc tacttgagga   4020
ggctgaggca ggagactcgc ttgaacccgg gaggtggagg ttgcagtgag ccgagatcgc   4080
```

gccattgcac tccagcctgg gcaaaaagag tgaaactcca actcaaaaaa aagaaaagaa 4140
aatggaatgc acacacacac aggattagat gacctaccca cagtcactca ggcaggaagt 4200
ggttgagtca gaattaagtg aatgaggatg atgatgatga ccatggcagt gctggtggtg 4260
gtggtggtgg tggaggagga agtggcagct agcaattatt gagggatttc tttgtgccag 4320
gcactgatat gcattttctt gtttaaactt taaaacaatc ccagtacttt gagaggccga 4380
ggcaggcaga tcacctgagg tcaggagttc gagaccagcc tggacaacat ggtgaaaccc 4440
cgtctctact aaaactacaa aaattagcca ggtgtggtgg caggcacctg taaccccagc 4500
tacttgagaa gctgaggcag gaggatcact tgaacccagg aggcagaagt tgcagtgagc 4560
tgagattgca ccactgcact ccagcctggg cgacagagcg agactctgtc tacaaaaaaa 4620
aaaaaaaaaa ccttaaaaac aatcctgaga ggtagttact agtattattc ccattttaca 4680
gagaggagaa tcaaggccct gagatgttaa gttacttggc caaggtccga cagctggtca 4740
gtggagcaaa gaggatttca ctcaggtctg tctgattcca aagccttctt ctcaagatac 4800
tttgcatgca cctctccagc acactcagct gattgtagtt cattttatta tcacttttta 4860
aaagtcctgt ttccctgcct gacacttcag cttcttttac caactaccct ggatccagac 4920
cttttgtcct ccagaggaaa tagataaaaa ctgtgtctca ttctcctctt gtgaagctgg 4980
tgctgaaaac actgaagttc ccttgatgtg tcccagttag atcctgcatg gaaattcagt 5040
gagtcagagc catgtgtctc ttctagataa aaccatgtca gtttgtgatc tgagaaccac 5100
tcccctcatt tctcaaagga accctgactc ccactcatcc ccacatccca cagctggggg 5160
ctccagctca ctgccgctct taactcctaa gactggggca tatttacagc aatgaggagc 5220
attttcagaa cacagtcgat gaaacgcgca tgttgaagag ctcagcttcc ctttcaagtc 5280
ctcgctgagg ctggtgcaca attttcaaca atcacgagaa atgatgcttt atgctggaca 5340
aagagaatta gacagtgaga cctgcgtctt tgttctcgct ctttctcacc tcgcccctgg 5400
cagtcagaaa caatgcattg taaaaatgct tgtccaattt ttccaacagg atcaatttgc 5460
tgtactttta ttaaaagaaa aaaaggtggg agcattgtca aacatcctcc ctctcctctc 5520
ccttcccctg cctccacctc tcagaatccg tgcccctgcc aggagctgca gtcgctgcag 5580
cccgtgggtc ggacatgaga agccgggagg ctctgcatgc tgagagccgc gtgcagttgg 5640
cacattgctg gaccaggttt caaagacatg cacggtacct cccccgtgta tgtttctacc 5700
ctggctattt aaaggaagtc aaagagggca gcatttgaag tgacagcaac aaagaaaatg 5760
agaaagaaaa aggaggagga ggaggagctg ccatcatccc atccagagat gggatgacat 5820
gttccctttt tctcatgtcc tctaaaaggt ggtagctgta ttggtgaact tctgaaagca 5880
acaagccagc tctcatccca gttttgcctc ccttttgggt ttccctttte tctccttctg 5940 ccaccagtta aacttcaaga aaggtcaaaa agttatttcc ctaaagccaa aaaaaaaaaa 6000
aaaagatctg agcaacacca cgtgccctgc ttctctgttt ctgttcatcc ctttgcagat 6060
gccctggatg gtctctgagc acagtcctgt gggtataggc ttacatcaaa ttactcaaca 6120
cagatattta ccaagtgcct gccaggtgcc cagtgctgtt cccaatgctg gggatatgtc 6180
aatgagcaaa acacgctaaa caaacatccc tgccctcagg aggctgactt tctggtgtcg 6240
ggagaagggg aatcagcaat aagcaagaca tatgacatgt cagatgggga caaatcttag 6300
tggaaaagag agggcagaat aaggggacag ggaacggggc cggccaggaa agattcatgt 6360
ggaggcaaga gagtaagcca tcaggtatct gggggaagaa cattctagac atcaagacac 6420
agggagcagc cagtgcaaag gccctggggc aggagtgtgg gaaatgggaa atggcaagga 6480

```
ggccagagtg tggtaaacac aaacagcacg tggtatgagc agcaatgagt aggagaccag   6540
atgggacaag tgagagtgtt gtgggcacct gtcatggagg gcttgtcagc cactggaagg   6600
gttttggctt ctattctgag tggaattttc tctttacctt gtgaaatgaa tgagaaatta   6660
ccataggagt cagggagggg ctcacgatga gcttcctaaa agtcttccaa agttcctcgt   6720
ggctgatagg ctaaagtaga agtttccagt ttcctccggt acctgctgtt tccctatgta   6780
agcccttagt gctgtgaagt cttccacctc ttctaacagg tcttcttcta ttttcactcc   6840
cttagcaaat tcacccagtc ttgggtattt attgcgtctc cattctaaca actgcccatt   6900
gtaaatacct agtccagact catcttctaa actccaggct cttacagcca actgtctact   6960
cagtgctcta ctgggatttc caataaatat cacacacaca aaatatccaa aactgaactc   7020
atcgtttttc tccacaccca aaacctgccc tgctcacagt gtcttcttct cagaagatgc   7080
tgaccacaga tttccagctg cacaggcctg gtcatcatcc ttcctccttc tcttttgtat   7140
ttttccatgc tccctatgtg atccatcagc aagttctgtt ggctctgcat tcaaaatacc   7200
aatgcactga gcacttctca ccacctcctc tgctgccctg atctgagcca ccattagtga   7260
ttgttgcttt gaaaactata actgcctcct aacagagtta ggagttttta cctacttaga   7320
ccccctcctc aatatagaag ccagaatgtc tcttctctgc tcaaactctc catagctccc   7380
cattccactt ggagtaaaag ctaaagtctc taaatttgct gttcacttag aactttttgc   7440
agtgatagga acgttctaga tgtacactgt ccagtatggt agccactggc cacaggtggc   7500
tactgagcac ttaaaatata actcatgtga ctaaggaact acatttgcaa ttttgtttca   7560
cgttaattaa tttaaatgaa aatagtcaca tgaggcagtg gccgccatat tggacagtgc   7620
aggcctacaa tgcccaacat gagtgggtcc cttcataacg ctttgacctt ttcttttctc   7680
ccctacctct tatagttacc ccacatcacc aacgctgacc tctcactgtt tgttcctcaa   7740
aagcacaggc tctacactct gttgtctgct ccttcttccc ggagggtcct tcttcagcat   7800
gtttaacatc tcacctcctt cagcgcttgc cttttcagtt catcccaacc acgtcccacc   7860
cccatctact cccaacccca ctgttctggc tctacttttt tctttctcac tgcacctctc   7920
cccctctaag aggttacata atctacttat tcgttaggtc tgttgttcta ttatgtctgt   7980
ttgctagaac accagctcca ccaaggtgaa catctttatc tgtctagttc actgcatgtc   8040
cccagcactt taaagaattc agccacaaag aaggtactct gtaaaaaatg tgcactaatg   8100
accatgactt tgacaaatgc taaccttggc aggagggtga tattctaggt gacggagact   8160
gcccgcaact cctctccgta aattacctgg cggaggattc cagtcctccg tgggttgata   8220
agagatgcag agctttgtac tgacagctgg agagactttg gcagaaataa attctttgct   8280
gtagacatga aggatcgggc gtgttctgct ctcttccggg aactaccata ttggattgtc   8340
aattcccatt catatgtctg tcttctgcat ttagtgacta gctcctcgac aggaacccca   8400
tcctactgaa gcaagaacct ctaatgccta attcagtata tgacactttg tggttgctca   8460
aaaagatgtt tgaggaatga ctgattaagt catgcttaga actggctaca taatttgcag   8520
gggtcccagt gcaaaatcaa aacataaggc cccttgttca aacattatta ggaatttcaa   8580
ggcagccaca gcagagcatt aaaccaagca tggtgctctt ctgttttggc agaggggatg   8640
ccgtgcatag gtcactcatc catgaagcct gtcctggtca cctgtgacat tctgtgaatt   8700
cccaaggcac actacacatg ttaagtcagg tgtccaggtc tatgacttag caatagaaaa   8760
ggcatcacgt tcaacgcaga tgagtgacgc agacaggttc tgagggctgg cagcaacctt   8820
```

-continued

```
cttctctcct gctgttgtct cagtgaacca caatcacccc cagtccccag atgactagca   8880
ctgatcatat gcaggacaga gtatgcagtc cattaggatg tcatggcctg tttgcttctc   8940
tgagcacctg atggactgac agctcctgga ggacaaggac caggcctctg aagccccagg   9000
gccttgagca gcccctggac catcttcagc tcttaatgat tgttaaatga ctggaagata   9060
cattaattaa gctcagaaag caactttggc ttcttatagc ttatgatagg ctttttcaag   9120
tctatcttct gaattaactt ccatgagaat actcatatat atatatatat attactttaa   9180
accctgaaac taaagttatg ctgaacttcc attagcatta tctggaactg gacttcccag   9240
tatgttgttc cgggcagcag cggcagcggc agcagcagca gcagcagcac ctgggaactt   9300
gtgagaaact cagattctca tgccctaccc tggacctgct gaatcagaaa ccctgggcgt   9360
gaggccagcg acattttaca agtcctccag gtgattctga ggcccctcaa gtcttgagag   9420
tatttgtgtc ctaaggaaca gagtttggaa agcagtgact tatgctgttc tcatcagata   9480
cgtttggatt ttaacacaaa ttaattgttt gcagctgcaa ccctcaaatg tctcagagga   9540
ttaaaatttt ttggtgcaat tttacatagt gagtcaaaat cccataaagc tggctcatga   9600
tgggggcatt tattcaactc agcaagaagg acatttgggt gagaatgaga aataatggtg   9660
tatgctcaca ttaaatatac tttttttaac aaaaaagaaa ttgttgaaat aaagcaaaaa   9720
ggagagttgg gaggatagat gtgtatggta aaggcaacac tggacccgta gccagaagat   9780
ctaagttaag taagcttgag caagtcaagt aaccttctga gccttaattt cttcacctaa   9840
gaaattgaga gactacccag ggctgccatg tagggttgag caggttgtgc actacacaag   9900
ggaacccagc tgaggagcaa gtgggagctg aagtccagct gagctaggct ttgtcccccct  9960
gcaggggaag ggacatcttt ctaattgact tagaaatgcc ttacaaacca gatgaggttc  10020
tgacaatact cctgcccacc tcacagagtt gcaaggatca gaaaagatga tgatttagaa  10080
agcctcattt gaaaattaca aggtgttata caaagagaag attggatatg atttggattg  10140
cggctttggc aatatactta tacttttgac catttcactc aggctgacca aatgcctgat  10200
atgctaattg gacacaaatc actacccatc taccaaggct tgtgctttaa aattggggct  10260
cagagaaatc agcaagactt ttagctgcag gaacagggac tgtcatagaa gctcactatg  10320
cccttggagg ttttgctgct gtatgagatc gtcacagagg acctgctgaa acccctaacc  10380
gtctatagct gttgcagcta caccttctca accagcaggc ttgggtgccc agaagtagct  10440
ctgtggggac tcagcttgtt gctgctgggt taacctggtg gggtgcaccc gataggaaaa  10500
gggtcagaag caccagaggc cacagacact tggaggtgag ccaggcctgg aattccattt  10560
attttgtgcc taagaggaaa gaagacctgt cctgaaattt ccatttgggg gctgaaactt  10620
tcttgttagg acactacaaa aatccctgtt ggcctgattt cataagtgtc agtacctaaa  10680
actgagcacc gaaagcactt cccataaaag caaaagtggt cttgttcatt gccgccttgt  10740
ggcagtttag ccctacagca ccagccaagg tgagctggcc cctgctcccc gacacgtggg  10800
tcatttatag gatcaccctt ctcaggaatg ccacatctgt tttcttttca ccagtctttc  10860
ttttgggaac tcatgcacca ttagcttgtc tcattgagct gtttgggtga acttggccaa  10920
tcagtcaagt ctttctctgg tccccatttc tcttttctac ctcaacccac cctccttgaa  10980
ttacataacc tttaagattc ttgcaaccgt gaaatgtttt ggctcttcca aacgtgatct  11040
gggcttccca agtaatatat taaaagaaag gttttatttt gtattgtttt gttttgcaaa  11100
tcaaaaaaat aaatctcaag tctctcccga atgggcccca gtgctctgca agaacagctc  11160
cccaaggatat ttctgcacca tgagataagg tggctggctg ccagaggggc cactggatct  11220
```

-continued

```
tcaaaggctg cctaattaag ttccagccag cagtctacct ctgtgggcca ggggctcttg  11280
ggagataaga cacgagacac atccagagat ggaggatgga gctttgctcc agtaatgaaa  11340
taaatcaaga gcagcccacc tcgtttgcaa atggaaatca ttctaacagg aggcctgcag  11400
tcatctgaga gagcaaggga gagtctccat tggattggag gcccctggcc ttcctgccca  11460
ctctccaggg ctctgatggg gtacaattat ggtgttaact gggatgggaa gataaggcaa  11520
gatgtcatta atggaggaga gcatgttttc ttaattccag aagctaatcc ccagtgactc  11580
actcctctcg agcctcccac agggatgtgg aggcattaaa ggtgcattgt ttattcatgt  11640
gacctaagta ttttgctgct ttccttagac ttctgattac attctgtggt cttcctgctg  11700
ccaaaatggt atagcagcat tttgctataa ttttatagca ggattgttct cctttttttgc  11760
actttgaata aaagagttcc cagggcttcg actatccttc aagtttcaat tttttttgta  11820
aatcctaagc agagccacca cctgagagat cacaagattt gctcaactta gaagacaggt  11880
aaattgaaag ttataaaaca aggaatctgg ccacctcaac tcctgtacta actgcagagt  11940
atatattttt tctcattgaa cctacctgga ttataatagt agagttttct ttaatagact  12000
tcaaagtatg ggttcagaca cagagtaact ctcaaacttt gaattgcaaa ggctttcact  12060
gcaaaccttc atgagatgta catatacccc ttatggaaaa tgatatcaaa atccactgca  12120
gcagtgatcc ttacctgatg gtttctttgg tgtcacccgc cctccaactc gctcatctcc  12180
aaaataaact aaattcatga tttttttttt tttttttttg ttagatggaa tctcgctctt  12240
gtcacccagg ctggagtgca atggcacaat cttggctcac cgcaacctcc acctcccagg  12300
tccaactgat tctcctgcct cagcctcccg agtagctggg attacaggtt tgagccacct  12360
tgcccggcta attttgtatt tttagtagag atggggtttc tccatgttgg tcaggctggt  12420
ctcaaaactc ctaacctcag gtgatctgcc ctccttggcc tcccaaagtg ttgggattac  12480
aggcgtgagc caccgcgtcc ggcccgattc ttttttctgc tctattggtg ctcgcttcaa  12540
ttcaccccga cgtctgggta gaatcggggt tcttcagtgg atgcagcttg ggtatttact  12600
cctggagtgc atgagatttc ttcaggacct cgaaatttaa atttgttcta caccaaagct  12660
atcacatgtc tcacctttaa ataagagccc aaaacattta tatatctaat caccgcacta  12720
gcctcatatc taccctgaaa acattaggtt ttagttacaa atagtttcat gttatgggtt  12780
gaatttgttc cccccaaaat tcacatattg aagccctaaa ctctggtact cagactgtga  12840
atttatttga agagaaagag gtctttaatc aagttaaaat gaggtcatta gggtgggctc  12900
taatccaaca taacccgtgt gctttttttt ttttgagacg gagtcttgct ctgccaccca  12960
ggctggagtg cagtggcgtg attttggttc actacaactt ccgcctcccg ggttcaagct  13020
attcttctgc ctcagcctcc caagtagctg ggattacagg catgggccac catgcctggc  13080
taatttttgt gtttttagta gaggcggggt ttcaccatgt tggccaggct ggtctcgaac  13140
tcctgacctc aggtgatccg cccatctcag cctcccaaag tgctgagatt acaggcatga  13200
gccactgcac ccggccaact ggtgtgcttt taagaggaga aaatgtggaa acagacacat  13260
atgctcgggg agatcagcac acaaacacac aagccgagaa ggaagtaatc catctatgag  13320
ctaaggaatg tcatagattg ccaggaaacc accagaaact gggagagagg ctggaattga  13380
ttcttcccta cggctttcag aaggagccag ccctgcccac accttgaacc tgggcttctg  13440
gcttccagga ctgtgagaca ataaacttct gttgttgaag ccccccgact gtggtatttg  13500
gttatggaac accaacatgg tggtctggga agcctggctg gtgattagga aagtgaaggc  13560
```

-continued

```
agtcagtaaa ggtgctgtat tgactgggat tgtactgaga acacctgagg ctcaatgcca  13620
ctggggaact ctgggagaca gcatagaaca cacatattgg agtgatccca gccaagatga  13680
gagggagccg gggtattcac cttccatctc ccatttgtct ctagcgcagg ctcccagggt  13740
tcccgccagc agggagaaaa cccttacgct gagcattgca tgtgtttgaa gtatgaagcg  13800
gttgaggctg ggcacagtgg ctcaagcctg taaccctgca ctttgggagg tcaaggtggg  13860
aggatcactt gaggccagga gttcaagact gagcaacatg gcaagacccc atctctacaa  13920
aaaaaaaaaa ttaagttagc caagtgtgct ggtgcacacc tgtaggccca gctactcagg  13980
agactgaggc tggaggatta cttcagccca ggaggtccag gctgcagtga gctatcatca  14040
tgccactaca ctccagcctg ggccacagag caagaccctg tctcagaaaa caaaaaaaga  14100
attggttgac attactggaa tgctgcgtgc taatttgagc aggggaatga cagcattggc  14160
cacacacaaa aaattaaaaa ataattgaat cccaccctag ataccttatt ccaagcccag  14220
tgatgttccc agggcccagt acatagcaat gcagacggac tttctgttgc caaagactac  14280
agcagggatc tagtggtatc taagaaaagg aggatgaatg gaaaatatct tggttttagc  14340
ctccctagga tgctagtggg tcaataacta tagtctcaat ctatgtggac tctaattcaa  14400
ttgggaaaaa tctcctctgc catggttaat tccagtatga gctaaaccat ggaggctagg  14460
gttggcagcg gtggtggtct cagtcaccta tctcactcga ggtaccattc ttccccatcc  14520
aacgtattca aaatctcttc atttcttttt cccccttgaac cctaggtgag agggctccag  14580
ttcttcattc gcaggtagct cagtctagtg caaacctctc cacagtggca agtccaagtc  14640
ctttgccacc atcacaattg ctggtgcagc agcctgtcct gtgggattgc tggggcttga  14700
ccctgcctct aaggaaagat ccccatccct accccatatt tatttcagct ggaaaattgt  14760
gctccatgga ttcctgaatg gaagcacctt taaaaaaaaa ttcaactttt attgcatata  14820
cagagggcac atgtacaggt ttgttatata gggatgttac atgatgctga ggtttggggt  14880
acaaatcccg tcacccagtt agtgagcata gtatgtgata ggtagttttt caacccatac  14940
ctctcatctt ctttcctccc aagtagttcg cagtgtgtaa tgttcccata tttatgtcca  15000
tgtgtgcttt atatttagct aaagccagag cctctggtat cctagtggga acccataatt  15060
cttctagttc tcccttggaa catggcgttt ccaccacatt attattatta ttattattat  15120
tattattatt attattatta ttattattga ggcagaattt tgctctgtcg cccaggctgg  15180
agtgcagtgg cgtgatctca gctcactgca agctccacct cctggattca caccattctc  15240
ctgcctcagc ctcccgagta gctgggacta caggcgcctg ccaccacacc gggctaattt  15300
ttttgtattt ttagtagaga cggggtttca ccgtgttagc caggatggtc tcgatctttt  15360
cactcggtga tccacccgcc ttggtctccc aaagtgctgg gattacaggc atgagccacc  15420
gcgcccagcc ctccaccaca ttttaacaac ctagacattt agaattacct gggcaatgtc  15480
catcctctgc ttcattttcc cctgtttttc ctcactttta atttttatct gctgtattta  15540
ttggctatgg ttagtcatcc taaagctgag attctggctc aggaattcat ctcgtctcct  15600
cagccatggg gttgggggtc tctcattctg ggaggggggcg ctgtcctaag tcctttagat  15660
gccctgacta cttcaaatct cacaacaaca tcaaagggtg gattagatca gcattttgca  15720
gctaaaaaag aaagaagcta aaagaagtta aataatgtgc ccaagagctt ccagctaaaa  15780
agtacctgaa aagaagttag aacccatttc tgtcaccacc acattataac ctaaaacctg  15840
gaacagaggc aggaccagga gctgcaggat agcaggagag agtaggggac ctgtggtttg  15900
agctctgcac tgtaagtaaa caggataccc actcagaagc ttgtccacag gacaaactgt  15960
```

ggttaagatt gttctcaaca agccctggta gcattgactg aatagcagcc atgcgctgag 16020
acctgctgta agcactttgg acatctcccc tttcaatctt catacaacac tccatcttac 16080
agaggagggc actgagactg agaagactag gtcactagct caagatcaca ccattggtaa 16140
ctggcagagc agggacatga cctctgatct ttctggtcca aagcccaggt ataaggcacc 16200
acacagtgcc atcgtcacag ctatagaatg agaaagtggc aaaggccaag agggagaatg 16260
ggaaggagca atccagcagg acgtgttcag atactttctg tgtctgtgct aaccaacaga 16320
taactggaag gtgtcctcca tcaccaagat gaatctgcag agtatacatg gtcatctgac 16380
tgtattgctg gactctttct tcccttttaa aaacacaaac aaagaggagc caaggcaagg 16440
gctctggatg ccactggctt agcaaatcta ctaaatgcac atcctggatt gaagtcactg 16500
cttagggatt cccaacaact cttgactgga caccagcccc agagaggaag taatagatta 16560
ttggcacagg aatggccctg tacagaatag caggcaacag aagcaaaatg gtccaacacg 16620
gagttgggcg agggcaggca caagggaccc caggcaaccc aaacaagacg cctgactccc 16680
tcacctctcc agccctgcac aggcaagcac acttctttgc ttctcaaccc ccatgacatt 16740
cacacgtgac tgatgggcaa ggtcatgctt ctgcctcctg tcatggagtt tgagaactgg 16800
aggaagctag aatgcatctt acccaatccc cttattatac agatggggaa actaagaccc 16860
aaagaagaga cttgcaggga ggttttcgtg gtagaatctg atctgcattg aagacttctt 16920
agctcctggc ctgacacatg gtccacgaca atgttgatga ctatgtgggt tgtaagtaac 16980
agaaatccaa ttcaaatgag ctttaaccaa aagggactga ttagctccca taactagaaa 17040
attcaaggag gtgatggctt cagtaatgcc tgatttcaag aacacagacc atgccatgag 17100
gacttagtct ctcctccttt tctctgatgt cttctggttt ggcttcatta tcaagtaagc 17160
tgccccacga gttgctggaa tggctgctgg ccatcctgga ttcctctcct tgtatctggc 17220
cttatccacc tctaccactt tgctttagtt gtttgcgtct tttcctagag acttagaaat 17280
tttacagaac cagaatattt tgccatcacc ctcagaaacc tggatgatgc tcttgcactg 17340
accttgagct taaagcttct taatttgggt ggtgattggg gtccatgcct ccctgggcag 17400
caggaatagg aatattgtcc taaatgaaac tctatgcaaa atagtgtgtg cttatacata 17460
tggaattttt cgggaggaga gagtagtata aagcttttca caccttggaa cacatgttcc 17520
ccaagaggga aagaactagt aaaaccaaaa ttcactatgg agattgtttc aataatttca 17580
tgtaggatga gggctgactt tgaattttat ggtcttcaat cagtactacc tagaaacaat 17640
gaatgttttc aagatcaggg atcatccggt ttgctgcttt ctgaacaatg ggctgatacc 17700
aagcgatgat tcctccctga cttcatctcg gttatttcaa atgcatttgg agaaatttgt 17760
gagtttaatg agccccttct gactctaagt ttgagaaaaa tgaggggata cattcccaga 17820
ttcaagtaaa atcatggtaa aaggaatttt acccagtttt taactcttaa tggccccttt 17880
caggagggtt ttatggtttt gtgcctgtct ccaacttggt gctccaattt gctcaccctg 17940
tgcaaatgct ttcatgcaaa tcttagccac agcatgctct gggagcttca ggagatgctg 18000
gggagagtgc tgcccccccc gcctgcagtc tctctctgcc tgtcatccaa ccacacctgt 18060
cctttctttt cttggccggt cttcatccct cttgcttcac atttaatttc tgttttctga 18120
gcttccaaat gatttgagga ataggatgct gtttcatgat aagctagcac agggcacctg 18180
atataaacag agctgctgtg tctgggcgca gtggctcatg cctgtaatcc caacactttc 18240
ggaggccgaa gcgggtagat cacctgaggt caagagttcg agaccagcct ggccaacatg 18300
gtgaaacccc gtctctacta aaaatacaaa aaattagcca gacgtggtgg caggcacctg 18360
taatcccagc tactcaggag gctgagacag gagaattgca tgaaaccagg aggcagaggt 18420
tgcagtgagt ggagatcatg ccattgcact ccagcctggg acacagaaca agactccacc 18480
tcaaaaaaac aaacaaaaaa caacaacagc aaaacagagc tgctgcatgg tagtgccatt 18540
gtgatattgt gacgatggtg gggcgtggga aaaatgatgt caactaccac tttgccaagt 18600
tttacaaacc ccggacatca agtgtgggga aggaggggta ggctgtttga aattgcaaag 18660
gaaagactga gaagagggtg cttggctgct gatatagttt ggatgtcatc ccctctaaat 18720
ctcatgttga attgtaatcc acagtgttgg aggtggggcc tggtaggagg tgactggatg 18780
gtcgtcctag gtttctgatg aatggtttag tgtcatcctc tcggtgctgt cctcccgata 18840
gtgagccagc tctcacaaga tctggctgtg taaaagtgtg cagcatcttc ccctcacttt 18900
cttgctccct ctcacaccat gtgacatgcc tgccccaact tcaccttctg ccatgaataa 18960
aaactccctg aagcctcccc agaagctgag cagatgctgg caccatgctt cctatacagc 19020
atgcagaacc acgagccaat caaacctctt ttctctataa attacctagt ctcaggcctt 19080
tctttatagt aatgcaagaa tggcctaaca cagttgctaa gtaccccaca aggactgtcc 19140
aaaacacaaa cccagccccc tcagagacta ggctctgaaa cagtgtcatc tacccatgat 19200
tcatacctac tgggtgggaa ttatattggt acctcaaaaa ggcaatcagt aagaatgtag 19260
acttagattg cttatctaag cgcccagctc agggcttact ttctgtggga gcacatggtt 19320
acagacaaca gaaaccaaca gctgagactg agtttctgga aggtctcagg cccacagaat 19380
tgatgggagg cgagatgtat cagtctgggt tctccagaga aacagaaccc acctatgttc 19440
tccagaacag aacaaaaaca gaccagcagt ttcagaaaga gagagagaga gagagagaga 19500
agagagaaag aagagagagg atataaggat gttttaaata cttgctttta attgtgatgg 19560
ctgagaagtc tcaagatttg cagtcagcaa gctgaagacc caagagagtg ggcggtatag 19620
ttccagttca agtccaaaga cctgaaaacc agaagagctg atgatggtgt aagttctagt 19680
ccaaatccaa acccaaggga ccagagaagg ctaatgttcc acccttgaag acagtcaggt 19740
agactgagtt ctcccttctc agccttttttg ttctgttcag gcacttggca gattggacgc 19800
tgttttggga tgagattaac tctttttgt tttgttttgt tttgttttaa gatggagtct 19860
cgctctgtca cccaggctgg agtgcactgg ctccgtcccg gcccactgca gcctccgtct 19920
cctggattct agcgattctc ctgcctcagc ctcccaggta gctgggatta cagacacgcc 19980
ccaccatgcc tggctaattt ttgtattttt agaagagatg ggtttcacc atgttggcta 20040 gactgatctc aaactcctga cctcaggtga tctgcccacc tcggcatccc aaactgctag 20100
gattacagac atgagctacc atgcctggcc aactttgaat gggtagacta aggaaagctg 20160
atggccactg acctggccag gcaaccttga aaagcactct ctgaacttcc attttctttt 20220
ctgtttgaaa tccttaccta gggcctctgg tgagcacagg catctcatta cacatctagt 20280
cactttacag tgagttccat ttttaaaaaa taagtttggt tttgctttta tccaagagaa 20340
tgcatttatc aaagcctggt caatctgggc tgcaaggaca ggcaaaaggc gctcagtcac 20400
aatatacctt gagggtttgg atttatgact cttcatcaag accctccagg tatatatagc 20460
aagtggccat ttggctgagg caggaccttg agtggcaggc actgtggaat tggcatacag 20520
ggaagagtca gatggaaagt gcctaaacct agaagacagc cagcgcaaca gcctcactcc 20580
tggactcttc tctatccatg tgtgaagaca ctctagttaa gttgcccttg accgcatttt 20640
atgaggaaat tgatatgcta cggtgaggac caagcatcaa gggattccca ggagtcttgg 20700
gaaatagccg cctttcttga gctctgctgc tggggttgta gactcaaatg catacaggag 20760
ccagacaagc cacagtaatg agtaaagcag gccaggaatt aatgtgttcc aatccacact 20820
cttcttgaaa taggcctctt ttgttgttgc tgttgttgtt gtttgagatg gagtctccct 20880
ctgtcaccca ggctggagtg cagtggcgca atctcggctc actgcaagct ctgcctcccg 20940
ggtttatgcc attcttctgc ctcagcctcc caagtagctg ggactacagg cgcccaccac 21000
tacacctggc taattttttg tatatttagt agagacaggg tttcaccatg ttatccagga 21060
ttgtctcgat ctcctgacct cgtgatccgc ccgcctcggc ctcccaaagt gctgggatta 21120
caggcgtgag ccaccgtgcc tggccaaaat aggcctctct tttactctgc tttttattct 21180
cccatttttg atagcaacat gagtaaaggg aaatgtgtct ctattataag agattttttt 21240
aaaagtgttc cttagctgta atacaaaggt aataatcaag agtacaaatt ttcaattatt 21300
gcttaattaa aaacaataac ttcaacaaca aacacaaggt gaatgccaaa tttagtctaa 21360
aaaaagtact actctaagac atctgggata ctatggatat aatgcctgct ccaccatgtg 21420
cacgccacat tcaatagtct atctgcccag gcatggtgtc tcatgcctgt aattccagca 21480
ctttgggagg ccaaggtggg cggatcactt gaggtcagga gtttgagacc agcctggcca 21540
acatggcaaa accccatctc tactaaaaat acaaaaatta gccaggtgtg gtggcatgcc 21600
cctgtaatcc cagctactag ggatgctgag gcaggagaat cgcttcaacc tgggaggtgg 21660
aggttgtggt gagccgagat tgcaccactg cactccagcc tgggcaacag agcaagactc 21720
tgtctcaaaa gaaaaaaaaa atagtcaatc tgccataagc ccaatccaag aatataaatg 21780
ggggtaggag agaaaccaca tagaacttcc actatggcat cttctattac catattcaac 21840
aaagacataa aaggccttgc aaaaaagaac ttttacagca tgtattttta ggacaatatt 21900
atagtgaggt tctggtatat ttcacaggca atgagccttt tctttcaact ggacaatagg 21960
gtggtataaa ccaatatagg aaatcctcca tggagcttta cagaagtgag aaattttgga 22020
ttaattttct ctctgtgcag caaggagcta ggagaaagag atatcacttc tccaaggcat 22080
ggaaagagag gggtttgatt gttattttgt tttgtttggg aggtgttttt ctccaatgag 22140
ttgttgaaat ctagagaaca taaaagaaaa aaatgaggat ctgatttaca cttacacaca 22200
ttcaacacca tttagtattt attaacaacc atatatccat tcaattgtca aattctaacc 22260
atgtgctgag agtatcatct ttatttgttt ctgatttaca agttttctct cctcaattag 22320
agtccaataa gcaacttgag gacaaagata tcatgtctca ctgtcttcag aattccccac 22380
ctcttctgga actttccatc ctgcattata atcacatgtg taatagctgc cccttgaaga 22440
gaggatgcat ttgttcatct ctgtgtccta tcccatgggc attgccttta ccatagttag 22500
tgagaggcca ggaaatgtta cttggctgaa tacataaatg aattctactg accttggggc 22560
atatacatta ttgaggatag cagtggtact catgaatgtt cactaacaaa caaataatct 22620
ctggactgtg aaggtgttgg ccatgcttgg tcagggaaga aaataagaga ggtgtgtatt 22680
agttatccat tgcttcataa cacattacct ccaagatctt agcagcttaa aacaacaagc 22740
atatatttaa tattatctca gagtttctga gggttaggaa tctgggtgtg gctcaatggg 22800
atgcctcagg ctcagcatct ctcatgaggt tgcagtcaag cttgcaggca cctgaaggct 22860
tgaccagggc cagaagcagg aagcctccat tcctcacctt gtgggcttct ccatagagct 22920
gctcatgact tagcaatgag cttccccaga gaaagagatc caagaaaaag cgagagaggg 22980
tccaggatgg aagccaacat cttttatgct ctagtctcag aaatgacatc gcaatgtggg 23040

-continued

```
agggagctgc ataaggagtg aatctgattc atacttacac aaattccaca ccatttagta  23100
tttattaaca accatatatc cattcagtta tcataaaaat atcaaattct aaccatgtcc  23160
tgagagtatc atctctattt gtttctgatt tacaagtttt ctctcctcaa ttcaaatcca  23220
ataagcaact tgaggacaga gatatcatgt ctcactgtct tcagaattcc ccagctcttc  23280
tggaactttc catcctgtat tacagaatac cgggatgcgg ggatcactgc gggccatctt  23340
ggaggctgcg tttgttaaat tgggatactc agtgttccag tgttgtttgc aaagaggctt  23400
tgagacccct accttaggaa acataaaatt atcttttcta ccagaattgg gaattttgac  23460
atatttgcat gaatatggac agtgatctga aagaaaaaat aattctgtaa gttgacctgg  23520
catgtggtgt tccagaagag acactgaggt gacagcctct gcctccaacc tcacaggacc  23580
aacctgaagc tcttgatcta cctgcccctt cagaaataag cttgccactc aaacatgagg  23640
agttactcta accagaggaa ttcttcagga tccaactcct caaggaaagg actgtgccca  23700
tttatgcccc tctggctcag agggagtttg actgtgaatg caaaatggtc attttctgtg  23760
aactttctga agacatattt tgctgaaaaa gaaatgtccc ttagagatag cactcagtga  23820
attattgtgg agtgaacaag aggccacaag tcagatgcta tctcaacaga ccaaaattgc  23880
agatgttagt ttggtcctga atattggtgc tgactcaaga agatagattt aaaaatgaat  23940
atcaccaaga tttcaagaca agctgtgagt ttaaaatgcc tcatgaaaag tgcatgagca  24000
tgcgtttata taaatgtgca ccttcgtatt tgtgtgttag ttatccatta ctatgtaaca  24060
cattgccccc ccaaacccta gcagcttaaa acaacaagca agtattatct gacactttct  24120
gagcatcagt gttcttctac ttcccttgtg gacctgatca gatttcgtga taattacatg  24180
ttcattaaag tcttttctga tagcctggag attccctgaa gacagaaatg ggtctctctt  24240
gtttacggag gtctctccag tatttggtag gaatagtact cttagtagat attcgaaaaa  24300
tatttgttga gttttttttt tatgttgaag cttttatttg tagacgttta tacctgttct  24360
tacaagatat gtattgtctg gcatgtatag atttttaatt catgtaggtg acgttgtatt  24420
atagatctca cagtttctta ttttttaatt cagcacagtg ttgcaagatc catccacatt  24480
gctatgcggc ctccatatgt tacttctaat atctgcaaaa tattacatgg tatgcaagca  24540
ctgtatttca cttaagcaga ttatctccct tcttctccac aaacaaagca ccgatgagca  24600
ttcttatatg cacccttca taggggtatg ttaaaatttt tcttaaggtt atatgcccac  24660
aggtaaaatt actgggtcaa aaaaatatgc agccgggtgt ggtggctcac acctgtaatc  24720
ccagcacttt gggaggctga ggcgggtgga tcacttgagg tcaagagttc gagaccagtc  24780
tggtcaacat ggcaaaactc tgtctctact aaaaatacac aaattagctg ggcctggtgg  24840
tgtgtgcctg gagtcccagc tacttgggag gctagggcag aaaaatcgct tgaacccggg  24900
aggcggaggt tgcggtgagc caagatcgca ccactgcact ccagcctggg tgacagagcg  24960
agactctatc tcaaaaaaca aacaaacaaa aagaagcata tatttaattt gactaaatac  25020
agctgaatgg ctgtccaagg cttccacaaa gtggttcatg aggcttcacg tatttccact  25080
ttaccaccaa actcggcatt atccaaggcc taaattttgc taatatagtg ataattcact  25140
gtggtttatt ttgccttact aataaattta agcatctctt catatgcatg ttaaccctat  25200
agagtttctc ttctctaaaa tacctgttcg ttcctttccc aatttctcta ccagggttgc  25260
ctgttttctt cttgattagt agaagttatt tgtacatcta tattctatat gtacaattca  25320
agatatttgc agttttactc aatacaaatt tcttctttct gtcatctgct aactttattc  25380
ataatgtcca tttttgaaca gaaataattc atgcacgtgg ccctttctat tttattttat  25440
```

tggtttcatt gttcttgtac cttacagctt ttattattta ttatagtaca ttttaaattt 25500
ttcaagtaag ttatcaagtt cttggaaaaa aaatcaaact gaaattttta ttggttttca 25560
atgaatttat agattaagga ggattgttat cactataaga ttagttcggc ccagctaagc 25620
atgggacaga tcatattgca tgttctttaa ttacagcgtt tttaaatttt cttcatggaa 25680
gtgtagaata ttcttttttg ttgttgtttt ttgttttgtt tttttttttg aaacggaatc 25740
tcgctgtgtc gcccaggctg gagtgcagtg gtgcaatctc ggctcactgc aagctctgcc 25800
tcccgtgttc acgccattct cccgcctcag cctcccaagt agctgggact acaggtgccc 25860
gccaccatgc ctggctaatt tttgtgtgtg tgtttttagt agagttatgg tttcactgcg 25920
ttagccagga tggtctcaat ctcctaacct catgatcccc ctgccttggc ctcccaaagt 25980
gctggaatta caggtagagc caccacgccc agttgacgta tagtatattc ttaaacaaat 26040
tctcaattat gttatagttt ttgttgatat tttgaatgac atcttatttt ttataaaact 26100
gtctatttga ttattgatgc tataaaaaaa ttctaatggt tgagagttta tcatatttct 26160
agcaaccttg ctaaactctt tattcattga gagcttacca tatttctaac aactatgaaa 26220
aactcttcat tagttctaat agtttgttga ttatcatggt ctttctaggt ataaagtaat 26280
ctcttctgaa agtaatcgca gtttttatttt ttcccttca attcttccat ctcttctttc 26340
tttcttttcc ttgtaatctt ggccagtgct atgacaaaca gcaatggtaa tggtggttat 26400
tctcgtcttg ttcttgtctt agagatagaa taaattctag ccgcaggatg gtctgagtag 26460
ccccttttct ccggggaggc tcttgaggag agtctgctgc tgtaaaggtg ctgggacctc 26520
cacttatggc tcataatctt tctaaaaact tctgttcaaa catgttaatt tacatttgct 26580
ggtggcgttc aagggttctc attttgtcaa gaacatttgg aagtggcaga cacttcattt 26640
aaatttgtta ttcatggggt cagagactcc gtgcccatga tgggatattt tagcacaacg 26700
ggtgccatga ttatgaagaa tttaggcaaa atgatacttt ttttccatat tcaataaata 26760
tttgttgaat gaatgagtga agaaataatc ctagaaatac atctaactta aaattggact 26820
cagtctttgg agggtcttaa gttagccaac tctgaaaaaa tctcaacttg aagaagaggg 26880
aagctatggc aacccttgtt tcctttttgt ttgtcaaact gggtggcccc gttacttgct 26940
tcctgcctgg cagcttcagt gattggactc ccccaagctt tggcccattt cctcagctta 27000
aatccagaga gaaatagaca ccactgaaca cgcaggcttc ctgtgctcac taggagggta 27060
tcttcatata ctttgccatt tccccctacc ctgttatgtc agacctcctg ctggcctagg 27120
agttaagatt caagggggat atggtgtgtg tgcgcgtgtg tgtgtgtgtg tgtgtgtata 27180
catgcccaca cacatttgca caagcccatg tgtgtatgaa tgcagtttcc agcatctttt 27240
gcttctccac agtgagctaa ggctctttgt gtgattaatg tgaggcagaa attgtggcca 27300
aggggaaaaa aaaaaggcag ctctgcactc ttcccccaat cagattaacg tggggtagag 27360
aggatttaaa tcaaagatgg cgcatcgttt ttatctatta tcccagttgc aatcaattgg 27420
tattggctgc ctggactgct gcgtcatgaa ggattctgag gctgggttcc agcctatctg 27480
gaaagcatgc cacaaccaat taaccatgtc tcccctgggc acaggacggg tgagtagcaa 27540
ctcacaagcc aaatgtaagc tgcagcagga gatgttggtc cagtatgcct agagcaatgg 27600
aagaactgga atgttctaac ctccgagggc aaacaagggc ccttgtctat tgcaaaagaa 27660
acatatactt aaatagcatc tgtaaacaga atcattgggt ggtattttca caatagaaag 27720
gaagaaagga aagaaaggca agattttggc tgctgtcacc catgttttaa tttctgtggg 27780

-continued

```
atttttttt ctctttcttt ctttcttgca ttcatgtgag cccatggaaa ccaaagcccc  27840
ctgagtaata aatacttaac tagtagagta agctttaggc aggtgatacc gtcagagcag  27900
aaatagcaaa tcagtattcc cttacccacc agctccaatc aattaataga agcttatctc  27960
cagctcctgg atttctgatc ctggaaggtg tttggatgcc caagcctggg cctggtcgac  28020
tggcactgtg tctatgcatt ggtgtagcat caccattctg acaggtatca aagggcacct  28080
ataacccaca agacaccatc tggccaagaa ctctgggaca catagttccc ctctgacttt  28140
tctaaccaac tccatgctgg atgtcgggct tgggcatccc caccaagctg cccccaaggc  28200
actgggcatt gtctgaggct tcccttattc acatgggcaa gtgtgctaag cccagctggc  28260
aggccctaca cacagcttgg cagcagccgg gagcttgagc aaggcggtga ggatccaggc  28320
ttggggctgt tcactccctg gggatgttgg cttctctctc tggttctgct cagccttcca  28380
gggccaccag caccagactc atcttagacc ccaaacaagt ttccccaggc atgtctgtga  28440
acctgtgccc tgatcactca gtaattactg caggcctggg atactcctct cctcctctat  28500
gacaatcttt cccctaatgt actttaagtc actgtctggg ataccccatc atccccacac  28560
atcaaccaga agtcccatgg ttgactgaag aagataagga gtcccttcct catcagggtc  28620
ctttggtcag aaaatcagaa atagaggctc cttgggaaaa cagagatact tcactttccc  28680
acggcatttt acagttcacc aagagcattt tagcaagtgt gatctaatca caaatttgat  28740
ctcattaaag cacaaagtat cttcaagata aggagtttat actcattttt ccttctgaga  28800
actgagtctc agaaatgtga aagaactttc ctgagcccat gcagcatgct aaggacagag  28860
gccaggctca aacctagagt atctggaccc tgcgctgtcg tctgcctgcc ataaccaggc  28920
tggctagttg gactttttat ctgtcgctat ggtggctata agttttggag ccttgtgaaa  28980
tttgtcactg ctttttaaac ccacagaaat cccatttcct cactgggacc tggaatccag  29040
caacagcatc cgcccttgag ttcagcatta ccctttcctg gctgtcatct ctttcacagg  29100
gttcaaaatt tctgggaggg tgatgtggtt tggctgtatc cccacccaaa tctcatcttg  29160
aattatagct cccataattc cctcatgttg taggagggac ccagtgagag atgattgaat  29220
catggggggc agttcccgca tactgttctg tggtggtgaa taagtctcac gagatctgat  29280
ggttttataa ggggaaaccc ctttcacttg gctctcattc tgtcttgtct gccaccatgt  29340
aagtcgtgcc tttcaccttc tgccatgatt gtgaagcctc cccagccaca tggaactgtg  29400
agtccatcaa accttttttt ctttataaat tacccagtct caggtatgtc tttatcagca  29460
gtgtgaaaac ggactaatac agagggataa gacattaaga taattagaat ttaagtgcaa  29520
ttagtttatt tgcttccctc ttctgaactg aggggacaag acatgactaa agccagcact  29580
gccgagaggg gtggtgactg gcaggtggtg tggttacaca aatgaacccc acctatttct  29640
tcaccttgcc ctagaagtca ccatccaggt atatccaaaa ttgtgtatac cctgcatgta  29700
gccaggaagg ggttaaaata aattaagaaa acagaaactg aaaacattcc tgggagggac  29760
ctgcttgaca ctgaggccat cagcctaaga tactctccca aaagtctccc cttgggaaaa  29820
caaaaatatg aattctctcc tgggtgatat ggtttggctg tgtccccacc caaatttcat  29880
cttgaattat agctcccaca atttccatga aaatgggaat atttcctatt tccagtttcc  29940
tagaatattg ttctaggatt gtgggagaac aataacattc aaagctaaaa gtctcctctt  30000
gggaaagcaa gaggagactt ttagctttga atgttgttct cccacagttt cacaaaatgc  30060
taaatggctg tgctctttca ctctttgtaa gagacaggag taaactgcat tggtttctct  30120
tgttttttca ccaaaattcc tggccactag gacaagggac taagagtgga gaccgtttgt  30180
```

-continued ggtttacaca gggagcccct agatttccac catacaaacc tgggtcctgg aagctttcct 30240
gtgcaggaag cagattttct tcccctgtct gttcaccaac tgctgttcca cttgtatatt 30300
tcaaaagtaa taaaggtcaa cattttaatt aaccccactg atagaacctc attctgtcag 30360
acctagaata ttgttctagg atttcataac cttgatccta aagtcctttt gcttgggggg 30420
cttagcctgg gagagttttt ggctttgacc agtgtactag tttgttctca tgctgctaat 30480
aaagacatac ctgagactgg gtaatttaca aaggaaagag gtttaatgga ctcccaattt 30540
cacatggctg gagaggcctc acactcatgg tggaagataa ggaggagcaa agtcacatct 30600
tacctggatg gtggaaggca aagagagttt gtgcagggga actcctcttt ataaaaccat 30660
cagatcttgt gagacttagt cactatcatg agaacagcac gggaaagacc tggccccatg 30720
attcagttac ctcctgcagg ctccctccca tgacacgtgg aaattgtggg agctataatt 30780
caagatgaga tttgggtggg gacacagcca aaccatatca cccagcaaag aattcaagcg 30840
tgagctggtg gtgttagaca gcaatctttt attgaacagt actgctcctt gtggagcagg 30900
gctaactcat aggcagtggg cccaggattg gcaacttacg agctcttggc aactgcattt 30960
atattcactt aaacccactt ttaattacat gcaaattaag gggtgggtta atgcaaattg 31020
aggaatggat tatttagaac tttctaggaa aggagcttta acttctggat cattgctacg 31080
gaaaaaggtg gtagcttcag ggttgttgcc atggcattct taaactgtca tggtgctggt 31140
gggagcgtct tatgctaatg agcaatgagg acagctaggg attggttttt tgccatctgc 31200
tggcttcttc actttatctt gtctggacca gattctgtat tggtcagcag ggttgtgaac 31260
agaaaacaag tcctgtgggt ctcctatctc actttaatcc caacctcttc actctcctcc 31320
acatcaagtt tcctcaacca gcccaggttt accttattga aattgctcta ttaagattag 31380
tatatttcta taaggtgctt ctaaaacagt tgctgacata cagtaagcac tcaataaatg 31440
ttagtgatta ttattagcaa tatagtcctt agaattggca gcctgtgtgt tcttcctttt 31500
aattatactc tctcaagatt ttgatatata ctatgacaat ttccaaatga tgttctgtaa 31560
tcaattactg tggcttctaa attaaaaaaa tgagatgaaa tccaggcacc gtcctcagcc 31620
caagcgtctc tcaggcatca gtttatatgc tttcccttac cataaaaaat gtggggtaca 31680
tatcagtgtt actagcaagc agaaataaaa cagaaaaaag tcctgctact ctcaatgaag 31740
ccctggtgtg gagtcagaga tacctcccct gccccatcct atggtgaccc aggcattccc 31800
aggagtcaca ggctgcagtt ctgttaattc tgggaagttt cattctgaga gcttggaggg 31860
gcccttaggc cgtatcattt tcacttccgt gaaacctaag gaacactagg aagaccatct 31920
gtctgggaat tctgtcttga ccaagtagtg tggggcagtg acaaaagtcc tgagccagga 31980
ggcaaagacc tgtgctccgg gatctttcag aacattaatc cacggtggaa cttcgtgcaa 32040
cacatgctcc ctccctggac tactgttttg tcatgtataa ttgagagagt tgagccagat 32100
cagagatcag aaactagtag tagctgggga gaaagtacag actgcagatg tgagttactt 32160
ggcttgcaaa gtagtgttat aatttttatt aattagtcct caacagttaa aaattcaggt 32220
ttttgcatga aatctgactg ctcttgaaaa gtctggcaac actcagattg cgtttcctta 32280
gagaaataat tggcctttct ctccagacat gacatatgct ctttggttta cccaagtcct 32340
ccccttccct ccagatcatt cacttacatc acctgcttag ttagcactta ttggcatttg 32400
agtttgagac ccctagtcta aataatttct tttttttttc tttcttttt tttgagatgg 32460 cgtctcactc tgtcacccag gctggagtgc agtggcgtga tttcagctca ctgcaacctc 32520

-continued

```
cacctcctgg gctcaagcaa ttctcctgcc tcagcctcct gagtggctgg gactacagat  32580
acatgccacc atgcctggct aatttttttg tatttttagt agagacaggg tttcaccata  32640
ttgatcaggc tggtctcaaa ctcctgacct caagtgattc acctgcctcc acctcccaaa  32700
gtgctgggat tacaggccac catactcagc ctagtctaaa ttatttctag tggtccctcc  32760
tgcttgggcc agatgaatgg ggtcatatca ccttgttaca tagcatgttg ctgcataaca  32820
gctgtgtacc caatacacag tgacttcaca taaccagtgt ttattatatt acatctcctg  32880
attttgtgag tcaggaatcc aacaaggagg attaggtgaa cattttttct gtctcacacc  32940
atgtctgcag aggtcatttg ctgctattta gctggcaaat gagctggcac ggatggtcca  33000
agacagcttc acccagccag gtgcagtggc tcatgcctgt aatcccatca ctttgggagg  33060
ctgaggcagg tggatcacga ggtcaggaga tcgagaccat cctggctaac atggtgaaac  33120
cccatctcta ctaaaaatac aaaaaattgg ccaggcatgg tggagggcgc ctgtagtccc  33180
agctgcttgg gaggctgagg caggagaatg gcgtgaaccc gggaggtgga gctggcagtg  33240
agctgagatt gtgccactgc actccagcct gggcaacaga gcgagactct gtctcaaaaa  33300
aaaaaaaaaa aaaagcttca cccacaagtc tctcgcttga cagggatggc tggaagtctg  33360
gattctgctg tacctatcac ttggagcacc tgcatagctt ccctagcaca gaaccaaggt  33420
agtaggactc aaatggtagc ttagggctcc cagagcgagc attccagggg acccaggccc  33480
aaatcacaaa gcctcttgag acctagcctc agaaattgca gaacattact tctgccacat  33540
tctgttggcc aaacaagtca ctgaggccag tcttgtcaag gggagggaac ttggactcaa  33600
caggcagagt agaaaagaat ttgtgccagc ttcactttac gacatgtcag ttattcaaat  33660
tctgctgtcc tgaattaaag gatactgatt aggccaaata aaaaatgtct tataataatc  33720
cattatatag ttatgcacca tataatgaca ttttggtcaa caacagacca catacacaac  33780
agtggtcccg tatgattata atactgtatt ttttctgcac cttttctata tttaggtatg  33840
tttaggtaca cacaaatact cctcattatg ttacaattga ctgcagcatt cagtacagca  33900
acatgctata cagatttgca acttaggcac acacaggcgg ctataccata cagtttaggt  33960
aaataggaag ctatatcatt taggtttgtg taagcatgct ccatggtgtc acctaacaac  34020
atatttttca gaacatatcc ctgtcggtaa gcaacacatg actacacaag aattatgtcc  34080
ctgccgccaa aagcagaaag acaggtttgt agaagagaga gctcactcta cactgtgccc  34140
actgctcatt ttagtggctc cctatgacat gcagtatcac acaggacact ttgagttata  34200
aggaattgaa cttcaagttt ttataaggaa aaaaaaaaag gagacgtgga tggagctgga  34260
agccatcatc ctcagcaaac taatgcagga acagaaaacc aaatgctgcg tgttctcact  34320
tataagtggg agctgaacaa tgagaatgca tggacacagg gaggggaaca acacacactg  34380
gggcctctca gggagtgggg tgaggggagg gagagcatta ggaaaaatac ctaatatgtg  34440
ctgggcttga cacctaggtg atgggttgat agctgcagca aaccaccatt gcatacgatt  34500
acctatgcaa caaaccttca catcctgcac atgtacccca aacttaaaac taaaatttaa  34560
aaaaaaaaaa aagaagaaga aacggccagg cgcggtggct cacgcctgta atcccagcac  34620
ttcgggaggc cgaggtgggc agatcacgaa gtcaggagat ggagaccatc ctggctaaca  34680
cggtgaaacc ccgtctctac taaaaataca aaaaaattag cctgttgtgg tggcgggcgc  34740
ctgtggtccc agctacttgg gaggctgagg caggagaatg gcgtgaaccc aggaggtgga  34800
ggttgcggtg agccgagatc gcgccactgc gctccagcct gggcgacaga gtgagactct  34860
gtctcaaaaa aaaattaatt aaataaataa accgaagaaa ctattgattc acagcaacaa  34920
```

-continued

```
aggtaactac attagtaaac ataaaagaca gtataaatat atttttgtaa ttccttctat  34980
ctgattttaa aaataactac ataaagcaat tatgataaaa ttgtgccaat gccttataat  35040
gcataaaatg taatttgtat gacattaaca gcacaaaaga ggagggaggg tattgtgctt  35100
tatttgaagc aaagtttctg tatactgtta aaattaattt agcattaatt tgaattagat  35160
tgttttaagt taagatgcta attgcaatcc ccagggcaac cactaagaaa ataacttgaa  35220
atatattata aaaaaaaaac aacaaggaaa ataaaatggt aagtagaaaa tatctattta  35280
acacaaaaga agttagtaat cgagaaatgg tagaataaaa aagacttaag atatacagaa  35340
aacaaatagc aaaatggcag atgtcaatta tatcctatca gtcattatat tccatgtaaa  35400
tgggttaaac actctaagca aacagtagaa agattagcag agtggctttt ttaaacgacc  35460
caattatata cattctacaa gtgacaaact ttataatcta agacataaat cagttgaaag  35520
cattaataaa aagatggaaa aagaaatgcc tgattcatgt atccaaaagg caaaaaaaaa  35580
aaaaaaaaag taagacttta catcgccctc agttgaatcc aggagttcaa atgatgctgt  35640
tgggattcag ccttactcac ctaaggtttc ttctctgtta attccactct caggtgtttc  35700
agcctctcat gatggccccc agaagctcca ggcttagcaa ctccaataga acgtaagctt  35760
ctttttctct actgtaccag caaacttcct ggtttgagtt tcattggcct gcttgggtca  35820
aatgtccaca cctgagctag tttccaggcc cacgcataaa tcacgtgctc ttctctggag  35880
agcagtttgg cttagcttct tctgaccaat atggtctgag aggaaatgag gtgtgttcct  35940
acaatgaagg ccaagaggct atcaccagaa gacaggagag tggatactta gctggctaat  36000
aaaccacaag cgtctactac acatggtttt tgggttggag ggacatggaa aaaaagtcaa  36060
gctaaaaaat ctatgaggtg ttcaaacgtt tgtctttatg ttcatgtttt aattgtccaa  36120
aagaatttcc acactaactt taaaaatctt tttagctctt ttgatacatg aaacatgctt  36180
gaattgaatt cttagagact gggaaaaggg aaaatggaac ctcacatcaa gaagcacttg  36240
ctctgcatca ggcccccttta tatacccggt cttactcaag ccatgaaacc ccaggaacta  36300
catggggctc tcagactttt gaagatgagg agactgaggc acaggaagat cagcgatcta  36360
gccaacgtgc ccactttgca ggaggtagta tggattcagc acagtcccag aacctagggt  36420
ccttttccct gcactgtgct acctacgtca tattgcacat catgctatag ctatgagtct  36480
tcctacatgt ccacattcca ggaagaaccg ggaagaacac atttgccctg ggcatgaaca  36540
ttagaatcaa agctaaatta ggggtattgg agattgagtg caggcaaggc acaaagttag  36600
aatttcttgg ttttcacttt actggaaagt tatttcacca tcagtgtctg gttggtggtg  36660
gtttgtgtaa gctgtacatt tatattttgc ccgcccaggc atctctgcgg gtaggcatcg  36720
tcaaccgttt gcaagatggt ctcgccttgg tgatgggtca tgattctcgc tttcatttgc  36780
ctcttggttc caactcaggt cacacccaat tttcagtctt tggcttcatc ttggtatcag  36840
ggatgaatca tgatgaatac tgggattgtt acagtttact gtctctttct atcctcattc  36900
tcctgcttct tcgttggcag aggctgacaa ccaatgttga aatcagattg ttcccttcat  36960
ccagatcttt ctttgaaaat gcttctctca tttctggtgg attaaggcaa cagtttccat  37020
aatgtgtgct actggacaca accactcaga atctcagcca taaaaaaggt ggggtgctac  37080
aaccagatta tgggggaatg tgtgtcacgc aggtaaaaaa aaatctgcta tattccccat  37140
gaacgtataa agtgttccaa tagatctttc ctattgacat tatttagcca gtagtctaag  37200
gacagcaata gtctaaatgt aaaatgtagc acttttattt atcaggaatg aaaaaccagt  37260
```

ccccacacac agctagtgaa aactaaaaat taggaacttg gctttgtagg agacatgaaa 37320
cctctttcac tccattccat tccagcccat ttttaaaaaa tgaaacggaa ggttattttg 37380
ctagcagaaa actgttattg ttgctgaagt tgctaagaaa attgggcagt ttatcagtga 37440
agatggcaac agcaaatata cagcgttgcc agaggcatta ttttgccatc ctaggcagca 37500
ttaacaagtt aaaaaaattc taggttccag gatggcaata atgaattttg gtctcatggg 37560
caggaaggca gatggtaggt atattttccc ttgaacatgt cctgatggat aacaggcttt 37620
tctggaaaag aggccacgat gtcagattct tattagcatt aatgatgggt tgttcaacaa 37680
aatctctgca ccttgcacta cgaatatccc tggaagattt gggactaacc tcagacataa 37740
gtgactattt gcacttgcca ggttagctct tctttatcgg tattctgtgt tggtttttgg 37800
ctttgaataa tgtcttgttt tataaaacac gaagaaatag tgtcatggtt gggagccaaa 37860
tggatggtgt tgcattgata cagcgaacac tattaggagg gagtaagtga gtctgggtgg 37920
tgataatgtt gaggagcaaa gctgttgtta ttgaccattt tataggaaca ggttcttttt 37980
aaggctgcat gcctacatat ttcaaacaat gcgcttgaga aatgtccaaa gacatacaac 38040
aaacagaatg agaataagtg ctgagttgag acagatagcc cagcttgaaa attctgttat 38100
gaaaaacagg aaatatagat acaggcagaa tattatgtca actagactga taaaacatga 38160
agcagcctcc ttagaagagg tgttttcacg gtcccctaag taaaccctta gcacttgggg 38220
atagcaacaa attaccgggg aaggtagtaa aaggtgtggc cttggaatta gaccagggca 38280
caagaaagaa ggcaagagga agggaaacta accactctac atacaccaaa gcagagagaa 38340
aggttatgcc aaatccacca tttgacagtc tggtcatgtc aattacagtg ggcagttttc 38400
ttgggacaaa atgttgcact aagtgaagag ttttttctct tagatagaag agccacatta 38460
gccaacaatt tggaccctat gcagagagag agaggatata tttttcttct tggaaagcct 38520
gcgtaagtga gcacctttct ctgttgagca gagtttactt tgtttgcagg aaaaggaagg 38580
tagaggtgga tatgaagagt gtgggcaagc cattttcagt tcctttgtgt gctcctccat 38640
ggcctgcacc atattctgct ctgtagccag tctccaggat ggctccccaa gacccctgct 38700
cccatgactc tcggctttgg gtagttccct tccacattga atagagtatg acttttgaga 38760
ctaggctaaa ggctgtggct tccatctggc tctcttggat catttgctct gggggggagcc 38820 agctgcatgt tgtgaggaca ctcaagcagc tttttggaga ggtcccatgg tgaggtattg 38880
agatttcctg ccaatgtcca catgagtgag ctcccttgga agtgagtctt tcacacgcag 38940
tctagccttc tgatggctgc aactccaacc aatatcgtga ctgcaacctc atgagagacc 39000
cggagccaga actacccagc taagacattc ccaaattctt gacccacaga aactgagaaa 39060
tcataaatgt tattgttctc agccactata ttttagggta gtttgttata cagcaatagc 39120
taatgaatac ggctggctat cattcttgat taaggatttg cctctataat tataatttca 39180
aagtatttca gacttttata ttagaatata atagaaaata acacatattc aggcataaaa 39240
ggtaaaatta catgtcctag cacactattc tatacaataa aagtcaaaga aaatggtgtt 39300
tttgtgtgca atttcatctg aagggctgaa gctacagcgc acacacaggg acattgcatc 39360
gactttggct tttgctctga ttgagctatt ggcttttgct tccattgagc caatggaaga 39420
accattgggg aacgttgagt agaggcgtga caatgctgaa ctgatgttcc agaagacagt 39480
ctatgtaccc agaccaccat gtacccaagt acgtgccagg gaatacaaat gacctgcccc 39540
tgccctcaag gtgttttcag gctcatttat actcagccac actggaaaag ctatcagtct 39600
tccctcccac ttagtctgta tcttggggtt aacccttaaa taggaagaga gagctaggag 39660

-continued gagagtcaga gcattctgtt tgcccacaag tgttcagaaa ggcatgaaca atttgttctt 39720
tggctgtgaa actgcttaac ttaggtctaa agacccgttt gaattgttac catgttacag 39780
agtctcagaa gctctaggac tatgtattag tctcttaccc gctgctatca caaaatacct 39840
ttgagtgggt aatttacaat aatggaaatg tattacttat tgtcctggag gctaggaggt 39900
gtaagaccaa ggcaccagac gattcagtgt ctggtgaggg ctcacgttct gcttcaatag 39960
atggcacttt cttgctgctt actcacatgg cagaagggtg aacaagattc ctttggtttc 40020
tttcataagg acactaatcc cattcatgag ggctctgccc tcatcactta atcaggtcct 40080
gaaaggcccc acctgtacta cggacacatt gtagattagg tttcaagata taaattttgg 40140
ccatacagaa acgttcagac catagctaag tgtatcagtc agttatgcta tggtaacaac 40200
cccaaaactc agtgcttcaa atgacaaaca ttttactctt gttcatgttc catgtccaat 40260
gcaatgggga agagtctatt cacggtaatc attctggggc ccagactgat ggaggctcta 40320
ccatcttatg acaatgccat atcaacatga ggctggaatt aagtgttttg cccaaggaat 40380
ggaacagggc ctttcttttt tatctttcgt tggccaaaac aagtcacatg gccaccccat 40440
cttccaggag ggtaagaaag tgttattcca cacatacctg gaagtagcag aaaacagaat 40500
attaatgagc atcagtaatg cctacagcaa agaagcttct tttttttttt ttccttcaca 40560
atttgctgga aaaagtaagg agagagaaag acaggaatca cagcttgatt ccctgagatc 40620
tttgtctctg tgagatagga atacagtgag gtgaatccta aactggcttt ccttattctc 40680
agtaaatttg tgtttttgtt tttgttttct taccaaagac ctatatatgt tccaggtgct 40740
gtgctgggtg ctatagaaga gatacaaagt cgattagata tgggccctcc cttaagggag 40800
gcacatggcc tctcagtttt aacatagtta ggagagtaaa ttgcctggaa taattattta 40860
gtatgttcca gagataaata cacctttcag tttcctaatg tctttttttct ccaagtagat 40920 ggtaatggaa tgatcattcc attaattacc agttcaaatt tcttctccga attattctcc 40980
gtgatcaggg aatggaaaca tggtccagag tgctgagata tgccacacct tgattaggtt 41040
tgagatgtta tctttaaaaa gggctgcaaa ataaaataca ggatactcag ttaaattaga 41100
atttcagatt aacaacaaat aacaaatgct taggacatac ttatctaaag gtttatttct 41160
tgtttatctg aaattctaat ttaaatgggt agcttatatt gttatttgct aagcctggca 41220
actttatctt aaaaactctt ggctgggcgt ggtggctcac gcctgtaatc ccaacacttt 41280
gggaggccga ggtggacaga tcatgaggtc aggagtttga gaccagcctg accaatatgg 41340
tgaaacccca tctctacgaa aaatacaaaa attagctggg catggtggca tatgcctgta 41400
gttccagcta cttgggaagc tgaggcagga gaatcgcttg aaccggggag gcagagattg 41460
cagtggccga gatcgtgcca caagatcgcg ccactgcact ccagccttgg gacagagaga 41520
gactctgtct acaaaaaaaa aaaaaaaacc aaaaacaaaa aaaaactctt catcatcaca 41580
gaagcctcaa ccacttctaa tctcattctg ttccacttcc ctcaccatct ccacatgtct 41640
atgccgcacc agccctacta gcctcgtttc tactccattg agaaacctgg catgtgtcta 41700
ccgcagggcc tttgcaagtg ttgtttcctc tgtatggaac cctctggtta tctgggaggc 41760
tgactcttcc tctttattct cctcagctca aatgctggca cctctgaaag gctttccttg 41820
atcaggtgat ctgaagttgc accctcttgc cctgtttcca tcattcccgg tcacatcact 41880
gcatttattt atagaaattg ctactctaaa attatcctag ttctattgtg tgtgtctcat 41940
tcttcattac aatgtaagct cagtgagatc agggactatg tctgtcttgt tctttgccaa 42000

```
atcccagcac tgataagaga acctcctaga aggtagtggg tgagaaataa ccatttatga  42060
gttgagttat gctttagttt gctgaaggct cctattttct agtacatgca aatacctaca  42120
cataagggag ataagagttt agggaaagga gaatagacaa ccaaatgata taatttatga  42180
taggggtaaa cgtactttaa aaaaaaaagt agaacagtga actgaagacc aactactttc  42240
actgcgttct actttcgttg aagttattag aaaaagcact tctgattagg tgatgtgagc  42300
tgagttctac ataatgagaa agaaggagct atccaagggg agactattca gggtatagta  42360
gcagttgaaa cactcctgaa ataagaacgt acttggctta tttgaggaat aaacgaacag  42420
ttgaccggca tagctggcat agcatgagcc agagagtaac ctgtgtgaga ggtggtcgga  42480
aggacaacca gagcagtctt aaaactttta ttggagtttt actttaaata caatgacaat  42540
atatttaaga gcttgaattt ggggaaataa tatgcccctt ggtagctgtg atgaaaatgg  42600
actctagaat agaaagcatg gaagtaggaa taccagatag gaggccattt cagtcatcca  42660
gccaagagtg ggatggtggg ttcgtctagg ttttagcatt gacaatgaag agagaagggg  42720
gcaagttaag atgtaatagt gaggcatcac caacaaaaat tgattattta attaatggaa  42780
agaatggaag aatgcattgg tggatgtgag ggtggataaa tagattcatc aatggatagt  42840
gggtggatat tggatggatg gatagatgga tgaatgggtg gatgaatggt agatggatat  42900
tggatggatg aatggatgga gggataaatt gtagatggat attggatgga tggatggata  42960
gatgaatggt agatggatat tggatgcata gatgacggat gaatggatgg atggtagata  43020
gatattgaat tgatggatgg atggatggat ggatggatag tggaaagata gacaaaggaa  43080
agatattggg tgatgtgtgg gtgatgaagt agaaaatgct tattaaattc tcaggctcca  43140
gaccaatctc cttttgaacc ttatagctga cacccttatt aacagagaaa tcttgaagaa  43200
ggaattaatt aagaagcctc actttcttca tctgaaaaga ggactttaat atatacgttc  43260
ggaaaataat gtgaagaata aaaggtataa aacctactga tccattacac cagtgcccag  43320
gacacagtag tcattgttat tcacctcccg tatcttgtgt atcgatttgc aactttcaag  43380
ttgtcttttc gtcagtctct ccatcagcta gtttacactg ctcagactca gagacttcac  43440
taaaacccag caaaacaata acatttatat caaatgttta gattttttaa tgaaagggag  43500
aaatgatgga gcgtgggaag tgttataaac tattcagtat ttcaattttt taattcacaa  43560
tcctgaattc cctttgatgg ttttttaata tagggagggc tcttgtgagt atgtgtgaat  43620
aattaaactt tttagaattt gaacataagt tggaagaagc tcatttcact gtcaatgatg  43680
tgaggcaaag gaaagcccaa tgggcatctt ttttacgcta aataattttg tgggattttt  43740
tttttaattc ctgtcttctc agatagtctg agaaagaaag ccttcggaag gttacttgtc  43800
atgctcttct tttgtgttat cttgataaat cctgattgaa ggggaaagaa gagaaggagg  43860
attgagacaa taatgaggtt atcattgttt gagcatttac tacacagact ctctcgcctt  43920
tggtccctca gcagcccaac aggcaggtaa tagtactctg cccattgtgc agatgggtca  43980
tctgaggttt tcacaggtta tgtggcacgt acagcacagg tgcacattcg gactggtttg  44040
atttcagtgc tgggactctc tactatttcc ctaggctgct ccttggttgg ttggttggca  44100
tcaagccatt tctcagcatt atttactgtg tttattcatt ctcctccctc cctgttggct  44160
gacagctatt gatttctgtg cgtgattctg cccttggtct caaatagttt tgcaatttct  44220
tgcccaattt tcaagtgaac tttatcatcc ctttgcttag tgaagctcgt ctttgttcct  44280
tgggcaataa tggatgatac cataaatggc atgtcacaga acagaagtga gggcgacctt  44340
tattagatta aatatgtttc cccacccagt gctctgcaga tcgtgggatt tctatcagaa  44400
```

```
gacagacaac agggactgaa ctgcatgcag ccaagagctt cccaaaattg tactggtaat  44460
tacttttctt gatataataa caattactga taatgatttc ctagaaattt taagagttag  44520
tatatcaatg caatccagat attatatatt cagtttgctt aaaagctcct taagattgtc  44580
actggattct tggatgctgt catccccctc gtagagggaa gactgatagg aatttgtggc  44640
tatgatgatt caactcacag taggattcca aattctttgc tgcacccaca ggatctgatt  44700
cctgtctact tcctttcttc cattctcttc tttgtccact tctctctagc cgtggcgata  44760
cctttttgtt ctccgactat accaagcttg ttcctgccac aaggcctttg cacctcatgt  44820
tccctctgcc tagagtgttc ttcctgaata cctgtgcctg gctgaagact ttttatcatt  44880
catgtctcaa tgtaaatgtc accaacctgg aaaggcctaa ctaaaatatc tcacccattg  44940
atatggtttg gctgtgtccc cacccagtgg gatccccggg taccgagctc gaattcgccc  45000
tatagtgagt cgtattacaa ttcactggcc gtcgttttac aacgtcgtga ctgggaaaac  45060
cctggcgtta cccaacttaa tcgccttgca gcacatcccc ctttcgccag ctggcgtaat  45120
agcgaagagg cccgcaccga tcgcccttcc caacagttgc gcagct                 45166
```

<210> SEQ ID NO 7
<211> LENGTH: 32692
<212> TYPE: DNA
<213> ORGANISM: Homo sapiens

<400> SEQUENCE: 7

```
ttctgcacaa tgtcctctcc tgcctttcag atgtgtctag gctgccctgc tacctgcctt     60
tgcctatgtt ctttttctg tctggaatgc tcttctgtgc ttggttcatg ccctaattgt    120
catcttggct cagagaaata atcctggcaa caaattacct cctttgaatc ctaatcatag    180
tttttgtgt gatttttctt ttttggattg tcctctccca tgagattgta ggctccagga    240
gagcagaaac tgtaaatatg tgtgtgaata tgtatatgta catctgtttg tatccatggc    300
tatcagtata accatttgca catagttgtc tctcaataaa agtttgttga ataaatggat    360
gaaggaagtg gtgttttact ttgggaatat tttcataact ctccaggagg aggcattgct    420
tttattcagt ggttccatct atctattgct tcacacccat cacacaaaga atatgccagt    480
ttgaaaaata cagcctagtt ttgtgtgttt ggctactttg ggccactccc agattttcca    540
aaggtacact tgcattcacc tttatggtta gaggcacttt cttagaatct gagtttaaga    600
aacggtatgc tattttaatt acagtaagta ctttatcaag gtcagttgtc ttagaatgtg    660
gatttatatg acatagtctc taatacattc tgtttggcat gtattacagg gaaaaaccaa    720
acagtcctgt ttgcagccaa agattgcaag atggtggtag gtgtgtagtt agagcacgag    780
actttctttt gctcacatgc ataggtcagt tctcttcttt cctgtcttgt cagttctctt    840
ggatgagcaa ctgtgtttgg tcatgggggc aaggcactga ccttggagct catgtgcagg    900
tcactgtggg ccatagcaag tctgcctgaa ctttttttcc ccgtctgttg atctgtgcat    960
tcttgcttat gcttgagctt tttttcagtt tgtttttaat ctttgcttcc tcaagttaac   1020
ataagtagca gggtagaatg atctgccaca tgaaagtcat ttctgtctca aagtggtctt   1080
ggagaaacct gaaatttttc agtgtcttgt ttgggatgag gattgggatg agctctcatt   1140
tgaaacacat ttatttgcca ttttatattg ttgcagctca acatattgac cacctttttgg  1200
gtagtaccag ttctgtgctt tacaagcatg atttctagct ctcataacaa ctttgaggag   1260
aaggtattct cattctaagg ctgaggaaac agatatgtta agtcacttgt caggagcatc   1320
```

-continued

```
tgggaagtct gtgctggact tgaacaccta ggcctcccag ctctcaagtg ggatcatgtt   1380
gtactttgtt ttccaagtgt tgctagaggc agcttgtctt tttgcacatg tgtcattcac   1440
agtcctcctt ggtctgtgat accattcaaa tatagtggcc tgacctctga gcagtgtttc   1500
actacttctg aatgtattat gttttatttt tttctctttg ataagtagta atggatgtgt   1560
aacccattca cgatatagta ccttcttgtt ccttggagct gatactacac tcagttgagg   1620
gtgacttttt ctttgttgga catttacaaa taatttcagt cacaacattt agtgacataa   1680
atactttgac ttgaaacaat taccattttc tcgattttag tgggagactg gggcaatgtg   1740
tgtaggacat ccttcagaaa cagatgagta taacaagctg tgtgaggcag tagaggtgca   1800
cacacctcag ttactggaag gcacaacttc gagttcttgt ggattgtgtt ggcagccctg   1860
tagatagatt cagcagatgc tgtagacatt ctcttactac cgaattatag cttaaagacc   1920
taactcttag agcaagcctt aaaatgtgct ttccccgctt tgttttagga aactcttctg   1980
tttgctgatg aggaaaggtt atctttccag gcagcatcca ggaatggtct tttgaatgtc   2040
ttcatgcctt cttgtgacct cattcctgct gccatcgtac ttatccctgc tcagattaac   2100
tgcctgcgtg ttcaacttta ttccatagtt ggatctacct gtagcatttg cagctttctg   2160
tgtagactgg gcacaagtta aaagcttagg aagtctatat aactcaccat aattttagca   2220
ctttaactta ttaaggtaca tgttttggtt atctgattta tagaagtacc atgtaaaaat   2280
ccacctatgc tgtacaattg ctgaaatact gagtaagctc tgcattttat gaccaagtta   2340
taggatgaat aattactctc tggagtgaat ggttcaaaat gaaataactg tatgccttag   2400
gtgtgacgtg acacgagatg tatttaagcc ccaaaagtat gtaattatca cactactctt   2460
gcatagacac acaagtacat ttttgcttat ggcaagagtt ttatgtgcaa aagaaaactc   2520
actttctggt aagcgaagga acagtccatt atttttgagg ggttcataag ttgtttggta   2580
ttagaggctc catttcaatc cccctgcatt tctttagggt ctaatttaaa ttcatacatc   2640
acttgattct agagtaaacc attatcatac cctggatttt gaatattaag gacagttgag   2700
ggagtttctc aaagcaccat tttatgactt atagtctgcc tctgtattca gtgacttatt   2760
atatattcca ttcttagact gcattttgat catcaactgt attaaggcaa tatatgttgt   2820
actttatttt actttctact gaaagtaaga gctattttgt agtctattta gatttttaat   2880
tttataatct ggtctcattt tacagatcat gagtaattaa aggtatctca agctgatttg   2940
tcctgttttt aattcagtat taaagtatta ttttaatcac attaaaaatg tgactgatat   3000
tttttgttta tcacaattct actagcccca ctgagtaact gctgctgttg aattagtgat   3060
ggggttatat cagtttccct tgtcaaagga ccagatacgt cagcttgggt atttagcttg   3120
gtagttgtga cttagttttc tgttctcaag cccaggagat gagaattcct tattctgggt   3180
gccagtggag gcctacagtg gctcctgggt gttcctttgg gctagagaaa gtcaagttga   3240
gatgcccccg gctttcagac tagaaaaata aatagcagtg atggtattga tgtagctaag   3300
tgatgtagct tacctgttta cagtgcgaat ctcttgagag gtgtgtgtgt tttaaagtct   3360
ctcaagagat tcgcactgta aacaggtaag ctacatcaat tagctaaatc acacacacac   3420
acacacacac acacacacac actattagat ggcaggagcc agaatgttaa cttagttttg   3480
taactaagtg ttagagaaca atacatttaa agctttaaac ttttaaaaaa tataatttac   3540
aagtaatttg tagaaaagga tagtagattg ctaccattat gctaaatatc aatctgttca   3600
gtaaagagac tggcaaattt taattcatct ataattttgc tgtctgatgt ggtagccatg   3660
tggcaggctg gaattgagat tactgaaagt gtaacacatg caccagagtt tgaagactta   3720
```

```
gtgcaataaa aagaatgtaa aacattatga acaatttatt gaaatgataa tatttgtgtt   3780
aaaagtatta ttagaattaa tttagcctgt ttattttaat ttttaaaatg tgactactag   3840
gaaatttaaa attacatagt ggcttcatta ttttttaatt agtgctagtc tctaggccct   3900
ttggtctcat aataagttct ttctgtttat gtatacaatt cagttatgat ttgattacat   3960
acttgatttt aactttttgc cagcataaat ctaaacactg tagtgattct taaaccttag   4020
tttcaaaaca ctgtgtgtgt gtgtctgtgt gtgtgtttcg gcagagatgg agccttgctc   4080
tgttgtccaa gctggagtgc agtgtcagaa tcatagctca ctgcagcccc gaactcgggt   4140
tcaagtgatc ttcctgcctc agcctcccaa atagctggga ctacaggtgc acgccaccat   4200
gcccagcttc aaacactttt tttaagttgc ccttcacatt atttgagact gttttttatc   4260
ttaaatttta aggcagaaga accatctgcc aattgattat tttgtaggtt tcagacttca   4320
ttggctgagt tatttacaat gagttagaat tcattttatt ttcgtagaag ttcagtgggt   4380
tggttatgat atttgggatt ttatttctgg taaaatacaa tgaatgctat taatgaaatt   4440
attgaaagta agggcaaaaa ctgcaattac ttttgcacca acctaatata tttactttaa   4500
aaaatcattc ctttggactt ggctgtgaaa attaaaaaag agaaaaccct cattccttaa   4560
aaacgttggc ttttatagta ataagctgtc ttacaggttt gatatatata taatatatat   4620
aacataatat ataatataca tattttatat atataatata tataacataa tatataatat   4680
atatattata tatatatatt atatataata tgtataaatat atatataaat attttatata   4740
taatataaat atataattga taaataaaaa atatatattt tatatataat tatgtaatat   4800
atataatatg tatatagtgt aaagacagaa gaagtatggg ttttcttgag tttcagtgtt   4860
tcttggattt tactatccag tttataaaaa ggaggagaaa cagaccaacg taagatggtc   4920
aattctttgt tttttgtagt atttttcaaa atgtagtctc cggttcaata gcatcatcat   4980
cacctcttaa tttgttagag atacacattc ttgggcttca catagacata ctgactggga   5040
aactctggag atggggccta gcatctgggt tttaataagc attccaggtg attctgatac   5100
gcacagaacc actggcctaa tgtagtggtc agggtccacc caggaaaaga gaaactaccc   5160
ttaagttttt gaaacaggaa ttcagtgcag ggtattggtt attcaggtta tgcagctgaa   5220
acagcaaggt agattgaatg atgagggctt ttaaagcagc acgaaaataa tacacaaaga   5280
taatacagtc actagggtta ggctatggga atttaggagc cagggttcac ctcaggagac   5340
tgaaacctcc tggtaggggc aagtaggagc tggagccatg gaagcaatgc agccattgct   5400
ggaaacacta cctaaagaag agatggaagg agtgggagaa atgttgtgaa tccttccttc   5460
tcaccttcca gttttgcacc agtgcctctt gtagactgaa cccagagaaa agccagctga   5520
tctagtagcc tgagaaatgg ggtctggcag tgatcagctc acttgagata tagagctctc   5580
agagtgtatc tgtgggtaaa cacacccaga actggctcat gtagtaatta cagtttaaaa   5640
caaaacattc taatataatt aaaaaataat ctcagaatag aagacagtct tcttaatgga   5700
ataatcatag ctttatgaaa actaaaccat ccttttataa tttctctgtt ggctagggaa   5760
atgttttcac aagtgtctgt aaatttggaa accttacctt acacctttga aggattaaaa   5820
aaaaatttcc tgtttactcc aggacctgtt ttagccctac tcttcctagt tgatgagtta   5880
ccaagctgtc cttggttgtt agcgccatct tatggcagac gtgggaaagt tgcctcctca   5940
atttttgaca actttcctgg aacatccctg gatggttttt cttatctctc ctctcattta   6000
ttgcttaaaa ctaagttcca ccattttgta tgtcttcttt gcctctagtt atttccttgc   6060
```

-continued ccccttttact tttccagtgt tctctttttc ctgttctttt tgtttcaatt gtgattatac 6120
atggctgata aaagttacta cagtgatagc cctgtaacaa ggaaaatgca gcttgtagaa 6180
ttttaaagtt agaaataatg tcttgaacct tttaagccct tgaaaggatc ttgaagatcc 6240
cccaaaatct gcaaaaaatc atgtatttcc tcattctttt aagttaatgt ttttttccag 6300
acagtagtat ttaactgctg ttatttgaag cagtattgtt ttaaagtatt tataagaaat 6360
ggaagcctaa gaagctaacc acaattttcc cacttgatag ggaactgtgt tctgaattcc 6420
agttgactgt cttagaatcc agttatgtgt taaatggtcc aaaataaaat ctaatattta 6480
cgaatacaaa tgagtctgga acatatagtc gtcttatatt taaaagttct gtgttttcat 6540
tcattaactt ttattcactt tccaaatatt aagaaaattg taaataggtg aggaactggt 6600
atggttttac ttgagagctt ttaccagtac aaggaaatgc tgctagtaaa aatttggaaa 6660
tggagaagga gttctttaca tttcttgagt tctggtggaa gaccagtgct gttgttttgg 6720
tttaaggtgc tgagccagac gctatagagc agtgcttccc agtctctttt acctcatagc 6780
acacagaaaa taatttgtac tgcactgggg taggaggtga tttctaattg tagataagct 6840
gctaacaggc tagtgattgg acactactgg ctttggctgg ctcaagagct gaggttttgc 6900
tgtctgggaa ctttaatctc tcatatgggg aagctctgct gtatagagga catttcaggt 6960
gtaatgaacc ttagtctcat taagagcgca atacatataa cacacatagt ggtaaattat 7020
gatagtgatg gtttggtgaa atgcttaaga agaataagag aagttagctc tcaatgagat 7080
ggaaaggata aggctctgca gtgggagtgg atcagagagg gcattccatc cagatatgga 7140
gggaccaaag gggagtttg gggaatgtca gagatttctc atgtggttgg ggtgcaagat 7200
ttgaggatgc aaataggaga caggtatagt gagaactact gttaagaaag aaggcagggg 7260
ttcaggaagg ccgtatgtgg ctgaatggac ttgtgacctt gggcatcact ggtagttttt 7320
atgcggtgaa tgacgtgatc tgaccgctct cctccccttt aaaaaaatat tctagggcac 7380
ctgtagaatg acctggaagc tgcaagcaga gaaatccctg gggagggga gtgccttcat 7440
ccaagctagt taaaggcgta caccaggtga atgaagatgg gtggacttgc taaagaggga 7500
acccgcagat tttgcttatg atgtgaagaa aaccacctca gatttggagc ctgggtgagg 7560
gaaaggatga tgggactgtt ttcagaatta gattctgttt gggagacaag gaactcaatt 7620
ttggatgtgg gtttgatgct tgaagagcaa caattgttaa tattgataaa gtgctttcta 7680
ggggccaggt agtgatctaa agtctttact ttctaaactc attttatttt caaaacgact 7740
gtaagaagta ggtgctatca gttagtgtcc agtcaggaaa atggaaaaaa aacaaaacaa 7800
aacaccaaaa acctaccatt agatagatgt tttcagcaga gaaagattta atgcagggta 7860
ttggttatag tgatgttgaa agggctggag gaacaaaaag aaaaaagtgt gtgttgggag 7920
ggtaatgttg gaccagaaaa gcagagagag agagagagag agagagggag aatgtgtaaa 7980
tgaatgttga ttgttgaatg agtaaaaagg agaagaggat gttatcaagt gtcaggtgtc 8040
cactgctgca taaagtgcat gccctgcagg tctgctggag atcttcattg gttctgctgc 8100
tttggagcca ccacagatga tgatggagcc tacagttatc tgttgctgct gttggaggta 8160
tcgctagaac caggaaacaa aaaaaggccc cttttctttc tctcaccttg cagtctgttg 8220
acagtgtttc ccatgggtgg aacccaactg gaagcaagtt gacaagggag tttggaaaat 8280
atagtttata gacttctagc cccttgtaat gcggagaaga attgagaacc aacagaaaaa 8340
taactggcag aggaagtaat gtttttaagc ttgctttgca gatgtggaaa taggcatgga 8400
gaaggtaagt agttctccta aggtcacata gctattattt ggtagagttg ggatgtgaat 8460

-continued

```
ccaggcagtg tggtttcaga gcctgtgctc ttatctccta ctttttgatc ttgcccccac   8520
acatgataat tgtttgattt gtctccttac tgctgagcac ttcaaatgag tggctgtttc   8580
cattgatttt acttatctag cacttatttt tattttgact tctgttactg gctttagttt   8640
tttaccctca cctttggaat atctctcttc aaggtcacca ctgattttta tagccaatac   8700
aatgggttat ttaagcttct gtttctcttt gatcttttcc tggcttttga taacagtagc   8760
catttatatg gaattacaac tttgacttct gtgatgttga acttgcttgt tttcgccttg   8820
tctcactgag gcaccttggt tttcttcttt ctctacgcat tccttagacc attgccatct   8880
tttggattga gtttgaattt aggtgtgtta tataagaagc cccttaatgt taattttata   8940
tttaaatcag gacgaataaa aagatgaaat acatatatat tcttgtggtc tttttccttg   9000
tgtgtgtgtg tttgtggggg aggggggtaa agtcacagag gagtgggagt aggtcccaat   9060
gtggactttt ccctgggctg aaggagaggg acttactttt gaatacctac catgtgccag   9120
cactgtgcta agtgctttaa acacattgct tccttttaat tatcctgtgt gagattggta   9180
gttaccttta ttttacaaat aaaggtaact gaaactgact ttgtgtgatg aaaaagtaat   9240
agaagtggga ttgaaaccct catctaactg cttctgacag ccaggttctt tcctctggat   9300
cacctggaaa aatctccagt ttcttatctg ttaaatgagg aaacttggca agataatttt   9360
taaggcccgt ttttcagtat catcctcctg attctgtaac atactaattg tcctgagcag   9420
tagttacctc ttttctaagt aaatattgaa aaagaaagtt agcatcccac tacagaaatg   9480
tgctgtatta ttaagaccaa gagtactgac aggttatttg taagaagtta tgaactagac   9540
aaagacattt aaagtagtca tgatactgga ttttcatgtt tgtttccagg gaaccccccct   9600
tacctccaac tgaggctgct gcccagaaga ttagaagctg tggcttgtaa cgacaggggc   9660
tcaggataaa gccttgggac aactccagtc taaacaaaag gcaaccctgt tattctatta   9720
tactttatgt tgaaagcatt tgctcccagg ttattaacta ttatcctttc ctcacaggaa   9780
atttagtgtg aaatttgcaa gaagatcgtg gaaaatatac tttaaggaca agattcactg   9840
tggtgcagtt tggcaccttt agaacgctaa cagacaaacc taaaatgatt aaccattatg   9900
tgagtctccc acatgttttc acatatggaa ataggtggtt taaatggata ccaacatcct   9960
ctcttggtat acagtactta ccataaaata tcaagcgagt attcttagat atgtatcagc  10020
aaagtaagta aatttccagg ctctgtagca tcttttactg tctttacttt ataaacattc  10080
tccaaccctt cctcattcat gccttatttt tttaaaatgg gaaattgaga tatgccttct  10140
tactcacttt tttttttttc tgagacagtg tctcgctctg taccccaggc tggaatgcaa  10200
tggccccatc ttggctcact gcagcctctg cctcccggat tcaagcaatt ctcgtgcctc  10260
agccacctta atagctggaa ttacgggtgt gcgccaccat gctggctaat ttttgtattt  10320
ttagtagaga tggggtttcg ccattttggc caggctggtc tctaactcct gacctcaggt  10380
gatctgccca ctttggcctc ccaaagtgct gagattacaa gtgtgagcca ctgtgcccag  10440
ctttaacttt tagttttaca ggttttccct gcagtagaag aagcttgcac agggagcctc  10500
agctcatgat tttcctccca cctctctggc cactccttca ttgagttttg gtgcttcatc  10560
ctctatctgc cctctaaatg ttggtgtccc tatcgtctaa ggctgggcac ttttctccta  10620
cctgatgccc ttttcttaga ttatgccaat tatcccaaag ctttctgtgc catcaagtga  10680
tgactgcagt ttttatttcc aggtctgact gctctcctga ttgcttgctt atcttttata  10740
tctgtttagg tctggcaggc atttcaagcc atttttagac tgctacccct gtaaagtaag  10800
```

-continued

```
aaaatttaca tcacaaccca gtacacacat acgttactat aaataacaga aacagatttt  10860
cacaagacaa gacttatccc taaaacatgc catgcttgct gatgttctca ataatactgt  10920
ctcatttcca ttaaaaaatg ctttctgtga cacacagcat tggcctatga cctcttagtg  10980
gttcaggaac ccactatttg aaaaacactg ttcttgagcc actgtagatg tttttagaga  11040
tgttgtaggg agccagctta catattggag actgtgccct cctttcccca ccccacaggg  11100
ggcactgcct gcaaggaagg tgtttgatct gaaccctctg aggccaatca aatggaaaag  11160
gtttagtaca ggctaacagc accagtttac aaggctatcc atacaagaat gattacatca  11220
actcgtggaa agtgtcatca tggaatcaga gtaacctctt ggttatttga aattgtttgt  11280
tatatagaat tggtaagaat accctgtaat ctagtgacat atagaaccag ttttgaatag  11340
taacagaact gcctataaga ttttatagta cttaccttgc acacttctgc tgagttcaca  11400
aaaggctgac taaacccttg ttctcggcaa tctcatctct gatcccaaag tgttctcata  11460
cttattttag actcaacata ttttctaatg aagcttctgg aaatagctgg tatcatatta  11520
cggaaactta ttattggcac agtgccttaa tgattagttg gcttgggggg tggggagaga  11580
ccctagctat caaggatgga cgtaaaaata ctttgctaat atgagcactg ctgaggttta  11640
agtcattcct gaggtaagct aaaatatgtt taaaggttat taaaaaggca cacagtttct  11700
catttaacat tttggtatta actttagagg ccaagagttt taagtagtct ctgtaggata  11760
gtttgtttcc ttccttcctt cctcccttcc ctttcctttt ccttccttcc ttccttccct  11820
ccttccttcc ttccctcctt ccctccttcc ttccttccat tcttcctccc tccctctttc  11880
tttcttttct ttctctctct ccttccttcc ttcctccctc cctccctccc tccctttcct  11940
tctttctttt cttttctttt cttcctttct tctttccttt ttttctctcc tttctctctt  12000
tctttctttt ctgggtctca ctgtttcacc caggttgaaa tgcagtggca tgatcacagc  12060
tcactgcagt accaacctcc tgggctcaag caatcctccc acctccgcct cctgagtagc  12120
tgggactaca ggcacgcacc accatgcccg gcccatagtt tctatttcag aaaacataat  12180
agcatactcc atcccctcta gattcaaaag taacataatt ctaaaattgt agttggtagg  12240
tttttttgcat atacatgctt gaattagggc agcttagtat caaggatcag aaaattatgg  12300
cccacaggcc aaatctggcc tgccacctgt ttttgtgtag cctgcaaact aagaatgttt  12360
tttattttta ttttttagtg gttggaaaaa aaaatcaaaa gaataatatt ttgtgatgtg  12420
aaaattatat gaaattcaaa tttcagagtc tataaataaa gccttattgt aacacatcta  12480
tactcattag tttatgtctt agtcctttgg ggctactgta gcaagatacc ataaactgga  12540
tggcttataa acaacagaaa tttagtttcc tatagttctg gaggctggga aacccaagat  12600
caaggtgctg gcaaattcag tgtctggtgt gggccctatt cctggttcgt agatgacacc  12660
ttcttgttct gacctcacat gatgggaaga atgagggggt catgcatgcc tcttgtttaa  12720
ggacactaat cccattcatg agggttctgc cctcatgacc taatcgtccc tcagaggttc  12780
taccacctaa caccatcaca ttggtaaatt tggggggaca aaaacattca gaccatagca  12840
tttaatgtat tgtcaatgac taatttcatg gtctaatggc agagttgagt agttatgaca  12900
gaaactttgg ccttcaaagc ctaagatatt tactatctgg ctctttacag aaaaagtttg  12960
ctgacccctg ccctattatg gttcatagcc tttttgaaat gtgacacatg ccaggcacag  13020
tggcccacgc ttataatccc aggattttgg gaggggagat cgaggctggc ggatcacctg  13080
aggtcaggag ttcgagaaca gcctggccaa cacggtgaaa ccccgtctct actaaaaata  13140
caaaaattag ccagatgtgg tggcaggtgc ttgtagtccc agctgtttgg gaggctgagg  13200
```

-continued caggagaatc agttgaaccc aggaggcaga ggttgcagtg agctgagatt gcaccactgc 13260
actccagcct gggcgacaga gcgggactct gtctcaaaaa aaaaaaatta tatatatata 13320
ttttatcaat cagcttcttg gatagggaat ggctgacacc ttgaattttg aaaaatgttt 13380
gggaatggca gtttctatgg tgtgacacag aaatatagca gtccttgata tagttgctgt 13440
aataagaatg gaacattcta aactttgttt ccgatttgac agctctttta tttttgaggt 13500
atctcagata tattttgtat gatccttcca tttcaccctc ccttgtgtgc ttttatttta 13560
atccattgaa gactttgtct cacagtaaac agtgtgatta tgttctcttc taccacttag 13620
cggttttcag tacttaggtt tgtctaatgg gctcatcact gaaagatgga gtcaattccc 13680
tttgctgact tactagagag tgtgtgcaaa tagcattagg ttggcatagt gtactgaaaa 13740
gttctgtcag accaccatat ttggcagtaa gtttggtaaa tgtgtctaaa atgggcacat 13800
ctgcccaata ccttagttcc tcttctgtaa agcaccttaa acctccaaat gtatcgtcta 13860
tcaggtgtct tttttttaa gatggtctca ttctgtcacc caggctggca gtgattttgg 13920
ctcactgcaa cctccacctc ccaggctcaa gtgatcctcc caccagtagc tgggactaca 13980
ggcgccgggc accatgccta gctaattttt gtatttttaa tggagagtgg gtttcaccat 14040
gttgcccagt ctggttttga actcctgggc tctcagcgat ctgcccgcct tggcctctca 14100
aagtgctggg attacaagcg tgaaccacca cacccagcct aagtgtcatt tttaatttct 14160
tttaactctt agccagaaaa ggttgcatat gtttttatgc attttttgag caatctaata 14220
taccaacctg tacccacttt gcctctcttt gtcctgtata tttgattgga tgggatagtg 14280
gccgtgccac gttttagtgt gctccagcaa gaccaagttt atgtgtaggt ctgaaatgtg 14340
tggtatcctc agcattcttc aaacctcaca aagaaggtga ataagcaact caaactctaa 14400
aaagacaaaa ctagatgtta caatgtccac acactgaagt tttctctta gctaattgga 14460 aagacccaga atcttctctt agaatttgat attcctactt agaaattgtt ttagaaagtt 14520
tagccttcta gtttgtagtg tatttagctt tctagtttag ctttctagtt gataatgtat 14580
ttgaaagagg cacatgctgg gtgtggtggc tcatgcctgt aatctcagca ctttggaggc 14640
tgaggcggca gatggcttga gccaggagct tgagactagc ttgagcaaca tggtgaaacc 14700
ccatctccac aaaaatacaa aaattaacca gacgtgatgg cgcacacctg tagtcccagc 14760
tacttggggg gctgaggtga gagtattgct ggaacccagg aggtcgaggc tgcatgagcc 14820
ataatcttgc cactgtactc cagcttgggt gacagagcga tctgctgtct caaaaaaaaa 14880
aaaaaaggca cagaaggcaa tgccttatat acaggcacat ccccagacag tgtcagcttg 14940
attaagtgat agcatgagga agtaaaacct ttaaaaagaa agaagactta agaattcaac 15000
aagagcagtt tgaggccatt tggtgtggag ccatagcccc agacacctca ccatcccctg 15060
aggattcact gtgttacagc tgagagtttt gatccctaag cgtgagccag tcactgtttt 15120
ctaggcatta cgttttctct tcataacaat tctgcagtgt agaaatgctt acatcaggcc 15180
ttaagtgcct tttttctttt ctttttttta attgggacag ggtttcattc tgtagcccag 15240
gctaggtaca gtggtgcagt tatagctcac tgcagccttg tactcctggg ttcaagtgat 15300
cctcccaact cagcctcctg agattacagg catgtaccac catgcttggc tatttcattt 15360
aaacaaaggt tttttagaga tggggtatca ctctattggt cttgaactcc tgacctcaag 15420
tgatccatcc tcctgccttg gccttccaga gtcctgattt acaggcatga gccactttac 15480
ccaggtcctt acgtgccttt tgttgttgag aagtgcaaga acattttctc tagctttctc 15540
aagattgcat ctacaagcac aggagctagg atttgaacac aggtagtcag agtctggagt 15600
ctatgctttc tccattatct caaagccata caagagaaca ggtagatcac agaggccata 15660
tagtatagtg gctagacttt ttaccttcag atcccagttt tcttaccttc tgattggtta 15720
actaatgttt agtgcctctg tttccacatt tatgaagtac atttaaaagt tgtttgtggc 15780
tgggcatagt ggctcacacc tgtaatccca acattttggg aggccaagat gagacgtata 15840
acttgagaac aggagtttga gaccagcctc tgtaacatag ggaggcctcc atctctacaa 15900
aaaattaaaa aaataattag ccaggtgtgg tggcacatac ctgtagtccc agctacttgg 15960
gaggctgagg caggggggatc acttgatgcc aaaaggtcga gactgtagta agcagtgata 16020
atgccactgt actccagcct gggtgacaga gaaagcacct gtctcaaaaa ccaaaagttt 16080
ctacctacac ggtaggattg ttgtgaggat tcagtgagat ttcatgttta aatagcccag 16140
tgcccagcac atgataaaga actcaaaaca tgttagctgc tgtattttat ataaaacata 16200
attattagta attcatagta gataaaccaa taattctcca cacttaagat agatatttta 16260
aaatttagaa acattttact cagttgaaat aatttaaaag tattcatatt aattggtgta 16320
ataagttagg acttatttta ggactactgc caaatgacta tgcaaaataa ttggcatagt 16380
tattctagat aattgaaatg tcttgcttga tgtaaacagt agaaaacaag agagaaaaac 16440
ctctgagcag tctgcctttg gttttccctt atgttagccc ttgaattttt aaataaattc 16500
ttttaaaata acgtttgggc tttggctcag taggaggctt accttttaaa ttatcagttt 16560
gccttttggg taaaaatcta tggattttct attatggggt gttagtagat gaaacaactc 16620
ttactgctgg ccagctatca agaaaggaca tatatctggg atgtcatcag ataattttat 16680
tttgatcaca ttgcttgcac aagaagcaag tcagtcagct ctctgatgga gatctggtaa 16740
ggggaggaga agcaaatgag aatgtccttc accttggaag tgtagtttct gctttgacat 16800
ctagcagctg tatgaacttc tgtagctcac ttaagcttac cacttaccac acctatgatg 16860
gggtgataat acctgccttg cttaactaaa aaggcttctt tgaatatgaa gtggcatata 16920
atgtgtgaag ggagcatgtt gaaagataca aagaaaggtc tagatacatt ttagttacca 16980
aataatattt tgtatgtgat gtccttttta aactatagag tgtttacaca catattcatt 17040
ggtgctttta gtgtgttgta catcacttca ttgggcactg gatatagatt ataagcttct 17100
tcctactata ttgttctaag acctgaagac ccagtgactt taatagcaaa tgtagcagcc 17160
ttggttaact aaaatgcctc agtccctatt agagaattta tcttatataa catttatttc 17220
aatcaaaatg atctttgagc ataggtcagt gaaagccaag ttactatatt acagaattaa 17280
ctatgtaatt tggtcattgg atcaaactca aatacattct ttcgacatgt cccaataaaa 17340
gagcattctg tgttaaccac cactaaccaa aaggccaaat tctcagaatc cattgtagta 17400
atgtatactt tatggttggc tacagttgag tattccaggg ctcaggctta gatgacctgg 17460
gggcttgcct ggactgttta atagagggtg gggcgggggg tacccacctc ttctctcaga 17520
aatactttac tatcttagaa agatttattt gaaagtggac agccctattt atgtctgctt 17580
acttgagtgg tggtttatga tgatcctgac tgacggggca ttagtttttc cccttgtata 17640
cctcctcaag cacagctctg tatacttacg tgagaaccac ccaccatgcg aaaataaaat 17700
gcatccctgc catacctcag aaactgtcag tctagtaggg gagatgttaa gatttgcaat 17760
attactaaaa atgatttttt tatctaatga tgttagtttt ttagatcaag agttaagtgg 17820
tgtaaatggt tcttcctctt cccacagata tttcactgga catctgagat gtcagatttt 17880
accaaaaaac aaactacaaa acagaggcta tagcataaat cagattatgg aacattccaa 17940

```
cttaaaactc aaatggcttt ccaattgtat ttagaattaa ataacttctg agataacttc  18000
taagacccta agtgagatca taaccatttt ttcttttgca tcctctgtac aaaagaactt  18060
gaactacatc gaacaaatta tgaaacatcc ttatcattgc actgttattt ttgatttttg  18120
aaaaagtttc aaagaacact cagatttgta ttctatttta aatttgcaaa taccctatga  18180
aatcctcccc tcccattatt taaaagctgt ataaaaataa tagaagcaat gaaaccacat  18240
tttgaaacat gtgcaagata ctgggaaatg ggaaaagtca ttctatacca ttgtgttaac  18300
caaccatagt cactatttta gtgtttttcc tccttgtatt tcctatgcat taaatgcagg  18360
ttttcattat ttgtacattt ttatatctag ctctttttgg tttgacattg tatgataagc  18420
atttttctgt tatatacaag ttatgtgtaa acataaataa ttcagtggat ttatatttta  18480
tttgaccatt gtcttatttt ggacatttaa atttgtttcc aagttttcat tttatgcatg  18540
aggctcagat ggagtgtctt tgtgcatgtg gagtaagcac tgcccttcac tctgcccgta  18600
ttttctttcg cctttaatat agacttccag aagaggaaat ggtgggccaa agggcatgtt  18660
ggatgttttt atggcacttt ctatgtattg ctaaattgcc taccagtttc acacaccaat  18720
tgccagcaat ggatattagc atagttttac aatttttttt tgccaattaa cagcaaaata  18780
aaaaactaaa gaacccctac aagttacctg ttgttttaat gtgaaaattt aaagttactc  18840
acaaagttaa gtattttccc atatgtttgc gtattcattg cgtctcctag tttgtgaact  18900
ttactcctgt cctcttttttc atcagttggt aaaggttgtg gagggccata gtggtggaca  18960
gcacgagctc tggggacaaa ctgtcaggtc tgcacctggg ctctgcccca gggtggggaa  19020
tatgtcctgg ggacagagga gtggaatatt ttttattttt aggaattcaa tttctttcta  19080
ttattttttt tctaaactta gaaaaatccc ttgccttttt agatgtttag tcgccagttc  19140
tgaatttctt caagtttaga aagttctttt acctccttac tccacctaga ttttgtttta  19200
tatttcaaac tcttaaaatt gatgacttta tcaactatct acacttatta tgaagatgta  19260
acaggcattc cttagaaatg aaatttctca ctttgaaatt ataaaattgg cactgcattt  19320
atagtaaaac tagatgttca aaagtttatt gggtaatgat gtttaaataa ttggctaatt  19380
tctttaccta aattgctttt attttaaaga gaagcacgtc agaattttat taggcatatt  19440
agctagtgca tggcgtggtg atttgttagg ttttgggtat tgtaagagag ttttatttgt  19500
ttagaagtag ttggcaagat atttatcttt tgattttttt tcctaaaggt gagttttata  19560
taggaatctg tacctcggga tcacgtggct ttgtgtacca ggcgtccagg gagcaattag  19620
gagggcaatc tgttaagtct tttgcctcag ggcagaacca ttaggtgtgc tgtgtatgtg  19680
cctcaagggg tgtaaataac taagctattc atgtactcat cagtttcctt tcaaggcatc  19740
tgtgaaacct ttaatctgtg gaagaatcag agaaagttga cctattgtat tattatcctc  19800
cctcacctga atattttgat aaagtatatt ttagaattta cagattggac attaagcaca  19860
tgaactttaa attccacttt ccattttgat gtgaatgttc taaaagttcc ctatgattta  19920
aatgtaagca gatctttaat gtctacagaa gagattttttt tttttgttg atttattatc  19980
tttcggagtg aataaattcc atttactgat ggctgagatt tctcactgtc atactacaga  20040
aatgagcagc attccagttt gtttcctata ttaattttgg ggcattattg aaaagaaata  20100
atcattcgtt tccctttcta ccattgcgca taaatgccat ttaaatgtgg agaaatctct  20160
tccaccttaa aaaaaaagcc ctcctttgac actgagcctt tctaccccat tcttaccctc  20220
tgccctattt tttttttca tatccaaatt tcttcaaaga gtgatcacat tcactttatt  20280
```

-continued

```
tcttcacctt gtacttcatt cttttaactt tggtctgccc cagcactcca ctgaacctgc  20340
taaagatgcc agtgttgcta aattcagtgg gctcttcatt cttcatctta tttgacaact  20400
cagtagcact gaacacagct gaccactctt tctcataaca gtctttactg gactttggta  20460
aatcaagatc tgttggtttt tctcttacct ctttggtaac tccagtctta gttaagccac  20520
cttcctcttc ccgctttttg gaccctttc ctactctcct atactctcaa accactatgt  20580
accaggttca agtgttcact tctcctgagc tccagactcc tgtagtccac ctattcatag  20640
gacatcttta tttatttgtt acacttgtgc ctcagactta actattttcc tttcaaacct  20700
gcttttctct attagtttcc tagttctgta aatgacacca tcatttatat catttctgag  20760
ttgttcaagt cagaaaatta gcagcgtctt atcattttta cctcttcaat atttcttttt  20820
ttcatttagt tatttaattt agatatgaat taagattttt tgtgtttaat ttgtaggaac  20880
atttcttaaa aaattataaa ttatacaagt catacatgaa tatattctta taaaaataaa  20940
aatattacct ctttgttacc cataattttc acttcctttc tccagaacta accactatta  21000
tcagtttggt tgcatacttc cagaactctt tttattcatt tacgtttaaa aaattttaaa  21060
aaataccta tagagtgggg tcttagtatg ttgcccaggc tggttttgaa ctcctgggcc  21120
caagcagtcc tcccaccttg gccttccaaa gtgcttggga ttacaggcat gagccactgc  21180
acctggctct atttacattt aagtactgat ttattgaagc tttgctagaa tgtgtcagtc  21240
accactgggt cttttttgg agggggaata ttagaacatt ttgactacta aaatttcttc  21300
tactcagtat ttcttttttt tttttttttt tttttttttt tgagacggag tctcgctctg  21360
tcgcccaggc tggagtgcag tggcgcgatc tcggctcact gcaagctccg cctccccggt  21420
actcagtatt tcttaaatga atcctttctt catcatactg ctgctaccac tggtacccta  21480
agtctaataa tcacgtctgg ttcattgcag taacttattt tctctatttc cacccttgtc  21540
actgtgcaaa taaactatct tctacattgt taccaaatga tctttaaaaa tcatctaatg  21600
atcataatct tttcttgctt aaaatcttac tgatttttca ccattcttaa ggccaaagtc  21660
taaaattctt actgttgtct acaaggccct tcatcatctg gccccaccta cttctttaat  21720
atcatatctt actccccccc actcgtcaac agagaacttt tttttgatat ctaagatttt  21780
tagcattaaa attataggat gtagtagaaa tgaaagttta aaaatattgc ttgtaaaatt  21840
attcttcatt ttaatgtata ttcataatta gctcacttta tgcatatgtg tcaaatgaga  21900
tagtttttgt tagtgtttat gaactgtaaa acattaatgt aaaatattgt ttctctttac  21960
tttttgtttc tatcttgcct tttgctttca tctacttgat aaaagatact atacatgtgg  22020
taataattct gtaggaatgt tggagtagaa tggacatgat tttctaattt ggaatgtcct  22080
ttgaatggaa aattagaaaa cagtccataa aataaaccat tatgttaggg gtgatatgtt  22140
caaaagaaaa gatttttccg gatcatctgt agaggtcttt ttaaattctt tatgcctgtg  22200
tctttagctt ccattttaag aaaacatatg gccgccatag aattgtttct tatttatatt  22260
taatttatgg ataaactcag ggaatctgct attttaacag tacttttggc gttcatacat  22320
ttttcatata gcccttctgt ctgtaggagg gaggttaatg ccaaatacca ttattgcctg  22380
tgaggaagac catcatcttg tgattggacc catactaatg aaatatgaat gctctagttg  22440
agccatgaat cacatcattt gtacttggtg gagcaaaatt gccagctttt tattttattt  22500
tatttatttt attttttgag atggagtctc gctctgtcgc ccaggctgga gtgcagtggc  22560
ccgatctcgg cttactgcaa gctccgcctc ccgggttcac gccattctcc tgcctcagcc  22620
tcccgagtag ctgggactac aggcgctcgc caccacgccc ggctgatttt tttgtatttt  22680
```

-continued ttagtagaga cggggtttca ctgtgttagc caggatggtc tcaatctcct gacctcatga 22740
tccgcccgcc tcggcctccc aaagtgttgg gattacaggc gtgagctacc gcgcccggca 22800
gggttgtttc ttaaaggtaa ataagctccc taaatttgtc tgtaaattgg aagtaactcc 22860
agtgaaaatg ccaacaggaa tttttttttg gcttgacaaa ctaaggctaa aattaatata 22920
gaaatgagca tacaataata ggaacactat gaaaaagaag agtaatgaga ggtgggacca 22980
agtctataag atattaaagg gtaagtctct ccggcccggt ttccctcggt gtgctactgt 23040
gcgcgcgatc cagcaccatg gggaagcggg acaatcgggt ggcctatatg aacccaatag 23100
caatggcgag atcaaggggt ccaatccagt cttcagggcc aacaatacag gattatctga 23160
atcgaccaag gcctacctgg gaagaagtaa aagagcaact agaaaaggaa aagaaaggct 23220
ccaaggcttt ggctgaattt gaagaaaaaa tgaatgagaa ctggaagaaa gaactggaaa 23280
aacacagaga gaaattgtta agtggaagtg agagctcatc caaaaaaaga cagagaaaga 23340
aaaaagaaaa gaagaaatct ggtaggtatt catcttcttc ttcatcaagc tctgattctt 23400
ccagcagttc ttctgattct gaagatgagg ataagaaaca aggaaaacag agaaagaaaa 23460
agaagaaccg ttcacataaa tcttctgaaa gctccatgtc agaaactgaa tcagacagta 23520
aggatagttt aaaaaagaaa aagaagtcaa aagatggaac tgagaaagaa aaggatatta 23580
aaggactcag caaaaagaga aagatgtatt ctgaagataa acctttatca tctgagtcct 23640
tgtcagaatc agagtatatt gaggaggtgc aagcaaaaaa gaagaaaagc agtgaagaac 23700
gagaaaaagc aacagaaaaa acaaaaagaa aaagaagcat aagaaacaca gtaagaagaa 23760
gaaaaagaag gctgctagtt caagtcctga ctcaccgtaa cattaagaaa aatcaggatt 23820
cccttataaa gaaagtgcaa tgtctgagga aatttcaact gtgaaaacta caacatattt 23880
actaaaatgc atgaattttc ttgtttttag aattattcct ggactattca gtagccactc 23940
agatgccact gtgtgaaagg gccataaatg ttgcctgctg cttgaacatc tatttttttc 24000
tcttccagtg cttgataact ctgggagata atacactgca gtcgtactag tggttaagat 24060
atttgggaat aaaattaata cttttgacta gaagcgtcta aggataaacc aacagaaatt 24120
gaatctggat acatctttaa gatgtaatca gaaatgacca gatgactcta gttagaattt 24180
ttgaaggagg gattacatta atatttcaaa acccttactc tgtagataag tgtattttaa 24240
tttttccccc tcgtatactt ttatttacct ggggaaggag cttttagggt tggggggtgg 24300
tttgctatct ctttagctag cagaatagtg tgcctttgat cctcacacat ctgtattatg 24360
gacacagtag ccatgcttca cggggaggtc agagctggct accagcagtc ttgcccttta 24420
ctgagcttag tgtcatcttt ggatgctgtc atatgctgct ttgagtgaac cagagaaaca 24480
gccatttgca gcatgagaaa gccccaaaag ctctgggatt tacctccact tcagtaataa 24540
tgaatatttt ttagcattag aatgtgttat gtcatttgaa ttaattttga ctacactttg 24600
gcttgggaga ggaattattt taaatagaca ttggtacttt ttgaacttga tagctaaaga 24660
ttctaaaatg catgttttat actaagtttt aaccagtcag gaaaatttta tgtaactagt 24720
gatagtttat ttttttgtat gaattttgtt taggctgcaa tgtttagctt ttgttaactc 24780
ctcactcttg ctgtcttaag ttcattacta tgtttaatgg cctacttgcc aagatattta 24840
gcatgtaaaa agcagggttt tgattaaaaa aaaaaaggct tcatattgaa gctgagactt 24900
acaataacaa gttgagtggc aagcctggta tgctgtgtct tattgccaga atcttagtaa 24960
atgtaatgtt taaaaaaaaa gatattaaag gatagtaagc tacaataatt aaaactgtgt 25020

-continued

```
gatgaaggca catgtataga tctagatcag tgaaataaaa tatgaagaca ggaacctgga  25080
gactgcagaa cacacagaac atgataaaag tagcatttta aatcagtgag ggaatttatt  25140
caaagggtgt tgggataact gggtagccat ctggaaaaaa ataaagttgg atctataatt  25200
tatacctcca ccagaatgaa atttaaatgg atcaaacttt aaaaggcaaa gtcacaaaag  25260
aaatagaact aagcagggga gaaaacttgt atagtttaga atgaaagttt tttttttctt  25320
gacataaaac cctgaaacaa taaaaaaaca agattcataa gttagattgt ataaaaaata  25380
aaagattttg catacttaaa actaccgcaa gccactttgg gaggctgagg ctggcggatc  25440
acgaggtcag gagatcggag accagcctgg ccatcatggt gaaaccccgt ctctactaaa  25500
aacaaaaaat tagccgggcg tggcggcatg tacctgtaat cccagctact caggagactg  25560
aggcaggaga atctcttgaa cctgtgaagc agaggttgca gtgagccaag atcacaccac  25620
tgcactccag cctggcgaca gagcgagact tcgtctcaaa aaaaaaaaac cccacaaagt  25680
caaaagacaa gtttgaaaaa tgtttacagc tccacaaaga tagacaaatt tccttgatgt  25740
atgaaaaatg tcaacaaacc aataaaaaga ctaacaattc agtagaaaaa tggacaaaga  25800
acaaatatgg agattcatag aaatgagaga taaatgtaca tgatgagaag gtgaggtgct  25860
cacttgattt ataagagaaa tgaaaattaa aactacacca gatgccattt tttaaaaacc  25920
tattacattg atgaaaataa aaatttagca aattgttagc ctgaatgggg agataggtac  25980
ttgaattttg tgtgggaatg taaattagga cagtctttat ggaggataat tttatagaat  26040
ccatcagatt tataaatgca cagacctatt tgacccaaca atttaacatc cagattttta  26100
tcttatgcca aactgaaatg aagaatggcc aagttttatt gaggcatcat ttatagtagc  26160
aaaacactgg aaacaagcta aatgttcatt atagaagact ggttaaataa aaatttgtcc  26220
atcgaagatg gagtagcatg tagttattaa aaaagaataa ggaaaatact gatagaggat  26280
gatgtagata ttaaatgggg aaaaaagtaa aactccacaa gatgtagaac agtatatgtg  26340
ttttgctgcc gtttgaggag aaaggagaaa atacagaaat atttatatgt tgcttatgta  26400
tgcatacaac atttgtggat ggattcacaa gaaaatggta gccttaattt accttgagac  26460
aaactgaggg acaaggacac cctttaatac ctttcagata tttttttttt ttgagacagg  26520
gttttgctct tgttgcccag cctggagtgc aatagcgtga tctcagctca ccacaacctc  26580
cgcctcccag gttcaatcgg ttttcctgcc tcagcctccc aagtaggtgg gattacaggc  26640
atgcgccacc acgcctggct aattttgtat ttttttagta gagatggggt ttctcatatt  26700
ggtcaggctg gtcttgaact cctgacctca ggtgatctgc ccacctcggc ctcccaaact  26760
gctgggatta caggcgtgag ccaccacacc tggctaccct ttcagtttta agccataata  26820
aaaattacat gaaattgggc tgggcacgat ggctcactcc tgttatccca gtgctttagg  26880
aggctgaggc aagaggatca cttgaggcca ggagttccag accagcctgg gtaatgtagc  26940
gagaccctgt ctctacaaga agataaaaaa attagctggg tgtcgtggtg cgtgcctata  27000
atcctagcta ctcaggtggc ggaggtgaga ggattgcccg aacccaggag tcaaaagctg  27060
cagtgagcta ctgtgatcat gcctctctac tccagcctgg gcaatagggt aagatcctgt  27120
ctctgaaaaa aaaaaaattt tttttttttt tctttctttt tttttatttt tagacagagt  27180
cttgctctgt taaccaggct ggagtgcagt ggcacgatct cagctcactg taacctccac  27240
ctcccagatt aaagtgatcc tcctgcctca gccttccgag tagctgggac taccagagtg  27300
caccaccatg cccagctaat ttttttgtat ttttagtaga ggggggtttc accatgttgg  27360
ccaggctggt ctcaaactcc tgacctcagg tggtccacct gcctcagcct cccaaagtgc  27420
```

```
tgggattatg ggcatgagcc actgcgccca gcccaaattt tttctttcta cacataaggc  27480
atcacgactt tgctgctgtt attttggaaa actgaagaaa ttattaaaga aagaaccgtt  27540
ggcatcatta aaatctagtc aattttatta ctaattgcta tgtaactcta ggtgagtccc  27600
tcatcataaa taaaaatgca tcttaagatt ataaatgttg atcagagtac catgccaagg  27660
ggcagcagac tactcaattc ctttgaaaaa atatcagaga aaagttgagg tagaaaggat  27720
tgtctctttc taatccaaaa tattaaagat gcattttctg gctattttgt caccaaatga  27780
ctgacagcta tgtgtggaga gaatcggcat gcatgacaca gcatgcagga ccagccatca  27840
ccagccacac ttgtctatca gatgaacatg atgctactta gtcttggttg cattcatctg  27900
gaaaggacca gcttttggcc tgcattccag ttctcatttt cctcatgtat cggtatcact  27960
ctactgtcta tacctcaaca aaaaagaaaa agtttagcag gtggaccttt actagtacaa  28020
cacgttagct acaaccaaat tcatttgtta tatcaagaaa gatatatgca ttctacttcc  28080
acatgaaaag ccttagtaaa ttttacattt gttttgaacg gattgtatta catgtatcca  28140
cacaaaaaac tactatataa tgcactgtgt tggagggatc tattcactcc acactgcatg  28200
aatacctcaa ttactaaagg gaaaaagagc ccttcttgtg gcattcaaaa gggtgactat  28260
atggagttac agctgaacaa cagggaaaaa tatatcactc tgatgatcaa agaggtaata  28320
tactgtgtgt tagttttcca tagccaagta gccacatgtc acagaacaaa aaaaactatg  28380
gacaactgct caccactgag gcaagcatgt acttttattc atcctttaat atgaagccat  28440
gacacacata atgttacttt gagctttgtg taggatagat gtaccttgcc ttatttaaat  28500
tcaatagagt cataaaggaa aaaaatgctg aagataattt tcactttaaa aaagaatttg  28560
gaaaatactc tttaaaaagt aagtcccaga atgactcatt ctacaaatat attacatact  28620
acaaggaaca ataaatgttt atgaatacac atagcaggga ctacaggcgc tcaccaccac  28680
acctggctaa tttttgtttt ttgttttatt ttgttttgtt tgagacaaga ggctcactct  28740
gttgcccagg ctggagtgca gtggcacgat cttggctcac tacagcctct acctcccgga  28800
ttcaagtgat tctcctgcct cagcctcccg agtagctggg attacaggca cgtgccacca  28860
cgcccagcta aattattttt gtatttttag tggagacagg gtttcgacgt gttggccagg  28920
ctggtcttga actcctgatt tcaggtgatc cacctgcttc agcctcccaa agtgctggga  28980
ttacaggcgt gagccaccac acctggcctg tatttttttt cttttttttt tctgtactag  29040
aaactgcgtg tcgccatgtt gcccaggctt tcttaactcc tgggttcaag cgatccactt  29100
gcctctgcct cccaaagtgc tgggactata ggcgtgagcc acctcgcccg gcccataaat  29160
gattttatgc ttgtagtaac aattctaaac caggggttag caatctctgg cataaaaacc  29220
aaagagagca aaagtcaaca gtgaagactt aatggccagt gcataacagt ataatctccc  29280
ttgattcaag ttaacatttt ccagtaaaca tttcttgagt acctgctagg tgccaaacag  29340
tcctacctgg atcagcattt cctacaccta cacctcctga cttgacacac agaaaggact  29400
ctcaggcttc atatgaatgc tgacgctgat accatatacc caatacactc agattttgaa  29460
gtcctaaaaa ctatgagtgg atactacata ttagtactgg caaaaattag agttaagttt  29520
agcaagaaaa ccaatgtaca cagatgttaa ttgttaggaa aacttacaag agaatactta  29580
ctaatgactg tctgtgggct gggtgcagtg gctcatgcct gtaatgccag cactttggga  29640
ggccgaggca ggcggatcac ctgaggtcag gagttcgaga ccagcctggc caacagggcg  29700
aaaccccgtc tctactaaaa atacaaaaat tagctgggcg tggtggcggg tgcctgtaat  29760
```

cccagctact cgggatgctg aggcaagaga atcacttgaa cctgggaggt ggaggttaca 29820
gtaagctgtg atcacgccac tgcactccag cctgggtgac aggagcgaaa ctccgtgtca 29880
aaaaagaaaa aaaagaaatc tagtatgaag acagagtaat aaacagaatg aaatagtcct 29940
aaggctattc aaagtcataa agaataggca aaactatttt ctcaccttaa atatcacaca 30000
aacaggctta agagtttgcc tatcagatgt aacttggcat ttacattgct aatagtgctt 30060
tttcaaagag tgctcacact ttcagttcct tttgaatgat aatacctgga tctcctacct 30120
accctaggac tcagacatac taataatgtc aagctgcaga taagcatttt catgttcaga 30180
gcagaaattt tttgagggag gtatttgttt ttgtgggaag gcattgtata ggaaggttcg 30240
ttctgctttg ttctagtttt tactcgatac tccataaaca gtgagtgcaa ataaaattta 30300
tccctcatga aaagacatat atcacaagac aaaaaccaat ggaaatgaaa aattcctaaa 30360
agagctgttt tcagtacaca ctagaaaaaa ggatcctcac ttctttgtgg tattaaatta 30420
tttgtcttca tatagttttc aactcaaaac tagtcgtcca aagacccttt ggaaaaatga 30480
aactataaaa ggcaatggat tactcgacca caagtaaatc cctacaattt taaaatgaca 30540
gtctacttca gtgcaatcgt ttagacaata aagatttaaa ggaaaagaga ggcaataaaa 30600
cacttcacaa atcaaaaaaa ttgcttccag gatacaaaaa gatttcccta cacgaggtct 30660
agccttgaaa ttgcagtaag aaaaacattt ctgaagtaat aaactgaaga tacagactta 30720
atgttaactt ccaaactatt ctttatttat ctttttacta ttcgaaagaa agaaagaatt 30780
tggtgtttag agtgcatggg gaagtaggta ggaaattagg gagctaattt atagcagatt 30840
aagatacaga atgtccgcaa agtcagagaa cataggatgc atttaaataa catgctcagt 30900
gttattttct ttaatctcca aacacctttc caggtgaagt tcctttaatt tcaaatcatc 30960
gaatctcatt cttaacctga aagtggtaca ataaatacag tctccaaaaa gtctggacac 31020
acagggaaaa ttgtgtgtta ttcagtgatc atcttacttg aaaatgtaac ttacatactt 31080
ttaaaaaata agtttattgt atgtttattg aattttcaga taccctgtat tttgcttcta 31140
tttaggattt cctttctttt taagtttcag gcatagtgct aaaataacta ggtacagtca 31200
acaaagagac taggcagctg acaagcagcc cccaccccac tgggttaaag atctaggcag 31260
cctggaggtg ggaggataat gaaaggcagg tgatgggagt ggaggaccat gtgcctggct 31320
ggctttctct ttacctccag cagctggcgg tagtcataat tgaaatcttg atcttatttt 31380
gagtgaatga agaccaggaa aggttgataa ataacaatat ttgttaatat ttcttattct 31440
aatctggtac ctactgatgt agaagaactt tctctttttt tttttgagac ggaatctcgc 31500
tctgttgccc aggctggagt gcagtggtgc agtctcaact cactgcaacc tccgcctccc 31560
cagttcaagt agttctcctg tttcctcctt ctcaagtcct cctgagtagc tgggactaca 31620
ggcacatgct accacgtcca gctaattttt gtatttttag tagagacggg gttttaccat 31680
attggtcagg ctggtctcga actcctgacc tcaggtgatc cacctgcctc ggcctcccaa 31740
agtgctggga ttacagggat gagccatcac acctggccag aactttttct tatacatgct 31800
aatacctttt gggattggtt taagtaatag gacatcttat tttttaaaac aaaaaactta 31860
tgctaacatc agtaatattt ctactgagag tggccgggcg cggtggctca cgcctgtaat 31920
cccagcactt tgggaggccg aggcaggtgg atcatgaggt caggagatcg agaccatcct 31980
ggctaacaag gtgaaacccc gtctctacta aaaatacaaa aaattagccg ggcgcggtgg 32040
cgggcgcctg tagtcccagc tactcgggag gctgaggcag gagaatggcg tgaacccggg 32100
aagcggagct tgcagtgagc cgagattgcg ccactgcagt ccgcagtcca gcctaggcga 32160

```
cagagcgaga ctccgtctca aaaaaaaaaa aaaaaaaaaa aaatttctac tgagaaacac  32220

tactacttta ctgacaccta agaattctgc cagataaaat gttgctttct ttgctaaaac  32280

agagctcttt gatctttgct ggtaagaatt cttctgaact gaataaaagt ttttagaaca  32340

tgcatggtgg tgaaaagtat acatagccct ttgagtctgg gcagggaaga aagaaagttt  32400

cacaaaggct aaaacaagcc accactctca taaaacctga tgaacagttg agtctgaatt  32460

catgagatta tggggtttag aaagtgtgaa gatggatagg cgaccagttt ggctttagtg  32520

agattattgt ttctgtttgc ttggataaaa ctcaggtgct ggtggggtga ctttgaatgt  32580

tgatggaata ttagaacttt tgtgtccccc aaactgctta aatcttaggt ctgttggacc  32640

atatgtaaat ggccttcttt tcatattcac tttttttgct ctgccatctt gt          32692
```

<210> SEQ ID NO 8
<211> LENGTH: 26
<212> TYPE: PRT
<213> ORGANISM: Homo sapiens

<400> SEQUENCE: 8

```
Met Ser Cys Lys Lys Glu Ser Leu Gly Ser Lys Cys Asn Tyr Ile Leu
1               5                   10                  15

Leu Trp Tyr Gln Pro Thr Glu Ser Pro His
            20                  25
```

<210> SEQ ID NO 9
<211> LENGTH: 39
<212> TYPE: PRT
<213> ORGANISM: Streptococcus species

<400> SEQUENCE: 9

```
Met Pro Phe Glu Ala Val Gly Glu Ala Arg Leu Ala Ala Arg Thr Ser
1               5                   10                  15

Arg Pro Gly Asp Arg Gly Pro Gly Asn Arg Ala Glu Glu Ser Pro Asp
            20                  25                  30

Ser Ala Glu Gln Gly Gly Gly
        35
```

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct

<400> SEQUENCE: 10

```
ggatgtgctg caaggcgatt aagttgg                                        27
```

<210> SEQ ID NO 11
<211> LENGTH: 26
<212> TYPE: DNA
<213> ORGANISM: Artificial Sequence
<220> FEATURE:
<223> OTHER INFORMATION: Synthetic Construct

<400> SEQUENCE: 11

```
ctcgtatgtt gtgtggaatt gtgagt                                         26
```

<210> SEQ ID NO 12
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 12

taatacgact cactataggg                                              20


<210> SEQ ID NO 13
<211> LENGTH: 34079
<212> TYPE: DNA
<213> ORGANISM: Homo sapiens

<400> SEQUENCE: 13

gtctttataa ctttgagggg tcagcagttt aactgtgggc tgagtcactt gtcacaagtg     60

actccatttt gagaaattta ggatcataaa cagtaatata tattatcaac attaaaaaaa    120

gataaaattt taagcttttt ttcctgtaat catttaagat tttaggatat tagattttat    180

ctgataattt ttatctctga aataatctaa gctaaaattt aataaattag atttttttaa    240

aaaaacaaaa aaagggaaaa acatttcagt tggctgaaat gttctcttct ttccccaagg    300

aggatggtga catctctaat aaccattcat tttttctttt ctggtgttac attttaatat    360

tgcaagggaa gaaaaaaatc attcctctat ccttcataat tcctagctgg gacagaccct    420

tacaaaaaag acagattaac aggagaaaaa acaaacaaaa gtttactaag atgtataact    480

caggtatgca tgcacgatga cccagagaaa ttagtaaacc ccaagagtag actcaaagag    540

atgactttga cttcaggctt gaataccatc ctttgctgaa acaaggaaaa aagtatataa    600

agaaaggccc agttatgggg aggtggccag gaggagtact ataaacaaga gtaacgtgtg    660

ttatgcagat ttaaattcat gccatctcca ttgatcagag tctctagtga tttagagtca    720

tctttatctt cctggtactg ggagggagac atatagatgt aaatttctct ttaaaaaaaa    780

gggtaacttc tctgctctga gaaattctcc tttgtctgct atttctgaaa ataatcagct    840

caaaatggtc tttatactat atttgcagtg gaatattctg gtctcctatt gtaattatct    900

ttttgggttc ttcctgccca ctgcacacag aaaaccagtt cactgacacc gtcgtactgc    960

agtaaagaaa gagtttaatt aacataaggc tggacatgtg ggagaactca agttatcact   1020

caaattagtc tctccaaaga ctctgaggtt ggtgtttttc aaggacaatt tggtgggcag   1080

gggactagag aatggttgct actgattagt tggggatgca atcatagggg tgtggaaaat   1140

gtaatgagtc ctcctctggg tgggggacca caggacctgt ggaatcatga gtcatgagtt   1200

ttggtggggt tcctcagttg tcagaatgaa aaagtctgaa aaacatctca aaagaccaac   1260

tttaggttct acaatagtga tgttatctat aggagcaatt ggggaagtca caaatcttgt   1320

gacctctggc cacatgactc ctgtgcagta aaggattaca gtaactaagc ctacatttta   1380

gcaggattag ggtcccttcc ataatcctaa tcttgtggcc ttttataggt cttacaaagg   1440

tggtttcagc cctgaacaag gtggggatca attttaggaa gggcctatta tccttgcctc   1500

aatgttaaac tatatattaa atttctccca tggttagctt ggcccacgcc caggaatgag   1560

ctaagatggg ccacctatga ggttataagc aagatggagt cagttgtgct aaatttctct   1620

tgcttttgta atctttgcaa aggcagtttc attccagtca tgttttgggg tggcatgtcc   1680

tgaattccat cagtgtgata aagtttattt tattttaatt caaatttaat atatgataaa   1740

attacatgac atcacaaact aaaaaggcta ccttgttctt tttgaaatta tttgtgttca   1800

tgaaaattaa ttggttatgg ttattggata tatatgctta taataaatgt ctgagttttt   1860

aaaaagcata agacatgttt tgtaaaagag atgtgaaaag tatacaaggt attggtgcta   1920
```

-continued

```
atggaataaa agaaatacta aaaagtaact tctcagtgaa ttttataggg caataacaat   1980
ttatagagaa gtttcttatt tagccaaata agataaatgt gcatgagcat gtttcaaaat   2040
gacaaaaccc ctctctcaaa tgttagctaa ttaagactta tttttatcta ctgaaacttc   2100
agttgcattt caactaaaaa ccattctgaa atattgaaga taaaatttga agattgaaaa   2160
gtggctgact actggtgact aaagtgtggt cattattaca tctaaaatgg cgttctgttc   2220
tacaggaacg cgtgtgtgca tatctttaat gtcagccctt gcctctggga tgacacttat   2280
tagatttaat ggtgtcatgt gctatttcaa gattggcata gtggttttta taacacaatg   2340
tgctaatatt ccacttatta tttaaagtgt taaaagaaaa actatagaca aattaaattt   2400
agcggagttt aattgagcaa agaacaatac aagaatttga cagcctctag aaccaggaaa   2460
ggtttaataa gactccaggg ctctcatgtg cctgaataac atttatagac acaaaaagga   2520
aagtgacata cagcaagcag aaatgaggta cagagatagc ctgattggtt aaagctccct   2580
gtttgtccta tttgaatttg gtttgaaccg ttggctgcct gtggttgact taagtccagt   2640
tgctgtgact gatttagatt ccgctacttg ttatacagaa agtaacagtc tgtttacaca   2700
tcaagttacg ttacagttta ctatgtatgc ggaaactttt aggccaaatt taagataggt   2760
aggaggtagc tttaggctaa acttaattca atttaataaa aatagctgtt aaagctcaaa   2820
tcttattgtt ttgctcacgt ccatatgtac tatgatcact cgattctgct ttagttttaa   2880
aatacaaaat tctgaaatac ggtagaatga attagtacag ttacttattt aacttagaag   2940
tcatatctgt gaaaaataat tatttgcatg tgtattgaga attcccaggt gtctggcaat   3000
gacgaccctc agaaaattgc tgataaataa taagacacaa tctcttaggg aatttgttgt   3060
gctagtatat ggtataactg tcctacactc ctctgctcaa aagaaaagca gaggaggccc   3120
aaagagacat cccaggccaa ctgatgcttt aaaaaaatct ctcagtaaaa ttctttctta   3180
ggctgcagct ttttttaca gtcacagaga gagaaaatgt ggatgaataa tctatctact   3240
tcaatctatt tgtctatctg catctatcaa gtggcccaaa gggataagga gacttgctgg   3300
gttttctgcc ttcacatagg gaatacactg ttatacagca tacctgaatc aaggtagatc   3360
tagagttatg gcgtcactat agataaatta gaaaaaatta tgctaggata atttaggaac   3420
tgtccaataa attctataaa cattacctaa aagtcaatga taaagaaaat ttaaaatatc   3480
tagaagggtt atctgtctat attagccttc caacttgtat gcccacttcc accccaacac   3540
acataccctg cacaattaca atcatattga tattgatgtc gtctgcaacc atcaccccac   3600
tatactcaat ttctcctaaa ttctacatgt cttggtttat ctataacgcc ttggaccttc   3660
atataattta tttacttatt tttaatttgg gaaaggctta tttgccttta aatcagataa   3720
tttataatta aaataattat tatcaaggtg ttttggtact gtcattcaat aaacgagtga   3780
atatgcattt cattttgtct tattttgcat tttgcatttt aagatattaa gtgtctctgt   3840
tgggagccta tcaacttctg gtcattttgt caccctgttc ttcccacaac tccctgagct   3900
gtttcacttg ttagagggaa ttggtttagt tgtgcctgtg cagagaggtt tttgtttgtt   3960
tggtatttgg gtttgttttg gtttgttttt gtttttgttt tttggtgtaa gactttctta   4020
acttgtgggc ttcctttgta gtaagtttct taatttcaaa aatagtgata atcacctggt   4080
cctgtgatat gttaaaacaa agtgttgttt aattttaaat gccactgaga atgttagatt   4140
tgttaggaac ctatgaaatg tctattttgg aggtataagt ggagatagca cgattaatct   4200
caccccccat cttttaatat atattatcta ttaaacattc acttgtatca ccaaggaaag   4260
ggttacttgc aaagagaaga gaaactctgc tttaaggaaa atgatatatc cagatgccta   4320
```

-continued aagaagatga cctgtgatcc tgtgatttta attgaatata gcatatcgtt ctcaaatgtt 4380
atggccgaag gacttgatat actaaaaatg agaattaggc agggaaaaaa aagacaaaat 4440
tttgtcctca aagtggcatt ctccatgtag aatcaactta atccaatcta tcgctggttc 4500
ctcaattaac tatagcatgt cttaacttca tattttggct cacactatgt cttttgatgt 4560
tatgtgttgt tggaaaactt gtaactgatg catgagtgtg ctctctgttc aaactgtttc 4620
taatatataa ttttcttgtc cagtgttctt tcaataaggg tacctagtcc tttgaggata 4680
tcttgctaga atgatgcaaa tgaagatgtg gactatttaa ttatttgtta aaacatatta 4740
tattgcaaca ccctagttat cacaggttct gtaatgaaga ggacaatgtg attattattt 4800
tttggcaaag tgaagtactt agtttaaata agcaatggga agtaatggat aatctaacag 4860
gagtaatcct ctactgagat atccttttgt gggggacatt tggaaaggtt atgacctgga 4920
aaacctaagt taagaatctt cctggtcacc cttaccctac ccaccaacta cagtattttc 4980
tcccccaaga aataaacatt aataaacata catttattta aatatgactt tctatctcta 5040
tgtacttctt tttttttttt tttttttgag atggagtctc gctctgtcac caggctggag 5100
tacagtggcg tgatctcggc tcactgcaac ctctgcctcc cgggttcaag cgattctcct 5160
gcctcagcct cccgagtagc tgggactata ggtgtgtgcc accacaccca gctagttttt 5220
gtatttttag tagagatggg gtttcaccat gttggccagg atagtcttga tctcttgacc 5280
tcgtgatcca cccacctcag cctcccaaag tgcttggatt acagtcatga gccaccacgc 5340
ccggtaatta atgtatttca ctataccgct cccccacaaa aaaaaaaaat gctcttagga 5400
aaataaaaca tgagaaaatg catatcactc taaactctct ctctatatat ctcagatggc 5460
acaagcaaaa gaactggatt ggccccatta ggtagtacaa acacactgga gcctcccaac 5520
aatggactgg ggcatgaaag atccatgcgc tgaaaaaatg acactaagtt gaacttctca 5580
gactaccctt ggtaagaagt gaggagaaag aatctgaaat tgcccggctt ctgtgtgctc 5640
catttgaact taagaagtgc atttgctttt gaactctaaa gcttcaatct cagtctccag 5700
ggtgcttact tcccctgttt tgtgtgaacc tttccttgta gacacctgtt gaggactgta 5760
ttaataagac acattgtaga aagagaaaat gcattttcta agccaagaag gtgaaagcta 5820
ctcttttcta gggctcttgt taatctttgg gagcccagca tcttctgtgg cagaacaaag 5880
atgatacagg tgtaaattct tatttttttt ccccgctccc acaaagaaaa tgttgttgat 5940
gtgtcagtgt tcagctacat ttctcttaag ataaacaaca gagtatttct tccttctatc 6000
ctgaggtttt acaactggat tcccattgct ttctagcatc attctaaata gaaccccact 6060
gtctggccac ggccagaatt agctcgaatg gtacctgtta ttgaaaggga gtctgtattt 6120
gcagtaatac agagaatgcc agtttagaaa tgagcctgat tgcatggttc attttgttct 6180
cctttgtaga gccaggctgc ggcccactac aaaggcacga aacatgccaa gaagctcaaa 6240
gcactggaag ccatgaaaaa taagcagaaa tctgtaactg ccaaggacag cgcaaagact 6300
accttcacct ccatcactac caataccatc aataccagct ctgacaaaac aggttaagca 6360
atgatctttg ttgttgttgt cctcgtcgtc gtcgttgggg attccctccc ttgtctagcc 6420
ccatgtctgt ttacttatgt gcctgccata ttgattcatg cttgagccat ctttctgtat 6480
aatggtaatt gtttcctctc atttttccaa acccctgcaa gattaagata atcactaatt 6540
atattccaga ttttgcattt tgcaagagtc ctgtggctgt ttcagaggaa tagtcataaa 6600
aggcatttga agccatgtac cccataactc tttttgagaa atgaaccttt tcagtgtgca 6660

-continued

```
gcatttgcat cttgtatgca gcaccttagc ttataactgc atggcagatt taatttaatt   6720
gtgagtacac agcaaagtat gctaaatgaa ttgagaaggc cccaataagg gcattattac   6780
agaaagcctt tattgtcata aattccaaat actgcattgt tttaagtagt ggctgtgtga   6840
tactgggctt gttatggctg ggtaaccttc cctctgcaaa cacaggtaag tgttattgat   6900
accaattact ctttttaaca gaggcttcac ggtgaaataa tggcctctga atggcccctt   6960
gggatagctc ctgccaacga ccagcttatt cataataggg gaagctagtg aggtttcccc   7020
aagctgacat tttaaatata agaccactgg ttttcgaaat ctacagagaa aatattcctc   7080
tgtgattcat ggatatacct ctaataaatc actttctaga acacagagac tgttacacct   7140
caattgtttt ccagtccatg tgaatggcaa tggtaaggaa acgttcatat catcaccaat   7200
gatagtgtct taactgaaag aggatcttct ggatatgact gatgaaaaca gaaaataaac   7260
agtgaatgaa tagaatagat tacgacaacc ttattacaca atgtaacatc cttattacac   7320
aatggacaca tatcagctct tccaaggact ggggatgctg caagtgaatc tgtaagggat   7380
aatgatattc ttagttcctg tggcattttg tattttcttc aggtattatt gtagatgcat   7440
catgctgccc tccctaagag ccctgtgttt tccctcagcc tgaatacatg tctcatcttt   7500
gtatgctggc aactggtctg gcatgggata aatgctgagt aaaatgtctg ttgaatgact   7560
gagacttatt tcactccttt ggtttggttc tctgatatag ccaagtttgt gccaccacat   7620
actaaagagg aaaaaaaaag acaggcttgt catattcact tctttgttat ccagagcaag   7680
agctggattg tgccatttta ttaatttaga tttaaacctt ttagggaaag ctttggtctt   7740
ttctctaata atcgaagact acctgcttta ttttgagggc tgaaagagaa tgagtggtaa   7800
tgaagcaggt aagtgtaatt tctgctcccg gatattgggt cacaggtggg gatccccaaa   7860
gcagcatctg gcatagagaa gtgcagaaaa atcctgaagc cttttgatgc aaagaaggca   7920
gtaggtaggg agaacaaaga gatgagtttg atgtaaaggg ttaaagtgac gtttttcctt   7980
gctccaaatt ttttctactt ttagactttt taaatcaaca attcatcttt gggttatctt   8040
gacttttttta aaatatgaaa atatgtgttt cattaaggat gcacatcatt taaaaatata   8100
tatatgtgtg gtaggtagag ctgctaactt gagttaagaa aagccccccg gagcttgctg   8160
tgagccgaga ttgtgccact gcactccagc ctgggcgata gagcgagact ccatctcaaa   8220
aaagaaaaag aaaaaaaaaa aaagcccccca ggtgtgttgt ctctgttaag taaatgggtt   8280
gtgactagat actttcatct cttaacttag agactagaat acgtcaacct agaataatcc   8340
aaagggtcag aatctagttt aaagagagtt tatccaagtg ttaagttgga gaatggctgc   8400
ccagaaaaca cagattccaa agaatggaag tcagtattcc aaagtgtaga agtttagtat   8460
catttttata gacaaagttt agggaagttt aacagaattt caacacctct ttctatataa   8520
ggcttaatgc ttagttacag taatctgaca ttggttgggg tggtcttatt cttttgggaa   8580
aggtatattt aacattttat actgaggatt taatactcat ggggtctttt gcaccatcta   8640
gtcttaggta caggacaata aaggatgtag ttaatatata acaaatatca gtaattggaa   8700
gggggaggca gtctggtgtc tggtctctcc tagtcattta cagaacaaga aaatgaggaa   8760
gagaattaac cccaaagaag cagaaattgc aaacatgtta tgtgactcag acaccagtgc   8820
ttaacacccc caccccaccc cttggcataa taaatttaga gggtccttaa attttatttt   8880
cttttacaac tttgaagggt ggcagtcttc caggatctgt cctttcagaa gttgagtggt   8940
aacaaacttt ggatttgtct tttgaagata acataaacat gccagaactt acctaacagt   9000
ggaaatggtg ttgagatgat gaagcaccct tccaagctgg agctagagaa aatttcaaaa   9060
```

-continued

```
gggcagaaga gatagtaaag tctgtaaagt tggtgcagat attctaaagc caaaagaagg   9120
aagcgatgga cattaggaaa gacattgctt tcctaatcca tgaggaccta tatcaggaaa   9180
aaacaaaaca aaacaaaaaa acaaacaaaa aagcaagtta tataggttga gaggctaaga   9240
gttccagcac actcatcaga tattttgagc caaattctct ttaaactgaa tttacacaaa   9300
actctctatg agaaaagaca cccatttcgt agacccttat tctatttgta ttgcagtata   9360
aacctgaggc atctaggcta acaaatttga gttttcttaa agcaattaca tgttcttttt   9420
attactatgt gcttcctcat actgattagc acaactctga aaacaaaatg agtctgagcc   9480
tggcacagtg gcatgtggct atagactcgc ctacttggaa ggctgaggca caaacaattc   9540
cttgcatctg ggactttgag actggactgg gcaaaataag tgagacctca tctcaaaaca   9600
aaaggactct gagctaattt tgtagaatag ttaaatactt ggcagaagga gaagaagagg   9660
tagataagac tctagaatca aagatcatgc attttttaat aataaaaaga aaatttctgg   9720
taatgcacaa gaatcttttg tgatttgtag gcttgtccat atataaaaga tagagacaca   9780
tgaaatcaca ttttagtaat ttatcaaatc attttaatta aaaaatctat atgaaaagag   9840
taatccaatt atatatatat tttaaaaacc caaactaatt cctttgaaaa atgttaaaca   9900
tgtcatactt tggtaaatga gaacccctgg agagggttgg ggcaacaata gtgaaaaggg   9960
gaagaaatgg tatggccttt aattagaaaa ttgatttggc ggttttctct aaaatgtaag  10020
aaatagaaag aatactcaca gaaactaaat tttcattgta aacctagttg actgatataa  10080
agacaatttt gattgataat tcctcttaaa ttttcaagtc atatattatt tattagtata  10140
aataataagg ttttatctgc tgccttgggg taacacatac atctaaacca tggggttagc  10200
tcctattcac taactttatg atcttgggtt tttgtgttgc ctttttctct aattatgcca  10260
gtctgctaga gtgctgagca gaaaattgta ttcagtgatc agccactgac tattcataga  10320
aagaatgcct agttcatcta tctcaaggca aaaacacact tcctaacgtt aaagaacaat  10380
tttagttctt gtgatctaat gaagagtgtt aggttggtga atttacttgt ataaaagttt  10440
acaggtaaaa gtaatatttt taaaaaatat attgagcact ctaaattgct gataagagtg  10500
gttactattt gtcacagaat atttcataga gcatttccaa agatagccag aataattgtc  10560
taatctagca agtgttttta aataccaagt tttttattta gaaaaattaa tggcaaaatt  10620
ttaaaaatta tactcaaagt aactaggcaa gtgtaactaa cttgtgttgt ttgttcttct  10680
atgaaatgac aaattcagat ttgtctgaat aagttctgta caaggtcatt ccctgatctt  10740
tctttacttt tgattcttag ggaatctcat tcacattgtt tatcagttag gttaggctag  10800
gttatattgc agtaataaac aacctctaaa atcctagtgg cttttgcaat atctaattat  10860
ttcttactca tactacatat cagctgtggt ttttctttca tcttaattta actccaggac  10920
taggctgacg aagcaaccac tagctggaga attctatgga agaggggaaa aggctcttag  10980
agctttttag tggactgaca cgtaatattt ctctcacttt tcactggtaa gttacatggc  11040
caagcctgat tacaatgggg caggcaagaa taattctcct ctagagaagc aaaacagata  11100
ttagtcagca attatataac attctattgt taacttcaat cactagacct acaaatttgg  11160
agagaagagc tttatttctt atagttacag cctgcagggt ggccatcctg acagtctggg  11220
aagcacagcc tccatcagag tctgagaata ggtacttcga gggaggagag ataaaacagg  11280
aatttatgct gaaacggttg gccaagtata catattcaat gagatatagg aggagctatg  11340
aatattgaca aaggggggat gtatgcatgc atactaagga aacattcatg ttacatatga  11400
```

-continued

```
cccatgttca ttttggggtg gagactttaa ataaattaca attaggtcct ttgagtcaaa  11460
agctgaaaca gggacatgaa ggcacttaca tatgcagcct ctgtaaactg gccagaacca  11520
gtccatggcc agtgttctct tattaagaga aagttactga agtcgatttc ttgtccagtc  11580
aaggctgtag ttatggcttg tgaaaagttg gggagtgtta ggcaatgtct ggtggtcagt  11640
gagctgcaat tgtttcaata ttgcttatct tgagtccagt gcttgtttag ctgctagaga  11700
aaagaaaaat gttgtgatag ttagaacagt tagaacatag tttactctct acgtgtaggg  11760
gtgtgtgcct taaactttgt caggcatggc cttagttgtt atttagaatt ttgtatctta  11820
ttgccacaaa gagtctgttc cttcaatctt atggtctcta tttgaacact atcatggctt  11880
ccttcaagta tcacttgtgc ttagatgtct taagattctc ttgccctgtc cttctcctaa  11940
gtccagatct gcttttccat ggcccattgc tcacttactt ggatggcttt caagcatcaa  12000
tacttaacag attcaaaaaa caaacaaaca aatgaaaaaa accagtcctc atcctgacca  12060
tcatcgttta ttttgagttc tgcacttccc agatttgaaa gctttctagt tgtcttttcc  12120
tctcctaagt tctcacttct attcaattgc tagagtccac ttccctccca ttcctggaat  12180
ggttcatgct tttacatgtt gttactaccc acatcctggc cttgtagatc tatgtttttc  12240
acatacattt gccctagcct ctatgcaggt ctaactgcct ccacacctgt gtcttgacaa  12300
ccatgttctt cattttactc tccagttata ctctacagta cataaaccac atctcttacc  12360
cattcagaaa tctttaatgt acctctgtgc tggaccccag gatcacaacc tacctttcca  12420
atcttctctt ccacggcttt cctgcaatat tttccactag aggcacacct tgtttttcca  12480
ttgttgtttc ttgtactgta gttctaaaac acggaaaatt ctttcacttt tcttcctcct  12540
gcctataaag ctccataaaa ccaattcctt tctagttgcc ctatcatatt cttgctaaag  12600
ggaagttttc tgcctttacc ttctctcatt gctagagggc atgcctcttg agagtactcc  12660
cttgattaat tattttgctt atgtttttat ttacagagta ctttttatat aaaagatagt  12720
aagtcaagag ttttaaaact tggaacaatc agttttgtgt ttctgttctt ggattgaagc  12780
atggtaaagc tttagacttt tgtatttgtg tataggtggt ttcacgaaag aacagcggtt  12840
ctcattaaaa caggggattc tgtgatattg ctcatcaaat ttcagagttg caagttttat  12900
taaaggtcat caagtctaac ccctaaagga gattgttgtt gttgttgttt ttggtttttg  12960
agattctcta gtcctacaag taaagaacac ttgacatttc taatggccct tcagtgacta  13020
tcaatcagga gttaattagc ctattgagta tatggatttt ccttagtcat ctaattggta  13080
aagtctgaga acatttctcc ctggttctat tacataattc tctttatcac gtctcactga  13140
attgcaaatg tattcatcag ataaagctac taattacaat ttaaatttgc acttttcact  13200
catgactcag tcttctttgt atccagtttc cctttttctc ttttaatttt gaaattgtaa  13260
accagggatg ttgtactcat cagacttaaa ggtaccaaaa gtaaaatact tttgaatgta  13320
ttgctaagaa ggtctatgaa tgcaaaggaa cttttatttg ctcttgattc ataattgact  13380
gtaagtgttt attggaatgc acattatttg ttcagggact tagagtaata aagataattt  13440
tctaatgata aagaagatat ctgatggaaa atgatggcca gtgattgaaa acaaatacac  13500
ctggaaacaa agactcatag gaaggtcagt caattttaag gtcacaaatc tggattcttt  13560
tatttcctgc acattaccct cctgaaccag ctgtttacct caggcccagt gccagacaaa  13620
tctaggtgca catttttaaa aaaattcatt tagatagaag ccaaattatg acaatagtga  13680
acaaatgaga aatgtagtag aacaatagtt tgtaaggaaa aatcaacctc aatatccttt  13740
aggaaacaag caaatagttt tctatggagg gcaactgtaa attagctttt gtgtctgttt  13800
```

tcctaaggaa ggttggaaga gtttgctttt cttgacttag agttcaaaca aatgcagcaa 13860
atattaaaaa taacaaaata caagctgggc ttgatttcag aaagacatat atctcatatg 13920
tttgtatata ggatatattg tacatgaata caaatataca catacattga tttttatgta 13980
agattctgtc tttaatacct gttcctgatg tacgctacta ttccaagtct tcataatcag 14040
tgatgcatat tttcttttaa gatagacaaa tgcttttgtg ggttatgaat ctatacctct 14100
gttgaagttt atgaggcaat ataaagttat ttgaaaaggg cacatttcca tcagctctta 14160
tagatctgct gcagtggtgt acaaatgccc ctcttatcaa tgtggaaatt gtgctaactc 14220
ctggggtctt tcttttccta cccattctcc ctaacaaagc atcactggaa caataactgt 14280
catgataaaa gacccactgc atacgtcttg gcacaggagt tgaagcacca ttgtgaaacc 14340
atttgtgcct ggagtgcttt ttcttttctt agcactggct catgacatgc ttcagattgg 14400
tcaaagaaag agattttatc aagtgttccc ttctcaagat gtgtgataag tgctagcaga 14460
gtgtgctggt agcagatctt tagagattga aaaagagaag ggaaattcag aagtggggga 14520
aaaagctaaa ccttatttga atattgtggt tctaggatct ttgtatgtga atcagtgatg 14580
ataaatttca cattaggaat gacataaaag taacaaaata ttatattctg ttctttgttg 14640
tgcatgagga aattatgatg aatgatattt ggctggttct atttggctga taaaagtttt 14700
gacctagata tattatgtat ataactgctc cctgcatcac ataaaaattt tagaacaact 14760
ggattcctta cctatgtatg tgcacatgta tgtatcctgc agggagggaa aactttcagt 14820
ggaatctaga aacttacaga tccttttcac aggggagagt ggaacaggga tgtaagcaac 14880
ttaggagaga gtaaatgatg ttggagggaa aataaatgga ccctcgaaag aataggtaat 14940
aacctgtgac aaagtctgtc ccggtgtgat gctgacttac agtctccact cctgtgatct 15000
cccctggttg atgagatgtc ttggaagagc cttaatgaca actgagttcc ttttggaaga 15060
tctatcccta gacagataag aggagttcag agaaagcacc cccacccctg catttgctgt 15120
tccccagttg ccttactgaa gtaatcagca taccaaagca acatattttg gggtggcatt 15180
tgctgaactc cttcagtgca tatgcatgtg agtatgtgta tacagtgtgt ttttgactgt 15240
ctttctttac cagagatttt acatctataa agtacctgaa aagctgaaca cctaagaagt 15300
atttatgata taatagacat ctggatgaaa tttaaaaatt aaattaaaac tcccagtagc 15360
tttgtctgca gatgccacac ttctggaaac atctgtgtct ttgtgtgttt gggtgtgagt 15420
tcatggagag tttttcctcc tcatttttat gtgattctta ggaattgagt agacataagc 15480
ttacataaca aaatatttca actgcaaaaa aatgattctt aaaggtagaa atcttaaata 15540
ttacaaaaga gttgaacaat gataaaatat gacagaatgt caaatgagta tctatgaaaa 15600
catgcagaca attagagaat tttgtctcca atatggaaaa gtgaacgggt tgatatttaa 15660
tagtaataga catgaaatgt gaaacaaaac atgcaaatag tacatttctt gcagtcagga 15720
gacagtgttt ctactgagtt cgttgtaaaa acaaaaccca aactcagaca aatatttgaa 15780
ttaagaatta cacttgcatt tttcttttat gaattccaaa atccattaca tggcattgat 15840
atggctctga tgagtagagg aacaccaggg ttcttggtcc tcatgctagt ttagataaaa 15900
agacatggac acacatgtag tgattttaag gagtggagag tttaataggc aagaaagaag 15960
gaagacggca gaaggaagaa gctgtcccgt acagcgatag agggagtggg tctccaaagg 16020
caaaagagga gaccccaaat tgaacggaaa ccagccaggt atatatagag gctggaggaa 16080
gcggtgtctg cttggcacag ggcttgtggg attggtttaa ccaggcatgt tattcatgta 16140

-continued gcctgcgaaa aaagctggcc ctcccaccct agccttctaa tgcaaatgcg gggtgcagtg 16200
atgttctaca cacgtgggga tatgtggggg cggctgtgtt gccaggcaca cgtggggcaa 16260
ggacaagaag gccacgggaa ttgccttgtt tgggtggacc cagtttctaa ttgcctgcat 16320
ttgtatatca aagattgcca ccaggctcta agctggggct ttccagctaa acaagaaatg 16380
tctttaaaaa cgaaaacttc ccaaggaccc attttcctct ctgcctaaaa taatttctta 16440
gtaactccta ccacagcatc agaactcttt agtgatctaa cccttgccta tcatttttgc 16500
cagtcttaca catttcttct caactcctgc ccaattacct cacttgagga ctgaaagcaa 16560
ggtgtgtatg ttcttttgcc tggaatattc ctccatcata cctcacccca tcccacactt 16620
cacatgctaa cgcacaaaag aatgcacatg ttgtgtgcca atgcatatgt gcctgggtgc 16680
acagaaacat gaacaaatcc attcatattc ttagttggct cattcctact tctaggcttc 16740
tgcataaact cattcctagc actcactgaa attgtattat cctcctgctt gtcaacccca 16800
tgaaatttc agcttcttga tgaaggatac accttaattt catacatctt tattctagca 16860
actagcacag ttttacatta aacctagcaa atagtactgt attatttttg tttctatgaa 16920
gatcttgcta ggaattattt taatagtaaa aactaacaca taccaaagta catagtaaca 16980
acttgaatgt acataatcaa taagttttac taattgaact ttattacatt taactacttt 17040
gtgatacaaa tcaaaggtat taaccagtgt agctcagagt ttgaatgtgc caccattggg 17100
ctgagcattt cccagagaca gcataaaatt gctattttaa ttatcataat tgcattcaga 17160
ttcatcacta aattagtgag ctacttcagt ttctaatgag agttaagaac attttaaaaa 17220
gctctattga gtcggattga ctatgtatcc aactttgcgt tgtgacatgg gtatgggttt 17280
aaatctgagg gcagaaagca tattaatccc atgggtaggg tctatgccac tcttccagtg 17340
tataaccagt ctctagtttg ctttactttt gttatgactg agtttgtggg gtagccttaa 17400
caatatttta tatttacgtg attgctcaaa ccaattaccc acaaactaat agctgatgcc 17460
tggccaaacc taaagatgaa ggtcagaatg cagaatgtgt agcagtaatg atactgaccc 17520
atttgggcct tattttattg tttttcgttt tttggttttt ttttttcaaa ttaaaaaccc 17580
ttttattagg tttagtggtg catttgaagg tttgttatac aggtaaattg catgtcacag 17640
ggtttggggt ccagtttatt tcatcaccta ggtaatgagc atagtaccca atatgtagtt 17700
tttcaatcct cacccttctc ccaccttcca atctcaaata ggccctggtg tctgttgttc 17760
ctttctttgt gttcatatgt aatcaatatt tagctcccat tcataagtga aaatattcag 17820
tatttggttt tccatccctg tgttagttcg cttaggataa tggcccccgc ctccatccac 17880
attgctgcaa agacatgatc ttgttctttt ttaatgttta catagtattc catggtgtat 17940
atgtaccaaa ttttccttat ccagtctacc attgatgggc attaggttga ttccatgtct 18000
ttgctattgt gaatcgtact gcaagtaaca taatggatgc atgtgtcttt atggtagaat 18060
gatttatgtt cctttggaga tatactcaaa aaaggggttg ctgggtctaa ttgtaattat 18120
gttttacatt atttaaggaa tcaccagact gctttccatc atggctgaac tagtttacac 18180
tcccaccaac agtatataag tgtttttctc cacaaccttg ccagcatctg ttattttttg 18240
actttttttt tttttttttt tttttttgag atggagtctt gctctgtcat caggctgggg 18300
tgcagtggtg cgatcgatct cagctcactg caacctctac ctcccaggtt caagcgattc 18360
tcctgcctca gcctcccaag tagctgggac cacaggctca cgccaccacg cccagctaat 18420
tttttgtatt tttagtagag acggggtttc accatgatgg ctaggatggt ctcgatctct 18480
tgaccttgtg atccacctgc cttggcctcc caaagtgtga cttgttatta atagccattc 18540
tgaccagtgt gaggtggcat ctcattgtgg ttgggatttg catttctata atgattagtg 18600
atgttgagca ttttttccta tgtttttggc catgtgtatg tcttcttttg aaaattgttc 18660
atgttctttg tccatttctt aatgaggttg cttgtttttt gcttgtaaat ttaagttcct 18720
tatagattct agatagcaga acttcatcga attgatagtt tgcaaatata ttcttccatt 18780
ctgtaggttg tctgtttact ctgttgacag tttcttttgc tatacagaag ctctttaggt 18840
cccatttgtc aaattttttt tttgttgcaa ttgcttttgg catctttgtc atgaaatctt 18900
tgtcagatcc tacgtccaga atggtatttc ctaggttatc tcctggtgtt tttctgtcat 18960
tttagatttt acctttaagt ctttaatcca tcttgagttg atttttctat atgatctaag 19020
gaaaatatcc aatttcaatc ttctgcatat agctaactac ttatcccagt accatttatt 19080
gaatagggag tcctttcccc atggctcgtt tttgtttatt ttgttgaaga tcagatggtt 19140
gtgggggtga agcattattt ctgggctttc tattctgttt cattggttta tgtgcctgtt 19200
tttgtaccag taccttgctg ttttggttac tgtaggcttg cagtttgaat ttgggtaatg 19260
tgataccgcc agctttgttc tttttgctta ggattgcttt ggctatttgg gttcttttct 19320
ggttccgtaa gagttttatt atttttattt tttattatat ttttgagaca gcgtctcact 19380
ctgttgccca agctggagtg cagtggcatg atctccgctc actgcaacct ctacctctca 19440
ggttcaagtg attatcccac ctcagcctcc tgagtagctg ggactacagg catgagccac 19500
ctcacccagc taatttttgt atttttagta gagacagggt tttgccatat tgcccaggct 19560
ggtctcaaac acctggcctc aagtgaatta tctgcccacc tcagcctccc aaattgctgg 19620
gattacaggt gtgagccatc gcacctggcc atatgaattt aaaaaaaatt tttttaaata 19680
attctgtgaa gagtgtcatt ggtagtttga taggaatagc attgaatcta tcaattgttt 19740
tgggcagtct ggccatttta acaatattaa ttctttctat ccatgagcat ggagtgtttt 19800
ttcatttgtt tgtctcacct atattttatt tgcacagtgt tttgtaattc ttgtagatat 19860
ctttcatctc ctggttaact gtatttccag ctattttatt cttttcttga ctgttgtgaa 19920
tgggattgca ttcttcattt ggctctcagc ttggatgttg tttgtgtgta ggaatactac 19980
tgatttttgt acattgattt agtatcccaa agttttgctg aagttgttgt tagatctagg 20040
agcttttggg cagagactat ggggttttct agatacagga tcatatcatc tgcaaatagg 20100
gatagtttga attcttctct tctgatttag atgccttttc tttctttctc ttgcctgatt 20160
gctctggcca ggatttccag tgctgtgttg gataggagtc gtgagagagg ccatccttgt 20220
cttgtttcgg ttctcaaggg taattcttcc agctttgccc attcagtatg atgttgggta 20280
tgggtttgtc atgcacagct cttaattatt ttgaagtatg ctcctttaat gcttagtttg 20340
ttgagagttt tttataagat gcgatgttaa attttattga aagtcttttt tgtatctatc 20400
aaaataatca tgcagttttg tctttgttct ctttatgtga tgagtcacat ttattgattt 20460
gtgtatgttg aaccaaccct gtacttcagg gagaaagcct atttgattat ggtagattcg 20520
ctttttgatg tgctgctggg ttaggtttgc tagtattttg ttgaggactt tggcatctat 20580
gttcatcaag gatattgacc tgaagtatat cagatatata tgtgtgtata tatatatgat 20640
atatatatca aatatatgtg tgtatatata tatgatatat atatcaaata tatgtgtata 20700
tatatatgat atatatatca aatatatgtg tatatatgta tatatatgat atatatatca 20760
aatatgtgtg tatatatatg tatatatgat atatatatca aatatatgtg tgtatatatg 20820
atatatatat caaatatatg tgtgtatata tgatatatac atatatactt gatacctaaa 20880

-continued gttggcagag ataaagagta aataaatata tataatacat aaatatatgt aaataaatat 20940
atatataaat tatatatata tttatttact ttttatctct gccaacttta ggtatcaaga 21000
tgatgctggc ctcatagaat gagttgggga gaagtgcctc cgcctcaagt tttttagaag 21060
agtttcagtg ggaataatac ctgctcatct ttatacatct ggtagaattc agctgtgaat 21120
ttccctggtc ctgggctttt tggggttacc aggcttttta tcactgattc aattttggaa 21180
cttgttattg gtttttttcag ggattcaatt tcttccttgt tcaatcttgg aagattgtat 21240
gtttccagga atttatccat ctcttctagg ttttctagct tgtgtgcata aacgtattca 21300
tagtagtctc tgagggtttt gtgtatttct gtggggtcag tagtcatatc tcgtttatca 21360
tttctgatca tgtttatttc aaacttctct ctttttttctt tcttagtcta gctagtgttt 21420
tatctatcta ttaattcttt caaaaagcca actcctggat ttgttgatct tttgtatgtt 21480
tttttacatc tcactttcct tcagttcagc tttgattttc tttatttctt gtcttctgcc 21540
agttttgggg ctggtttcct cttgtttctc cagtttctct aattgtgatg ttaggttgtt 21600
aatttgatat cttctttact tttcaatgtg ggcctttagt gctataaatt tccctcttaa 21660
actgccttag ctgtgcagag gttgtggtat gttgtacctt tgcactcatt agtttcaaag 21720
aatttcttga tttctgcctt aatttcatta tttacccaaa gtaattcagg agcagggtgt 21780
ttaatttcca tgtaactata aggttttgag tgatattctt aggattgatt tctattttca 21840
ttgtgctgtt ggaacttatg ttattttttg ccatactttc tatttctctg ccagctctct 21900
agtagaatta ggtaaagcta gaaagaaaac aatgctttct tctacactgc ttattaagta 21960
gaagagtttg tgggaaaaaa aaaaaatcat tcttaccctt cactgaaata gggatttgag 22020
tctgactgat ggaactcgag gttatttatt tttcctttta tctatctatt aattcatatt 22080
cattcttaaa tctacaaata ttgttgtaat atatgagata tcgaagcaat gaaaactaat 22140
gcagaacagg agttctagcc ttaagatatc ttcactctgg atggtacaca aaatataatc 22200
cagggtagaa aatatttgtt tgaagaaaat agcagataca gtgccatgaa cgtctagagc 22260
aactgaaata atcttttcct ataaaggagg tagacgggga cacagatatt gttaaccagt 22320
atttgttaaa cttaatgtca agggtatgta atttataaaa taaatccttt gatgaaatgt 22380
ttcatttaat caacattgag tactcagtat ttctagtcat gagatgtagc ttctgtcctc 22440
tagtgattca tttaaatgga ggagacagag aacaaaaagc tgtgataaag tggttgagaa 22500
gttttgtgct agaggcttgt aaagattatg ggaataccta actcttggag gtaaatgttc 22560
ttaaatttac agataaagaa accaggttct gagttaggaa aattgaccaa gataaaaaat 22620
ccgtaagaag tggagctaga gtttgagtgg cgttttgatt cctcccgggg cctttgcctt 22680
gctgtctcct gttaggcagc aaaacactta aacttaatct tcccataatc ctccttagca 22740
ctaaccccaa ttttggttgc taactgatat caccatgtct gctatattac tcaaggtagt 22800
tcctttcatt ttacagaacc ctcaaacact cctaaggatt ttggtgtaaa tactattctt 22860
tacacataag accctgtaac tgttaaaagg ctctaatgtg cctgcctaca gtttatgttc 22920
ttcacatatt tattgtggtt ttcacctgca tgggagctgg taagagaaga taaggtcaag 22980
gaccaagtct ttttctcggt ttacattttg ttaataaaaa tcatgctatt attttgccag 23040
aaagaaaagc tctgtgggta attggaaagt aacatctttg atctctttgt gtaaaattta 23100
tagtagataa ttttggattt gcatgagaaa tcatttcaac tttggttttt ctatttatgc 23160
ttgctcttgt aatgctatct agacgatgac agaattctct ggaataacaa aacccaagtc 23220
ttaaagacaa aggaaaaaaa agcctgtttt tcttgcagtc aaatgttaat ttttcaatat 23280
gaatatacag aattatcagc taaagataca agattaccta cattgaaaga gattagagtt 23340
ttgcaggata tgtatgatct ccttggaatt attgctttgg aaaagtgctt taattctttt 23400
aggcaactaa ggtgatcttt agtacagtaa ttttgacaat taaaaatcta ggctgggcac 23460
agtggctcat agctgtaatc ctaacacttt gggagcagag atgggaggat tgcttgagac 23520
taggagttca agaccactct ggccaacata gccagaccca tctcaaaaaa aaaaagaaaa 23580
aatccattaa cctaaaaggg atttgttcat ggcccataaa tgcatgcttc tccctatatt 23640
actaagacat tttagatcag tatatagtgt tacttaaaaa taagttagtg tagtccagag 23700
ttcagaggtc atagtttttc atacaaaggt gtcaatttcc taaacatgaa taaaagtata 23760
gttttaattt atatagcttt ttaaacattt caatatggca tcatctaaaa tattacattt 23820
tagcctcatc caaaaagaga aagcttaaaa gttatttcta agttatcaac atttccattt 23880
taaagaattt gcttcacaga agaccatgaa tataagaaat gggacagaaa tcatagttat 23940
ctctctacta gtagaaacat aaatctctca tttgctaaat aatacagaaa aaatatgttg 24000
gtgacttagc atctgccttc ttgttatttt cagttattga tacatactag tatgtatcaa 24060
tttttgtgtc ctagtcagga ggaagtactc accatcctga gagatgaatg gatctttaaa 24120
aagtgccttg ctctagcaag aatagataaa atcagtttct ttctttagtg tagtccaaga 24180
ttctaaccag attatatgcc tttgtattaa aaaactaacc taataactat aactggaata 24240
atgatataat gcattatttg tcatggtatg aaacccattg gtaacttctg ttcactatta 24300
ttccctttat tcaaaaaggt aaaggtaaca tcttccatca aacttgcaat taatggggga 24360
tggtcagata gtttttctca gttgtatcct gccaaaattt atttatttat ttatttattt 24420
atttatttat ttatttttga aacagagtct tgctaggctg gagtgcagtg gcacgatgtt 24480
ggctcactgt aacatctacc tcccaggttc aatcaattct cccgcctcat cctcccgagt 24540
agctgggact ataggtgttc gccatcacac ctggcgaatt tttgtagttt ttggtggaga 24600
ggaggtttca ccgtattggt caggctagtc tcgaactcct aacctcaagt gatcctcctt 24660
tcttggcctc ccaaagtgct gggattacag gtttgagcca ccatgcccgg ccattttttt 24720
tttttagta atacgaagag tagtaaaaga aatcaaatgg gagtatattg acaaagtttt 24780
tttttttttt ttggtcttgt ttcttgtttg tttgttttg tttgtttata aaaaaccatt 24840
tagaatccgt aaagcaaacc cattcaattt gtgggcactt tgtcatcaag ttgattcaat 24900
ttagctattg gtttttaata attggttatt tagctattga tttttaagct attggttttt 24960
aagaatattt gtcattactt aaaaacctta gaaagacttt gctttattct catcaaaatc 25020
ctactcaatg taagcttctg cacaaggagt ttctgattgt atcagccatc tttttattta 25080
ttgcaaaaag aaaaataaaa catttattat aatgtgtcac ttcctggttg ggtcagtgag 25140
tgtatttgct tttgggcacc tcagttcaac atcagcatta tgaaaaatta catatatggt 25200
atttagaatc tctatggtat gttgtaattt aatgaaagct ttatctaaat gtgtgtgtat 25260
gtgtgtctgt gtgtgtgtag ctttaccttt agtgtgcaaa taaaagtaaa attttacata 25320
gctggatagg atacaagtac tttaggttcc agcatggtaa atatccactg tcaaaagtag 25380
aaaaagagaa gtcatccagt tggctattac gtagtgttta gcaattattt tttctgcaag 25440
ggatcatgta gtaagtattt tagcctctgt cataactatt caattctgac acttgcatga 25500
aagcaaccat tggcaacatg taaatgaatg agcatggctg tattccaatc aaagtttctt 25560
taccaaaaca ggcagcaagc ctactttggc catagtttgt aaatctctaa tttagatacc 25620

-continued

```
tccaaatatt aagctattta tgattgttcc agttatctgt gtatgcagac aaaccaactc  25680
aaacttggta gtgaaaaaac tctatcattt attattaata tctttaatga ttctggtggt  25740
taactgtgat taagtaggca gggttttttt cttagatggg gaataggggg tgtttctttt  25800
atgttatagt taaatggcag tttgtgtaga gtcatctcaa agccttcctg acttatgtca  25860
agctgttgat gctgcccatt attgatcatc ctccctatga tttgttactt gacagatgaa  25920
gaaaattaaa tggtacagct gagattagaa acctaatgtc tgagtccaaa tctcatcttc  25980
ttttcccaaa aaaaaaaccc ctttatctga atcccactac caccatcacc acatctgtac  26040
cacccctttt gcctgtactt ttaggcacac ctcacagtat ttacatttca gttttctcta  26100
ctaagcaaga ctgaaagctc cttgatagca atgaattatc ttaaaacacc tacctaacac  26160
aggatcctgt gttaggattg ggtcaccagc tgatgatttt tatagctgcc aatttagaag  26220
ttggccgtct ctgaaaactg gcttagcaga gagattgaaa caatttatct agagagtcac  26280
aaattcagcc gatgaccagc tgagtggaag tgatgctcag tgaataatga ggctaatctg  26340
actgatgatc aagattgagt catgcatgca tatgagcacc caacttgaaa tgaggtatca  26400
ctgtacgcat taatttataa ctacatatga agaaaaggag ccaagtctca taaacccaag  26460
tgctggcctt tcaaacacac acatttcatt cagagactca aatttgacaa tgatacctga  26520
taaaggctca catcagtcat atcacagctg gggctgtctg ccagagtacc cactagtgac  26580
ctctccatac atattgccta ggctttttca caatatcaca tctgagttac aaaaagacag  26640
ctaggctgaa gctgtatttc cttttatgac ttttactgta aagtcacaac accctctcat  26700
catactctat tggttgagac aggcataaag gggtagggga tagattccat ctgatgatga  26760
tagagtgaca gtcacattgt attgtaagaa gagcacgtga ggtgggaatt aaacctagca  26820
tcatgatatt ttttatttga aaattttttt ttggattgga ataacagcaa gagcaaaaga  26880
agagccagac gtggtgacac acacctgttg ccccaactac tcaggaggct gaggtaggag  26940
gatttcttga gcctaggagt ttgtggctgc agtgagctat gattgcacca ctgcaatcca  27000
gccttagtgg cagagttaga cacctcagct ctaaaagtat aaataaataa aaatataaaa  27060
aatacaaaag agatgagtca ggacaacaag agttggagag caaaggaaaa actgggacaa  27120
taggaaagac atgttgataa tgatagctaa ggaaagcaga ggctaaattc agatttatat  27180
aaggtttaag ctatgtgttt gcttcaaacc agagccatgt gtttgaagca aaagaatttt  27240
aggaacttat gtaaaggatg aatggtagcc tctcaagtgg tcagaagaag gttgtgttca  27300
ggtccagaca aagaaggaag tcagaaagag gtctccataa ccagaagatt ggtatgccct  27360
tcatattagg ccacattctg acccaaccag gagcttcaca atgtgctgga ggtctggaac  27420
caggaacttc ctagacttct agaggtccat aacccattgc ccatcaaggg caacctgtag  27480
cacaggatgg ggcagatatg aggcagataa atgaatgcct ctagctggaa aaacactagt  27540
gttgataagt gaagttgaat ccagacaggt gtcacaaaag ccaaaatctc actgaaatga  27600
ctgcatcaat tggttggttt gacatcacat gtctaaaaat agatagaaat aacccatctg  27660
ggaagttaaa gaatgaggaa agtctttaaa actctatccc ctaacttctt tcatttttgt  27720
gctcaataag ccattttctg cattagagcc ctcagaagag ccctttagag catgcacctg  27780
atacgagagc cctgagacat ctgctgtgcc atttaaatcc tctctttgct atacccagct  27840
ttctctgtct atggaccaaa tgtgcctatt ttttgctcca ctgatttaat agccccagga  27900
aagttgataa tgtaatcata gaagttctat ctgaatggaa catcttgagt tctatctcca  27960
gtctttcttt ggggcttcct ggaccgtgta gactctaact ttgctacgtt gcagctgctt  28020
```

ttggtgcaga gcttattgga atcattccct ctacttagtg tgtgtgtgtt tctgttagtc 28080
tatcaactgc cagaaaaatt tgccttatta tttagcagca ttttaacagg tttcagtcca 28140
ttaaaagcaa aagagagcat taaatggcat tcttcggctg ttaaccagtg agctttcatc 28200
agtttattaa tagactctaa ctgcaaatgt gctcgttacc tgctagggct ttagactgac 28260
tctagcggca acaatggtat cctctgggac tagaaatcca attctaagtt ctaccttcag 28320
gtaatgcttt tggactgctt tggaaagtta aacaaataaa tgctgaaact ttccttccag 28380
agagctgaaa ctgactagat ttattcatgc tttaaaaact ctggcctaag aaaaaaatag 28440
ccaagactaa agtagcaaac tgaccagtgg gcctaagtct cttccagttg ccattttttt 28500
aatgccattt ctatcctgtt tctacagagc tattacaatg gatggacaga aagctgagat 28560
tcaggatgat tgggaggata cacatggttt ctcacagaga gagtcaaatt cactagaaca 28620
gtattaagaa ttttgctttc atgagagagt agtaaaagat tctactccag agatgtagac 28680
acatgtggcc actagaaaag ctaaattaat attagcttct ggtggaactg gcatgctttt 28740
gggcacctca actgatagtt caacattagc attatgaaag tcacatatac agttatttag 28800
aatctctgtg gtgtatggta atttaatgaa ggctttaccc aagtgtatgt gtgtgtgtgt 28860
gtgtgtctgt gtgtctgtgt gtagcttatt agattcaatt taaaaccctg gcatgcttcc 28920
tccttttcct gataagagtt gtgtttccat ttttgccttt actgcaagat tagaagaaat 28980
cttatcaaca attgtaatcc tcattgaagt acatggcagg gaaaaggaag aggtagatca 29040
agcacaagaa aggaacgaga catataattt tatccctgtt tcaaatagtt aaaaaaaaat 29100
atatccaaaa gggactattc aaccaggaaa gagtgtgacg atgtaaatat gtaagttcaa 29160
ttttcaaata cgtccaccca tcctcttcca atatagcatt gtggaagctc ttgaggaaaa 29220
ctggcttgat tttaacaact aaagaaattt catttgcatt gcacattctt ataatagtaa 29280
caatagctta cacatttgta gcacatagta caagttaggc attctgatgt tttacatgaa 29340
ttgattcatt aaattctagc aaaagttcaa caaagatttt taatttcatg ttgtgaataa 29400
agatataata caaaggaaca cagaagttag gtacttgccc aaagttacac atctgataga 29460
gatttagctg gaaccaagat gtgacgtcag caaatccagc ttcagaggac tgatcctgag 29520
tgctaagcat gttgcttctg ttagggaagg ttgtgatcta gctatgtgta ttatattttc 29580
agcaagtatg tttgattctc attcctcaat caaattttct ccattttatg actatattaa 29640
tgttatgcat gagtatatta tatggtgtgt gattgcattt ggaagcatca gtaaatacat 29700
aggattgaca atgaggaaga ttatagtgtt attagaccta ccatcatgat gttagataag 29760
atttgtaatt tgaagtagag acagtgctta ccaaatatct attattcccc tacatgtttg 29820
agcccctcta acatttatat tggggccata taattaattc taacaaatgt gataataagc 29880
aaaagtaact aattgtgaac tgcatttaga aaaaaaaccc actacaatgt aggatcagag 29940
tagcaaatga aaggccacaa tattttatgg aatgttaaag agttagaaaa aacactggag 30000
gcatttttcc tggaaagctt gagggtaaag tgcgagttgt cctaaaatat ctggtgtgtt 30060
acagtgtaga ggaatgaaaa gccttattct aatggcgtga aagtatatag cagagctaat 30120
cagtgaaaaa tacagaggaa cttattagat tcaatataaa taagaacttg cttttgatac 30180
cacatgtggg accctgcatt acatttgtaa atcatttatt tttcggtttt gccattgtct 30240
gccacttcca gtagaataga agttcttcaa gaatatgtat cttgttcata gctattttcc 30300
taatgctttg catggtccta gccagtttaa aaaaaagtat gatatgaata gtcatcatac 30360

-continued

```
aaatatatga gtgaatcaat gaacaaataa acattctatc aaatagagca ctctagatat  30420

tttcctgact ttggaggaat tctaatacag gctatgtgat tggttgctag gaatattttg  30480

gagcaacttc cagctctgga ttgtggtcgt actagatgtg acctaatgtc tgtcccaatg  30540

cccagattct ttcattttta tattttacat ttgaactttc ctgatcatta aagccttttg  30600

ctttttactt cccagcagat aggaaattca gtcaagatgt ttgttgttgc aaaaccacaa  30660

agaaatattg caagcatttt tttagcccta cctgtttgca agcacattta tcatcttttg  30720

ataacatggc atcctattca gagaaatgga cagtatgcac tttgtaatca ggatggaggc  30780

tgtgatatga ctgatgtgag cctttatcag gtatcattgt caaatttgag tctctgaatg  30840

aaatgtgtgt gtttgaaagg ccagcacttg ggtttatgag acttggctcc ttttcttcat  30900

atgtagttat aaattaatgc gtacagtgat acctcatttc aagttgggtg ctcatatgca  30960

tgcatgactc aatcttgatc atcagtcaga ttagcctcat tattcactga gcatcacttc  31020

cactcagctg gtcatcggct gaatttgtga ctctctagat aaattgtttc aatctctctg  31080

ctaagccagt tttcagagac ggccaacttc taaattggca gctataaaaa tcatcagctg  31140

gtgacccaat cctaacacag gatcctgtgt taggtaggtg ttttaagata attcattgct  31200

atcaaggagc tttcagtctt gcttagtaga gaaaactgaa atgtaaatac tgtgaggtgt  31260

gcctaaaagt acaggcaaaa ggggtggtac agatgtggtg atggtggtag tgggattcag  31320

ataaagggtt ttttttggg aaaagaagat gagatttgga ctcagacatt aggtttctaa  31380

tctcagctgt accatttaat tttcttcatc tgtcaagtaa caaatcatag ggaggatgat  31440

caataatgca attaaggcct ctaacataag gcctgccaca tagtaggtgt tctgaaatga  31500

tagaaagtta ctgttactat ttattatgat cattattatt aatgtgaatt agaattttga  31560

ggcagaggtg gaatatccca cttctctgta atcctcacag atgggaaaaa tggtgaaagg  31620

aggaatcaaa gagatgttat ctatattaaa aaaacataga ggaagatgat agctaaccta  31680

gcaagagcag aaatgatggt atagcagaaa agagtgccaa ggcattccag gtcccttgat  31740

gtgccagaaa ggtaagaatc aatgatgcct aatgggcatt tgccaccacc agctggcagt  31800

ttaggacaat tcaagttgtc ttctcaagtc ggctccagta tttagtagag cttgcccttc  31860

ataataacat aagtgtctct ctaatgtttg cattaggacc catctccagc tttatcaagt  31920

aagtgagcct gtggatcagg ataagcattt ttttagaagg catcttcctg agccagctga  31980

tcatgtaaca ctgtggctca gaaacacgta catgtgaaat aaaccttgac gtgtttctag  32040

caaataattc agtttaaact taggacatgg aaagtttctg gttcaaaaga aaatggagta  32100

aactcatttc accttatttc tcctgcatta attatgaata taaagtctgg acagaacaca  32160

taagccaagc attaggagac tttgaagaaa gagaagtagg gagagaggta ggactgtcta  32220

gcagcctcaa gacttacagg atgactcagt gataagttcc ccatttttgg tttgtttcct  32280

ttattttgtt ttgtttgcct cctatatatg ccggtctggg cacaggagca gtctgcaagc  32340

tagaagtacc aatgggttca gacaaaatag tcccaagaca agtctgctct tttcagtcat  32400

attctaaact tggaagagac agccttgtag gatgggactc ttttgattat acccactgta  32460

ttccaggaga gcatctcaaa cctaccacac ctctccctct cctccctgac acttcagaat  32520

ctggatcaaa gagtcctgct atttgtgctc agcactaatg caagcagagg cagtcccccc  32580

tccaaagggc actggtaaaa ctgcagggca ggacactctt gaccattccc atcttgtgac  32640

aatggatcta gaccctttac atatccttct ttataagctg gcatgatgtt aacctttgtc  32700

agcaggggc actggagaga catcgcagga ggaagaggtc tgtcttcttg gtcttggatg  32760
```

```
ttcactgacc agactcctgc ggtgcagata gcttcttcga aagatgccca gcttgtgcag  32820

tgcatggtgt ccagaaatgc ccacagacta gtggcctctc tcaacacacc cctaaagcag  32880

ttttgtaaca ttgtgcctct agtgagacat tttcctatga accacttcta ctggcaccct  32940

agagggttag caagttccac ctgtgatgcc tcatggcaac ctctctacca ttcagtgagc  33000

cacggtcaaa ccgtgtccaa caaggtctag agctcagccc tgggaagggt gagctctttt  33060

ctctaagcac attatttcag ccctaggtag gcatgactgc tccttatatc tgctattcat  33120

atattatttg gagatgtctt tatttcttac tatacaatcg tcattaagca atcccttgtt  33180

acagttaaca ttaaatttcc cctgtccaaa ttacgatgcc agtttctctt ttttgattgg  33240

accctgactg acaaagaatg atgccaatag catgatccgt aagagaaaaa aaaagataaa  33300

ttggatttca tcaaaattaa aaacttatgg tctgcaaaaa agaaatatta gtccaggaga  33360

aaatttttta attcacatat ctggaaaaga tgttatatct agaatatata aaaagtactt  33420

taaacttgac agcaagaaaa caaataatcc acttagaaaa tagacgaaag ccatgagcag  33480

acattttgtc aaataatgca cagatggtac aatgaaaagc acataaaaag atattccaca  33540

ttattagcta tcagggaaat gcaaatcagc acattataag atacctctac acacctatta  33600

gaatgtgtaa aataaataac aaatcccatc aatgctaagt tctgataagg atgtagagca  33660

tcagggagtt ttatacattg ctggtgagaa agaatttggc attttcttgt aaaagtaaac  33720

atatacttgc catatgaccc agcaatctta ctgctgggta tttactccag acatttataa  33780

cagttctgtt aatcctcaca tacagtagaa acaacctgtc tttcattggg caagtggatt  33840

aacaaactgt gatacagaga tacagtggga taccactcag cagtaaagag gaataaacta  33900

ttgatatgta taatttggat agatctcaag gacattatgg tgagtgaaca aaaccaatct  33960

caaagtgatc catcttttac tattccactt atgtgacatt ctccaaatta cattgaagac  34020

atagcatagt tcccaggatt tagggttgga ggtaagctat gactttaatg ggtagtac   34079
```

<210> SEQ ID NO 14
<211> LENGTH: 27661
<212> TYPE: DNA
<213> ORGANISM: Homo sapiens

<400> SEQUENCE: 14

```
aaaagtgtgt tttttaggaa atacttgttc tgccatctcc cccatagttt tacaaagtaa     60

atcacgttgt gcttggaatc gtccctgcct acgctcgaga actgttcact tagaaaataa    120

acatgtgggt aagcattggt ccatacgtat aagcgatcaa gagaccctgg cccccgtgga    180

aacatgtttt caggcaatcc agctctggta ctctttgagc tgcctttcta ttttacggca    240

tgttcagaag atgaatctac cattacgctg actaacgaag tctagtcata gcgatagcgg    300

tgtcttagca gcagaagtga tggttggtta actgagcgtg ttttagacgc catctgcatt    360

acaaagtatc ttccatgggg taggccatgg agtcagcacc actgttctcg aggggcagtc    420

tctagctcct catcttacaa gggcaactga cgctgacatt caacaactgg tgcaatgtca    480

gctgcaggcg agtaggtgga gcaggaccta ctcagcacca ggcgggctgc ccctccacag    540

tttgcggtga taataaggca ctttacagag gatgctacca tacttggtat agaaatcttg    600

aaaaagtgga tgctccggtg aagctcagag aggctgtgtg gggtacccgg ggtgcacagg    660

cacggacctc agacgcaaac tcaacacatt catgcccatc tttccattta tgtttggttg    720

gatcagccta atttgcttgt atggaatgaa attcagaaaa aaaagaagga tgatttattt    780
```

-continued

```
ttacagcctt tgaaatgtcc ttagtcatgt acttgtactt ggtttgaaat cgtatcataa    840
attggaatca gggaatttga agggaatttt caaagtccct tgtgactctt catgtgcaat    900
cttcagcatc gagtattccc caattttcca caggggatac acttttctat catgatctgg    960
gcccctgtcc tgcccttcag ccacagttca tctttcctga ccattctgtc ctatgataac   1020
gtctcccttt aattttctcc gtggctcatt tgacagctaa cctgtgtcca cttttctgtt   1080
ttaacagcta gcttctttac acaaggtatg ggtgtctcaa atgtttaggc acatatgtga   1140
aattctaatt ggttgattgc tttgccagaa atgaccctat aacctgggcc agattaccag   1200
atgtgccaga gtgtgctcca gtcggtggga tatgcccctg ggccagccag ggtgtatctc   1260
agccagacag ccacaagatg cagtgctgga caccccagtc ctgagttgat ggagctgctg   1320
actttctggg tttcagctgt atcatcagta agagtgctgt atctattcag gcagaggaga   1380
tggtctctcc agctccacta gagatcttag atctgtgatg cacaggtaat tactcctaaa   1440
attacctgag acgatttctg aaatcatgag ggagtggctt cctgaggagc gatgattaca   1500
caaacccggg aggacctgga ggtcctgctt ctgtcactgg ctgggctgcg tatcatacct   1560
tttcataact acaaaccctc cctgaaggtc ttcccaaggt gaaatatcca agaacaagta   1620
gactgtattt gctcttgctg ttgttcccca tggtggacgc ttgccataaa tatggtggtg   1680
gtgtctgcaa gactggctac gttcatgact gctctcacat gcttttctga agcatagatt   1740
aagtggcagc tctacaaaga gtgagattta tagcctagtt tatgtttttt gggggtaaga   1800
aattcttcag tgtttctaga agctacttaa ccttggttga tgtcacttaa aggagaggaa   1860
aattctgggt ttgcaagggg agcctcctgg tgttttgagt aggtcagcat ccacattacc   1920
agatggtaaa gacactttgc taggaccttt gacaagctaa gtactcgagg ggctgtgata   1980
ctgaaggggg tggagaatgg aggtggctca taaataatgt ggtgctggta ggctgcagcc   2040
cagacatgac cacagcgcag ggaaacgcac ctccgccagt cttggcgaac ttcacagcac   2100
cttcccatac aaaagtggca gatactgatc taactgcatc agaagtcctt gctattggtc   2160
cgtgaaaggt ctaagttaat ctgtccctta ctatcttaaa ttaaacgggc acatgactcc   2220
accgaccgtc cacgaggtct ttcctggagt gaagctttaa ttctctgtcc gcccactgca   2280
gtcccggata ggggagtaag aaggtctgac agttaatgac acttgaggaa gatgtgcgtg   2340
cctggagctt ctcagcagtg ggacatttgc ccctagcaga gggtcgaggg acactggcaa   2400
atgctgacgt ggatgtagca cggtcaccaa aaccccgcgt gtccgagatg gtggagcagc   2460
ttttcccggc tcatgtgagg gctggccagc cacacagcac caggctgact ttagcagctt   2520
ggtctcccaa gccgaggcta tctgaaggac accagagagc tgcgtttctc cttctgtgcc   2580
aaggtgaaca cacaacgctt cagatgttcc gctctcccct cgtgagacag acggcccggc   2640
ttctgtgtgg ctttggggat gggagtgcca gtcactggcc acagaatgac aaattgcctc   2700
cctgccaata tcagagcagg gacagttctc gccacagcgt cctccagatg ggcccaatta   2760
aactattagc caatgagcaa ggtctgatgg ctccattagg aacccccctg tgcttaaata   2820
aacagctcag aatacatagt ttctccatcg agccctggct cggcgaaggc cccatctggg   2880
caaggtctcc aaggttggcc ctggcgagcc ccagggggtg ttggggtggc tggggcaggc   2940
cgccctccct ggttctcagg gtcctgcaag ccacaccgca gtgggtgatg tgagagaggg   3000
ggcagcaccc ccacctgcca tggccagggc caagttctcc accagctgca ccccttttgct  3060
tgtgcacgcc tagacaacca cactccctga ctggatggaa cttccagaac cagcccctga   3120
cctcagcaca ctagtccctt gccagctgtc tttcccacat acagaaattt caggcccgtg   3180
```

-continued

```
ctgtttggct gttcatcatt tgtaattact gccaagcaag gggcacattt cgtgcagaat   3240
aaatgaagac agcagacagc gaagcggggc cttactgcct gagcgtggtg ggcgtgactc   3300
tcggggggag cgggggctgc ctgcttatgg gtgctgcttt ctctctgccc gtgaaggtga   3360
ccatcacaca ggcccagggc ccctcagggc tcttctcacc ccacacgacc cagggttggt   3420
tcccagtggg agcagagcct gcccaggaga gaccgctatc tccactggtc cagcttacac   3480
aaagatccat cgaaaagcat cagttcttga gaaaaacgac actataaata aaatggtttt   3540
caatacagag agctgggctc catcaaccct gctgagatcc ttggggacgg ggctgcgcct   3600
ttctctttgt gattatggtc actgtattcc agtaatttgg gtgaactctg attggccatc   3660
caatatcttt gatgttctag gaggtcacac actgcaaaaa gcaaagcggg tctgtcccct   3720
gcttgcttct attgggaggg gccacctcac gccctgcagc acagccctgg ccagtgacag   3780
ctcagcatgg ctgcccagtc tcagctttta actggggcat ctgttctgca aatgctcctg   3840
agcacccact gtgcaccggc cctgctaggg acgtagcagt gaccaggact gccaaggccc   3900
ctactgggtt taattcattc cgtgtaatct caggctgctg ccagctcccg ggaagaccaa   3960
gccatctgtg ctcctcccgg gagcatccca cttcctttcc agagctcggg gctcaccttt   4020
tggattctgt cctcctacca ctgacatctg ctcttagggg aggaagagaa acttcctcgg   4080
ggggcaaatg agaaatagct aatttgtgcg gtgtgcaaaa gaaagtcatt gcttgctaga   4140
attgttgcta tgatttttcc ttattcatta atttcctttt gctactgggt agcatattgt   4200
tgttcttggt ttgtgttgac cttttcagtc ctcatgaaaa caagccgtcc tgaggcaggc   4260
cttctttgca caggtcagca tcagcaagga aggctcatta cccattttta atgcagttag   4320
atggtgctga acttgactgt gtgctttcac tccaagattt gccctcttat caccccccaa   4380
gactaaggtc ttggcctagg actgataaac aaaccagccg atccgtgaca gtgatggaag   4440
ggtgcgtgtg tgcagagttg gggggcatgc acgctttctc tgctctactc ctcttctgcc   4500
aaggccagtg tcctccctga gatgccaagc ccctcagacg atggaggcct cctccccct   4560
gggatcctga tgacaaccat ctcaggcacc caatcacaga gtgcttggaa atggccactt   4620
agagcttccc tgcaaaaggg tggctgatcc caatgtgagg ctgttgttgt ctccaagggc   4680
caccttccca cggaggtgac ttgcacgagg gtgtcagcgt ccaggggaaa tatggggctg   4740
ctgccacagc ctagagacag acaggagatg gcgaggaggg agactggtgc ccaggcgctg   4800
gcttgcctgg ggtcccagtc atggcagaag gacttgggga gacagcatgg aacaggaatc   4860
cctgctcaga gctgctgttg agacacagaa agaacctccc ttgctggtgt ctggcagagg   4920
gtgttgatga cagtccaggg gcatgaagag gctggggttt gaggctgctg taggctctgt   4980
ggggtcccag gaatgttggg gggcccagga atgtgcccac tttcaatctt ggtcagcgct   5040
ctccacccga cgccttgtgt gcctgcagag ccgcagtctc caccagacgc ctcgtgtgcc   5100
tgcagagcca cagtctccac cccacgcctc gtgtgcctgc agagccacag tctccaccca   5160
acgccttctg tgcctgcaga gccgcagtgt ccacccaaca ccttctgtgc ctgcagagcc   5220
gcagggtctg ggttttgtgg caccacatgt tcggtctcat ctcctcccaa atcctgttaa   5280
atttccctga atttaggacc aggcccaatg ccatggacac agtagaccct caataaatga   5340
gtaatcaaat tgatggtgaa gaactgattt tttttcctgt taaccctccc tagcagggtt   5400
tttattaatg gggttttcag cagcttgcga ttgaaaggcc gccttgcccc agggtacaat   5460
gaagtcagga cccccaggag ggaggctccg tgtggctggg ggaggggagt aacagaatga   5520
```

-continued gcataaaatc gcagggagat gccccacagc tgccccgggg gtcctggggg ctggctctgt 5580
ggaggtagag gagcagaggt gccttcagca tccgatgctc ctgcctgtgt ctgtgtctcc 5640
tctccacgcc tgctccttcc ccatcaccct gttctctgtg gccattgcag gtgttgtaag 5700
ccacatcaaa tccacttgaa atggggtgaa atgaatctac caatacctga atcagtcagt 5760
agcaacctga ggtgatcatg tagttttctg gttgcctgag gcttgcattt caggctcagc 5820
ttcaacaggt tccagtggcc atggggacag gaagtgcacg cctcccccga gggtcttagc 5880
tcacccaagg ctgcagtgtg agggccacat ttcctggggg ccaccccatg gcactggcta 5940
ccccaggggt gctgagacag gcctgttcct ggagaccacc tagaccctcc aatatcacct 6000
gcttctgtct aagctctgaa atccccttct ggcgtggtgg tgcctcccct gtgcagcccc 6060
acccagaacc cctctttcca cctgtgcagt gtgccccagc ttccccgcag ggtggcagtt 6120
cagggctcac tccccagctt cccacttact gcccacctac ccctctagac agaggttctg 6180
ccagggcggg gctttcctgt ttcctttggt tctgtcagat cccagcatgg accgatcccg 6240
aagtgcagtc cctcagaggg tggagtgggc atttatgtgg gctatttggt aatggcagca 6300
atgtcgcctc tccctgacga ctctaccagg ttggccctgc atgcttctgt gtgctgcagg 6360
tgagcttggc tcatggctgc tgatcactgc agccccttcc cagccacacg ccaggcccaa 6420
ggtgatgcat gctgggccat gccaggcacc tgtgatgaaa tgctcagttg tgtgaaggtg 6480
ctggccagcc cacgagagct ggaatgccag agtcacattc agttacaagg tggagccatc 6540
agcacagcag gcaggcgtga gggtgaggac gcggtcggga ggaatctcac ttcccctgca 6600
gacccttggg agagatgcag gggacacagg gcgaggactg ggaggtgagg ttccagcagg 6660
ggcagggtta gccctgcatg gggcctttcc ttgaggtttc tctgtagggt gtcccctgag 6720
ccctgaggcc acacccctcg gctgctgaac ctgcctgtgc tatgacagtt cattgtcctg 6780
gacaataagg cactagaaca gagggggtgt tgataattaa gccaagctcc atgctgtgga 6840
aagcgggtgc ccactcaaca ccccagggtc taaggggacg tggcaggttt cactcccaga 6900
ctggccctaa tgcagaagag aagggagaaa ccaccaggtt cccacattgc catccaggca 6960
tcttttccgg gctgagtttt ctgcaaggct tgtcgggtcc atcagaggta aaaactgcaa 7020
cgcacaccta attataccta atttgctatt gattaactat ttattctaac agaaccactg 7080
taaaactgtc ctgtgtgttt aactatcaaa ataaaggagt gctggcacct tctgcatttt 7140
caaacattct atgctctagg tcaaagttca gcatttttat tgactctaaa caggagatgg 7200
aaaaccacat tagaaaaagt ggaattaaaa aaaaaagaaa actggaaatg ccttttttatt 7260
agaaaatggc ctcatgggca tggctggctt tcaggagtaa gttcatggag gatccctttt 7320
gatgtgtcag tactggaaca agcgaggttt tgagtatttt cagtagcatc tttgttcaaa 7380
gttaatcttg tggatatcaa accacctctt ggaaggagga agaatatcta ttttcatgtt 7440
tacattacaa aagagcttat aaattagtgg gtttcactaa aagttgtatt gaagtaagct 7500
gtgggttttg tgtgaggtgt gaggtgtgcc cacacaccta tatatctcgt ttatctagct 7560
tcatccagac aaaacagtgt tcacatttaa tttttcagat aactgaaata aagctgtcta 7620
agagtaaagt ctttataaaa ttgtaagcac ttttattaat gcacttctgg gatatttttc 7680
ttactccccc tgcttttgaa aacagaaact acggaaagta actttgaaat aatccccctt 7740
gtgttagtag aacaatgtat gctcatctgg ggcctcagat gacgtcgaac ctagggactc 7800
atggcgtctc ctccaccagg aatccctgcc agcctcccag ggtccacgtg taattctact 7860
tttctcttct gccatgactc ctagcccaaa gacaaatact tctttgcaat ctcatattgt 7920

-continued

```
gctaatttta caacatctga tatttttggg gtggtattag atagcttcac tttcatactg   7980
gttgagaggt tgggggaaag agagagaggg aaagagagaa aaagggagag agagagagag   8040
agagctgcta ataatataca actctattcc tctagtgcgt ggtcttgtga atgacgcaca   8100
cttgttgcat aaaaggcctt tctcttcata ttggggtgtt ggctatgact tgagatttgg   8160
gactctcacg cgtcttcatg tgggatgtgc cagctttgac tctgtgacta gaactgactt   8220
ctttaggcca atgtgctcaa agataataat ggtaattaat ctttttttaa tgtgcctatt   8280
atatatggga aggttatctt aaaattaaaa ttatcttcaa ggcttattta tcctgttgcc   8340
cagagaatgc tgtggatttt ttttccatgc catgaagtag aggcattagg atgggccaga   8400
aaaaaacaaa gcaaattcct tcaaagataa gatactttaa gttgaaaaat caaggaactc   8460
tctcttccta aagcagtggt acccatctag tgttttgtgt gtgtgtgtgt gtgtgtgtgt   8520
gtggtgttta acaaaagttc tcataaaact tagggtttct gattaactca gtgatgccaa   8580
attctatttt tttttccaca acgtacacca tagaaagcat gcagccttgt gaaaagttcg   8640
aaaagaggtc ttcagattca gagtctccag gtggccaatt tcttctgatc tagattttca   8700
aaaaagtatg aaagcagcaa aaagttatta agcaaagctc aatggcacag ctcaacttca   8760
gtacgttgct tcttgtagta ctgcaaattc taattaatgg cttgctcatt gcacacagga   8820
agtgagattt agcctaggga aaagaaagca aggagtaact caaggaattt gataaatcat   8880
atttttttat gtttttatgt ttaaaattcc ttctttttaa aagcggtgaa aatgtaacac   8940
tttctcttcc tcttactgga aattttcaaa taattttgtc tttcctcctc tcttggcctc   9000
agacagatta tggagataat gcactcacca tccctctccc ctctgaagcc acggtttcct   9060
gaaggtctcc catttctgga gtctctcgag gcctccaaca gaaggcagca tctcctgtgc   9120
tgcaggcggt taccaagtaa cagacctcag aagccttcca aggtccaagg atgtaaatgc   9180
agtatgtcct ctaagccgag cgcagggtgc tggaatccga gagccagggg ccatggtgag   9240
agcttccttt gctgggaggc acggatggga tgaactccct ggaggtggaa gggcagcctc   9300
cctcccggtc tttctctcct gtctctccct ctctatctct gtctctgatt ctctctcttt   9360
ctctctgctc tcagtttctc tctggttctg tttctccccg tctctgtctc tctttatctg   9420
attctctgtc tctctttatc tgattctctg tctgtgtctg cctcagtctc tctctctctc   9480
tttctgtgtc tctctgtctc ttatctgatc ctgtgtgtgt ctgtgtatct cttctgtctc   9540
tactgtctct ctctgtgtct ctgtgtctct ctgtctgatt ctctctctct gtctctatct   9600
gattctgtct gatgctgtct ctctctctct ctgtatctta ttctccctgt ctctctgtgt   9660
ctctctatct ctatctgatt gtctttttct gtctctctct gtctctatct gattctctct   9720
ctctctgtat gtctctctgt ctgattctct ctgtttttct ctgtctctct ctctatgtag   9780
ctcttctgtc tctctctatc tgattctgtc tctctctgtc tctatctgat tctctgattc   9840
tctctgtttt tctctatctc tctgtgtatc tcttgtcttt ctctgtctct atctgatact   9900
gtctctgtct gattctctct gtttctctc tctgtgtatc tcttttctct ctctgtctct   9960
gtctgattct gtctgtctct tttctgtctc tatctgattc tgcctgattc gcgtctctct  10020
ctgtctctga ttctctctgt ctctctatct ctctctcact ccattggcat cagcacagga  10080
cccagtggtg caggggaagc tcccagccat acaggacaag cctctgtcac gacagccctt  10140
gctggtgtct gcatcaggag gtctccttgg cgatgaggtc taaggagcaa ctggcatcag  10200
aacagagcct ccaacctgcc ttaggtcgtc aagactttga agcaagagcc tcagatgcaa  10260
```

-continued

```
ttagcaggac ctgcctttgt gtcgtgtgct ctgagctagt ctcgcggagg ctgctattgt  10320
ttggggttca gctgtcagta ttgttatcct gcaaaatctc tgaatttcca cttctctgtc  10380
caagtgccat gaagccagcc aagtggggag aaagggttct tctgagattg attttttccc  10440
agacactgtg gttctgttca attgaattca ctcaagttgt ggttaacata agcactacgg  10500
agagtatgac atgtcaaatt agcagctttg caaatctcct gttaattgtc agcctaatta  10560
aaaaattgct aattataatg tttataactt caaataactg ctcagctata aagtaggcct  10620
gtcaggtgta aacaggggac tggagggaaa aagtcaatcg acatctgtta atttatcagc  10680
ggcagtatac caaattgaaa aatagattgc ctattgcact gtaaatctgc attacaatga  10740
aaagaccgaa tcattccaca cctgctaaat aaacggggat gggagtcctt cctggcctgc  10800
cccgggctcc tctgctgctc acatccccgt cctgtctatg agctggggga aggccggagc  10860
caggcacagg gacagaaaat gggggtcccc acgcgacatc taaaaaacga aaaaaccaaa  10920
ctgactaaaa cgtgcacaga aacacgattc agacagtggg agcggggtga tccctcttcc  10980
ctggaaggag cctggagccc cactgccggc cccggtcact ttagtctgaa ttctcagtgc  11040
gtctccagct gcagaacgat gaggctggaa tacaacgcct ttgtctctaa gatccgggca  11100
atcccagccc aactttcaga gcctggtgaa ctcgcctatg cccacatctg caggggtagt  11160
tcctgctggg ccctgcccca tctgggcaac ccatcatgct gcttccagta gttcctccgc  11220
ctgccttccc tcctctcctc cagtgtcctg tgagactccg gggcaggggc tgtctccacc  11280
ctcttcctcc attgcctgcc ctgcctgggc gacccatcat gctgcttctg ggttcatctg  11340
cctgccttcc ctcctctcct ccagtgtcct gtgagactcc ggggcagggg ctgtctccac  11400
cctcttcctc cattgcctgc cctgcctggg cgacccatca tgctgcttct gggttcatct  11460
gcctgccttc ctctcctcca ctgtcctgtg agaccccggg gcaggggctg tctccaccct  11520
cttcctccat tgcctgccct gcctgggcaa cccatcatgc agcttcctgg ttcatccgcc  11580
tgccttcctt gctctcctcc agtatcctgt gtccaccctc ctcctccatc gccccccttcc  11640
agtctgggga gtggagcatg cagaatagaa gctccctgtg accgagcctg tgctcacaaa  11700
gcactggcta cttcctggag gataatcatc aatccccttc tgcaggtgca ctaacagcac  11760
ttgggtgttg tttagtttgg ttcaacaaac atttattgag catttcactc tgtgtcagga  11820
attattaatt attaatatat tcagatgagg gaagcaaagt cggtcgtaag gtcccacctt  11880
tgggaagttt acagatgagt gtgactatgt atgttggatt aaactggggt ggaatggtgg  11940
ccagtcatgt cagccacagg taactgcatg taatgagggg taaagaagga acgaatagct  12000
ccagtatctg ggctccaga gcccctggga ttttgccctg tcaaccagaa cacgtaaggc  12060
ccaagacccc agaaaaaggg tggatttgtc ttataattgt gcccctctga tgtttcctgt  12120
tgggaccccg tgtatcaggt gagcagtagc agagttggat ccagtgtcgg ggtatccatg  12180
gacacctgcc catccccagc cctgcacctt ggccccaaag tctctgaact tttgatccgc  12240
actgtgtcag tatacgtctg gccttgcctt cattccactg catgtttaac cacattctga  12300
tagagcagga gcatcaccat cttggacaaa tgccaccatt ttaagttctc cttgattaaa  12360
aaccacctaa atccagcccc aaaacatcag cctaatggct aatgtcagca tgaccagaaa  12420
cattccaacc ctgagataaa cccccccctct gaccagaaac atgccaaccc tgagataacc  12480
tcgtctccaa acagaggcat tccaaccctg caataaactt tccctcacac agaaacattc  12540
cgagcctgcg ataagctccc ctccctaaac ccttaaatac ccttagtctg taagagagtg  12600
ctcctgaccg aaatcagcca gaagcccctc tcaggtttat tttccaaaat aaacctgtct  12660
```

-continued

```
ttgactgtga agccactttt catgtttcct ttcttctttc tttaactctt acacattccc  12720
caggccctgt ccccgtcgtc actttctctg ggtcataatt gggtacattc ccagtggttt  12780
tgtgtacctt agctagaggg agggtgggtt tccacggttt cctgagtcac agatggccta  12840
tgtctcacag gttatccctt tcttccccac ccaaacgtcc tctcatctca tctcccaata  12900
gaggagaaag agaattagaa agcttcactg ccttgggcca ggtttctttc cttcatggtc  12960
tttattttac aggatgcctt ggaagttgtc tgtctgaaga ggcagctagg gttgggggag  13020
ggccccggca agcacctaga gtgcagacaa gttaagcaga gggtgggctt tagccaggga  13080
agcagagcca gggtggggag tacagaacca gcccagagca gagacagagg gagggcacca  13140
tgtgagggtc ggcattcacc gagcagacag gaaccagcag tcacactgcc caggatcctc  13200
ttccaaacct gcctcagata atgtcacaat cactcccatt gcacagacag atacttcagg  13260
cactgacttt cacacacttg ccctaaattt cccaagtgca aagggacggg gagaatcagg  13320
cactcaagtc tctgggcagc ttcaccgtct tccctctacg gaaccgcact gctgctgggg  13380
agggaaaggg gctaggagct ataaatcagg ctgaagaaag ggaaatgcag gcactgaggc  13440
agcggcagac gctctgacag atgaacctgc actgcagctg ctcctctcag ggcatgtgca  13500
ttgagcccag gagtccccag ggaggtccac accctaagcc cgggacccag acatgttact  13560
tttcagcgtt gaaggtgctt taaggatgtg gttaaggtta ctgaccctgc agtgggagga  13620
tgtcccagac tattcttgga agggttattg gcccaatcca ataacccttc aaagcagaga  13680
actttctccc actaaaatca gagaggtttg gaggtgaggg gagcccggtc cacgggtttg  13740
aggaggaatt catccaggca gcctccagga gcccaggctg gccccagcgg agaggagatg  13800
ggcctccatc ctcggcctca ggaactgaat tcagccagcg ccctgattga actggggcag  13860
ggccctcgga gccccctgca gagcttcccc atggacccct tcccccaccc agagcctgac  13920
ctgcctgctc ttggttccgg ccttgcaagg gtttttcaga ggactcagtg cagccacgcg  13980
ggcccagact tctgactcac ggaaccatga ggtaacaaat ggcgtggttt tatgctgctt  14040
agtttgtggt aattttacca cagctattaa aaactagagc gagtttattt cctgttccag  14100
aactgtcaaa tctgggtgag gctagggtct gcagtgaact acggcccctc gaaacccatg  14160
gcttccagca ggccagagac agaggacagc agggaggagt ccgcaggctc cggttgcaac  14220
aattcacatc atttccgctc ctgctgtgac cacgccgggt gcccagggtg ctgggcagga  14280
agttggggcg acgtctccca gcagtgcccc tctaggggaa gaagcactgg ctcctgacgg  14340
gcagcggcca cctctgctct ggtttctacg gaccagacat ttgtacacat gtggcctggg  14400
agcatcagca gaacgccagg gtgtgaccca gagaactgcc aatcaaccag acgcggaaca  14460
cgacatcacc aggcagacac aggacaaagc taaatttaag tccagtggat gtgattagct  14520
gcaatgttca gttgaattat ttggtaaact cagttaataa attttataaa ttcaatatat  14580
tttatagtgt gcaattaaag tattttaaaa gtgatcaact attttagagc agttttcggt  14640
ttacagaaaa gttgagcaga aagtacagag acttcccata catgccgcct ccttgtacac  14700
agtttgtcct actattaaca tcttgcatcc atgtgcgcat tgattacgat tgatgaagca  14760
gtattgatgc attattattg gctctattta catctgggtt actctgcgtg gtgcggctct  14820
gagaattgcg acaagtgcat ctccccgccg tggctgctac agagcgctgc cacagagcgc  14880
tgccactccc gaaacgccct ccgtgctccg cctgctcatc cctccctccc cgccacccct  14940
ggcaaccatg aatcttttta ctgtctgcgt agtttcgctc ttttcagaac atcatagagt  15000
```

-continued

```
tgaaatcaca tagtttgtaa cctttgcaga tgggcttctt tcacttaata atgtgcattt  15060
aagctttctc tatgtgtctt catgacttga caaatgaatt ttttttttt tctttgagac  15120
agagtctcgc tctgtcaccc aggctagagt gcagtgacgt gatctcggct cactgcaatc  15180
tctgcctcct gggttcaagt gattcttctg ccttagcctc ccaagtagct gggactacag  15240
gcacatgcta ccatgcctgg ctaatttttg tatttttagt agacagggtt tcgccatctt  15300
gaccaggctg gtctggaact cctggcttca ggtgatctgc ttgcctcgga ctcccaaagt  15360
gctgggattg caggtgtgag ccaccacgcc tggccaggtc atttcttttt agcatgaaat  15420
atcattccct ggtccgaacg tgctactgtt tatccattca cccactgaag gacatctggc  15480
tgctgccgag ttttggcaat gatgaatagt gtggctgtaa acagctgttt ctgtgcagtt  15540
tctgtgtgcc tgtgttttca cgcctgtggg tcagtgtgcg ggtttgtgtg tgtccgcgtt  15600
tccatgcctg ttggtcagta tgtgggtttc tgtgtgcccg tgtttctgtg cctgtgggtc  15660
agtatgtggg tttctgtgtg tccgtgtttc catgcctgtt ggtcagtgtg tgggtttctg  15720
tgtgcccgtg tttccatgcc tgctggtcag tgtgtgggtt tctgtgtgcc tgtgtttcca  15780
tgcctgtggg tcagtatcaa ggtatgcact tgctgaatcg tatgaacaga gtgtgttcag  15840
ctttgcagga aacttccaga ccactctcca cagtggctgc accatcctgc actcccacca  15900
gcaatgaatg agggtttctg ttgctccaca tccttcaaag acctgaccta acgacccaca  15960
aatgctgctg tcacggcttc tttctaagag gcttcacggt ccagagaaat gcatttcacg  16020
aatggccttt agcagttggt aagaagaatt gctgtttacg gcgagcaggc tgtgtgctgg  16080
gcatctctca tgttcatcat ctcatttcat catctcggtc gtctggtagg agtgcactag  16140
cctccctcaa tttctgacaa gtagctgaag actggggaga tgaagtaact tctcaaagat  16200
cacagtcagc agacggcaag gggaacgtgg gactcccatg cggctgactc tgggggccct  16260
gccatcccca gcctagggcg ctgtgtgctg catcctcatc gctctgttgc caaatggctc  16320
ctcaagactg ccagagttct tctgtgcccc actgagttgc gtgggcttaa ttgcttagaa  16380
tgagatggca gaagaaatgt tgagaaggga aatcaagaaa acagatggca tttaggaggc  16440
cacagaaccg aaagaaagaa caccagggac ccatgagatt caaggtgagt catgccgaca  16500
ccttgaccag gggcaagggg gaaggagccc ccgtattttg tcattaaaat ctctagagtt  16560
gccagaactt cttgtattaa gtttcacttt tcccacagga agtactggaa tcataattaa  16620
aggaaaaaaa agcttaggtc actgctaact tccaacttca acatctttaa ttttagttat  16680
ttcccctggc tccctggctt attgccctag atctttcctt aatatttaag acttcatata  16740
acaattaata taaaagcttc accgccgttt ccagctcatt ggaaatgcac gtgagtgggc  16800
gttgtgcgca gacactgagc gtggctgggg gagacgccac agaaacagag gacgcacccc  16860
gacgtgggga actcgcatcc acccagggaa cggcacacat ctgcctccac tgccaatgca  16920
ggagcactgg gcccacccga gaggacctcc acgaatgcct tctgcatgcg gggcacccga  16980
ggcccagaga gggaatcccc aggcacccca cccaggcggt gcatagacag tgctaggccc  17040
tgcatgccgg ggtccagccc agggctgtgg cctgtgccaa atgccaagaa gcaatcgtct  17100
actgggaggg gaaatgtcag ccattctgag gcagctcagg gaaatccaac tcctcggtcc  17160
tgaggacatc aagagaaaaa ggagtgatgg cacaggccgg ggtccggggg aagggagggg  17220
catttctctg ggaagcccct ggagatgaca cttccctggg ggccttgtgt cccccagaga  17280
aggcctcagg ccagtggcat ggatgcttcg aaggcttctt gggtttgcag catctcaggg  17340
ctcaccagag gcctccaggc ccacagtaaa tgagggtgcg gcacgggggc gtcagaggac  17400
```

ggacaaggat agcacagcaa cgaagcactc caagggctta gcccgacatt cagggaccca 17460
cagagtggcc tgcagggagc tggggcccag ccacagtcct gccaggtgga aggaccgggc 17520
atggaggctc caggctgaga ccagcattgg atagggtggg tgggcaggga ttacttaggt 17580
gccaataacc caggagtaga ggagatggca ccgctataaa atgccacgag aggtgcgcac 17640
aagggttcag ggctgcatag aaccgggagg gagaggaaga ccccactgga gcaagtgcca 17700
gggtgacaga gccagaggac tttctgagat agcacagccc cgagggtcgg cagggcactg 17760
agggccacct gccctgcctg ccccgccagg gcgagcatct gaatccacat tctcctgggc 17820
cgcagctcat ctgcgagtcg gagcctccga aggggggcca gtagcacatg tcccagcctc 17880
tctcgcccag gtgatcctca tgaccagacg cggctttgct acaagacagc tcagactgtg 17940
ttcccccaat cgtgttcccg caggaaagct gcccgaggat ttttgtcatg cacacgccgc 18000
tgccagccca ttagctctcc ctgcttccca tggtctgccg catctggggt atccagcgtc 18060
ctcctgcagc cgagggggaa ttctgaatgt tttgctagaa accgtctcat caacattcag 18120
tttcctaaca ttggttccaa tcctgatttt tagcttcatt ttttttgagg ggcgagggca 18180
tctgggcact ggaaatgcgg gaacccacac gcagctcatc cacccatagg ctctgacatg 18240
tttaacttat atctgaaaga ctctgagact cgagatggcc aatgtttaac ggcatcagct 18300
ttgaccagca cagttgcaat tatttgacat gatgtgttca acccatcaaa gttgaccaag 18360
ggttttgtag acccatttgc tcagggtaac ataagatctt ttgacaaaca tgtctgttta 18420
cgtactttca gaatttgtgt agactctgaa aagacccctg atgtaatcta ctaaaaacat 18480
agagggtttt taagttattg ttatgtaatt aacatctgta acggcagttg acttaaggaa 18540
atgtctttgc acttacagta agtacatttg tgtgaggaat tatttgcgta aattgtccca 18600
aatagaattt aatttaaaag catagatttt atgatcttgc tcatgaaaag ctgagaatga 18660
tgaatcaaac attaagttaa atgtcacatg ataattagtc agatattgcg agcttacaac 18720
taggatcttt ctgattctct gtctcttctt taggcatcag gactgaatca tatgttttat 18780
gaggcctata aaacatgcaa acctctgatt tagctatttt taaggactgt agagacactc 18840
aaatttggtg tatttaagtt gaactcacat ataggatatg taaaattgca tacaaaattg 18900
caaatggggt tctctgtaaa tatgtttgct aatgagaata ttttaatttc atagatcata 18960
ccaggaagat aaatcatcca tttacaaaca gcagttgctt aaaagatgtg gactaggcaa 19020
tttttccatc tccagtggaa ctgagaggtc cttgttttca cagctgaata ttcaaagggg 19080
tgtttatcat aattggagga tgcttgacag tttatgcagc ccacacttag caggcttcaa 19140
aatacatcct gaattatttg ttgcaaaccc ctagataaac aagcaagaaa tgctgctcaa 19200
ttgtcctaaa aagccacaaa ttagaggtat tttgggttac tcatagtgat ttctgaatgc 19260
agtggtaaaa ttctgatttc catttgtatt aattctcttt gtgaacttta aaagaactat 19320
ctttcaagtt taataacctt tctgaaaaaa atcataactg tagatattaa cctgaaacac 19380
aagaaaatgg atcaggtggg gcatcacctg tgaagccttg ttgggaatat gttgggtgag 19440
aacattaggt cacttctctc tgacaaggac accctccttg gctaaaggct ggttgggtcc 19500
tgtgagccct ccctggatga ggcgttagca ggaatcccgc tgagatagtg ggctggacgc 19560
tcaccctcac ccttagtgat attaaccgag ggcctctgtg attttctctc caggccctcg 19620
ccccaccact cggctgtcat ccccactggc cgctggtgca tttggacttg ggttcagtct 19680
ctctctccgg ttgcaatagt tttgagtgaa gtcttccttc tttgcttaac tggtgtcata 19740

-continued caatttttct tttgcatgtg ttacaactca ttagaaccca gtcatgtgac atactgctcc 19800
ctctaggaat gaggcacaaa ggacattgga acagtcaaaa tacacttctc aaactttagg 19860
cactgacatg tgtgctgtta gtgcagtgga aaacccctca gatatgaatt cagagacagt 19920
ttgccaatat tttagttaag catctacaaa gcttggattc atgtgtggtt ttccaagtcc 19980
cagggcatgc aaatgagcca attagaagca gtagtggggc tgatcggctc actggaggtc 20040
aggaaaagtg gtgtgaatca cccacgttca ggtcaagaac tcaaacagca aatagcaatt 20100
agggctgaac actgaaggga ccaacaccgt caccatctca agaggccccg tgtgcactgt 20160
tctgcggcac tttatgagaa ccaattttca taatgataag ccctggtccc caaggaaaga 20220
ttgatttatg tttcacatat ttattaatgg aaggagaagg gcattctaat ctgttcgaga 20280
gctttctttc taaataaaac agtcctcccg ttgtgctgct cacaggctgc ttctgttaca 20340
tccaggagga ccatcttctg tgagctcctg gtggcaaagg tgttattatg tgtgacagag 20400
cctggttagg tggcaccagc cctgtaggaa ggaccagtgc agtagctagt ttattttcac 20460
cttgggctgg ttggccgtga ccgtctcccc ttggcccctg gggctggcct gaggacaaca 20520
ctggggaatt acaaatggag aggacatttt atgcagcaag ccaagcccta gcctactgcc 20580
tgcctaatgt cacagtgaga tgagaagccc aggtctgcag ggtgaggtgg tacctcccag 20640
gtgccctaca ggtgagagtc ctcatcaggg cttcaccagg atccctcagc tccacgaaga 20700
gctgtgcagg gctagtgagg cctgaggaga tgataccacg cgtgtctccc agggggggttg 20760
acaccaaccc ctagaaggga acagaggtct cagagtcagc cgatcccgag gacttgaaag 20820
tcaggctccc tggaagctac caccacccac ctgccttgtg tgaaagcagc acacacataa 20880
cacatagaga cacacacaga cacacacaca gacacatgca gacacacaaa cagggagaca 20940
caaacacaga cacagacaca cacacactca cagggagaca cagctagaca cacagacaca 21000
ctcacagaga aaacacaggc acactcagag agacacacac agacacaaac acacagactc 21060
actcacaaac acagacacac tcatacagag acacacagac acaaacacac acagacacat 21120
gcagatacac acacagggag acacaaacac acacagacac atgcagacac acacacccac 21180
agggagacac acctagacac acacagacac acagagacaa acacagacac actcatagag 21240
aaaacacaca gacacaaaca cacagacaca gtcacagaga caaacacaga cacatagact 21300
cacagacaca caaacagaca cactcataga gacacacaga cacaaataca cacagacaca 21360
ctcaccaaga caaacacaga cacactcata gagagatgca cacagacaca aacacacaca 21420
gacacatgca gacacacaga cacatgcaga cttgcacatg ggaagaaacc attcacgtgt 21480
gggtacaggg cgtctgtgag tctcacactt gaccgtgtct ccagtctgga gcctcaggcc 21540
ttcatgaagc ctcccaggtt cctaggggga agacatagcc tctgtggaac cctacactaa 21600
acattttgaa tatttggaaa gatatcttta taatccagcc aatatcaaac cttcactttc 21660
cttctgttag cagccaatat gtttgggtat aattttcata ctagtttgtg tcatagtaag 21720
ttaaagagat agtatttgga aggttttgca tcaagatttc cttcctagca catggaattt 21780
cagaaataat atttattaca tttcccaaag tttgaacagg ggtccttaga ggactgaacc 21840
cagcagcaga tggattttac ttagggcaca ttatttcaaa acattcagat gattcatcag 21900
cttataaact gagatttgtt ccagtaagat tttggctatt ggcttccctt gaaacaccag 21960
gagctcctgc ttccttgaaa ctgagttacc actgggagca gttgtcagat gctgaccggc 22020
agccacccct ctcccagtgg ccccggccct gccacacata ccagcagccc tgccacactt 22080
gactcattcc tggaaggaac ctggtgcctg gacacctgag tgtgcagcgc cactgaagct 22140

-continued caacgcttac tgtcgctcag ggcctcgagg ctcagaaagt gtgtgactta aacacgtcac 22200
ggaggccagg cacacagtgg ggccaacact acggcttcct gagctgtcca gcaggtttct 22260
gcttctcaac gcggccctgc ctggttctgt aagagcagga gcaggagcag gtgattagga 22320
cgtccgcgca ggagccgtgg caaaaacgct tccagacaat ggggaactca gacgtctgga 22380
agggacgggg gcagaacgtc agcgccacag acaaatgtga atcaggctta ttacacatct 22440
attgagtgag tcagctgcac acctcaagcc ttttcctgat tctgattttt aaatggaatt 22500
tcaaattctt tctttgaaaa gaaaaggaaa ggtcaaatac aggtaatttc atctccgtgc 22560
cgcgcatgca catttcaaat acaatcttcc agcttgctgc ctgttctcac acctcccggt 22620
tacttctcct cttcccaggg acccagacgg ggagagggtg ctgggcgccg gcaagccaca 22680
gcgtctgctc tcatgatctc gcccccaccc gccttgggcc cccagaggtc tgtgctccgc 22740
tcctcttcct cctcagaact ttctattcat tacatcccag cagagcacct caccacggtt 22800
gccccaggaa aggatgcatg tgtggttttg ctgtgctttt tgtttacaaa actgatcatg 22860
ttggttaact ccagcccaga tgttgcagag gttaagtctg ctatcaacct ggagatgttc 22920
ggaaggagac agccatcacc acccgtcaca cctgctttgc tgcttctggt aacatgcatt 22980
tgcctgcagg ctcagggcac gtggaaggag gtgtgagata gaatcgggac agggccaact 23040
tgcccatgga ggtggcatct ccctcgtgct tctctggatt ctgtcacctg ttccagtcct 23100
gggaatgggc tgacaattca tctcctcgtt ctgtgcctat aacattgcat tcccagagca 23160
tcggtgccac ctttccagct gcgacagtgt accctgtgta ccacatccag taacctgcaa 23220
taagagacgc tccatacgct gcgtcaaatt gaggaacatg cagcgaatct gccacagaca 23280
ctgacaccac gtcgcaccga gatgcccagg aaatcaggag ttaaggagac gtcgctgctt 23340
cccttttccc ttctcacttg cactgggggg gagtggggtg tctgtaccta aaagcccttt 23400
ctcactggct gtctttcggc aacatacttg ctcttgattc acatgcccct gttcatgcac 23460
acttcggggg gcggaggggc agagccctac cccatccccg agagtcagtg tgtgaggtgg 23520
gcatcaagca gagccctacc ccatccccga gagtcagtgt gtgaggtggg catcaagcag 23580
agccctaccc catccccgag agtcagtatg tggggtgggt gtggacagcg ggtgtggaca 23640
gcctgccatc gttttcctct atctctgtct ccacgggcac tgccaacgcc ccgtctttca 23700
acctcctttg cagcttgggg ctcctgtgga ctgcgggctg cccagggatg tgctgtgggt 23760
tcctgggaag ggcgctgggg tgtcgagcac cttggccatc ctaaacttaa acaccacgcg 23820
ggctcgtaat taatccttct tgaaggaacg ctgctgattc cctcgacatt accaacaatc 23880
tgcggttgaa ctacagacat acacccaagc gggcatactg agaaggaaaa caaaatccct 23940
ccgccaggaa ggtccacctc tgacggatgc cgcctccagg ccgcacttct ccaagagccc 24000
gccttttcct ctctgcaggc ctcgcgcagc tcctgcctcc ccccatgcac gcgcttcgcc 24060
ttcctccctc caagccccgc gcctgcctcc ctccatggac acactttccc ctcctccttg 24120
caggccccgc aaggctcctg cctccctcca cgcacgcact tccctttcct ccttccaggc 24180
cccccgcctg cctcctccac gcaccgcaag gctcctgcct ccctccctcc acgcacacac 24240
ttccccttcc tccctccctc taacacatat ccagcaacct ccacgtctgg ttttcctgat 24300
ggagtaagtt actgaggaca aatcatttta caaatgagac aactaagagc tagaaatgga 24360
gagtaattac tcagggtact gcacaaatcc ataggaggga aacacacttt taacctacgg 24420
gtttcatcca gggcttctca aatgccactg cacttagttt ccagagacac caacagcccg 24480

-continued

```
gaggggacca gggggatgaa ctgaggcgtc tgtttctgcc tcagacacac agttgtcggc  24540
tggaccaaat gggcttcacc tcattccttt tggtgtagcc tctcccaggg ccagtaatac  24600
tgacctgaga gttgatggat aacttgaaaa gtctgttatt ctggcattgg gaagacttcc  24660
aactcacatt gtaaaaacat gaattttatt ataataaaaa gtaaatatcg ttcagtgaat  24720
atacatgtat atgtataata gatcatatat atttcagatg cgtaacaagt gatttgtaga  24780
tttcatttta tgtgtgtgtg tgtgtgtgtg tgtgtgtgtg tgtgtgtatg tgtgtgtatt  24840
tagaggcact ttgtaagtgg gcaacttatg gtcaaagtct gggacttaaa atatcctaaa  24900
tgaacgttca taattttttt taagggaaat attgatgaag ccctgtcgtt gaaacaaaaa  24960
gtttgtaagg ataaatcttg caaaatgatt tctttacttt ctagtagtag tcacagaaac  25020
aaagaaacac gtcgcttaga ccttattgaa gtagctgcgt gggagacact tgattattcc  25080
aggaaagaca catggcagga tgagagtgtg aaaaatgaac actgagcact acgggaacgt  25140
cggatcataa cgatgacgaa ggaaagggcg aatccctcca atggagtctg ctgcatggac  25200
agggctcagg acggggaaca ggagccttca gggctgaggc cgtgcagcca ctgccaccgc  25260
tcactgccag gcaggccttg ctgggcatac caggaggggc agctgggctg tgtgcccact  25320
cagccacttc cgggatggga tcctaggccg gttaccgact tctccctgcc ttcatccttt  25380
cataaaatag aagcagcaat catatctgct tcatattaaa gaaaggttat tgggcagatg  25440
ttagaacagc caacataaat gtgttaaatg tgcaaaactg agaataacaa ccaaataatg  25500
tgttaataat cagagagagg ttctacagga gaaggtttag ctgctgcaat cccctgaagt  25560
cgatgtcaga cctgagggct gcaaggaggc cactgggaac ggccccgtcg gccgggggcc  25620
caggaatcag ccctgtgcag agtgcattcc gtaatgtgtg caccttctct acttcagaaa  25680
aaaatattct ttgaaagatc catttttaa agcctccaac cccctgtga gaaaattggc  25740
aactgtgggg gcccccgcag cctcaaattt accagtccta cgggtgtgac ttgagaggga  25800
gtttcctgct ggatttcaat gaatggctgc gtatgttggc actggctgca cttggcttcc  25860
tggacttcct tggtcggcat tttggaagct ttgggtggca ctgagatttt caataggagc  25920
tatttgttat aatatgggct tgaccaatat tgatctggct tgtagtaaaa agtcagaata  25980
aaaagcgtat acagcctagc atgaagtagt cacgatcgtg atttgataaa ctgtgcagat  26040
atcgttggcc aaaaacctca agttactcct gtcaagccct ttggttgtgt tgcggttggg  26100
aggtcacagg gtccggtttt gatttctagc ctttagatca ccgtgtgatg catctcctct  26160
acctgaccgg tcccggaggt caccttccac tcactcatca actgtaagtg agtaaaagtg  26220
gcgaaaatca tcatggggaa gtccaaaacc taaaataaaa aaactgggga aagtttaagt  26280
cattcaagtc ggaaagcccc tgaagacctt ttctgctgtc tgcaagattt cagaagcaat  26340
gggccttgtt caggaggttt gggttcaagg atgcatggat gttctggagg tttgggttca  26400
gggatgcatg gatgttctgg aggtttgggt ttgggggtac acggatattc tggaggtttg  26460
ggtttggggg gtacatggat attctggagg tttgggtttg ggggtacatg gatgttctgg  26520
aggtttgggt ttgggggtac atggatgttc tggaggtttg ggttaaggga tgtgtggatg  26580
ttctggaggt ttgggttgcg gggtacatgg atgttctgga ggtttaggtt cagggatgca  26640
tggaagttct ggaggtttgg gttcagggat gcatggaagt tctggaggtt tgggttcagg  26700
gatgcatgga tgttctggag gtttgggttc agggatgcat ggatgttctg gaggtttggg  26760
ttcagggatg catggatgtt ctggaggttt gggttcgggg atgcatgaat gttctggagg  26820
tttgggtttg ggggtgcatg gatgttctgg aggtttgggt tcagggatgc atggatgttc  26880
```

-continued

```
tggaggtttg ggttaaggga tccgtggatg ttctggaggt ttgggttgga ggtgcatgga  26940

tgttctggag gtttgggttt gggggtacat ggatgttctg gaggtttggg tttggggatg  27000

cgtggatgtt caggaggttt gggtttgggg gtacatggat gttctggagg tttgggttca  27060

gggatgcacg gaagttctgg aggcttgggt tggggggtac atggatgttc tggaggtttg  27120

ggttcaggga tgcgtgaatg ttctggaggt ttgggtttgg gggttcatgg atgttctgga  27180

ggtttgggtt cagggatgca tggatgttct ggctgacagc ctggagacct agggctagtt  27240

actcagtctc tgagctggtg atgtctcatc tgtaacaggt gagataacaa gggaggcctt  27300

tgcagggagt gaagggaagc cgtgtctcta atccctgcag gagggcagag gccagcctta  27360

gctctgagtg gcagctcaga ggaaggggct gcagaggtcc gcgtgggtca gagttgaatc  27420

tgctcagact tggagcccag ttagatgaag atgtggagta agggctgcat cccacccacc  27480

cccgactttg gtaagaggct gtgagtcagg gcgcgtttct aactcttgac ctgagcccct  27540

gtgcacaggt gcttctgagt ccaggatcca tccctgaagg tttgcaggca tattaggaca  27600

aaattgccat tttgggtctt ggcaaatgtg caatatgaaa ttaagtgagt taatcggtag  27660

t                                                                  27661
```